US010738086B2

(12) United States Patent
Leamon et al.

(10) Patent No.: US 10,738,086 B2
(45) Date of Patent: Aug. 11, 2020

(54) CONJUGATES CONTAINING HYDROPHILIC SPACER LINKERS

(71) Applicant: Endocyte, Inc., West Lafayette, IN (US)

(72) Inventors: Christopher Paul Leamon, West Lafayette, IN (US); Iontcho Radoslavov Vlahov, West Lafayette, IN (US); Hari Krishna R. Santhapuram, West Lafayette, IN (US); Paul Joseph Kleindl, Lebanon, IN (US); Kevin Yu Wang, Fishers, IN (US); Fei You, West Lafayette, IN (US)

(73) Assignee: Endocyte Inc., Lafayette, IN (US)

( * ) Notice: Subject to any disclaimer, the term of this patent is extended or adjusted under 35 U.S.C. 154(b) by 33 days.

(21) Appl. No.: 15/431,157

(22) Filed: Feb. 13, 2017

(65) Prior Publication Data

US 2017/0151340 A1    Jun. 1, 2017

Related U.S. Application Data

(63) Continuation of application No. 14/820,777, filed on Aug. 7, 2015, now abandoned, which is a continuation of application No. 12/666,712, filed as application No. PCT/US2008/068093 on Jun. 25, 2008, now Pat. No. 9,138,484.

(60) Provisional application No. 61/036,186, filed on Mar. 13, 2008, provisional application No. 60/946,092, filed on Jun. 25, 2007.

(51) Int. Cl.
| | |
|---|---|
| *C07K 9/00* | (2006.01) |
| *A61K 47/54* | (2017.01) |
| *A61K 47/65* | (2017.01) |
| *A61K 47/60* | (2017.01) |
| *C07H 15/24* | (2006.01) |

(52) U.S. Cl.
CPC ............ *C07K 9/003* (2013.01); *A61K 47/545* (2017.08); *A61K 47/60* (2017.08); *A61K 47/65* (2017.08); *C07H 15/24* (2013.01)

(58) Field of Classification Search
CPC ................................ C07K 9/003; A61K 47/65
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 3,632,622 A | 1/1972 | Moore et al. |
| 3,641,109 A | 2/1972 | Emerson et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,687,808 A | 8/1987 | Jarrett et al. |
| 4,691,024 A | 9/1987 | Sirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady et al. |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Feist. Molecular Systems Biology, 2006, 1-14 (Year: 2006).*
Raemakers-Franken. European Journal of Biochemistry, 1991, 200, 783-87 (Year: 1991).*
Grahame. Archives of Microbiology, 2005, 184, 32-40 (Year: 2005).*
Grahame. The Journal of Biological Chemistry, 1991, 266 (33), 22227-33 (Year: 1991).*
Beelen. European Journal of Biochemistry, 1984, 139, 359-65) (Year: 1984).*

(Continued)

*Primary Examiner* — Noble E Jarrell
(74) *Attorney, Agent, or Firm* — Barnes & Thornburg LLP

(57) ABSTRACT

Described herein are compositions and methods for use in targeted drug delivery using cell-surface receptor binding drug delivery conjugates containing hydrophilic spacer linkers for use in treating disease states caused by pathogenic cell populations.

21 Claims, 14 Drawing Sheets

(56) References Cited

U.S. PATENT DOCUMENTS

| | | |
|---|---|---|
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Glazier |
| 5,547,668 A | 8/1996 | Kranz et al. |
| 5,552,545 A | 9/1996 | Pearce et al. |
| 5,562,907 A | 10/1996 | Arnon |
| 5,574,018 A | 11/1996 | Habberfield et al. |
| 5,583,020 A | 12/1996 | Sullivan |
| 5,627,165 A | 5/1997 | Nelson et al. |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipsky |
| 6,344,452 B1 | 2/2002 | Shinozaki et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,548,505 B1 | 4/2003 | Martin et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,747,022 B2 | 6/2004 | Shinozaki et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,238,368 B2 | 7/2007 | Zalipsky et al. |
| 7,279,562 B2 | 10/2007 | Molnar-Kimber et al. |
| 7,582,744 B2 | 9/2009 | Manoharan et al. |
| 7,601,332 B2 | 9/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Dömling et al. |
| 7,875,612 B2 | 1/2011 | Green et al. |
| 8,044,200 B2 | 10/2011 | Xu et al. |
| 8,105,568 B2 | 1/2012 | Vlahov et al. |
| 8,288,557 B2 | 10/2012 | Vlahov et al. |
| 8,349,901 B2 | 1/2013 | Satyam |
| 8,383,122 B2 | 2/2013 | Dai et al. |
| 8,394,922 B2 | 3/2013 | Cheng et al. |
| 8,465,724 B2 | 6/2013 | Vlahov et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,546,425 B2 | 10/2013 | Leamon et al. |
| 8,580,820 B2 | 11/2013 | Zanda et al. |
| 8,765,096 B2 | 7/2014 | Leamon |
| 8,802,632 B2 | 8/2014 | Cheng et al. |
| 8,889,880 B2 | 11/2014 | Vlahov et al. |
| 9,061,995 B2 | 6/2015 | Chari et al. |
| 9,090,563 B2 | 7/2015 | Vlahov et al. |
| 9,138,484 B2 | 9/2015 | Leamon |
| 9,192,682 B2 | 11/2015 | Leamon et al. |
| 9,295,731 B2 | 3/2016 | Nguyen |
| 9,550,734 B2 | 1/2017 | Vlahov et al. |
| 9,662,402 B2 | 5/2017 | Vlahov et al. |
| 2001/0031252 A1 | 10/2001 | Low et al. |
| 2002/0151088 A1 | 10/2002 | Molnar-Kimber et al. |
| 2003/0022831 A1 | 1/2003 | Rothbard et al. |
| 2003/0086900 A1 | 5/2003 | Low et al. |
| 2003/0162234 A1 | 8/2003 | Jallad et al. |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2004/0247614 A1 | 12/2004 | Dorr et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Mancharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2010/0004276 A1 | 1/2010 | Vlahov et al. |
| 2010/0040669 A1 | 2/2010 | Higuchi |
| 2010/0048490 A1 | 3/2010 | Vlahov et al. |
| 2010/0074863 A1 | 3/2010 | Or et al. |
| 2010/0104626 A1 | 4/2010 | Leamon et al. |
| 2010/0129314 A1 | 5/2010 | Singh et al. |
| 2010/0144647 A1 | 6/2010 | Kratz et al. |
| 2010/0240701 A1 | 9/2010 | Vlahov et al. |
| 2010/0323973 A1 | 12/2010 | Leamon et al. |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0022245 A1 | 1/2012 | Low et al. |
| 2012/0065149 A1 | 3/2012 | Vlahov et al. |
| 2012/0122893 A1 | 5/2012 | Reddy et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon et al. |
| 2012/0259100 A1 | 10/2012 | Jin |
| 2012/0322741 A1 | 12/2012 | Low et al. |
| 2013/0029900 A1 | 1/2013 | Widdison |
| 2013/0116195 A1 | 5/2013 | Leamon et al. |
| 2013/0137139 A1 | 5/2013 | Vlahov et al. |
| 2013/0184435 A1 | 7/2013 | Vlahov et al. |

(56) References Cited

U.S. PATENT DOCUMENTS

| | | |
|---|---|---|
| 2013/0203680 A1 | 8/2013 | Leamon et al. |
| 2013/0217638 A1 | 8/2013 | Wessjohann et al. |
| 2013/0224228 A1 | 8/2013 | Jackson et al. |
| 2013/0252904 A1 | 9/2013 | Leamon et al. |
| 2013/0281678 A1 | 10/2013 | Dai et al. |
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |
| 2014/0073761 A1 | 3/2014 | Leamon et al. |
| 2014/0073763 A1 | 3/2014 | Low et al. |
| 2014/0080175 A1 | 3/2014 | Vlahov et al. |
| 2014/0107316 A1 | 4/2014 | Vlahov et al. |
| 2014/0154702 A1 | 6/2014 | Parker et al. |
| 2014/0193437 A1 | 7/2014 | Lin et al. |
| 2014/0213760 A1 | 7/2014 | Keanib et al. |
| 2014/0227295 A1 | 8/2014 | Cong et al. |
| 2014/0227298 A1 | 8/2014 | Cong et al. |
| 2014/0249315 A1 | 9/2014 | Vlahov et al. |
| 2014/0309406 A1 | 10/2014 | Li et al. |
| 2014/0323690 A1 | 10/2014 | Cheng et al. |
| 2015/0250896 A1 | 9/2015 | Zhao |
| 2015/0258203 A1 | 9/2015 | Vlahov et al. |
| 2015/0284416 A1 | 10/2015 | Zhao |
| 2015/0314015 A1 | 11/2015 | Leamon et al. |
| 2016/0002167 A1 | 1/2016 | Vlahov et al. |
| 2016/0108085 A1 | 4/2016 | Vlahov et al. |
| 2016/0129027 A1 | 5/2016 | Nguyen |
| 2016/0144050 A1 | 5/2016 | Kim et al. |
| 2016/0168183 A1 | 6/2016 | Leamon et al. |
| 2016/0220694 A1 | 8/2016 | Vlahov et al. |
| 2017/0151340 A1 | 6/2017 | Leamon et al. |
| 2017/0290878 A1 | 10/2017 | Leamon et al. |

FOREIGN PATENT DOCUMENTS

| | | |
|---|---|---|
| CN | 101784565 A | 7/2010 |
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| IL | 93983 | 2/1997 |
| JP | 59-175493 | 10/1984 |
| JP | 60-255789 | 12/1985 |
| WO | WO1985/05554 | 12/1985 |
| WO | WO 1988/01622 | 3/1988 |
| WO | WO 1990/12096 | 10/1990 |
| WO | WO 91/07418 | 5/1991 |
| WO | WO 1991/007418 | 5/1991 |
| WO | WO1995/15335 | 6/1995 |
| WO | WO96/36367 | 11/1996 |
| WO | WO 98/10651 | 3/1998 |
| WO | WO 1998/08382 | 3/1998 |
| WO | WO1998/08859 | 3/1998 |
| WO | WO 99/20626 | 4/1999 |
| WO | WO 1999/61055 | 12/1999 |
| WO | WO 2000/35422 | 6/2000 |
| WO | WO 2000/66091 | 11/2000 |
| WO | WO 2000/74721 | 12/2000 |
| WO | WO 2001/010468 | 2/2001 |
| WO | WO2001/13957 | 3/2001 |
| WO | WO 2001/28592 | 4/2001 |
| WO | WO 01/74382 | 10/2001 |
| WO | WO2001/82975 | 11/2001 |
| WO | WO2002/059272 | 8/2002 |
| WO | WO 2002/085908 | 10/2002 |
| WO | WO 2002/87424 | 11/2002 |
| WO | WO 2002/098868 | 12/2002 |
| WO | WO2003/050295 | 6/2003 |
| WO | WO2003/092742 | 11/2003 |
| WO | WO 2003/097647 | 11/2003 |
| WO | WO 2004/005326 | 1/2004 |
| WO | WO 2004/005327 | 1/2004 |
| WO | WO 2004/012735 | 2/2004 |
| WO | WO2004/022099 | 3/2004 |
| WO | WO2004/037210 | 5/2004 |
| WO | WO 2004/046170 | 6/2004 |
| WO | WO2004/010957 | 7/2004 |
| WO | WO 2004/054622 | 7/2004 |
| WO | WO 2004/069159 | 8/2004 |
| WO | WO04/100983 | 11/2004 |
| WO | 2005/089767 | 2/2005 |
| WO | WO 2005/074901 | 8/2005 |
| WO | WO 2005/112919 | 12/2005 |
| WO | WO2005/115912 | 12/2005 |
| WO | WO 2006/012527 | 2/2006 |
| WO | WO 2006/042146 | 4/2006 |
| WO | WO2006/089007 | 8/2006 |
| WO | WO 2006/101845 | 9/2006 |
| WO | WO06/105141 | 10/2006 |
| WO | WO2007/002222 | 1/2007 |
| WO | WO 2007/022493 | 2/2007 |
| WO | WO 2007/022494 | 2/2007 |
| WO | WO2007/022512 | 2/2007 |
| WO | WO2007/140298 | 12/2007 |
| WO | WO2008/057437 | 5/2008 |
| WO | WO 2008/101231 | 8/2008 |
| WO | WO 2008/112873 | 9/2008 |
| WO | WO 2009/002993 | 12/2008 |
| WO | WO 2009/026177 | 2/2009 |
| WO | WO 2009/055562 | 4/2009 |
| WO | WO2009/117531 | 9/2009 |
| WO | WO 2010/045598 | 4/2010 |
| WO | WO 2010/033733 | 5/2010 |
| WO | WO 2011/069116 | 6/2011 |
| WO | WO2011/106639 | 9/2011 |
| WO | WO 2011/130598 | 10/2011 |
| WO | WO2012/019123 | 2/2012 |
| WO | WO 2012/047525 | 4/2012 |
| WO | WO 2012/090104 | 7/2012 |
| WO | WO 2012/112687 | 8/2012 |
| WO | WO 2013/126797 | 8/2013 |
| WO | WO 2013/130776 | 9/2013 |
| WO | WO2013/149185 | 10/2013 |
| WO | WO 2013/170272 | 11/2013 |
| WO | WO 2013/173392 | 11/2013 |
| WO | WO 2013/173393 | 11/2013 |
| WO | WO 2014/009774 | 1/2014 |
| WO | WO 2014/040752 | 3/2014 |
| WO | WO 2014/062697 | 4/2014 |
| WO | WO2014/078484 | 5/2014 |
| WO | WO 2014/080251 | 5/2014 |
| WO | WO2015/106599 | 7/2015 |
| WO | WO 2016/147031 | 9/2016 |

OTHER PUBLICATIONS

Agoston E.S. et al., "Vitamin D Analogs as Anti-Carcinogenic Agents," *Anti-Cancer Agents in Medicinal Chemistry*, 2006; 6(1): 53-71.

Anderson et al., "Potocytosis: Sequestration and transport of small molecules by caveolae," *Science*, 1992; 255: 410-411.

Antony A.C., "Folate receptors," *Annu Rev Nutr*, 1996; 16: 501-21.

Antony A.C., "The biological chemistry of folate receptors," *Blood*, 1992; 79(11):2807-2820.

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.

Archer M.C. et al., "Separation of Folic Acid Derivatives and Pterins by High-Performance Liquid Chromatography," *Methods in Enzymology*, 1980; 66: pp: 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

International Search Report for PCT/US2008/068093 completed Sep. 23, 2008.

(56) References Cited

OTHER PUBLICATIONS

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).
Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.
Bavetsias, V., et al., "The design and synthesis of water-soluble analogues of CB30865, a quinazolin-4-one-based antitumor agent," J Med Chem, 2002; 45(17): 3692-3702.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.
Campbell et al., "Folate-binding protein is a marker for ovarian cancer," *Cancer Res.*, 1991; 51: 5329-5338.
Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid—polylysine-mediated introduction of c-myb antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
DeVita, Jr., Vincent et al (eds); *Biologic Therapy of Cancer*; 2nd ed., J.B. Lippincott Company; 1995.
Domling A. et al., "Myxobacterial Epothilones and Tubulysins as Promising Anticancer Agents," *Molecular Diversity*, 2005; 9: 141-147.
Douglas J.T. et al., "Targeted Gene Delivery by Tropism-Modified Adenoviral Vectors," *Nat. Biotechnol.*, 1996, vol. 14, pp. 1574-1578.
U.S. Appl. No. 60/946,092, filed Jun. 25, 2007, Vlahov et al.
U.S. Appl. No. 60/982,595, filed Nov. 25, 2007, Vlahov et al.
Eichman, J.D. et al., "The Use of PAMAM Dendrimers in the Efficient Transfer of Genetic Material Into Cells", Jul. 2000, PSTT, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and nonclassical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).

GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
U.S. Appl. No. 60/036,176, filed Mar. 13, 2008, Vlahvo et al.
U.S. Appl. No. 61/036,186, filed Mar. 13, 2008, Vlahov et al.
Gottschalk S. et al., "Folate receptor mediated DNA delivery into tumor cells: potosomal disruption results in enhanced gene expression," *Gene Therapy*, 1994; 1(3): 185-191.
Greene T.E. et al., "Protective Groups in Organic Synthesis," 2d edition, John Wiley & Sons, Inc. New York (1991).
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," Anal. Biochem., 1976, 73(2), pp. 493-500.
Hofland et al., "Folate-targeted gene transfer in vivo," *Mol Ther* 5(6): 739-744 (2002).
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Holladay et al., "Riboflavin-mediated delivery of a macromolecule into cultured human cells," *Biochim Biophys Acta*, 1426(1): 195-204 (1999).
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.
Jones T.R. et al., "A potent antitumour quinazoline inhibitor of thymidylate synthetase: synthesis, biological properties and therapeutic results in mice," Eur J Cancer, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.

(56) References Cited

OTHER PUBLICATIONS

Kane et al., "The influence of extracellular folate concentration on methotrexate uptake by human KB cells. Partial characterization of a membrane-associated methotrexate binding protein," *J. Biol. Chem.*, 261: 44-49 (1986).
Leamon CP et al, "Cytotoxicity of folate-Pseudomonas exotoxin conjugates toward tumor cells. Contribution of translocation domain," *J. Biol. Chem.* 268(33): 24847-24854 (1993).
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.
Leamon CP et al., "Delivery of macromolecules into living cells: a method that exploits folate receptor endocytosis," *Proc. Natl. Acad. Sci. USA* 88(13): 5572-5573 (1991).
Leamon CP et al., "Folate-mediated targeting: from diagnostics to drug and gene delivery," *Drug Discovery Today* 6: 36-43 (2001).
Leamon CP et al., "Folate-targeted chemotherapy," *Adv Drug Deliv Rev*, 2004;56(8): 1127-41.
Leamon CP et al., "Membrane folate-binding proteins are responsible for folate-protein conjugate endocytosis into cultured cells," *Biochem. J.* 291: 855-860 (1993).
Leamon CP et al., "Selective targeting of malignant cells with cytotoxin-folate conjugates," *J. Drug Target*. 2(2): 101-112 (1994).
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)Tc-Based Radiopharmaceutical," *Bioconjug. Chem.* 13(6): 1200-1210 (2002).
Leamon CP et al., "Synthesis and biological evaluation of EC72: A new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem*. 10(7): 2397-2414, (2002).
Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.
Lee, R. J. and Huang, L., "Folate-Targeted, Anionic Liposome-Entrapped Polylysine-Condensed Dna for Tumor Cell-Specific Gene Transfer," *J. Biol. Chem.* 271(14): 8481-8487 (1996).
Lee, R. J. and Low, P. S, "Delivery of liposomes into cultured KB cells via folate receptor-mediated endocytosis," *J. Biol. Chem.* 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pterolyglutamic Acid to Pteroic Acid by Bacterial Degradation," *Archives of Biochemistry*, 1948; vol. 19, pp. 311-316.
Levy, Carl C., et al. "The Enzymatic Hydrolysis of Methotrexate and Folic Acid", 1967, *The Journal of Biological Chemistry*, vol. 242, No. 12, pp. 2933-2938.
Lewis et al., "Receptor-mediated folate uptake is positively regulated by disruption of actin cytoskeleton," *Cancer Res.* 58(14): 2952-2956 (1998).
Li et al, "Targeted delivery of antisense oligodeoxynucleotides by LPDII," *J. Liposome Res*. 7(1): 63 (1997).
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).
Low P.S. et al., "Folate Receptor-Targeted Drugs for Cancer and Inflammatory Diseases," *Adv Drug Deliv Rev*, 2004;56(8):1055-238.
Lu et al., "Folate-targeted enzyme prodrug cancer therapy utilizing penicillin-V amidase and a doxorubicin prodrug," *J. Drug Target*, 7(1): 43-53 (1999).
Lu, J. Y. and Low, P. S., "Folate targeting of haptens to cancer cell surfaces mediates immunotherapy of syngeneic murine tumors," *Cancer Immunol Immunother*, 51: 153-162 (2002).
Lu, J. Y. and Low, P. S., "Folate-mediated delivery of macromolecular anticancer therapeutic agents," *Adv. Drug Del Rev*, 2002; 54(5): 675-693.
Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).
Mack D.O. et al., "The Carboxylation Activity of Vitamin K Analogs with Substitutions at Position 2, 3, or 5," *Journal of Biological Chemistry*, 1979; vol. 254, pp. 2656-2664.
Mancuso A.J. et al., "Activated Dimethyl Sulfoxide: Useful Reagents for Synthesis," *Synthesis*, 1981, pp. 165-184.
March, Advanced Organic Chemistry, 1992, John Wiley & Sons, 4th Ed., pp. 362-363, 816, 885, 896.
Mathais et al., "Receptor-mediated targeting of 67Ga-deferoxamine-folate to folate-receptor-positive human KB tumor xenografts," *Nucl Med Biol*, 26(1): 23-25 (1999).
Mathais et al., "Synthesis of [(99m)Tc]DTPA-folate and its evaluation as a folate-receptor-targeted radiopharmaceutical," *Bioconjug Chem*, 11(2): 253-257 (2000).
Mathias et al., "Indium- 111-DTPA-Folate as a potential folate-receptor-targeted radiopharmaceutical," *J. Nucl. Med.*, 39(9): 1579-1585 (1998).
Mathias et al., "Tumor-Selective Radiopharmaceutical Targeting via Receptor-Mediated Endocytosis of Gallium-67-Deferoxamine-Folate," *J. Nucl. Med*, 37(6): 1003-1008 (1996).
Mathias, C. J., "A kit formulation for preparation of [(111)In]In-DTPA-folate, a folate-receptor-targeted radiopharmaceutical," *Nucl. Med. Biol.*, 25(6): 585-587 (1998).
Matsui et al., "Studies on mitomycins. III. The synthesis and properties of mitomycin derivatives," J Antibiot, 21: 189-198 (1968).
U.S. Appl. No. 60/808,367, filed May 25, 2006, Vite et al.
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
McAlinden TP et al., "Synthesis and Biological Evaluation of a Fluorescent Analogue of Folic Acid," *Biochemistry*, 1991; 30: 5674-81.
McHugh M et al., "Demonstration of a High Affinity Folate Binder in Human Cell Membranes and Its Characterization in Cultured Human KB Cells," *J Biol Chem*, 1979; 254(22):11312-8.
Melani et al., "Targeting of interleukin 2 to human ovarian carcinoma by fusion with a single-chain Fv of antifolate receptor antibody," *Cancer Res.* 58(18): 4146-4154 (1998).
Melby, E.L. et al, "Entry of Protein Toxins in Polarized Epithelial Cells"; *Cancer Research*, 1993; 53: 1755-1760.
Mislick et al., "Transfection of folate-polylysine DNA complexes: evidence for lysosomal delivery," *Bioconjug. Chem.*, 6(5): 512-515 (1995).
Mock D.M. et al., "Urinary Biotin Analogs Increase in Humans During Chronic Supplementation: the Analogs are Biotin Metabolites," *Am J Physiol Endocrinol Metab*, 1997; 272: E83-E85.

(56) References Cited

OTHER PUBLICATIONS

Morshed et al., "Folate transport proteins mediate the bidirectional transport of 5-methyltetrahydrofolate in cultured human proximal tubule cells," *J. Nutr.*, 127(6): 1137-1147 (1997).
Nair et al., "Folate analogs altered in the C9-N10 bridge region. 14. 11-Oxahomofolic acid, a potential antitumor agent", *Journal of Medical Chemistry*, 23: 59-65 (1980).
Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).
Nair et al., "Folate analogs altered in the C9-N10 bridge region: N10-tosylisohomofolic acid and N10-tosylisohomoaminopterin," *Journal of Medical Chemistry*, 21: 673-677 (1978).
Nair et al., "Folate analogs altered in the C9-N10 bridge region: 11-thiohomofolic acid," *Journal of Medical Chemistry*, 22: 850-855 (1979).
Nair et al., "Folate analogs. 20. Synthesis and antifolate activity of 1',2',3',4',5',6'-hexahydrohomofolic acid," *Journal of Medical Chemistry*, 26: 135-140 (1983).
Nair et al., "Folate analogs. 21. Synthesis and antifolate and antitumor activities of N10-(cyanomethyl)-5,8-dideazafolic acid," *Journal of Medical Chemistry*, 26: 605-607 (1983).
Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).
Nair et al., "Folate analogues altered in the C9-N10 bridge region. 10-Oxafolic acid and 10-oxaaminopterin," *Journal of Medical Chemistry*, 19: 825-829 (1976).
Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," *Tetrahedron Letters*, No. 7, pp. 783-787 (1968).
Neuzil J. et al., "Vitamin E Analogs: A New Class of Multiple Action Agents with Anti-Neoplastic and Anti-Atherogenic Activity," *Apoptosis*, 2002; vol. 7, pp. 179-187.
Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.
Nimmo-Smirth R.H. et al., "Some Effects of 2-deaminopteroylglutamic Acid upon Bacterial Growth," *J. Gen. Microbial.*, 1953; 9: 536-544.
Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.
Nomura, Makoto et al., "Development of an Efficient Intermediate a-[2-(Trimethylsilyl)ethoxy]-2-N-[2-(trimethylsilyl)ethoxycarbonyl]folic Acid, for the Synthesis of Folate (y)-Conjugates, and Its Application to the Synthesis of Folate-Nucleoside Congugates," *Journal of Organic Chemistry*, 2000, vol. 65, pp. 5016-5021.
Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.
Oatis et al., "Synthesis of quinazoline analogues of folic acid modified at position 10," *Journal of Medical Chemistry*, 20: 1393-1396 (1977).
Olsnes S. et al., "Immunotoxins-entry into cells and mechanisms of action," *Immunology Today*, 1989; vol. 10, No. 9, pp. 291-295.
Patrick et al., "Folate Receptors as Potential Therapeutic Targets in Choroid Plexus Tumors of Sv40 Transgenic Mice," *J. Neurooncol,.* 32(2): 111-123 (1997).
Patrick et al., "Intracerebral bispecific ligand-antibody conjugate increases survival of animals bearing endogenously arising brain tumors," *Int. J. Cancer*, 78(4): 470-79 (1998).
Peltier, Hillary M., et al., "The Total Synthesis of Tubulysin D," 2006, *J. Am. Chem. Soc.*, No. 128, pp. 16018-16019.
Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Prabhu V. et al., "Arabidopsis dihydropteroate synthase: general properties and inhibition by reaction product and sulfonamides," *Phytochem.*, 1997; 45(1): 23-27.
Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Punt, V. et al., "Effect of Vitamin D Analog (1α Hydroxy D5) Immunoconjugated to Her-2 Antibody on Breast Cancer," *Int. J. Cancer*, 2004; 108: 922-929.
Raghavan B et al., "Cytotoxic Simplified Tubulysin Analogues," *J. Med. Chem.*, 2008; 51(6), pp. 1530-1533.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res.*, 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Remington: The Science & Practice of Pharmacy, 21th Edition (Lippincott Williams & Wilkins, 2005).
Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.
Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4. 3'-Ethyl- and 3'-isopropylfolic acids," *Journal of Medical Chemistry*, 17: 219-222 (1974).
Rose W.C., "Taxol-Based Combination Chemotherapy and Other In Vivo Preclinical Antitumor Studies," *J Natl Cancer Inst Monogr*, 1993, No. 15, pp. 47-53.
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Roy et al., "Targeting T cells against brain tumors with a bispecific ligand-antibody conjugate," *Int. J. Cancer* 76(5): 761-66 (1998).

(56) References Cited

OTHER PUBLICATIONS

Sadasivan et al., "The complete amino acid sequence of a human folate binding protein from KB cells determined from the cDNA," *J. Biol. Chem.*, 1989; 264: 5806-5811.
Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new lalpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-la,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins—Powerful Inhibitors of Tubulin Polymerization from Microbacteria", *Angew. Chem. Int. Ed.*, 2004, No. 43, pp. 4888-4892.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6- (trifluoromethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Theti, D. S. et al., "Selective delivery of CB300638, a cyclopenta[g]quinazoline-based thymidylate synthase inhibitor into human tumor cell lines overexpressing the alpha-isoform of the folate receptor," *Cancer Res*, 2003; 63(13): 3612-3618.
Toffoli et al., "Overexpression of folate binding protein in ovarian cancers," *Int. J. Cancer* 74(2): 193-198 (1997).
Toraya T. et al., "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh a. et al., "Temperature-sensitive differential affinity of TRAIL for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).
Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Wang, Xiu-Fang et al., "Vitamin E Analogs Trigger Apoptosis in HER2/erbB2-Overexpressing Breast Cancer Cells by Signaling via the Mitochondrial Pathway," *Biochemical and Biophysical Research Communication*, 2005; vol. 326, pp. 282-289.
Weinstock et al., "Folic acid analogs. II. p-{[(2,6-Diamino-8-purinyl)methyl] amino}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate

(56) References Cited

OTHER PUBLICATIONS binding protein (mFBP) in human CCRF-CEM leukemia cells," *Proccedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).

Wu M. et al., "Clustering of GPI-anchored folate receptor independent of both cross-linking and association with caveolin," *J. Membr. Biol.* 159(2): 137-147 (1997).

Zimmer H. et al., "Potential anticancer agents V., Synthesis of folic acid and pteroic acid analogs derived of caffeine and.theophylline," *Arzneimittelforschung*, 1966, 16(4), pp. 541-545.

Zimmerman, J., "Folic acid transport in organ-cultured mucosa of human intestine. Evidence for distinct carriers,"*Gastroenterol.* 99(4): 964-972 (1990).

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).

Wikipedia, Derivative (Chemistry), http://en.wikipedia.org/wiki/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, List of Purification Methods in Chemistry, http://en.wikipedia.org/wiki/List_of_purification_methods_in_chemistry, downloaded Dec. 16, 2009.

Wikipedia, Solution, http://en.wikipedia.org/wiki/Solution, downloaded Dec. 17, 2009.

Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.

Wikipedia, Conjugate, http://en.wikipedia.org/wiki/Conjugate, downloaded Dec. 17, 2009.

Wikipedia, Complex (Chemistry), http://en.wikipedia.org/wiki/Complex_(chemistry), downloaded Dec. 23, 2009.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-tert-butyl Diethylenetriaminepentaacetic Acid Its Derivatives" *J. Org. Chem.* 2000; 65:1562-1565.

Carl et al. "A novel connector linkage applicable in prodrug design" J. Med. Chem. 1981;24(5):479-480.

Coney et al. "Cloning of a tumor-associated antigent: MOv18 and MOv19 antibodies recognize a folate-binding protein" Cancer Res. 1991;51(22):6125-32.

Crapatureanu et al. "Molecular necklaces. Cross-linking hemoglobin with reagents containing covalently attached ligands" Bioconjugate Chemistry, 1999;10(6):1058-67.

Darnell, Ed. Molecular Cell Biology W. H. Freeman, San Francisco 1990;326-333.

DeNardo, Gerald. "When is Too Much Too Much and Yet Not Enough? Alas, a Plethora of Opportunities but Where's the Beef?" J. of Nuclear Medicine 2000; 41(3):470-3.

Dorwald, F. Z., "Side Reactions in Organic Synthesis: A Guide to Successful Synthesis Design," Wiley-VCH, Weinheim, 2005, pg. ix of preface.

Forgac. "Structure and function of vacuolar class of ATP-driven pumps" Physiological Rev. 1989; 69(3) :765-795.

Garrett et al. "Synthesis and characterisation of polyamine-poly(ethylene glycol) constructs for DNA binding and gene delivery" Bioorganic & Medicinal Chemistry, 2000; 8(7):1779-1797.

Henderson et al. "Mediated uptake of folate by a high-affinity binding protein in sublines of L1210 cells adapted to nanomolar concentrations of folate" J. Membrane Biol., 1988;101:247-258.

Huang et al. "Design, syntheses and sequence selective DNA cleavage of functional models of bleomycin-II. 1,2-trans-di substituted cyclopropane units as novel linkers" Bioorganic & Medicinal Chemistry, 1995;3(6):647-57.

Jansen et al., "Identification of a Membrane-Associated Folate-Binding Protein in Human Leukemic CCRF-CEM Cells with Transport-Related Methotrexate Resistance" in Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Kamen et al., 1986, "Receptor-mediated folate accumulation is regulated by cellular folate content" Proc. Natl. Acad. Sci., U.S.A. 83, 5983-5987.

Ke et al. "Targeting the Tumor-Associated Folate Receptor with a 111-IN-DTPA Conjugate of Pteroic Acid" Abstract No. 427. 48h Annual Meeting of the Society of Nuclear Medicine Toronto, Canada, Jun. 26, 2001, available May 4, 2001; 1 pg.

Kemp et al. "New Protective Groups for Peptide Synthesis-I The Bic Group Base and Solvent Lability of the 5-B enzi soxazolymethyl eneoxycarbonyl amino function" Tet. Lett. 1975;52:4625-4628.

Kutsky RJ. Handbook of Vitamins, Minerals, and Hormones, 2' Edition. New York: Van Nostrand Reinhold: 1981;263-277.

Lee et al. "Prolonged circulating lives of single-chain Fv proteins conjugated with polyethylene glycol: a comparison of conjugation chemistries and compounds" Bioconjugate Chemistry, 1999;10(6):973-81.

Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.

Mehvar R "Dextrans for targeted and sustained delivery of therapeutic and imaging agents" [Review] Journal of Controlled Release, 2000;69(1):1-25.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor—Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. Invest. 1971; 50(3):719-726.

Selhub et al. "The folate binding protein of rat kidney. Purification, properties, and cellular distribution" J. Biol. Chem. 1984;259(10):6601-6606.

Selhub et al. "Renal folate adsorption and the kidney folate binding protein I. Urinary Clearance studies" Am. J Physiol. 252:F750-F756.

Selhub et al. "Renal folate adsorption and the kidney folate binding protein II. Microinfusion studies" Am. J. Physiol. 252:F757-F760.

Sirotnak. "Obligate genetic expression in tumor cells of a fetal membrane property mediating "Folate" transport: biological significance and implications for improved therapy of human cancer" Cancer Res., 1985;45(9):3992-4000.

(56) References Cited

OTHER PUBLICATIONS

Stein et al. "Normal tissue reactivity of four anti-tumor monoclonal antibodies of clinical interest" Int. J. Cancer 1991;47(2):163-169.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94.
Toffoli et al. "Expression of folate binding protein as a prognostic factor for response to platinum-containing chemotherapy and survival in human ovarian cancer" Int. J. Cancer (Pred. Oncol) 1998; 79:121-126.
Westerhof et al. "Membrane transport of natural folates and antifolate compounds in murine L1210 Leukemia cells: role of carrier-and receptor mediated transport systems" Cancer Res. 1991;51:5507-5513.
Williams et al. "Renal tubular transport of folic acid and methotrexate in the monkey" Am. J. Physiol 1982; 242(5):F484-490.
Weygand, et al., Chemishe. Berichte (1950) 83, 460-467.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.
Bukanov Nikolay, O. et al., "Long-Lasting Arrest of Murine Polycystic Kidney Disease With CDK Inhibitor Roscovitine", Dec. 14, 2006; *Nature*; vol. 444; pp. 949-952.
Hay, Nissim, et al., "Upstream and Downstream of mTOR", 2004, *Genes & Development*, vol. 18, No. 16, pp. 1926-1945.
Kennedy, Michael D., et al., "Evaluation of Folate Conjugate Uptake and Transport by the Choroid Plexus of Mice", (May 2003), vol. 20, No. 5, pp. 714-719.
Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.
Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.
Piontek, Klaus B., et al. "A Functional Floxed Allele of Pkd1 that Can Be Conditionally Inactivated In Vivo", *J. Am. Soc. Nephrol.* vol. 15, pp. 3035-3043.
Shillingford, Jonathan M., et al., "The mTOR Pathway is Regulated by Polycystin-1, and its Inhibition Reverses Renal Cystogenesis in Polycyctic Kidney Disease", Apr. 4, 2006, PNAS. vol. 103, No. 14, pp. 5466-5471.
International Search Report for PCT/US2008/68093 completed Oct. 2, 2008.
Ke CY et al., "Folate-Receptor-Targeting of In-111 Using Pteroic Acid Conjugates of Benzyl-DTPA and Benzyl-DOTA," J. Nucl. Med., 2004; 45(5):457P.
Regueiro-Ren et al., "Synthesis and Biological Activity of Novel Epothilone Aziridines," Organic Letters, 2001; vol. 3, No. 17: 2693-96.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Elnakat et al., "Distribution, functionality and gene regulation of folate receptor isoforms: implications in targeted therapy," Advanced Drug Delivery Reviews, 2004; vol. 56:1067-84.
Sabharanjak et al., "Folate receptor endocytosis and trafficking," Advanced Drug Delivery Reviews, 2004; vol. 56: 1099-1109.
Paulos et al., "Folate receptor-mediated targeting of therapeutic and imaging agents to activated macrophages in rheumatoid arthritis," Advanced Drug Delivery Reviews, 2004; vol. 56: 1205-17.
Antony, "Folate receptors: reflections on a personal odysssey and a perspective on unfolding truth," Advanced Drug Delivery Reviews, 2004; vol. 56: 1059-66.
Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Paulos CM et al., "Ligand Binding and Kinetics of Folate Receptor Recycling in Vivo: Impact on Receptor-Mediated Drug Delivery," Molecular Pharmacology, 2004; 66:1406-1414.
Griesser uj, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Functional analog, http://en.wikipedia.org/wiki/Functional_analog, downloaded Apr. 7, 2009.
Wikipedia, Folic acid, http://en.wikipedia.org/wiki/Folic_acid, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Matulic-Adamic J et al., "An efficient synthesis of the ribozyme-folate conjugate," Tetrahedron Letters, 2002; 43(25):4439-4441.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:-"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake," Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).
Dube D et al., "Preparation and Tumor Cell Uptake of Poly(N-isopropylacrylamide) Folate Conjugates"; *Bioconjugate Chem*, 2002; 13: 685-692.
Evans et al., "Synthessis of biotin conjugates of the antifungal compound cymoxanil," *Pest Manag Sci*, 2002; 58: 392-396.
Rao et al., Journal of Medicinal Chemistry, 1985, 28:1079-1088.
Conrad et al, Journal of Medicinal Chemistry, 1979, 22(4): 391-400.
Wang et al., "Structure-activity and high-content imaging analyses for novel tubulysins," Chemical Biology & Drug Design, 2007; 70(2): 75-86.
Patterson et al., "Design, synthesis, and biological properties of highly potent tubulysin D analogues," Chemistry—A European Journal, 2007; 13(34): 9534-9541.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.

(56) References Cited

OTHER PUBLICATIONS

Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002).
Putnam et al., "Polymer conjugates with anticancer activity", Advances in Polymer Science 1995, 122, 55-123.
Umemoto et al., "Molecular design of methotrexate-antibody conjugates for targeted cancer treatment", Journal of Bioactive and Compatible Polymers, 1992, 7(2), 191-219.
Sanderson et al., "In vivo drug-linker stability of an anti-CD30 dipeptide-linked auristatin immunoconjugate," *Clinical Cancer Research*, 2005; 11:843-852.
Wu et al., "Enhancing the enantioselectivity of candida lipase catalyzed ester hydrolysis via noncovalent enzyme modification," *Journal of American Chemical Society*, 1990; 112:1990-1995.
Patterson et al., "Expedient synthesis of N-Methyl tubulysin analogues with high cytotoxicity," *Journal of Organic Chemistry*, 2008; 73:4365-4369.
Gabizon et al., Clin Cancer Res 9:6551-59 (2003).
Pouvreau, Isabelle et al.: "Effect of macrophage depletion by liposomes containing dichloromethylene-diphosphonate on endotoxin induce uveitis." J. Neuroimmun. (1998)86 p. 171-181.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.
Definition of derivative and analog, from http://cancerweb.ncl.ac.uk/cgi-omd?query=derivative and http://cancerweb.ncl.ac.uk/cgi-bin/omd?query=analog, pp. 1-5, accessed Jul. 7, 2005.
Kaneko, Takushi, "New Hydrazone Derivatives of Adiramycin and their Immunoconjugates—A Correlation between Acid Stability and Cytotoxicity", Bioconj. Chem., vol. 2, No. 3, pp. 131-141 (May 1, 1991).
PCT International Search Report/Written Opinion for PCT/US2009/061049, completed Mar. 15, 2010.
Polyak et al., "Introduction of spacer peptides N-terminal to a cleavage recognition motif in recombinant fusion proteins can improve site-specific cleavage," Protein Eng., 1997; 10(6):615-9.
University of Maryland Medical Center (UMMC), Vitamin B9 (folic acid), 2014, http://umm.edu/health/medical/altmed/supplement/vitamin-b9-folic-acid, pp. 1-4.
Cerner Multum, Inc., Drugs.com, Folic Acid, http://www.drugs.com/folic_acid.html?printable=1, 1996-2014, Version: 5.01, Revision Date Oct. 15, 2009, pp. 104.
PCT International Search Report/Written Opinion prepared for PCT/US2010/061897, dated Mar. 11, 2011.
Water, fromhttp://www.biology-ionline.org/dictionary/Water, pp. 103, accessed Apr. 24, 2014.
NIOSH List of antineoplastic and Other Hazardous Drugs in Healthcare settings 2010, pp. 1-16, published Sep. 20, 2010.
Chae et al, Recombinant Expression, Isotope labeling and purification of the Vitamin D Receptor Binding Peptide, Bull. Korean Chem Soc. 2011, 32, pp. 4337-4340.
Rudinger, peptide Hormones, JA Parsons, Ed., 1976, pp. 1-7.
SIGMA, 2004, pp. 1-2.
Berendsen, A Glimpse of the Holy Grail?, Science, 1998, 282, pp. 642-643.
Voet et al, Biochemistry, John Wiley & Sons Inc., 1995, pp. 235-241.
Ngo et al, Computational Complexity, Protein Structure protection, and the Levinthal Paradox, 1994, pp. 491-497.
Bradley et al, Limits of Cooperativity in a Structurally Modular Protein: Response of the Notch Ankyrin Domain to Analogous Alanine Substitutions in Each Repeat, J. Mol. Biol, 2002, 324, pp. 373-386.

Definition of moiety, from http://dictionary.reference.com/browse/moiety, pp. 1-3, accessed Aug. 26, 2010.
Muller, Prodrug approaches for Enhancing the Bioavailability of Drugs with Low Solubility, Chemistry & Biodiversity, 2009, 6, pp. 2071-2083.
Beaumont et al, Design of ester prodrugs to enhance oral absorption of poorly permeable compounds: Challenges to the Discovery Scientist, Current Drug Metbolism, 2003, 4, 461-485.
Hyo-Kyung Han, Targeted prodrug design to optimize drug delivery, AAPS Pharmsci 2000, 2(10), article 6, p. 1-11.
Yashveer Singh et al, Recent trends in targeted anticancer prodrug and conjugate design, Curr Med Chem, 2008, 15(18): 1802-1826.
Testa B, Prodrug Research: Futile or Fertile?, Biochem Pharm, 2004, 68, pp. 2097-2106.
Ettmayer et al, Lessons learned from marketed and investigational prodrugs, J. Med Chem, 2004, 47(10), pp. 2393-2404.
Machine Translation of WO 2004/005326, Jan. 15, 2004, pp. 1-5.
European Search Report prepared for corresponding European Application Serial No. 08841521.1, dated Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
PCT International Search Report/Written Opinion for PCT/US2008/056824, completed Jul. 24, 2009.
Vlahov I. et al., "An assembly concept for the consecutive introduction of unsymmetrical disulfide bonds: synthesis of a releasable multidrug conjugate of folic acid," 2007, J. Org Chem, 72, 5968-5972.
Wang, L. et al., "Synthesis, biological, and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase," 2011, J. Med. Chem., 54, 7150-7164.
Vlahov I. et al., "Design and regioselective synthesis of a new generation of targeted therapeutics. Part 3: Folate conjugates of aminopterin hydrazide for the treatment of inflammation," 2011, Bioorg. Med. Chem. Lett., 21, 1202-1205.
Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.
ENDOCYTE: Endocyte Enrolls First Patient in Phase 1 Study for the Small Molecule Drug Conjugate EC1456, a Folate-Targeted Tubulysin Conjugate in Advanced Solid Tumors. Dec. 2013. [Retrieved on Jun. 5, 2015).
Leamon, et al., "Patient selection and targeted treatment in the management of platinum-resistant ovarian cancer," Pharmacogenomics and Personalized Medicine, 6:113-125 (2013).
PCT International Search Report/Written Opinion prepared for PCT/US2015/020397, dated Jun. 18, 2015.
PCT International Search Report/Written Opinion prepared for PCT/US2015/25790, dated Jul. 7, 2015.
Zaragoza, D., Side Reactions in Organic Synthesis, 2005, Wiley-VCH Verlag GmbH & Co. KGaA, Weinheim, Preface, p. 9.
Attur, M. et al., "Differential anti-inflammatory effects of immunosuppressive drugs: Cyclosporin, rapamycin and FK-506 on inducible nitric oxide synthase, nitric oxide, cyclooxygenase-2 and $PGE_2$ production," Inflamm. res. 2000, 49, 020-026.
PCT International Search Report/Written Opinion prepared for PCT/US2013/065079, dated May 1, 2014.
Lorusso, P. M. et al., "Phase I Study of Folate Conjugate EC145 (Vintafolide) in Patients with Refractory Solid Tumors," J. Clinical Oncology, 2012, 30, No. 32, 4011-4016.
PCT International Search Report for PCT/US2015/051941 dated Dec. 18, 2015.

(56) References Cited

OTHER PUBLICATIONS

Christoper Leamon et al., "Folate Receptor specific anti-tumor activity of EC0305, a folate-tubulysin conjugate," AACR Annual Meeting, 2007, 67, 9, (abstract only).
PCT International Search Report prepared for PCT/US2016/030150 dated Apr. 29, 2016.
Dong, H. et al., "Self-assembled, redox-sensitive, H-shaped pegylated methotrexate conjugates with high drug-carrying capability for intracellular drug delivery," Med. CHem. Commun., 2013, 5, 147-152.
Beil,L. "Is your breakfast giving you cancer," Pre'vention, updated Mar. 29, 2010, available via internet at http://www.nbcnews.com/id/35874922/ns/health-diet_and_nutrition/t/your-breakfast-giving-you-cancer/⊇.V401rf1Vj21.
Adessi, C. et al., "Converting a Peptide into a Drug: Strategies to Improve Stability and Bioavailability," Current Medicinal Chemistry, 2002, 9, 963-978.
Weinstein, "Commentary: Three Decades of Folic Acid Antagonists in Dermatology," *Arch Dermatol*, Jun. 1983, vol. 119, 525-527.
Horvat S. et al, "Tumor-cell-targeted methionine-enkephalin analogues containing unnatural amino acids: design, synthesis, and in vitro antitumor activity" J. Med. Chem. 49(11), 3136-3142 2006, abstract.
Kawasaki, D. et al., Effect of Z-360, a novel orally active CCK-2/gastrin receptor antagonist on tumor growth in human pancreatic adenocarcinoma cell lines in vivo and mode of action determinations in citro, Cancer Chemotherapy and Pharmacology, 2008, vol. 61, No. 5, pp. 883-892.
International Search Report for PCT/US2013/027463, dated Jun. 27, 2013.
Berna M.J, Jensen R.T. Role of CCK/gastrin receptors in gastrointestinal/metabolic diseases and results of human studies using gastrin/CCK receptor agonists/antagonists in these diseases. Curf. Top Med Chem. 7:1211-1231, 2007.
Brand SJ, Fuller PJ. Journal Biol. Chem. 263 5341-5347 1988.
Caplin et al. Expression and processing of gastrin in pancreatic adenocarcinoma. Br J Surg. 87: 1035-1040,2000.
Chao et al., Constitutively active CCK2 Receptor splice variant increases srcdependent HIF-Ialpha expression and tumor growth. Oncogene 26, 1013-1019,2007.
Chao et al., Src Regulates constitutive internalization and rapid resensitization of a Cholecystokinin 2 receptor splice variant. Journal of Biological Chemistry 280 (39)33368-33373, 2005.
Currotto G. A chemical method for the preparation of novel 1,5 benzodiazepines acting as CCK-B Antagonists in high enantiomeric purity. Tetrahedron 53 (21) 7347-7364 1997.
Dufresne et al., Cholecystokinin and gastrin receptors. Physiol Rev. 86:805-847,2006.
Ferrand A., Timothy C. Wang. Gastrin and Cancer. Cancer Letters 238(1): 15-29,2006.
Grabowska et al., "Pre-clinical evaluation of a new orally-active CCK-2R antagonist, Z-360, in gastrointestinal cancer models," Regulatory Peptides, 14646-57 (2008).
Hellmich et al., Human colorectal cancers express a constitutively active Cholecystokinin-BI gastrin receptor that stimulates cell growth. J. Biol. Chern 275,32122-32128,2000.
Hur et al., Expression of gastrin and its receptor in human gastric cancer tissues. 2, Feb. J Cancer Res Clin Oncol. , vol. 132, pp. 85-91, 2006.
Kilonda et al., "The Synthesis of 7-carbonyl homolgues of 1-deoxynojirimycin," Tetrahedron Letters (1994) 35(48): 9047-9050.
Kobayashi et al., "Z-360, a novel Cholecystokinin-2/gastin receptor antagonist, inhibits Gemcitabine induced expression of the vascular endothelial growth factor gene in human pancreatic cancer cells," Biol.Pharm. Bull. 33 (2) 216-222 (2010).
Korner et al., "CCK(2) receptor splice variant with intron 4 retention in human gastrointestinal and lung tumours," Apr. 2010, J Cell Mol Med. , vol. 14, pp. 933-943.

Lauffer et al., A practical synthesis of (S) 3-tert-Butoxycarbonylamino-2-oxo-2,3,4,5-tetrahydro-1,5-benzodiazepine-1-acetic acid methyl ester as a conformationally restricted dipeptido-Mimetic for caspase-1 (ICE) inhibitors. Biorganic and Medicinal Chern.Lett. 12(8) 1225-1227, 2002.
Lee et al., "The Human Cholecystokinin-BI Gastrin Receptor," Journal of Biological Chemistry 268 (11) 8164-8169, 1993.
Miller L.J. Does the Human Pancreas have a type A or B personality? Gastroenterology 111, 1767-1770,1996.
Monstein et al., "Cholecystokinin A and Cholecystokinin-B/Gastrin receptor mRNA expression in the gastrointestinal tract and pancreas of the rat and human. A polymerase chain reaction study," Scand J Gastroenterol 31383-390, 1996.
Olszewska-Pazdrak et al., Agonist-independent activation of Src tyrosine kinase by a cholecystokinin-2 (CCK2) receptor splice variant39, Sep. 24, 2004, J Biol Chern., vol. 279, pp. 40400-40404.
Reddy et al., "In vivo structural activity and optimization studies of folate-tubulysin conjugates," Molecular pharmaceutics 2009, 6, 1518-25.
Reddy et al., "Preclinical evaluation of (99m)Tc-EC20 for imaging folate receptor-positive tumors," J Nucl Med. May 2004;45(5):857-66.
Reubi et al., "Localization of Cholecystokinin A and Cholecystokinin-BI Gastrin receptors in the human stomach," Gastroenterology (1997) 112:1197-1205.
Reubi et al., "Cholecystokinin(CCK)-A and CCK-B/gastrin receptors in human tumors," Apr. 1,,CancerRes., vol. 57, pp. 1377-1386, 1997.
Reubi et al., Unexpected high incidence of cholecystokinin B/gastrin receptors in human medullary thyroid carcinomas. Int. J. Cancer vol. 67, pp. 644-647,1996.
Rosario Herranz. Cholecystokinin antagonists: Pharmacological and therapeutic potential. Medicinal Research reviews 23 (5) 559-605, 2003.
Saillan-Barreau et al., Evidence for a functional role of the Cholecystokinin-B/gastrin receptor in the human fetal and adult pancreas. Diabetes 48 2015-2021, 1999.
Sethi et al., CCK-A and CCK-B receptors are expressed in small cell lung cancer lines and mediate Ca2+ mobilization and clonal growth. Cancer Res., vol. 53, pp. 5208-5213, 1993.
Smith et al., Characterization of the CCK-C (cancer) receptor in human pancreatic cancer. 2002, Int. J. Mol. Med., vol. 10, pp. 689-694.
Smith, "Quantitative analysis of gastrin mRNA and peptide in normal and cancerous human pancreas," International Journal of Molecular Medicine 2(3) 309-315 1998.
Sun et al., "Blockade of cholecystokin -2 receptor and cyclooxygenase 2 synergistically induces cell apoptosis and inhibits the proliferation of human gastric cancer cells in vitro," Cancer Letters 263 (2) 302-311 2008.
Tang C, Biemond I. Lamers CB. Cholecystokinin receptors in human pancreas and gall bladder muscle: a comparative study. Gastroenterology 111,1621-1626, 1996.
Todisco et al., Molecular Mechanisms for the antiapoptotic actions of gastrin. Am J Physiol Gastrointest Liver Physiol280: G298-G307, 2001.
Vlahov et al., "Carbohydrate-Based Synthetic Approach to Control Toxicity Profiles of Folate-Drug Conjugates," Journal of Organic Chemistry 75: 3685-3691 (2010).
Weinberg et al., Cholecystokinin A and B receptors are differentially expressed in normal and pancreatic adenocarcinoma. J. Clinical Investigation 100,597-603, 1997.
Zhou et al., Blocking gastrin and CCK-B autocrine loop affects cell proliferation and apoptosis in vitro. Molecular and Cellular Biochemistry 343 (1-2) 133-141 (2010).
Harikumar et al, J. Med. Chem., vol. 53, No. 7, pp. 2836-2842. (Year 2010).
Wikipedia, Wikipedia, Drug, 2018, pp. 1-8, recovered from http://en.wikipedia.org/wiki/Drug on Apr. 3, 2018 (Year: 2018).
Definition of "Adrenocortical hormone", The Free Dictionary, available online at: https://web.archive.org/web/20110929170055/https://medical-dictionary.thefreedictionary.com/adrenocorticoid, captured on Sep. 29, 2011.

(56) References Cited

OTHER PUBLICATIONS

Hofer, Kristi N., "Oral Budesonide in the Management of Crohn's Disease", Ann. Pharmacother., 2003, 37, 1457-64.
Lee et al., "Fluorescein aldehyde with disulfide functionality as a fluorescence turn-on probe for cysteine and homocysterine in HEPES buffer", Organic & Biomolecular Chemistry, 2013, 11, pp. 5012-5016.
Tyagi et al., "Binding of an indole alkaloid, vinblastine to double stranded DNA: A spectroscopic insight in to nature and strength of interaction", Journal of Photochemistry and Photobiology B: Biology 108 (2012), pp. 48-52.
Vlahov et al., "Engineering Folate-Drug Conjugates to Target Cancer: From Chemistry to Clinic", Bioconjugate Chem. 2012, 23, 1357-1369.
U.S. Appl. No. 60/590,580, filed Jul. 23, 2004, Vlahov et al.
U.S. Appl. No. 12/739,579, filed Apr. 23, 2010, Vlahov et al.
U.S. Appl. No. 12/775,824, filed May 7, 2010, Green et al.
Kim et al., "Synthesis and biological activity of 10-thia-10-deaza analogs of folic acid, pteroic acid, and related compounds", Journal of Medical Chemistry, 18: 776-780 (1975).
Kranz et al., "Conjugates of folate and anti-T-cell-receptor antibodies specifically target folate-receptor-positive tumor cells for lysis," Proc. Natl. Acad. Sci. USA, 1995; 92(20), pp. 9057-9061.
Kumar H.P. et al., "Folate transport in Lactobacillus salivarius. Characterization of the transport mechanism and purification and properties of the binding component," J. Biol. Chem., 1987; 262(15):7171-7179.
Ladino et al., "Folate-maytansinoids: target-selective drugs of low molecular weight," Int. J. Cancer, 73(6): 859 864 (1997).
Lambooy J. P., "Riboflavin Analogs Utilized for Metabolism by a Lactobacillus Casei Mutant," Int. J. Biochem., vol. 16. No. 2. 1984, pp. 231-234.
Landuer W. et al,, "The Interaction in Teratogenic Activity of the Two Niacin Analogs 3-acetylpyridine and 6-aminonicotinarnide," J Exp Zool, 151(3):253-258 (1962).
Langone, Li., et al., "Radioimmunoassays for the Vinca Alkaloids, Vinblastine and Vincristine", 1979, Analytical Biochemistry, No. 95, pp. 214-221.
Larock R.C., "Comprehensive Organic Transformations, a guide to functional group preparations," VCH Publishers, Inc. New York (1989).
Gubner, et al. "Therapeutic Suppression of Tissue Reactivity II. Effect of Aminopterin in Rheumatoid Arthritis and Psoriasis," Arch. Derm., Chicago 64, pp. 176-182. (1951).
Rees, et al. Aminopterin for Psoriasis a Decades's Observation,: Arch. Derm., Chicago 90, pp. 544-552 (1964).
Gubner, R., "Effect of 'Aminoptern' on Epithelial Tissues," Am. J. Med. Sci. 22, pp. 688-699 (1951).

\* cited by examiner

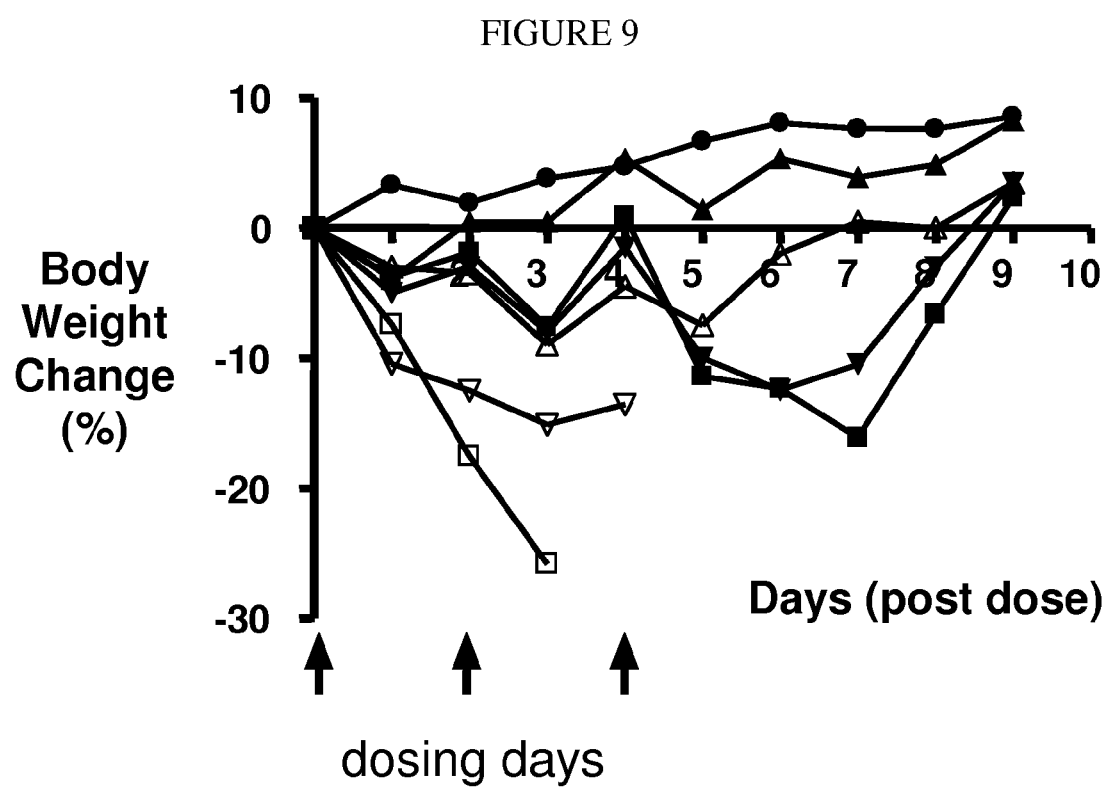

CONJUGATES CONTAINING HYDROPHILIC SPACER LINKERS

CROSS REFERENCE TO RELATED APPLICATIONS

This application is a continuation of U.S. application Ser. No. 14/820,777 filed on Aug. 7, 2015, which is a continuation of U.S. application Ser. No. 12/666,712 filed on Dec. 24, 2009, which is a U.S. national application filed under 37 C.F.R. § 371(b) of International Application Serial No. PCT/US2008/068093 filed Jun. 25, 2008, which claims the benefit of priority under 35 U.S.C. § 119(e) of U.S. provisional patent application Ser. Nos. 60/946,092 and 61/036,186, filed Jun. 25, 2007 and Mar. 13, 2008, respectively; the disclosures of which are incorporated herein in their entirety by reference.

TECHNICAL FIELD

The present invention relates to compositions and methods for use in targeted drug delivery. More particularly, the invention is directed to cell-surface receptor binding drug delivery conjugates containing hydrophilic spacer linkers for use in treating disease states caused by pathogenic cell populations and to methods and pharmaceutical compositions that use and include such conjugates.

BACKGROUND

The mammalian immune system provides a means for the recognition and elimination of tumor cells, other pathogenic cells, and invading foreign pathogens. While the immune system normally provides a strong line of defense, there are many instances where cancer cells, other pathogenic cells, or infectious agents evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects because they work not only to destroy pathogenic cells, but they also affect normal host cells, such as cells of the hematopoietic system. The adverse side effects of these anticancer drugs highlight the need for the development of new therapies selective for pathogenic cell populations and with reduced host toxicity.

Researchers have developed therapeutic protocols for destroying pathogenic cells by targeting cytotoxic compounds to such cells. Many of these protocols utilize toxins conjugated to antibodies that bind to antigens unique to or overexpressed by the pathogenic cells in an attempt to minimize delivery of the toxin to normal cells. Using this approach, certain immunotoxins have been developed consisting of antibodies directed to specific antigens on pathogenic cells, the antibodies being linked to toxins such as ricin, *Pseudomonas* exotoxin, Diptheria toxin, and tumor necrosis factor. These immunotoxins target pathogenic cells, such as tumor cells, bearing the specific antigens recognized by the antibody (Olsnes, S., *Immunol. Today*, 10, pp. 291-295, 1989; Melby, E. L., *Cancer Res.*, 53(8), pp. 1755-1760, 1993; Better, M. D., PCT Publication Number WO 91/07418, published May 30, 1991).

Another approach for targeting populations of pathogenic cells, such as cancer cells or foreign pathogens, in a host is to enhance the host immune response against the pathogenic cells to avoid the need for administration of compounds that may also exhibit independent host toxicity. One reported strategy for immunotherapy is to bind antibodies, for example, genetically engineered multimeric antibodies, to the surface of tumor cells to display the constant region of the antibodies on the cell surface and thereby induce tumor cell killing by various immune-system mediated processes (De Vita, V. T., *Biologic Therapy of Cancer*, 2d ed. Philadelphia, Lippincott, 1995; Soulillou, J. P., U.S. Pat. No. 5,672,486). However, these approaches have been complicated by the difficulties in defining tumor-specific antigens. Accordingly, additional compounds and methods are needed for selectively targeting pathogenic cell populations.

SUMMARY OF THE INVENTION

It has been discovered that therapeutic agents, diagnostic agents, and imaging agents may be conjugated to other compounds to control or alter their behavior, biodistribution, metabolism, and/or clearance in vivo. In one illustrative embodiment of the invention, conjugates of compounds are described that include a hydrophilic spacer linker. In one aspect, conjugates of compounds are described that include both a hydrophilic spacer linker and a targeting ligand. Illustrative of such conjugates are compounds of the following formula described herein

B-L-A wherein B is a receptor binding ligand that binds to a target cell receptor, L is a linker that comprises one or more hydrophilic spacer linkers, and A is a diagnostic, therapeutic, or imaging agent that is desirably delivered to the cell.

In another embodiment, non-receptor binding targeted compounds of the following formula are described herein:

L-A where L is a linker that comprises one or more hydrophilic spacer linkers and A is diagnostic, therapeutic, or imaging agent. In one variation, the linker L does not include a releasable linker. In another variation, the linker L includes a releasable linker. In another embodiment, at least one of the hydrophilic spacer linkers is formed from or includes at least one carbohydrate. In one variation, the carbohydrate forms part of the linker chain connecting B and A. In another variation, the carbohydrate forms part of a side chain attached to the linker chain connecting B and A.

It is appreciated that in each of the above embodiments, more than one receptor binding ligand B may be attached to the linkers described herein. It is further appreciated that more than one agent A may be attached to the linkers described herein. Such multi-ligand and/or multi-drug conjugates are also described herein, where the linker comprises a hydrophilic spacer linker.

In another embodiment, compounds are described herein that have reduced uptake by the liver and are less likely to be cleared by the liver. In one aspect, such compounds are preferentially cleared by the renal processes as compared to hepatic processes.

The agent or agents A include therapeutic drugs, diagnostic agents, imaging agents, and any other compound that is desirably or advantageously delivered to a cell by targeting a cell receptor. Illustrative drugs include cytotoxic drugs, anti-inflammatory agents, and the like. Illustrative diagnostic agents and imaging agents include PET imaging agents, fluorescent imaging agents, radioligands, radioligand complexing agents, and others.

In the embodiments of compounds, compositions, and methods described herein, the cells that may be targeted with the therapeutic, diagnostic, and/or imaging agents A include a wide variety, such as but not limited to cancer cells, bacterial cells, tumor cells, monocytes, activated macrophages, progenitor cells, such as endothelial progenitor cells, other inflammatory cells, atherosclerotic plaques, infections, and others. The targeting of the cell is accomplished by the appropriate selection of a cell receptor binding ligand B. It is appreciated that selective or specific targeting of a cell in vivo may be accomplished by selecting a receptor that is preferentially expressed or overexpressed by the target cell. Illustratively, the target cell preferentially expresses or overexpresses a vitamin receptor, such as folate receptors.

In another embodiment, the conjugates described herein are included in pharmaceutical compositions in amounts effective to treat diseases and disease states associated with pathogenic populations of cells.

In another embodiment, the conjugates described herein, and pharmaceutical compositions containing them are used in methods for treating diseases and disease states associated with pathogenic populations of cells.

BRIEF DESCRIPTION OF THE DRAWINGS

FIG. 9 shows the percentage body weight change of Balb/c mice having s.c. M109 tumors treated intravenously three times in a week for one week with PBS (untreated controls) (●), EC0436 (TIW 2 μmol/kg) (▲), EC0436 (TIW 2.5 μmol/kg) (▼), EC0436 (TIW 3 μmol/kg) (■), EC0305 (TIW 2 μmol/kg) (Δ), EC0305 (TIW 2.5 μmol/kg) (▽), and EC0305 (TIW 3 μmol/kg) (□).

DETAILED DESCRIPTION

Figure 1:
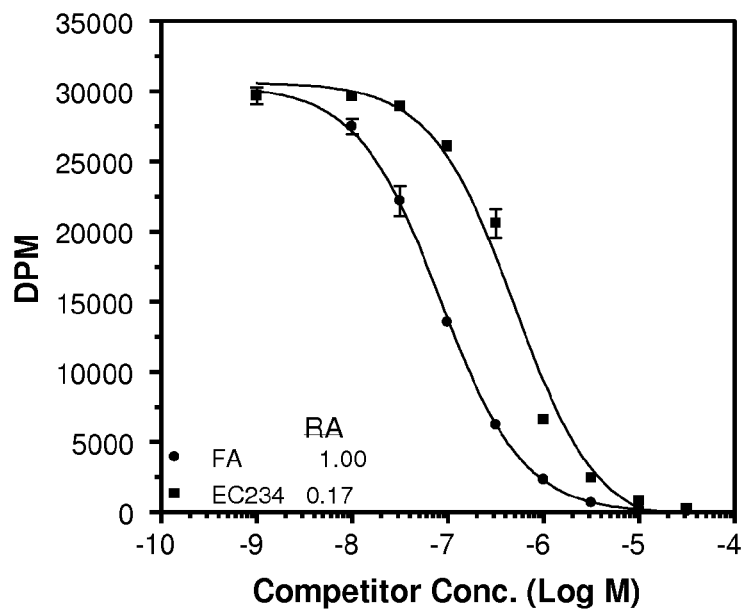
FIG. 1 shows the relative binding affinity of EC234, DPM for folic acid (●) and EC0234 (■).
Figure 2:
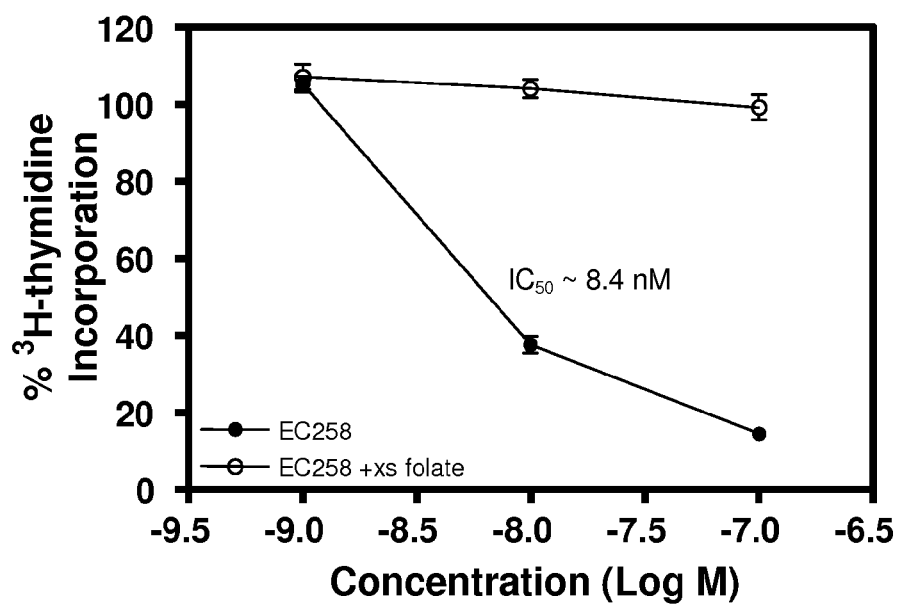
FIG. 2 shows the activity of EC0258 against KB cells (2 h pulse/72 h chase) for EC258 (●) and EC258+excess folic acid (○).
Figure 3A:
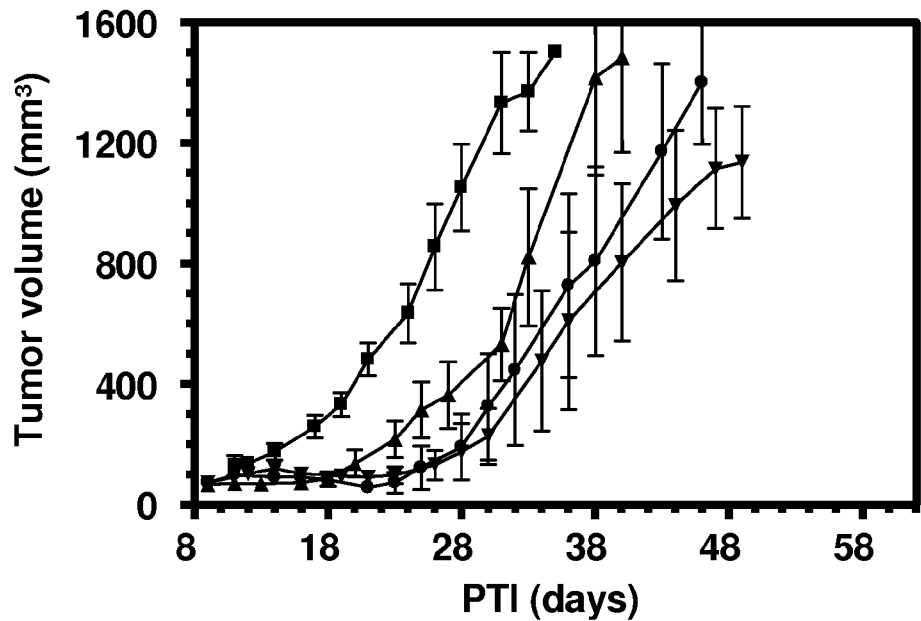
FIG. 3A shows the effect of EC0234 and EC0246 against M109 tumors in mice, untreated controls (■), EC145 standard (TIW 3 μmol/kg, 3 wks) (●), EC0234 (TIW 3 μmol/kg, 3 wks) (▼), and EC0246 (TIW 3 μmol/kg, 3 wks) (▲).
Figure 3B:
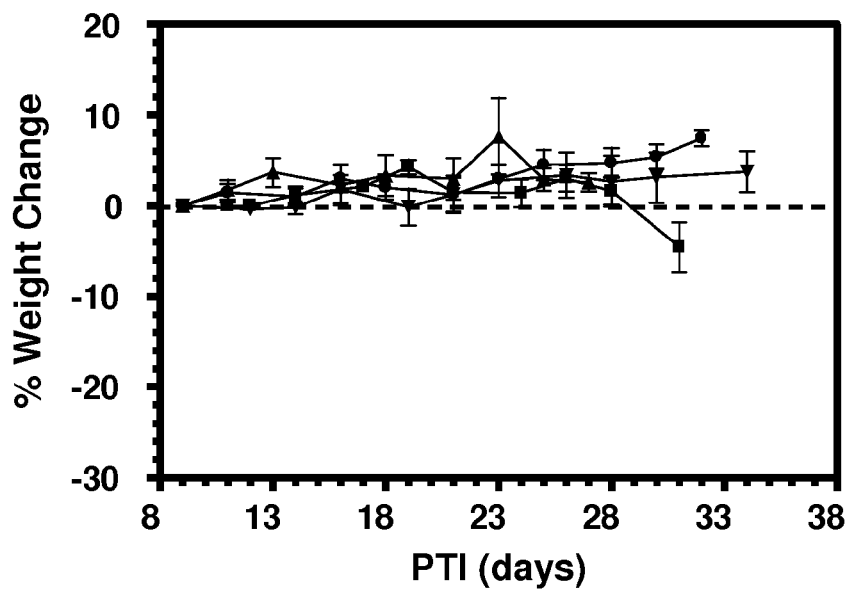
FIG. 3B shows the effect of EC0234 and EC0246 on percentage body weight change, untreated controls (■), EC145 standard (TIW 3 μmol/kg, 3 wks) (●), EC0234 (TIW 3 μmol/kg, 3 wks) (▼), and EC0246 (TIW 3 μmol/kg, 3 wks) (▲); indicating that no gross toxicity was observed during treatment.
Figure 4A:
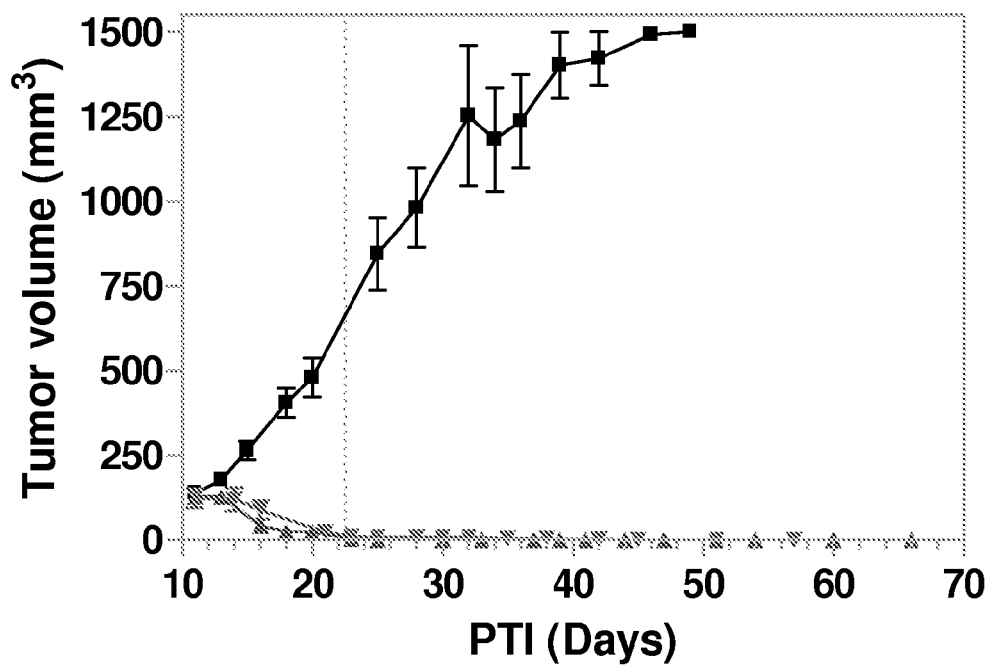
FIG. 4A shows the effect on KB tumor volume in mice of EC0396 (▼), EC145 (▲) and PBS control (■) dosed at 2 μmol/kg TIW for two weeks (the vertical line indicates the last dosing day).
Figure 4B:
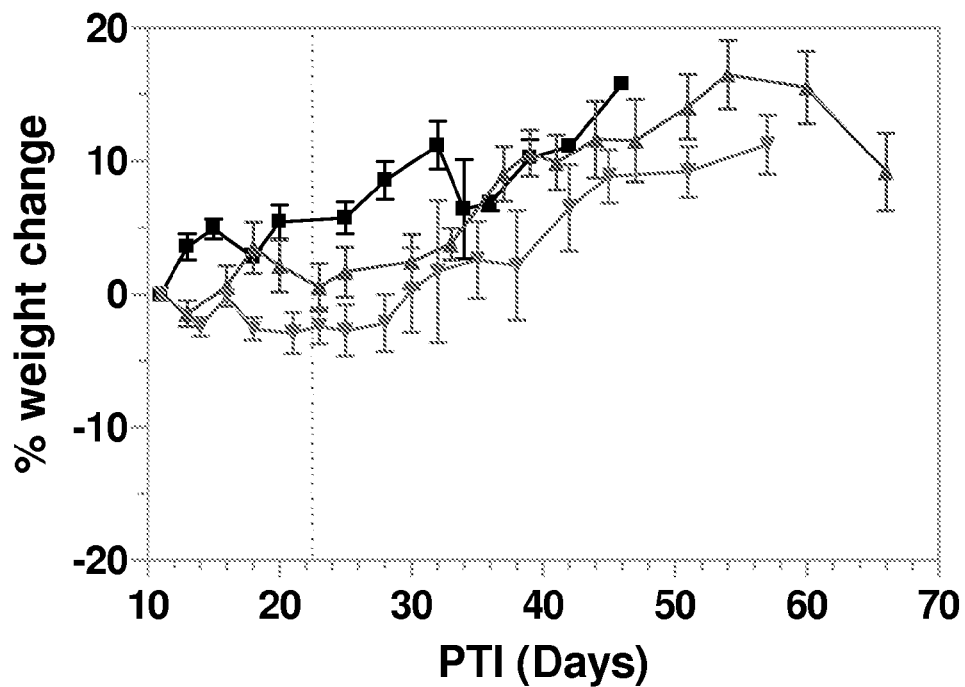
FIG. 4B shows the effect on percentage body weight change of EC0396 (▼), EC145 (▲) and PBS control (■) dosed at 2 μmol/kg TIW for two weeks (the vertical line indicates the last dosing day); indicating that no gross toxicity was observed during treatment.
Figure 5A:
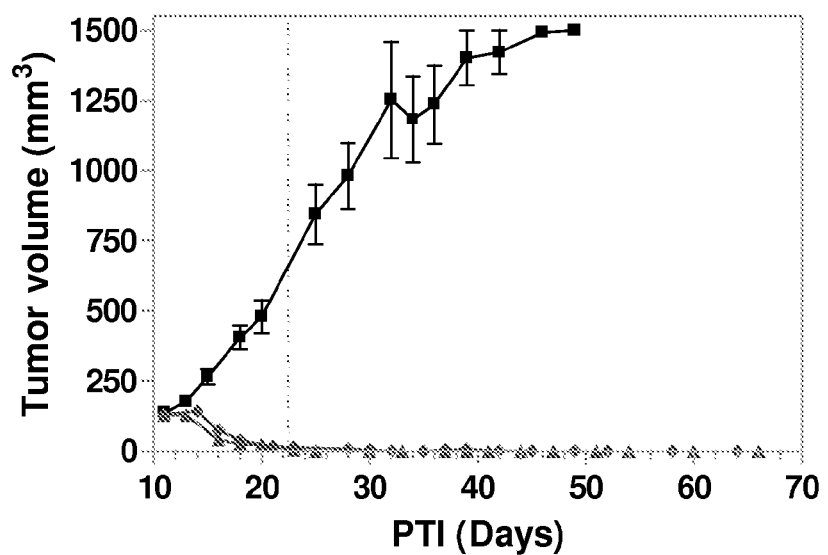
FIG. 5A shows the effect on KB tumor volume of EC0400 (●). EC145 (▲) and PBS control (■) dosed at 2 μmol/kg TIW for two weeks (the vertical line indicates the last dosing day).
Figure 5B:
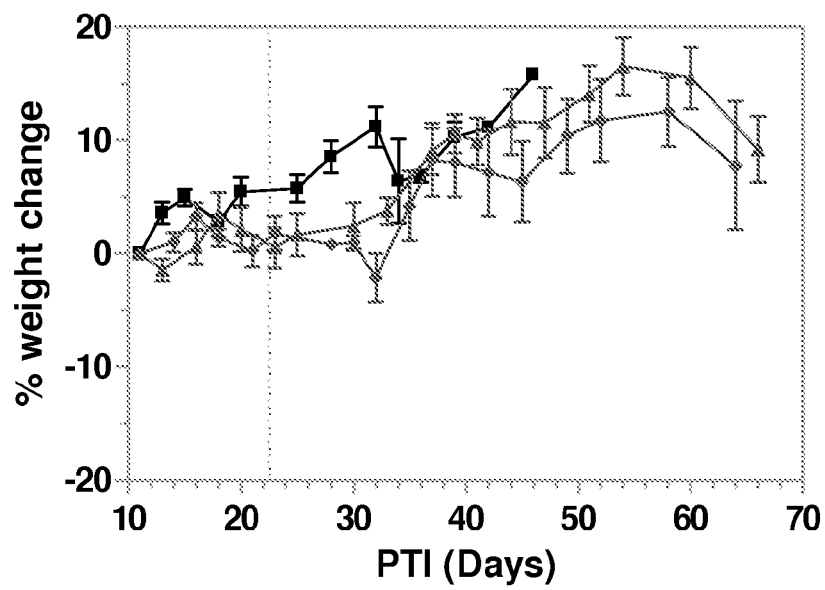
FIG. 5B shows the effect on percentage body weight change of EC0400 (●), EC145 (▲) and PBS control (■) dosed at 2 μmol/kg TIW for two weeks (the vertical line indicates the last dosing day); indicating that no gross toxicity was observed during treatment.
Figure 6A:
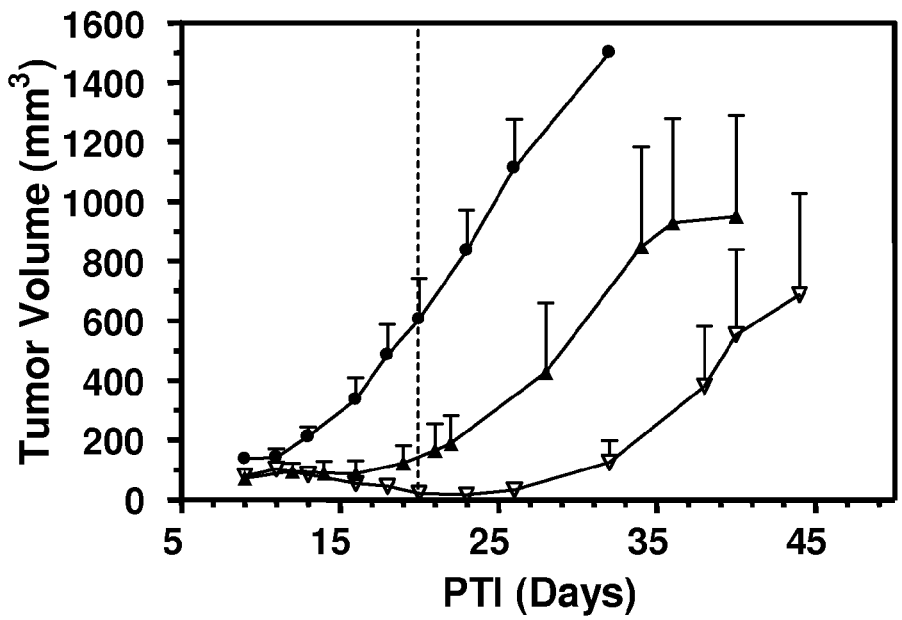
FIG. 6A shows the effect on tumor volume of EC0429 (▽) and EC145 (▲), dosed at 2 μmol/kg TIW for two weeks (the vertical line indicates the last dosing day) compared to untreated controls (●) for M109 tumors in Balb/c mice.
Figure 6B:
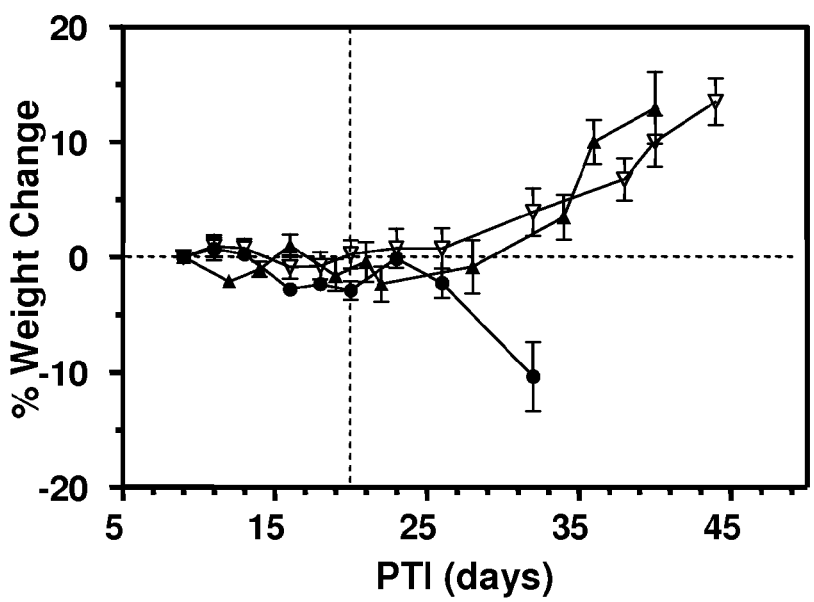
FIG. 6B shows the effect on percentage body weight change EC0429 (▽) and EC145 (▲), dosed at 2 μmol/kg TIW for two weeks (the vertical line indicates the last dosing day) compared to untreated controls (●); indicating that no gross toxicity was observed during treatment.
Figure 7A:
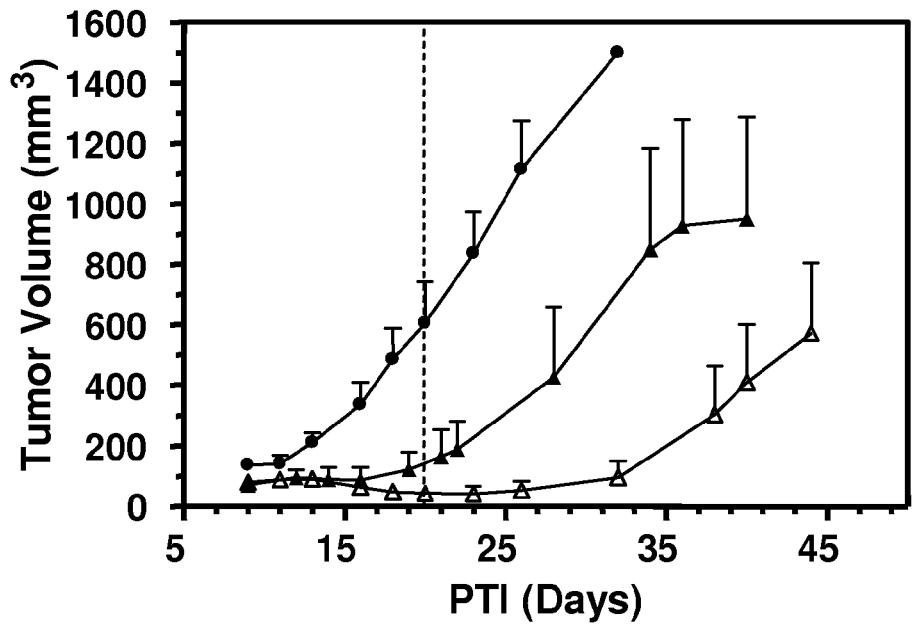
FIG. 7A shows the effect on tumor volume of EC0434 (Δ) and EC145 (▲), dosed at 2 μmol/kg TIW for two weeks (the vertical line indicates the last dosing day) compared to untreated controls (●) for s.c. M109 tumors in Balb/c mice.
Figure 7B:
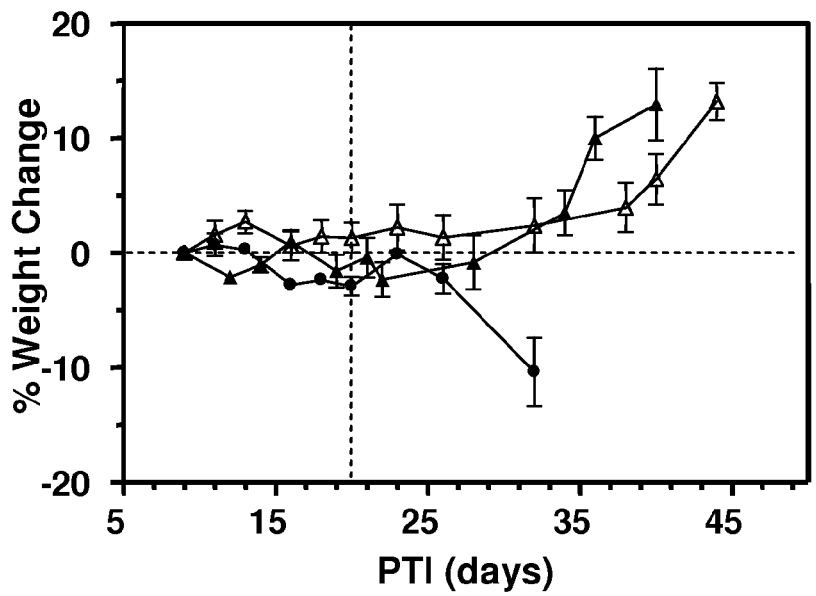
FIG. 7B shows the effect on percentage body weight change of EC0434 (Δ) and EC145 (▲), dosed at 2 μmol/kg TIW for two weeks (the vertical line indicates the last dosing day) compared to untreated controls (●); indicating that no gross toxicity was observed during treatment.

Drug delivery conjugates are described herein consisting of a receptor binding ligand (B), a polyvalent linker (L) comprising one or more hydrophilic spacer linkers, and a diagnostic, therapeutic, or imaging agent (A) that is desirably delivered to a cell. The binding ligand (B) is covalently attached to the polyvalent linker (L), and the diagnostic, therapeutic, or imaging agent (A), or analog or derivative thereof, is also covalently attached to the polyvalent linker (L). It is to be understood that the diagnostic, therapeutic, or imaging agent (A) includes analogs and derivatives thereof that are attached to the linker (L). The polyvalent linker (L) comprises one or more spacer linkers and/or releasable linkers, and combinations thereof, in any order. In one variation, releasable linkers, and optional spacer linkers are covalently bonded to each other to form the linker. In another variation, a releasable linker is directly attached to the agent (A), or analog or derivative thereof. In another variation, a releasable linker is directly attached to the binding ligand. In another variation, either or both the binding ligand and the agent (A), or analog or derivative thereof, is attached to a releasable linker through one or more spacer linkers. In another variation, each of the binding ligand and the agent (A), or analog or derivative thereof, is attached to a releasable linker, each of which may be directly attached to each other, or covalently attached through one or more spacer linkers.

From the foregoing, it should be appreciated that the arrangement of the binding ligand, and the agent (A), or analog or derivative thereof, and the various releasable and optional spacer linkers may be varied widely. In one aspect, the binding ligand, and the agent (A), or analog or derivative thereof, and the various releasable and optional spacer linkers are attached to each other through heteroatoms, such as nitrogen, oxygen, sulfur, phosphorus, silicon, and the like. In variations, the heteroatoms, excluding oxygen, may be in various states of oxidation, such as N(OH), S(O), $S(O)_2$, P(O), $P(O)_2$, $P(O)_3$, and the like. In other variation, the heteroatoms may be grouped to form divalent radicals, such as for example hydroxylamines, hydrazines, hydrazones, sulfonates, phosphinates, phosphonates, and the like, including radicals of the formulae —(NHR$^1$NHR$^2$)—, —SO$^-$, —(SO$_2$)—, and —N(R$^3$)O—, wherein R$^1$, R$^2$, and R$^3$ are each independently selected from hydrogen, alkyl, aryl, arylalkyl, substituted aryl, substituted arylalkyl, heteroaryl, substituted heteroaryl, and alkoxyalkyl. In another variation, more than one binding ligand is attached to the polyvalent linker. In another variation, more than one agent (A) is attached to the polyvalent linker. In another variation, more than one binding ligand and more than one agent (A) is attached to the polyvalent linker.

In one embodiment, the receptor binding ligand is a vitamin receptor binding ligand such as a vitamin, or an analog or a derivative thereof, capable of binding to vitamin receptors. In another embodiment, the binding ligand is a vitamin, or analog or derivative thereof, attached to a releasable linker which is attached to the drug through a linker that is formed from one or more spacer linkers and/or releasable linkers and/or hydrophilic spacer linkers. In one variation, both the drug and the vitamin, or analog or derivative thereof, can each be attached to spacer linkers, where the spacer linkers are attached to each other through one or more releasable linkers. In addition, both the drug and the vitamin, or analog or derivative thereof, can each be attached to one or more releasable linkers, where the releasable linkers are attached to each other or through a spacer linker. Each of these radicals may be connected through existing or additional heteroatoms on the binding ligand, agent A, or releasable, hydrophilic spacer, or additional spacer linker.

The binding site for the binding ligand (B) can include receptors for any binding ligand (B), or a derivative or analog thereof, capable of specifically binding to a receptor wherein the receptor or other protein is uniquely expressed, overexpressed, or preferentially expressed by a population of pathogenic cells. A surface-presented protein uniquely expressed, overexpressed, or preferentially expressed by the pathogenic cells is typically a receptor that is either not present or present at lower concentrations on non-pathogenic cells providing a means for selective elimination, labeling or diagnosis of the pathogenic cells. The binding ligand drug delivery conjugates may be capable of high affinity binding to receptors on cancer cells or other types of pathogenic cells. The high affinity binding can be inherent to the binding ligand or the binding affinity can be enhanced by the use of a chemically modified ligand (e.g., an analog or a derivative of a vitamin).

The binding ligand drug delivery conjugates described herein can be formed from, for example, a wide variety of vitamins or receptor-binding vitamin analogs/derivatives, linkers, and drugs. The binding ligand drug delivery conjugates described herein are capable of selectively targeting a population of pathogenic cells in the host animal due to preferential expression of a receptor for the binding ligand, such as a vitamin, accessible for ligand binding, on the pathogenic cells. Illustrative vitamin moieties that can be used as the binding ligand (B) include carnitine, inositol, lipoic acid, pyridoxal, ascorbic acid, niacin, pantothenic acid, folic acid, riboflavin, thiamine, biotin, vitamin $B_{12}$, other water soluble vitamins, the B vitamins, and the lipid soluble vitamins A, D, E and K. These vitamins, and their receptor-binding analogs and derivatives, constitute an illustrative targeting entity that can be coupled with the drug by a bivalent linker (L) to form a binding ligand (B) drug delivery conjugate as described herein. The term vitamin is understood to include vitamin analogs and/or derivatives, unless otherwise indicated. Illustratively, pteroic acid which is a derivative of folate, biotin analogs such as biocytin, biotin sulfoxide, oxybiotin and other biotin receptor-binding compounds, and the like, are considered to be vitamins, vitamin analogs, and vitamin derivatives. It should be appreciated that vitamin analogs or derivatives as described herein refer to vitamins that incorporates an heteroatom through which the vitamin analog or derivative is covalently bound to the bivalent linker (L).

Illustrative vitamin moieties include folic acid, biotin, riboflavin, thiamine, vitamin $B_{12}$, and receptor-binding analogs and derivatives of these vitamin molecules, and other related vitamin receptor binding molecules.

In another embodiment, the cell receptor is a folate receptor, and the targeting ligand B is a folate receptor binding ligand. In another embodiment, B is a folate, such as folic acid, or an analog or derivative of folic acid that binds to folic acid receptors. It is to be understood as used herein, that the term folate is used both individually and collectively to refer to folic acid itself, and/or to such analogs and derivatives of folic acid that are capable of binding to folate receptors. In another embodiment, B is a compound capable of selectively or specifically binding to a folate receptor, such as an antibody.

Illustrative embodiments of folate analogs and/or derivatives include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refer to the art-recognized analogs having a carbon atom substituted for one or two nitrogen atoms in the naturally occurring folic acid structure, or analog or derivative thereof. For example, the deaza analogs include the 1-deaza, 3-deaza, 5-deaza, 8-deaza, and 10-deaza analogs of folate. The dideaza analogs include, for example, 1,5-dideaza, 5,10-dideaza, 8,10-dideaza, and 5,8-dideaza analogs of folate. Other folates useful as complex forming ligands include the folate receptor-binding analogs aminopterin, amethopterin (methotrexate), $N^{10}$-methylfolate, 2-deamino-hydroxyfolate, deaza analogs such as 1-$N^{10}$-deazamethopterin or 3-deazamethopterin, and 3',5'-dichloro-4-amino-4-deoxy-methylpteroyl-glutamic acid (dichloromethotrexate). The foregoing folic acid analogs and/or derivatives are conventionally termed folates, reflecting their ability to bind with folate-receptors, and such ligands when conjugated with exogenous molecules are effective to enhance transmembrane transport, such as via folate-mediated endocytosis as described herein. Other suitable binding ligands capable of binding to folate receptors to initiate receptor mediated endocytotic transport of the complex include antibodies to the folate receptor. An exogenous molecule in complex with an antibody to a folate receptor is used to trigger transmembrane transport of the complex.

Additional analogs of folic acid that bind to folic acid receptors are described in US Patent Application Publication Serial Nos. 2005/0227985 and 2004/0242582, the disclosures of which are incorporated herein by reference. Illustratively, such folate analogs have the general formula:

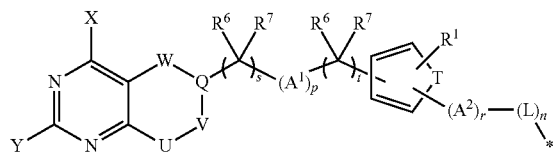

wherein X and Y are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$A^1$ and $A^2$ are each independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N ($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy, where Z is oxygen or sulfur;

$R^1$ is selected-from the group consisting of hydrogen, halo, $C_1$-$C_{12}$ alkyl, and $C_1$-$C_{12}$ alkoxy; $R^2$, $R^3$, $R^4$, $R^{4a}$, $R^{4b}$, $R^5$, $R^{5b}$, $R^{6b}$, and $R^{7b}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form a carbonyl group; $R^{6a}$ and $R^{7a}$ are each independently selected from the group consisting of hydrogen, halo, $C_1$-$C_{12}$ alkyl, and $C_1$-$C_{12}$ alkoxy; or $R^{6a}$ and $R^{7a}$ are taken together to form a carbonyl group;

L is a divalent linker as described herein; and n, p, r, s and t are each independently either 0 or 1.

As used herein, it is to be understood that the term folate refers both individually to folic acid used in forming a conjugate, or alternatively to a folate analog or derivative thereof that is capable of binding to folate or folic acid receptors.

In one aspect of such folate analogs, when s is 1, t is 0, and when s is 0, t is 1. In another aspect of such folate analogs, both n and r are 1, and linker $L^a$ is a naturally occurring amino acid covalently linked to $A^2$ at its alpha-amino group through an amide bond. Illustrative amino acids include aspartic acid, glutamic acid, lysine, cysteine, and the like.

The vitamin can be folate which includes a nitrogen, and in this embodiment, the spacer linkers can be alkylenecarbonyl, cycloalkylenecarbonyl, carbonylalkylcarbonyl, 1-alkylenesuccinimid-3-yl, 1-(carbonylalkyl)succinimid-3-yl, wherein each of the spacer linkers is optionally substituted with a substituent $X^1$, and the spacer linker is bonded to the folate nitrogen to form an imide or an alkylamide. In this embodiment, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

Illustrative embodiments of vitamin analogs and/or derivatives also include analogs and derivatives of biotin such as biocytin, biotin sulfoxide, oxybiotin and other biotin receptor-binding compounds, and the like. It is appreciated that analogs and derivatives of the other vitamins described herein are also contemplated herein. In one embodiment, vitamins that can be used as the binding ligand (B) in the drug delivery conjugates described herein include those that bind to vitamin receptors expressed specifically on activated macrophages, such as the folate receptor, which binds folate, or an analog or derivative thereof as described herein.

In addition to the vitamins described herein, it is appreciated that other binding ligands may be coupled with the drugs and linkers described and contemplated herein to form binding ligand-linker-drug conjugates capable of facilitating delivery of the drug to a desired target. These other binding ligands, in addition to the vitamins and their analogs and derivatives described, may be used to form drug delivery conjugates capable of binding to target cells. In general, any binding ligand (B) of a cell surface receptor may be advantageously used as a targeting ligand to which a linker-drug conjugate can be attached.

Illustrative other ligands described herein include peptide ligands identified from library screens, tumor cell-specific peptides, tumor cell-specific aptamers, tumor cell-specific carbohydrates, tumor cell-specific monoclonal or polyclonal antibodies, Fab or scFv (i.e., a single chain variable region) fragments of antibodies such as, for example, an Fab fragment of an antibody directed to EphA2 or other proteins specifically expressed or uniquely accessible on metastatic cancer cells, small organic molecules derived from combinatorial libraries, growth factors, such as EGF, FGF, insulin, and insulin-like growth factors, and homologous polypeptides, somatostatin and its analogs, transferrin, lipoprotein complexes, bile salts, selectins, steroid hormones, Arg-Gly-Asp containing peptides, retinoids, various Galectins, δ-opioid receptor ligands, cholecystokinin A receptor ligands, ligands specific for angiotensin AT1 or AT2 receptors, peroxisome proliferator-activated receptor λ ligands, β-lactam antibiotics such as penicillin, small organic molecules including antimicrobial drugs, and other molecules that bind specifically to a receptor preferentially expressed on the surface of tumor cells or on an infectious organism, antimicrobial and other drugs designed to fit into the binding pocket of a particular receptor based on the crystal structure of the receptor or other cell surface protein, binding ligands of tumor antigens or other molecules preferentially expressed on the surface of tumor cells, or fragments of any of these molecules.

An example of a tumor-specific antigen that could function as a binding site for a binding ligand-drug conjugate include extracellular epitopes of a member of the Ephrin family of proteins, such as EphA2. EphA2 expression is restricted to cell-cell junctions in normal cells, but EphA2 is distributed over the entire cell surface in metastatic tumor cells. Thus, EphA2 on metastatic cells would be accessible for binding to, for example, an Fab fragment of an antibody conjugated to a drug, whereas the protein would not be accessible for binding to the Fab fragment on normal cells, resulting in a binding ligand-drug conjugate specific for metastatic cancer cells.

The linker L includes one or more hydrophilic spacer linkers. In addition, other optional spacer linkers and/or releasable linkers may be included in L. It is appreciated that additional spacer linkers may included when predetermined lengths are selected for separating binding ligand B from agent A. It is also appreciated that in certain configurations, releasable linkers may be included. For example, as described herein in one embodiment, the targeted ligand conjugates may be used to deliver drugs for treating cancer or other diseases involving pathogenic cells. In such embodiments, it is appreciated that once delivered, the drug is desirably released from the conjugate. For example, in the configuration where the targeting ligand is folate, or an analog or derivative thereof, the conjugate may bind to a folate receptor. Once bound, the conjugate often undergoes the process of endocytosis, and the conjugate is delivered to the interior of the cell. Cellular mechanisms may biologically degrade the conjugate to release the drug "payload" and release the folate compound.

In an alternative configuration, the targeted conjugate may be used in immunotherapy. In this configuration, a releasable linker is generally not included. For example, conjugates of folate or other vitamin receptor binding compounds and immunogens, once delivered, will bind to the appropriated receptor and decorate or mark the cell with the antigenic payload. In another alternative configuration, the targeted conjugate may be used in a diagnostic therapy. In this configuration, a releasable linker may or may not be included. For example, conjugates that include imaging agents may be delivered to a target cell using the appropriate cell receptor binding ligand, such as a folate or other vitamin receptor binding compound. In one aspect, the conjugate may remain on the surface of the cell for imaging. In another configuration, the conjugate may undergo endocytosis into the interior of the cell. In this latter situation, a releasable linker may be included.

Accordingly, in other aspects, the conjugates B-L-A described herein also include the following general formulae:

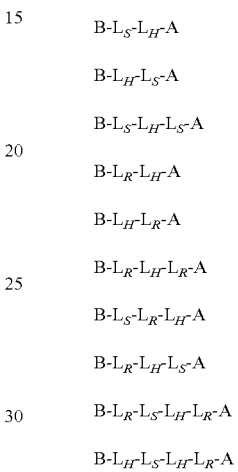

where B, L, and A are as described herein, and $L_R$ is a releasable linker section, $L_S$ is a spacer linker section, and $L_H$ is a hydrophilic linker section of linker L. It is to be understood that the foregoing formulae are merely illustrative, and that other arrangements of the hydrophilic spacer linker sections, releasable linker sections, and spacer linker sections are to be included herein. In addition, it is to be understood that additional conjugates are contemplated that include a plurality hydrophilic spacer linkers, and/or a plurality of releasable linkers, and/or a plurality of spacer linkers.

Similarly, in other aspects, the conjugates L-A described herein also include the following general formulae:

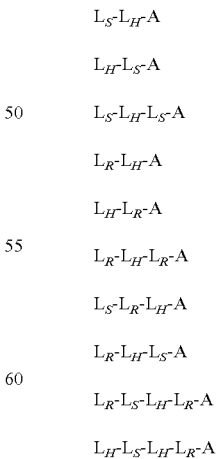

where L and A are as described herein, and $L_R$ is a releasable linker section, $L_S$ is a spacer linker section, and $L_H$ is a hydrophilic linker section of linker L. It is to be understood that the foregoing formulae are merely illustrative, and that other arrangements of the hydrophilic spacer linker sections, releasable linker sections, and spacer linker sections are to be included herein. In addition, it is to be understood that additional conjugates are contemplated that include a plurality hydrophilic spacer linkers, and/or a plurality of releasable linkers, and/or a plurality of spacer linkers.

It is appreciated that the arrangement and/or orientation of the various hydrophilic linkers may be in a linear or branched fashion, or both. For example, the hydrophilic linkers may form the backbone of the linker forming the conjugate between the folate and the drug, imagining agent, or diagnostic agent. Alternatively, the hydrophilic portion of the linker may be pendant to or attached to the backbone of the chain of atoms connecting the binding ligand B to the agent A. In this latter arrangement, the hydrophilic portion may be proximal or distal to the backbone chain of atoms.

In another embodiment, the linker is more or less linear, and the hydrophilic groups are arranged largely in a series to form a chain-like linker in the conjugate. Said another way, the hydrophilic groups form some or all of the backbone of the linker in this linear embodiment.

In another embodiment, the linker is branched with hydrophilic groups. In this branched embodiment, the hydrophilic groups may be proximal to the backbone or distal to the backbone. In each of these arrangements, the linker is more spherical or cylindrical in shape. In one variation, the linker is shaped like a bottle-brush. In one aspect, the backbone of the linker is formed by a linear series of amides, and the hydrophilic portion of the linker is formed by a parallel arrangement of branching side chains, such as by connecting monosaccharides, sulfonates, and the like, and derivatives and analogs thereof.

It is understood that the linker may be neutral or ionizable under certain conditions, such as physiological conditions encountered in vivo. For ionizable linkers, under the selected conditions, the linker may deprotonate to form a negative ion, or alternatively become protonated to form a positive ion. It is appreciated that more than one deprotonation or protonation event may occur. In addition, it is understood that the same linker may deprotonate and protonate to form inner salts or zwitterionic compounds.

In another embodiment, the hydrophilic spacer linkers are neutral, i.e. under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker is protonated in vivo. In another embodiment, the spacers include both regions that are neutral and regions that may be protonated to carry one or more positive charges. In another embodiment, the spacers include both regions that may be deprotonated to carry one or more negative charges and regions that may be protonated to carry one or more positive charges. It is understood that in this latter embodiment that zwitterions or inner salts may be formed.

In one aspect, the regions of the linkers that may be deprotonated to carry a negative charge include carboxylic acids, such as aspartic acid, glutamic acid, and longer chain carboxylic acid groups, and sulfuric acid esters, such as alkyl esters of sulfuric acid. In another aspect, the regions of the linkers that may be protonated to carry a positive charge include amino groups, such as polyaminoalkylenes including ethylene diamines, propylene diamines, butylene diamines and the like, and/or heterocycles including pyrollidines, piperidines, piperazines, and other amino groups, each of which is optionally substituted. In another embodiment, the regions of the linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In one embodiment, the hydrophilic spacer linkers described herein include are formed primarily from carbon, hydrogen, and oxygen, and have a carbon/oxygen ratio of about 3:1 or less, or of about 2:1 or less. In one aspect, the hydrophilic linkers described herein include a plurality of ether functional groups. In another aspect, the hydrophilic linkers described herein include a plurality of hydroxyl functional groups. Illustrative fragments that may be used to form such linkers include polyhydroxyl compounds such as carbohydrates, polyether compounds such as polyethylene glycol units, and acid groups such as carboxyl and alkyl sulfuric acids. In one variation, oligoamide spacers, and the like may also be included in the linker.

Illustrative carbohydrate spacers include saccharopeptides as described herein that include both a peptide feature and sugar feature; glucuronides, which may be incorporated via [2+3] Huisgen cyclization, also known as click chemistry; β-alkyl glycosides, such as of 2-deoxyhexapyranoses (2-deoxyglucose, 2-deoxyglucuronide, and the like), and β-alkyl mannopyranosides. Illustrative PEG groups include those of a specific length range from about 4 to about 20 PEG groups. Illustrative alkyl sulfuric acid esters may also be introduced with click chemistry directly into the backbone. Illustrative oligoamide spacers include EDTA and DTPA spacers, ρ-amino acids, and the like.

In another embodiment, the hydrophilic spacer linkers described herein include a polyether, such as the linkers of the following formulae:

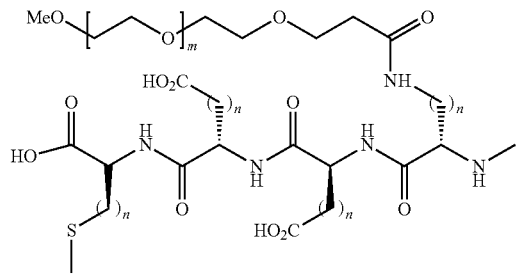

-continued

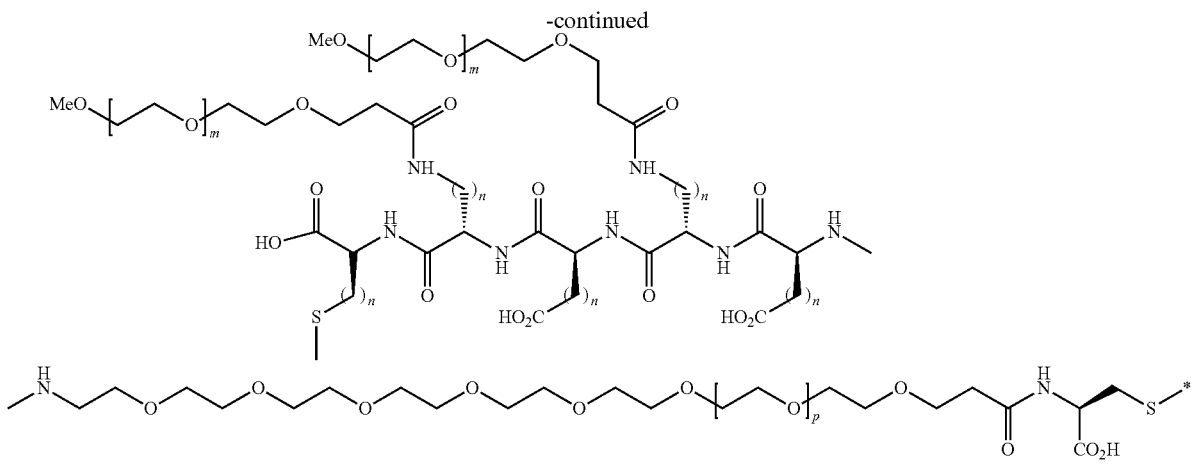

where m is an integer independently selected in each instance from 1 to about 8; p is an integer selected 1 to about 10; and n is an integer independently selected in each instance from 1 to about 3. In one aspect, m is independently in each instance 1 to about 3. In another aspect, n is 1 in each instance. In another aspect, p is independently in each instance about 4 to about 6. Illustratively, the corresponding polypropylene polyethers corresponding to the foregoing are contemplated herein and may be included in the conjugates as hydrophilic spacer linkers. In addition, it is appreciated that mixed polyethylene and polypropylene polyethers may be included in the conjugates as hydrophilic spacer linkers. Further, cyclic variations of the foregoing polyether compounds, such as those that include tetrahydrofuranyl, 1,3-dioxanes, 1,4-dioxanes, and the like are contemplated herein.

In another illustrative embodiment, the hydrophilic spacer linkers described herein include a plurality of hydroxyl functional groups, such as linkers that incorporate monosaccharides, oligosaccharides, polysaccharides, and the like. It is to be understood that the polyhydroxyl containing spacer linkers comprises a plurality of —(CROH)— groups, where R is hydrogen or alkyl.

In another embodiment, the spacer linkers include one or more of the following fragments:

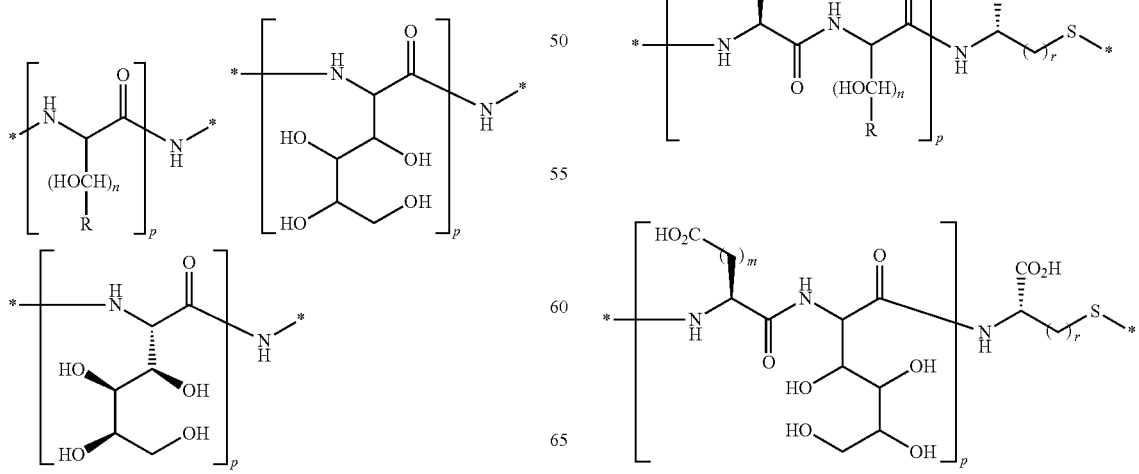

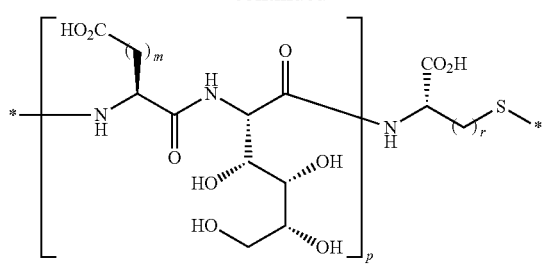

wherein R is H, alkyl, cycloalkyl, or arylalkyl; m is an integer from 1 to about 3; n is an integer from 1 to about 5, p is an integer from 1 to about 5, and r is an integer selected from 1 to about 3. In one aspect, the integer n is 3 or 4. In another aspect, the integer p is 3 or 4. In another aspect, the integer r is 1.

In another embodiment, the spacer linker includes one or more of the following cyclic polyhydroxyl groups:

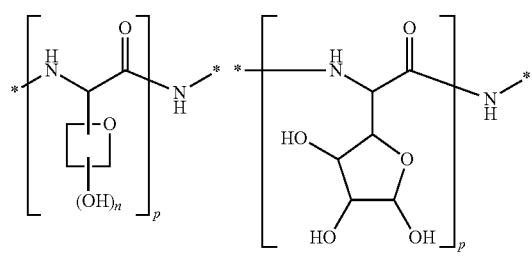

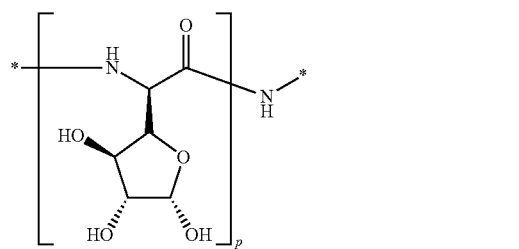

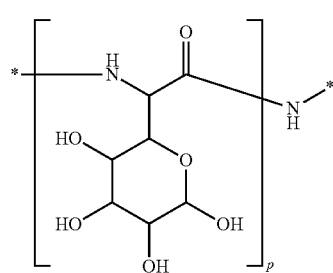

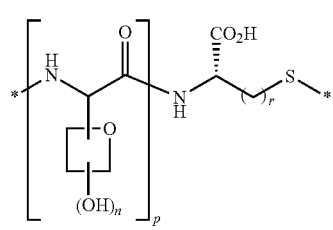

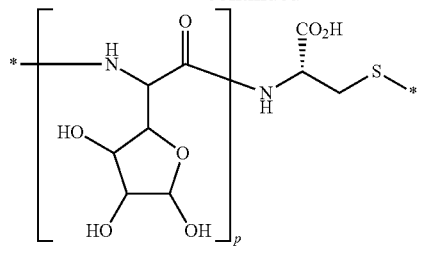

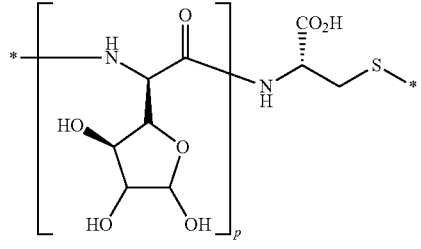

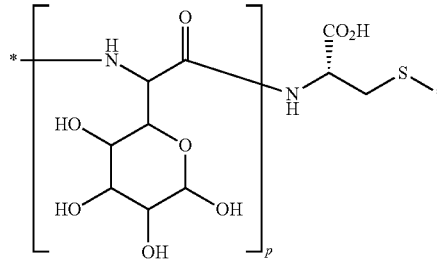

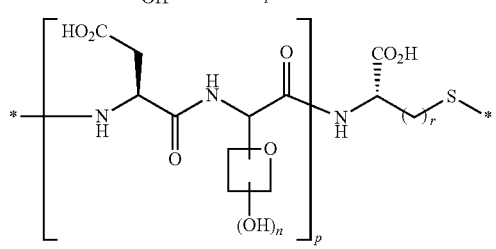

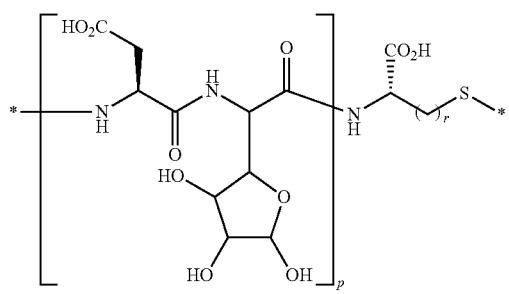

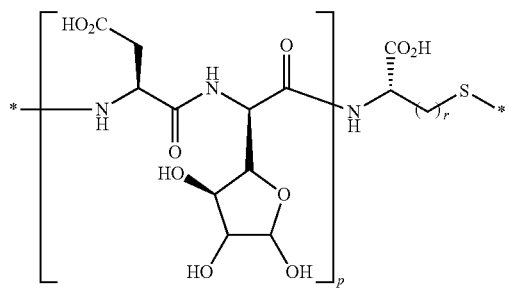

-continued

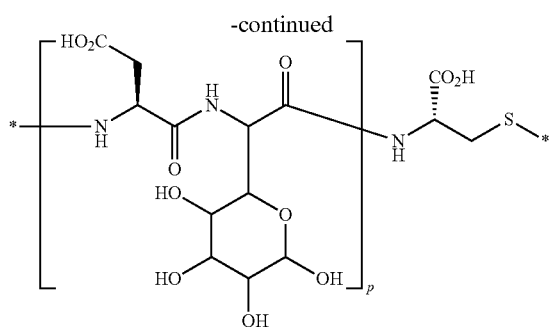

wherein n is an integer from 2 to about 5, p is an integer from 1 to about 5, and r is an integer from 1 to about 4. In one aspect, the integer n is 3 or 4. In another aspect, the integer p is 3 or 4. In another aspect, the integer r is 2 or 3. It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules. In addition, it is to be understood that in the foregoing formulae, various deoxy compounds are also contemplated. Illustratively, compounds of the following formulae are contemplated:

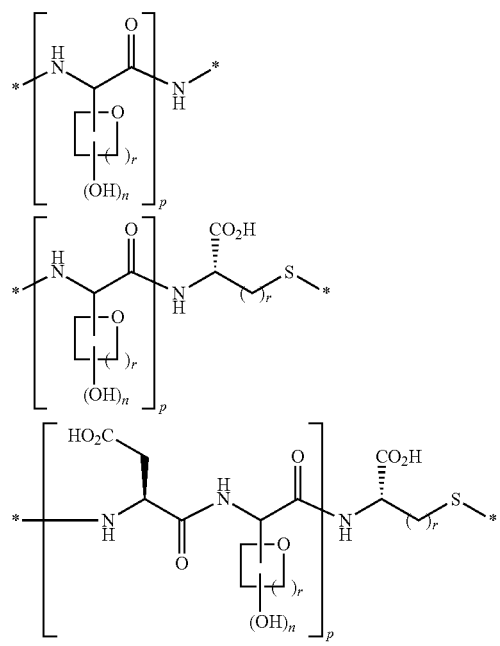

wherein n is equal to or less than r, such as when r is 2 or 3, n is 1 or 2, or 1, 2, or 3, respectively.

In another embodiment, the spacer linker includes a polyhydroxyl compound of the following formula:

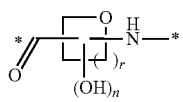

wherein n and r are each an integer selected from 1 to about 3. In one aspect, the spacer linker includes one or more polyhydroxyl compounds of the following formulae:

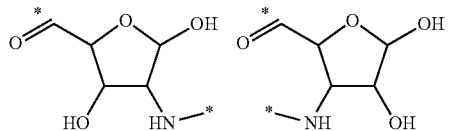

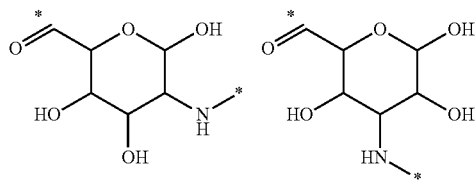

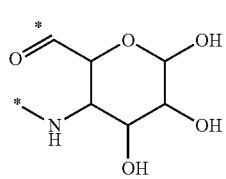

It is understood that all stereochemical forms of such sections of the linkers are contemplated herein. For example, in the above formula, the section may be derived from ribose, xylose, glucose, mannose, galactose, or other sugar and retain the stereochemical arrangements of pendant hydroxyl and alkyl groups present on those molecules.

In another configuration, the hydrophilic linkers L described herein include polyhydroxyl groups that are spaced away from the backbone of the linker. In one embodiment, such carbohydrate groups or polyhydroxyl groups are connected to the back bone by a triazole group, forming triazole-linked hydrophilic spacer linkers. Illustratively, such linkers include fragments of the following formulae:

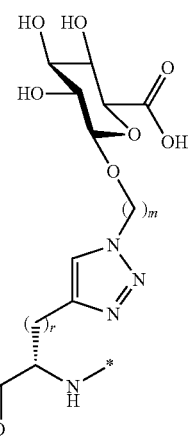

-continued

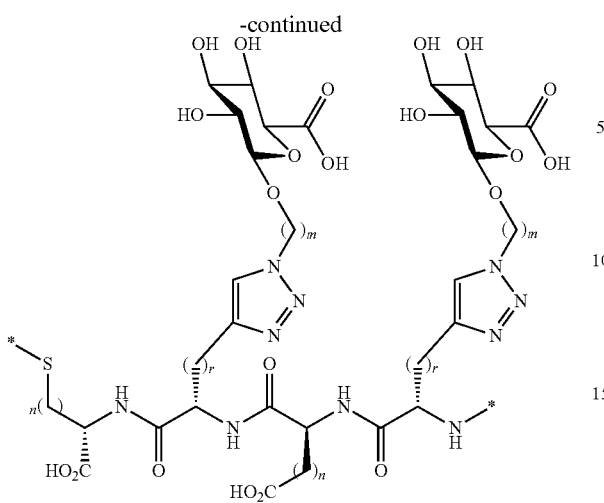

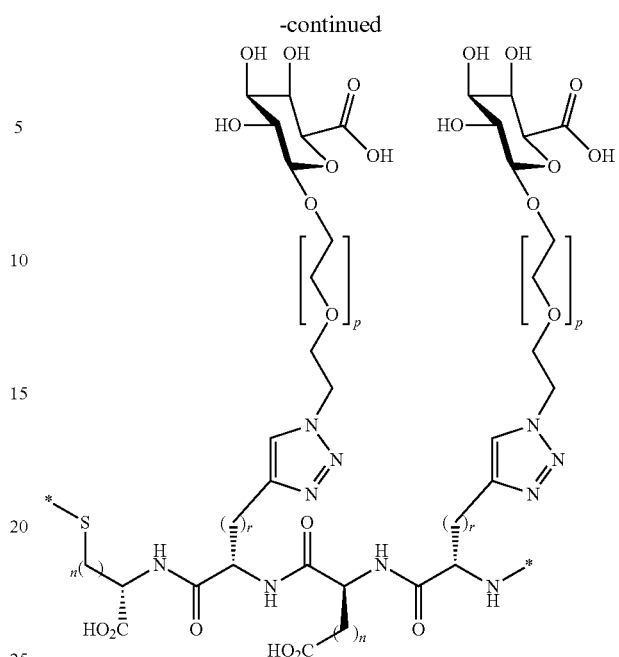

wherein n, m, and r are integers and are each independently selected in each instance from 1 to about 5. In one illustrative aspect, m is independently 2 or 3 in each instance. In another aspect, r is 1 in each instance. In another aspect, n is 1 in each instance. In one variation, the group connecting the polyhydroxyl group to the backbone of the linker is a different heteroaryl group, including but not limited to, pyrrole, pyrazole, 1,2,4-triazole, furan, oxazole, isoxazole, thienyl, thiazole, isothiazole, oxadiazole, and the like. Similarly, divalent 6-membered ring heteroaryl groups are contemplated. Other variations of the foregoing illustrative hydrophilic spacer linkers include oxyalkylene groups, such as the following formulae:

wherein n and r are integers and are each independently selected in each instance from 1 to about 5; and p is an integer selected from 1 to about 4.

In another embodiment, such carbohydrate groups or polyhydroxyl groups are connected to the back bone by an amide group, forming amide-linked hydrophilic spacer linkers. Illustratively, such linkers include fragments of the following formulae:

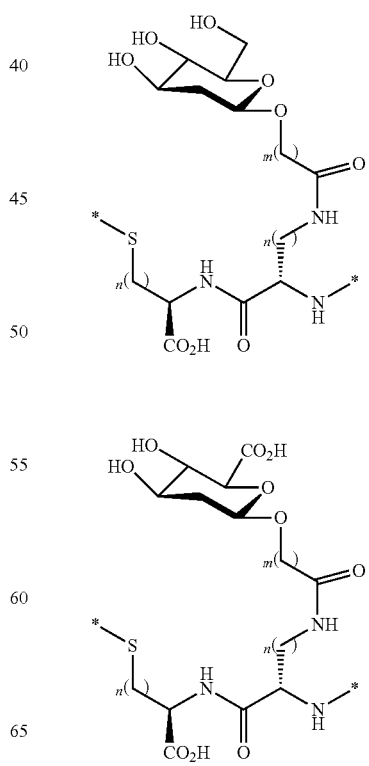

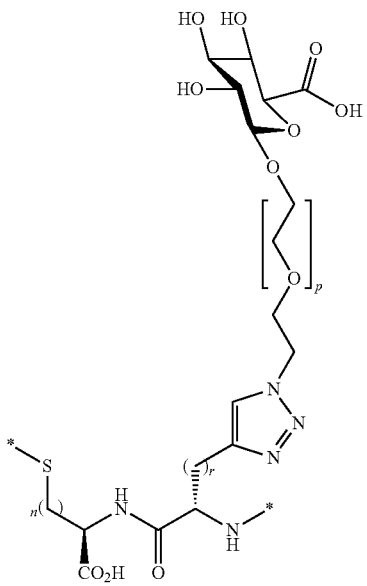

-continued

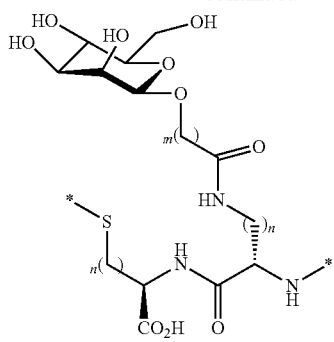

wherein n is an integer selected from 1 to about 3, and m is an integer selected from 1 to about 22. In one illustrative aspect, n is 1 or 2. In another illustrative aspect, m is selected from about 6 to about 10, illustratively 8. In one variation, the group connecting the polyhydroxyl group to the backbone of the linker is a different functional group, including but not limited to, esters, ureas, carbamates, acylhydrazones, and the like. Similarly, cyclic variations are contemplated. Other variations of the foregoing illustrative hydrophilic spacer linkers include oxyalkylene groups, such as the following formulae:

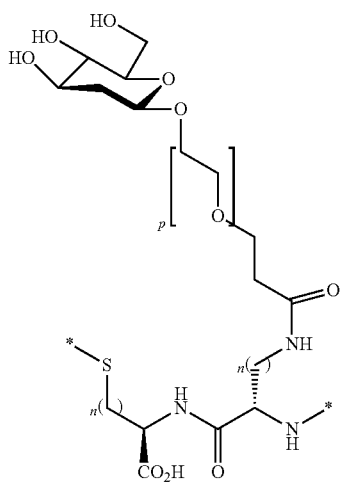

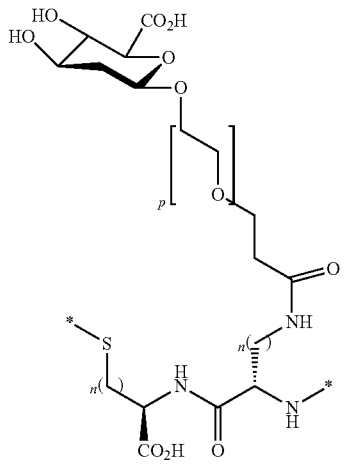

-continued

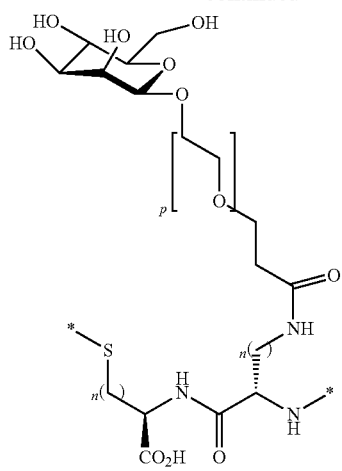

wherein n and r are integers and are each independently selected in each instance from 1 to about 5; and p is an integer selected from 1 to about 4.

In another embodiment, the spacer linkers include one or more of the following fragments:

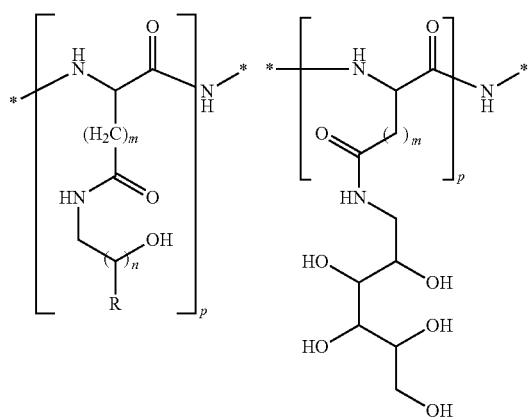

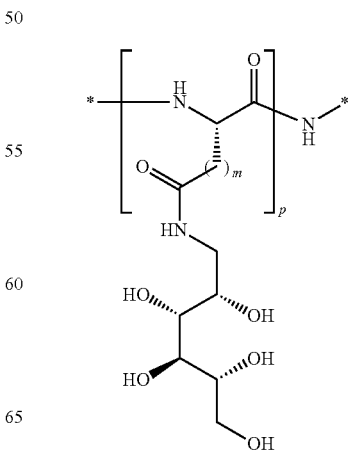

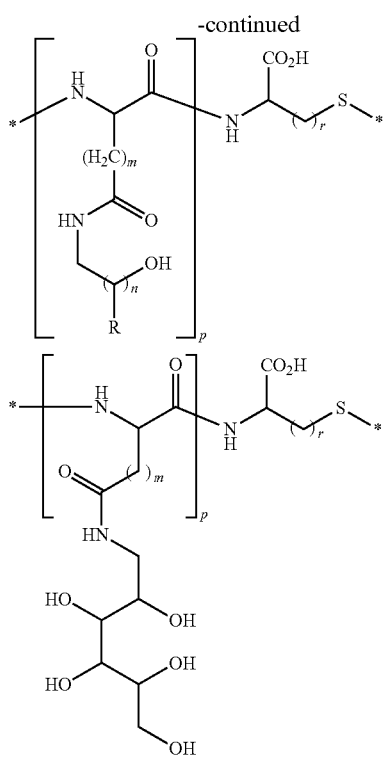

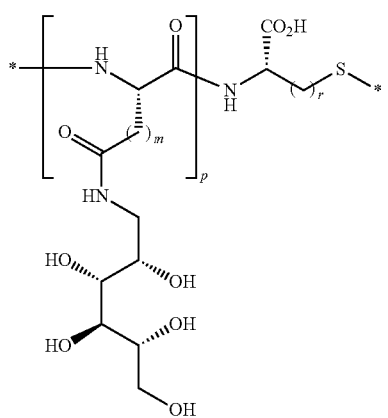

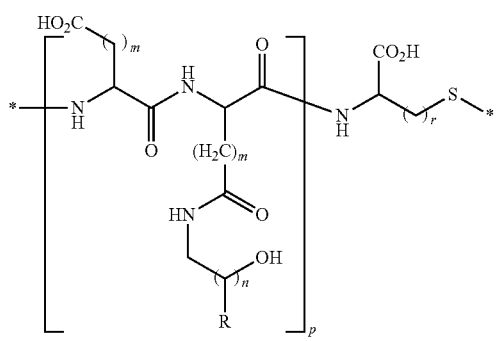

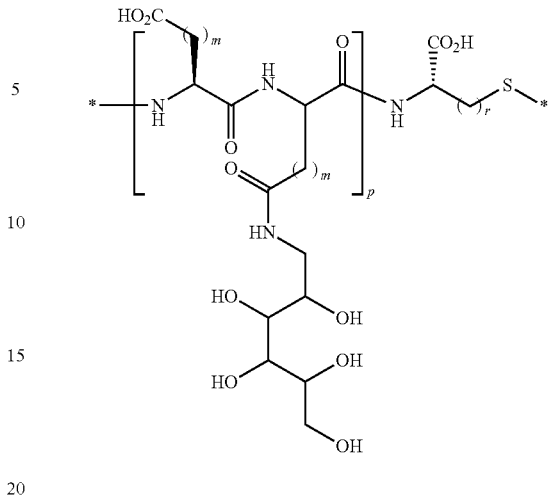

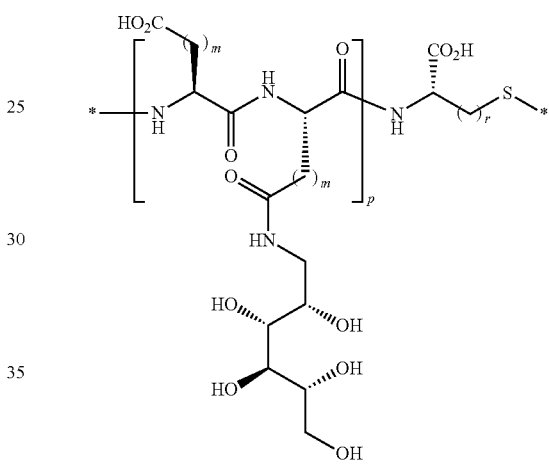

wherein R is H, alkyl, cycloalkyl, or arylalkyl; m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the spacer linkers include one or more of the following fragments:

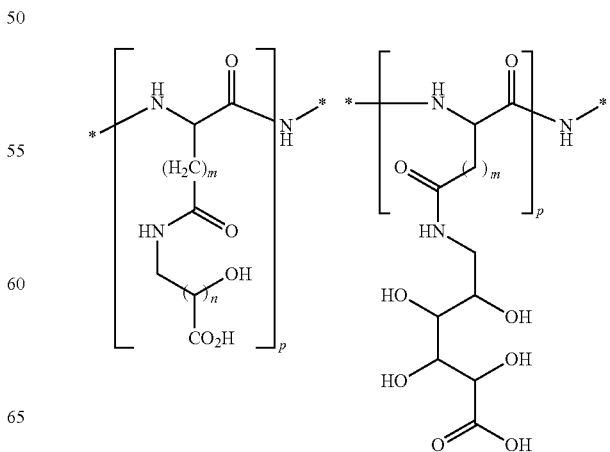

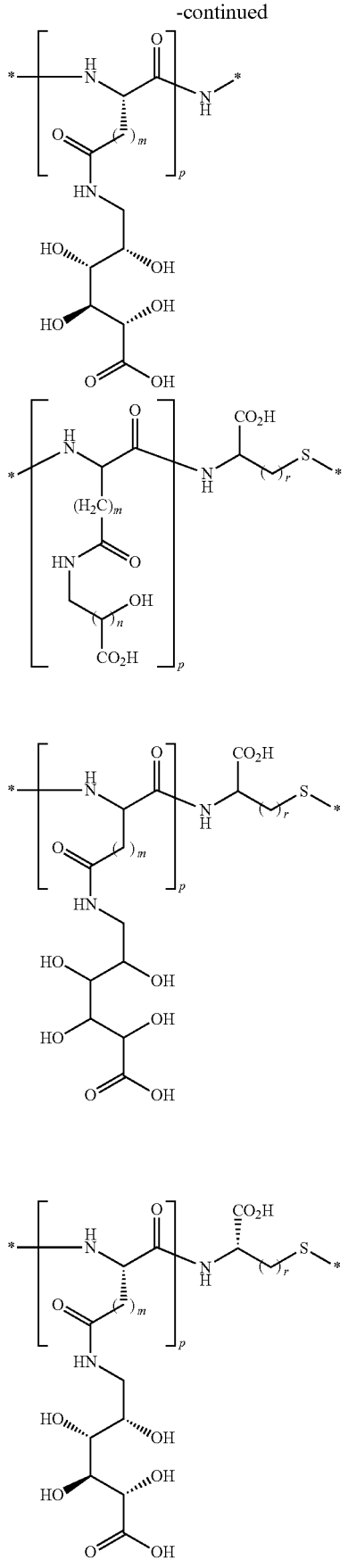
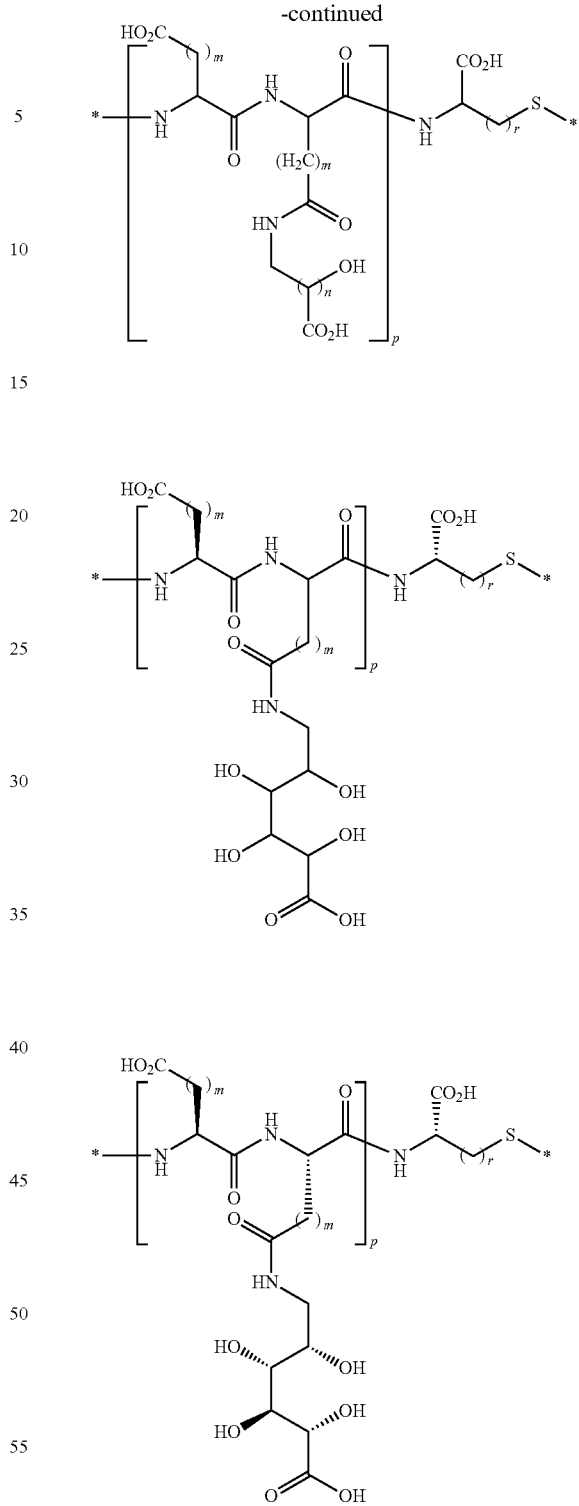
wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.
In another embodiment, the spacer linkers include one or more of the following fragments:

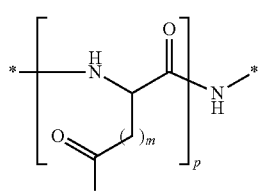
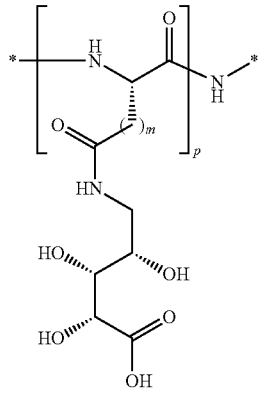
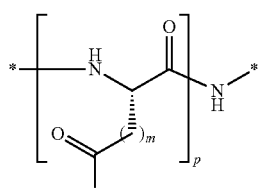
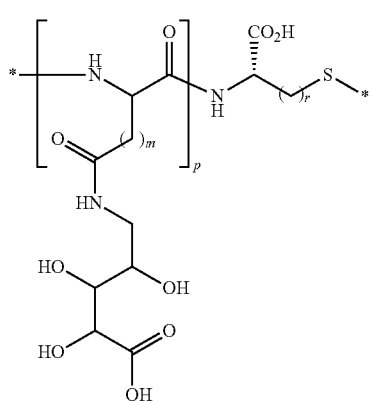
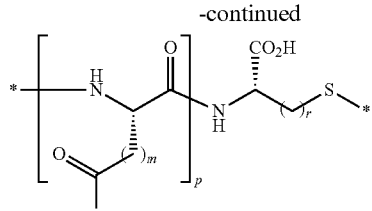
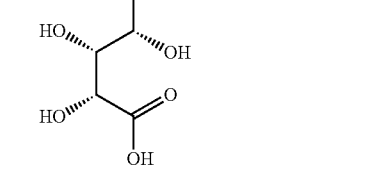
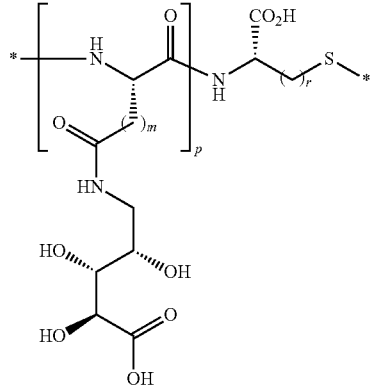
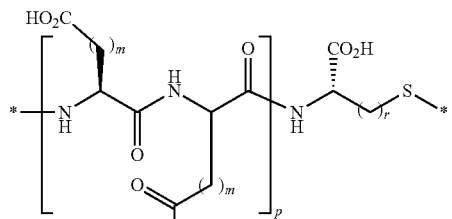
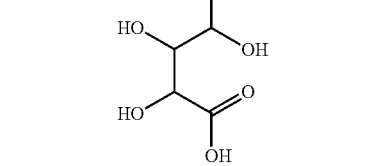
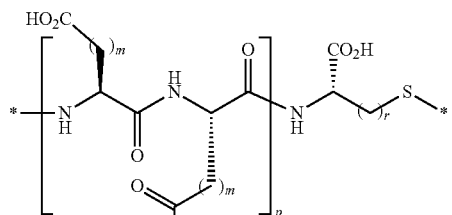
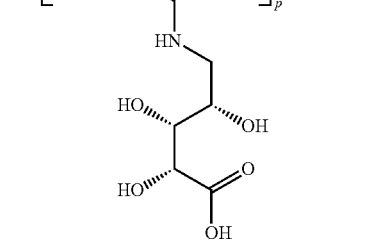

-continued

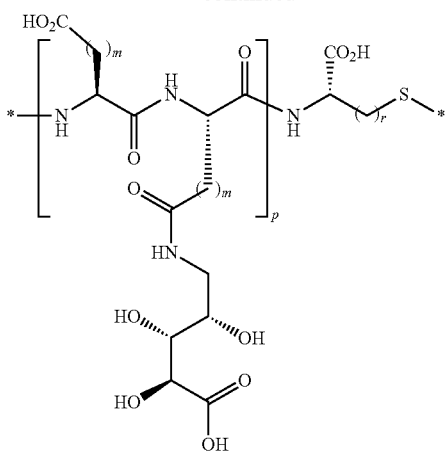

wherein m is an independently selected integer from 1 to about 3; n is an integer from 1 to about 6, p is an integer from 1 to about 5, and r is an integer selected from 1 to about 3. In one variation, the integer n is 3 or 4. In another variation, the integer p is 3 or 4. In another variation, the integer r is 1.

In another embodiment, the hydrophilic spacer linker is a combination of backbone and branching side motifs such as is illustrated by the following formulae

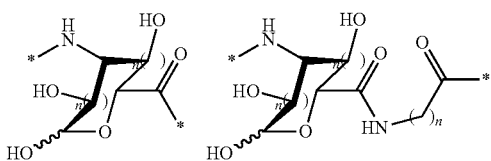

-continued

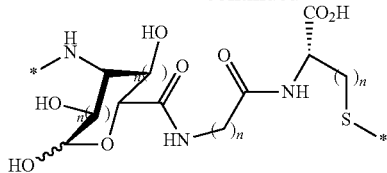

wherein n is an integer independently selected in each instance from 0 to about 3. The above formula are intended to represent 4, 5, 6, and even larger membered cyclic sugars. In addition, it is to be understood that the above formula may be modified to represent deoxy sugars, where one or more of the hydroxy groups present on the formulae are replaced by hydrogen, alkyl, or amino. In addition, it is to be understood that the corresponding carbonyl compounds are contemplated by the above formulae, where one or more of the hydroxyl groups is oxidized to the corresponding carbonyl. In addition, in this illustrative embodiment, the pyranose includes both carboxyl and amino functional groups and (a) can be inserted into the backbone and (b) can provide synthetic handles for branching side chains in variations of this embodiment. Any of the pendant hydroxyl groups may be used to attach other chemical fragments, including additional sugars to prepare the corresponding oligosaccharides. Other variations of this embodiment are also contemplated, including inserting the pyranose or other sugar into the backbone at a single carbon, i.e. a Spiro arrangement, at a geminal pair of carbons, and like arrangements. For example, one or two ends of the linker, or the agent A, or the binding ligand B may be connected to the sugar to be inserted into the backbone in a 1,1; 1,2; 1,3; 1,4; 2,3, or other arrangement.

In another embodiment, the hydrophilic spacer linkers described herein include are formed primarily from carbon, hydrogen, and nitrogen, and have a carbon/nitrogen ratio of about 3:1 or less, or of about 2:1 or less. In one aspect, the hydrophilic linkers described herein include a plurality of amino functional groups.

In another embodiment, the spacer linkers include one or more amino groups of the following formulae:

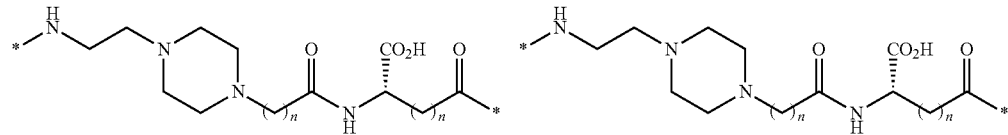

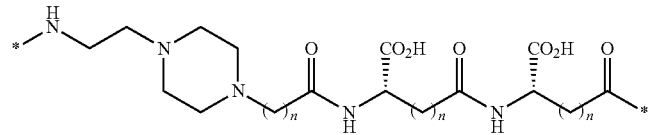

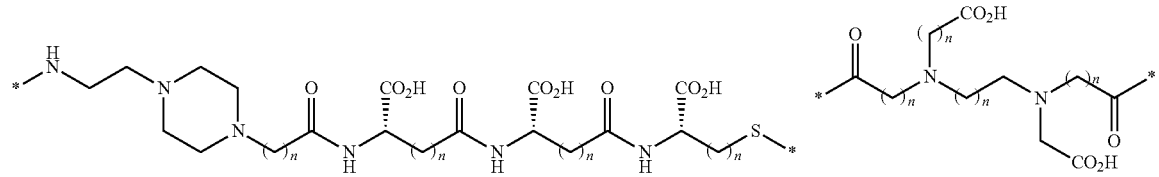

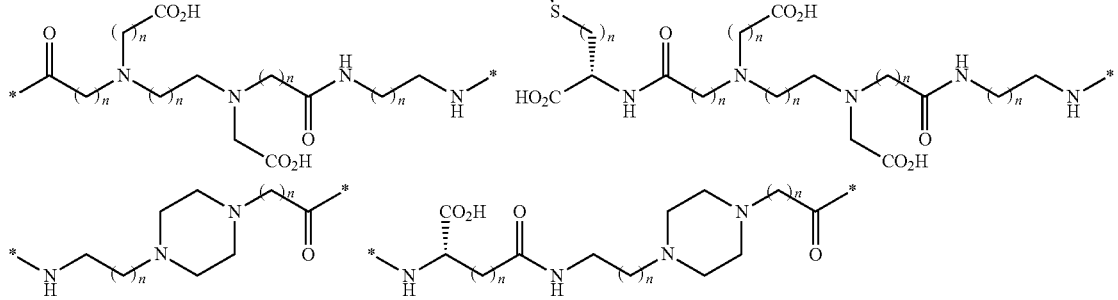

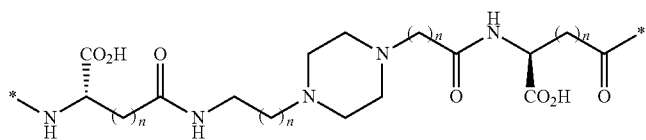

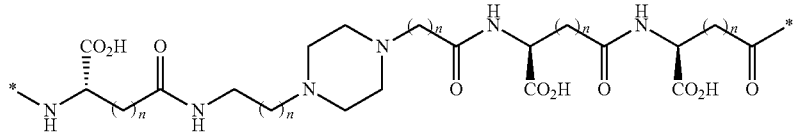

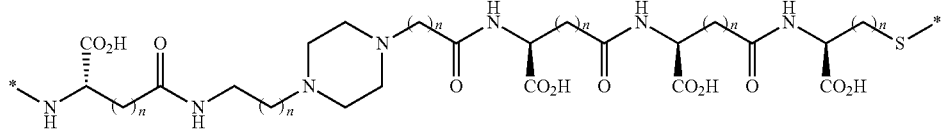

where n is an integer independently selected in each instance from 1 to about 3. In one aspect, the integer n is independently 1 or 2 in each instance. In another aspect, the integer n is 1 in each instance.

In another embodiment, the hydrophilic spacer linker is a sulfuric acid ester, such as an alkyl ester of sulfuric acid. Illustratively, the spacer linker is of the following formula:

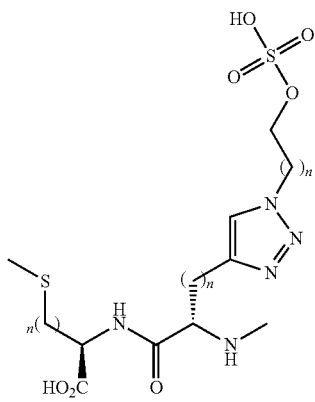

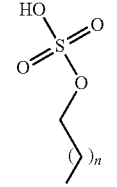 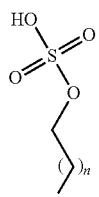

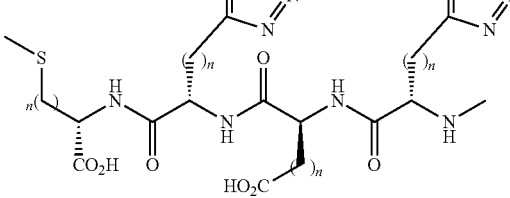

where n is an integer independently selected in each instance from 1 to about 3. Illustratively, n is independently 1 or 2 in each instance.

It is understood, that in such polyhydroxyl, polyamino, carboxylic acid, sulfuric acid, and like linkers that include free hydrogens bound to heteroatoms, one or more of those free hydrogen atoms may be protected with the appropriate hydroxyl, amino, or acid protecting group, respectively, or alternatively may be blocked as the corresponding pro-drugs, the latter of which are selected for the particular use, such as pro-drugs that release the parent drug under general or specific physiological conditions.

In each of the foregoing illustrative examples of linkers L, there are also included in some cases additional spacer linkers $L_S$, and/or additional releasable linkers $L_R$. Those spacer linker and releasable linkers also may include asymmetric carbon atoms. It is to be further understood that the stereochemical configurations shown herein are merely illustrative, and other stereochemical configurations are contemplated. For example in one variation, the corresponding unnatural amino acid configurations may be included in the conjugated described herein as follows:

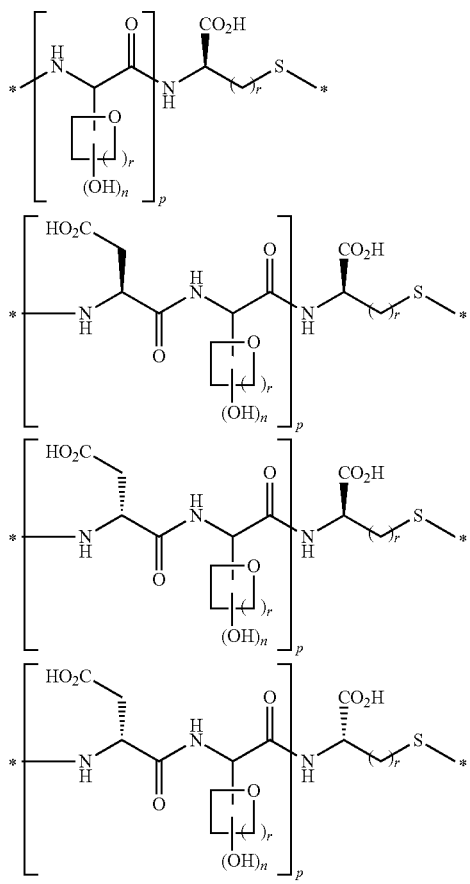

wherein n is an integer from 2 to about 5, p is an integer from 1 to about 5, and r is an integer from 1 to about 4, as described above.

It is to be further understood that in the foregoing embodiments, open positions, such as (*) atoms are locations for attachment of the binding ligand (B) or the agent (A) to be delivered. In addition, it is to be understood that such attachment of either or both of B and A may be direct or through an intervening linker. Intervening linkers include other spacer linkers and/or releasable linkers. Illustrative additional spacer linkers and releasable linkers that are included in the conjugated described herein are described in U.S. patent application Ser. No. 10/765,335, the disclosure of which is incorporated herein by reference.

In one embodiment, the hydrophilic spacer linker comprises one or more carbohydrate containing or polyhydroxyl group containing linkers. In another embodiment, the hydrophilic spacer linker comprises at least three carbohydrate containing or polyhydroxyl group containing linkers. In another embodiment, the hydrophilic spacer linker comprises one or more carbohydrate containing or polyhydroxyl group containing linkers, and one or more aspartic acids. In another embodiment, the hydrophilic spacer linker comprises one or more carbohydrate containing or polyhydroxyl group containing linkers, and one or more glutamic acids. In another embodiment, the hydrophilic spacer linker comprises one or more carbohydrate containing or polyhydroxyl group containing linkers, one or more glutamic acids, one or more aspartic acids, and one or more beta amino alanines. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more divalent 1,4-piperazines that are included in the chain of atoms connecting at least one of the binding ligands (L) with at least one of the agents (A). In one variation, the hydrophilic spacer linker includes one or more carbohydrate containing or polyhydroxyl group containing linkers. In another variation, the hydrophilic spacer linker includes one or more carbohydrate containing or polyhydroxyl group containing linkers and one or more aspartic acids. In another variation, the hydrophilic spacer linker includes one or more carbohydrate containing or polyhydroxyl group containing linkers and one or more glutamic acids. In a series of variations, in each of the foregoing embodiments, the hydrophilic spacer linker also includes one or more cysteines. In another series of variations, in each of the foregoing embodiments, the hydrophilic spacer linker also includes at least one arginine.

In another embodiment, the hydrophilic spacer linker comprises one or more oligoamide hydrophilic spacers, such as but not limited to aminoethylpiperazinylacetamide.

In another embodiment, the hydrophilic spacer linker comprises one or more triazole linked carbohydrate containing or polyhydroxyl group containing linkers. In another embodiment, the hydrophilic spacer linker comprises one or more amide linked carbohydrate containing or polyhydroxyl group containing linkers. In another embodiment, the hydrophilic spacer linker comprises one or more PEG groups and one or more cysteines. In another embodiment, the hydrophilic spacer linker comprises one or more EDTE derivatives.

In another embodiment, the additional spacer linker can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined below, and wherein the spacer linker and the releasable linker are each bonded to the spacer linker to form a succinimid-1-ylalkyl acetal or ketal.

The additional spacer linkers can be carbonyl, thionocarbonyl, alkylene, cycloalkylene, alkylenecycloalkyl, alkylenecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonylalkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)

succinimid-3-yl, and 1-(carbonyhetrahydrofuranyesuccinimid-3-yl, wherein each of the spacer linkers is optionally substituted with a substituent $X^1$, as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the additional spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined below. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$, as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the spacer linker can include nitrogen, and the substituent $X^1$ and the spacer linker to which they are bound to form an heterocycle.

In another embodiment, the releasable linker may be a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below.

Additional illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl(biscarboxyaryl)carbonyl, haloalkylenecarbonyl, alkylene(dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, iminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be iminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the drug can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the drug nitrogen to form an amide.

In the above releasable linker embodiment, the drug can include an oxygen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can form an amide, and also bonded to the drug oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the releasable linker can include nitrogen, and the substituent $X^2$ and the releasable linker can form an heterocycle.

The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

The agent A can include a nitrogen atom, and the releasable linker can be haloalkylenecarbonyl, optionally substituted with a substituent $X^2$, and the releasable linker is bonded to the drug nitrogen to form an amide.

The agent A can include an oxygen atom, and the releasable linker can be haloalkylenecarbonyl, optionally substituted with a substituent $X^2$, and the releasable linker is bonded to the drug oxygen to form an ester.

The agent A can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

The agent A can include a sulfur atom, and in this embodiment, the releasable linkers can be alkylenethio and carbonylalkylthio, and the releasable linker can be bonded to the drug sulfur to form a disulfide.

The agent A can be a mitomycin, a mitomycin derivative, or a mitomycin analog, and, in this embodiment, the releasable linkers can be carbonylalkylthio, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyesuccinimid-3-yl, wherein each of the releasable linkers is optionally substituted with a substituent $X^2$, and wherein the aziridine of the mitomycin is bonded to the releasable linker to form an acylaziridine.

The binding ligand B can be folate which includes a nitrogen, and in this embodiment, the spacer linkers can be alkylenecarbonyl, cycloalkylenecarbonyl, carbonylalkylcarbonyl, 1-alkylenesuccinimid-3-yl, 1-(carbonylalkyl)succinimid-3-yl, wherein each of the spacer linkers is optionally substituted with a substituent $X^1$, and the spacer linker is bonded to the folate nitrogen to form an imide or an alkylamide. In this embodiment, the substituents $X^1$ can be alkyl, hydroxyalkyl, amino, aminoalkyl, alkylaminoalkyl, dialkylaminoalkyl, sulfhydrylalkyl, alkylthioalkyl, aryl, substituted aryl, arylalkyl, substituted arylalkyl, carboxy, carboxyalkyl, guanidinoalkyl, $R^4$-carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

The term cycloalkylene as used herein refers to a bivalent chain of carbon atoms, a portion of which forms a ring, such as cycloprop-1,1-diyl, cycloprop-1,2-diyl, cyclohex-1,4-diyl, 3-ethylcyclopent-1,2-diyl, 1-methylenecyclohex-4-yl, and the like.

The term heterocycle as used herein refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

The term aryl as used herein refers to an aromatic mono or polycyclic ring of carbon atoms, such as phenyl, naphthyl, and the like. In addition, aryl may also include heteroaryl.

The term heteroaryl as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term optionally substituted as used herein refers to the replacement of one or more hydrogen atoms, generally on carbon, with a corresponding number of substituents, such as halo, hydroxy, amino, alkyl or dialkylamino, alkoxy, alkylsulfonyl, cyano, nitro, and the like. In addition, two hydrogens on the same carbon, on adjacent carbons, or nearby carbons may be replaced with a bivalent substituent to form the corresponding cyclic structure.

The term iminoalkylidenyl as used herein refers to a divalent radical containing alkylene as defined herein and a nitrogen atom, where the terminal carbon of the alkylene is double-bonded to the nitrogen atom, such as the formulae —(CH)=N—, —(CH$_2$)$_2$(CH)=N—, —CH$_2$C(Me)=N—, and the like.

The term amino acid as used herein refers generally to aminoalkylcarboxylate, where the alkyl radical is optionally substituted, such as with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like. It is to be understood that such amino acids may be of a single stereochemistry or a particular mixture of stereochemistries, including racemic mixtures. In addition, amino acid refers to beta, gamma, and longer amino acids, such as amino acids of the formula:

where R is hydrogen, alkyl, acyl, or a suitable nitrogen protecting group, R' and R'' are hydrogen or a substituent, each of which is independently selected in each occurrence, and q is an integer such as 1, 2, 3, 4, or 5. Illustratively, R' and/or R'' independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In another illustrative aspect of the vitamin receptor binding drug delivery conjugate intermediate described herein, the drug, or an analog or a derivative thereof, includes an alkylthiol nucleophile.

It is to be understood that the above-described terms can be combined to generate chemically-relevant groups, such as alkoxyalkyl referring to methyloxymethyl, ethyloxyethyl, and the like, haloalkoxyalkyl referring to trifluoromethyloxyethyl, 1,2-difluoro-2-chloroeth-1-yloxypropyl, and the like, arylalkyl referring to benzyl, phenethyl, α-methylbenzyl, and the like, and others.

The term amino acid derivative as used herein refers generally to an optionally substituted aminoalkylcarboxylate, where the amino group and/or the carboxylate group are each optionally substituted, such as with alkyl, carboxylalkyl, alkylamino, and the like, or optionally protected. In addition, the optionally substituted intervening divalent alkyl fragment may include additional groups, such as protecting groups, and the like.

The term peptide as used herein refers generally to a series of amino acids and/or amino acid analogs and derivatives covalently linked one to the other by amide bonds.

The term "releasable linker" as used herein refers to a linker that includes at least one bond that can be broken under physiological conditions (e.g., a pH-labile, acid-labile, oxidatively-labile, or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

The cleavable bond or bonds may be present in the interior of a cleavable linker and/or at one or both ends of a cleavable linker. It is appreciated that the lability of the cleavable bond may be adjusted by including functional groups or fragments within the polyvalent linker L that are able to assist or facilitate such bond breakage, also termed anchimeric assistance. In addition, it is appreciated that additional functional groups or fragments may be included within the polyvalent linker L that are able to assist or facilitate additional fragmentation of the receptor binding ligand agent conjugates after bond breaking of the releasable linker. The lability of the cleavable bond can be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like.

It is understood that a cleavable bond can connect two adjacent atoms within the releasable linker and/or connect other linkers or V and/or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, additional spacer linker, another releasable linker, the agent A, or analog or derivative thereof, or the binding ligand B, or analog or derivative thereof, following breakage of the bond, the releasable linker is separated from the other moiety.

It is understood that each of the additional spacer and releasable linkers are bivalent. It should be further understood that the connectivity between each of the various additional spacer and releasable linkers themselves, and between the various additional spacer and releasable linkers and A and/or B, as defined herein, may occur at any atom found in the various additional spacer or releasable linkers.

In one aspect of the various receptor binding drug delivery conjugates described herein, the polyvalent linker comprises an additional spacer linker and a releasable linker taken together to form 3-thiosuccinimid-1-ylalkyloxymethyloxy, where the methyl is optionally substituted with alkyl or substituted aryl.

In another aspect, the polyvalent linker comprises an additional spacer linker and a releasable linker taken together to form 3-thiosuccinimid-1-ylalkylcarbonyl, where the carbonyl forms an acylaziridine with the agent A, or analog or derivative thereof.

In another aspect, the polyvalent linker comprises an additional spacer linker and a releasable linker taken together to form 1-alkoxycycloalkylenoxy.

In another aspect, the polyvalent linker comprises an additional spacer linker and a releasable linker taken together to form alkyleneaminocarbonyl(dicarboxylarylene)carboxylate.

In another aspect, the polyvalent linker comprises a releasable linker, an additional spacer linker, and a releasable linker taken together to form dithioalkylcarbonylhydrazide, where the hydrazide forms an hydrazone with the agent A, or analog or derivative thereof.

In another aspect, the polyvalent linker comprises an additional spacer linker and a releasable linker taken together to form 3-thiosuccinimid-1-ylalkylcarbonylhydrazide, where the hydrazide forms an hydrazone with the agent A, or analog or derivative thereof.

In another aspect, the polyvalent linker comprises an additional spacer linker and a releasable linker taken together to form 3-thioalkylsulfonylalkyl(disubstituted silyl)oxy, where the disubstituted silyl is substituted with alkyl or optionally substituted aryl.

In another aspect, the polyvalent linker comprises a plurality of additional spacer linkers selected from the group consisting of the naturally occurring amino acids and stereoisomers thereof.

In another aspect, the polyvalent linker comprises a releasable linker, an additional spacer linker, and a releasable linker taken together to form 3-dithioalkyloxycarbonyl, where the carbonyl forms a carbonate with the agent A, or analog or derivative thereof.

In another aspect, the polyvalent linker comprises a releasable linker, an additional spacer linker, and a releasable linker taken together to form 3-dithioarylalkyloxycarbonyl, where the carbonyl forms a carbonate with the agent A, or analog or derivative thereof, and the aryl is optionally substituted.

In another aspect, the polyvalent linker comprises an additional spacer linker and a releasable linker taken together to form 3-thiosuccinimid-1-ylalkyloxyalkyloxyalkylidene, where the alkylidene forms an hydrazone with the agent A, or analog or derivative thereof, each alkyl is independently selected, and the oxyalkyloxy is optionally substituted with alkyl or optionally substituted aryl.

In another aspect, the polyvalent linker comprises a releasable linker, an additional spacer linker, and a releasable linker taken together to form 3-dithioalkyloxycarbonylhydrazide.

In another aspect, the polyvalent linker comprises a releasable linker, an additional spacer linker, and a releasable linker taken together to form 3-dithioalkylamino, where the amino forms a vinylogous amide with the agent A, or analog or derivative thereof.

In another aspect, the polyvalent linker comprises a releasable linker, an additional spacer linker, and a releasable linker taken together to form 3-dithioalkylamino, where the amino forms a vinylogous amide with the agent A, or analog or derivative thereof, and the alkyl is ethyl.

In another aspect, the polyvalent linker comprises a releasable linker, an additional spacer linker, and a releasable linker taken together to form 3-dithioalkylaminocarbonyl, where the carbonyl forms a carbamate with the agent A, or analog or derivative thereof.

In another aspect, the polyvalent linker comprises a releasable linker, an additional spacer linker, and a releasable linker taken together to form 3-dithioalkylaminocarbonyl, where the carbonyl forms a carbamate with the agent A, or analog or derivative thereof, and the alkyl is ethyl.

In another aspect, the polyvalent linker comprises a releasable linker, an additional spacer linker, and a releasable linker taken together to form 3-dithioarylalkyloxycarbonyl, where the carbonyl forms a carbamate or a carbamoylaziridine with the agent A, or analog or derivative thereof.

In another embodiment, the polyvalent linker (L) includes a disulfide releasable linker. In another embodiment, the polyvalent linker (L) includes at least one releasable linker that is not a disulfide releasable linker.

In one aspect, the releasable and spacer linkers may be arranged in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formulae:

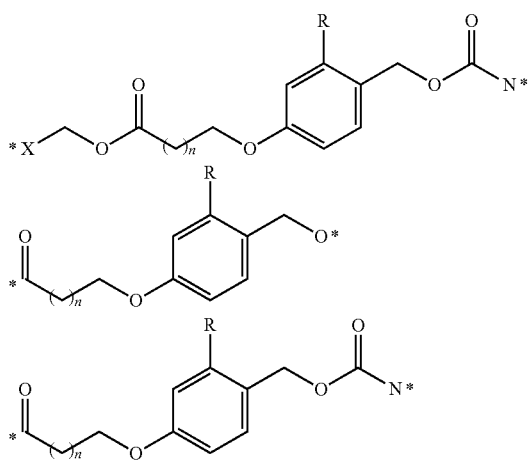

where X is an heteroatom, such as nitrogen, oxygen, or sulfur, or a carbonyl group; n is an integer selected from 0 to 4; illustratively 2; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the polyvalent linker, or alternatively for attachment of the drug, or analog or derivative thereof, or the vitamin, or analog or derivative thereof. In one embodiment, n is 2 and R is methoxy. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

Illustrative examples of intermediates useful in forming such linkers include:

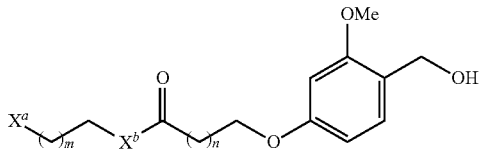

where $X^a$ is an electrophilic group such as maleimide, vinyl sulfone, activated carboxylic acid derivatives, and the like, $X^b$ is NH, O, or S; and m and n are each independently selected integers from 0-4. In one variation, m and n are each independently selected integers from 0-2. Such intermediates may be coupled to drugs, binding ligands, or other linkers vai nucleophilic attack onto electrophilic group $X^a$, and/or by forming ethers or carboxylic acid derivatives of the. In one embodiment, the benzylic hydroxyl group is converted into the corresponding activated benzyloxycarbonyl compound with phosgene or a phosgene equivalent. This embodiment may be coupled to drugs, binding ligands, or other linkers vai nucleophilic attack onto the activated carbonyl group.

Illustrative mechanisms for cleavage of the bivalant linkers described herein include the following 1,4 and 1,6 fragmentation mechanisms

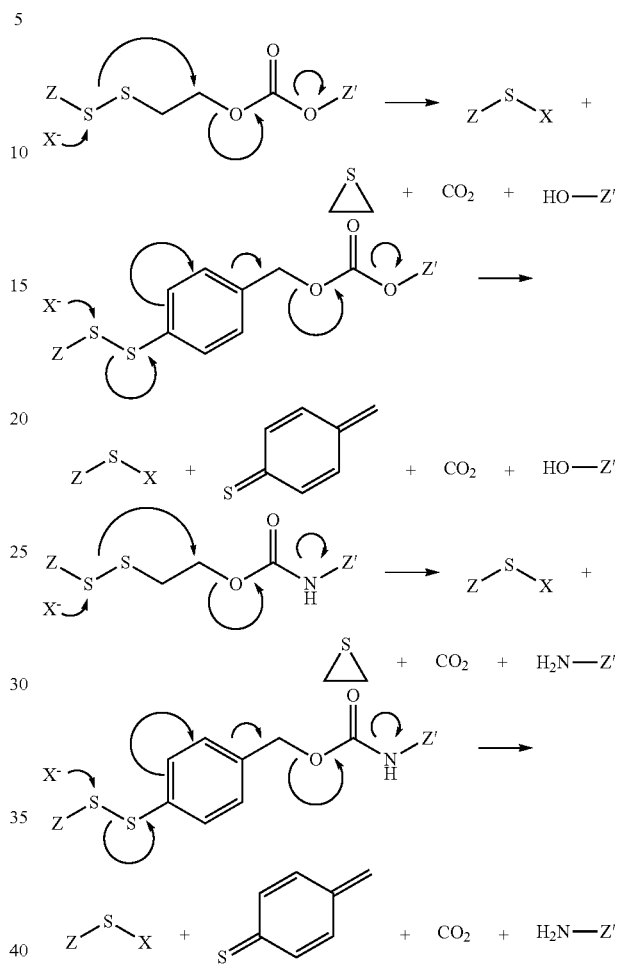

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

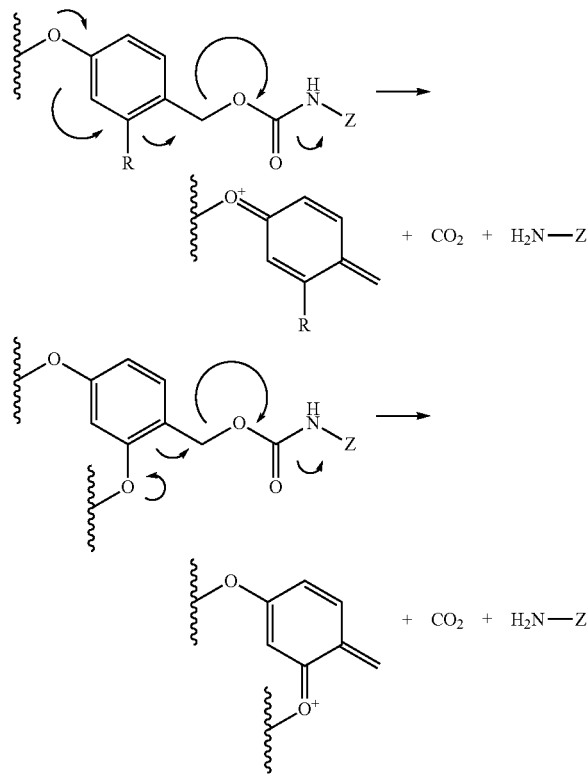

where Z is the vitamin, or analog or derivative thereof, or the drug, or analog or derivative thereof, or each is a vitamin or drug moiety in conjunction with other portions of the polyvalent linker, such as a drug or vitamin moiety including one or more spacer linkers and/or other releasable linkers. Without being bound by theory, in this embodiment, acid catalysis, such as in an endosome, may initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base.

Other illustrative linkers include compounds of the formulae:

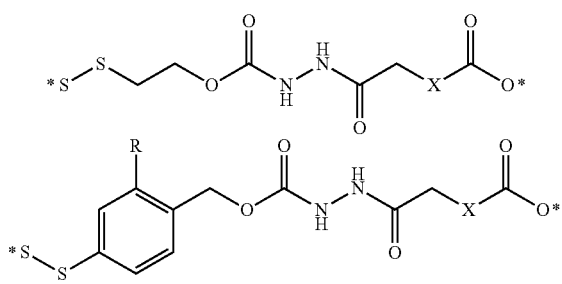

where X is NH, CH2, or O; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the polyvalent linker, or alternatively for attachment of the drug, or analog or derivative thereof, or the vitamin, or analog or derivative thereof.

Illustrative mechanisms for cleavage of such polyvalent linkers described herein include the following 1,4 and 1,6 fragmentation mechanisms followed by anchimerically assisted cleavage of the acylated Z' via cyclization by the hydrazide group:

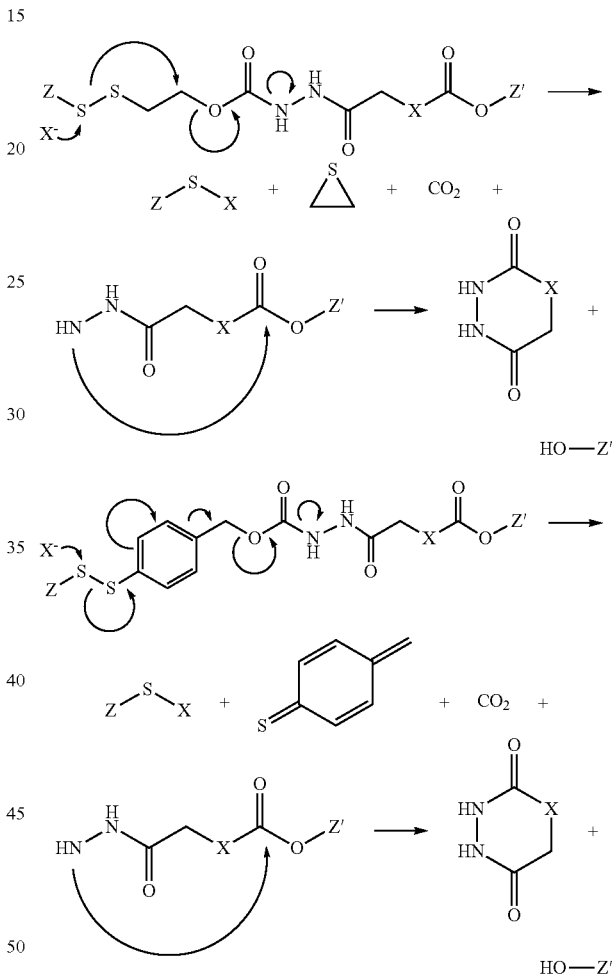

where X is an exogenous or endogenous nucleophile, glutathione, or bioreducing agent, and the like, and either of Z or Z' is the vitamin, or analog or derivative thereof, or the drug, or analog or derivative thereof, or a vitamin or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present. Without being bound by theory, in this embodiment, acid catalysis, such as in an endosome, may also initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base, as is similarly described herein.

In one embodiment, the polyvalent linkers described herein are compounds of the following formulae

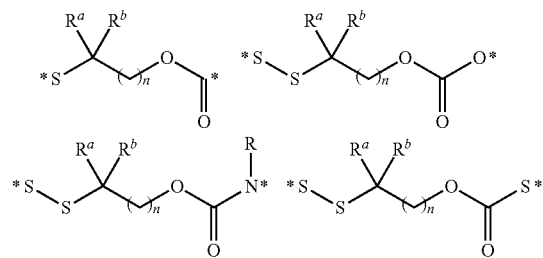

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

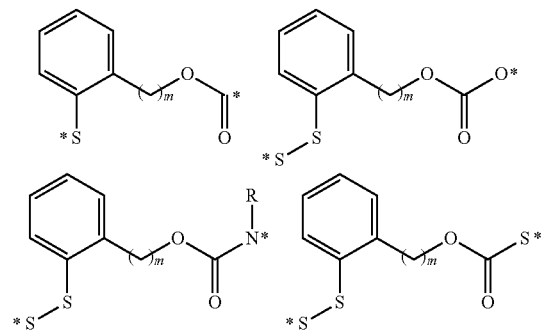

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

In another embodiment, the polyvalent linkers described herein include compounds of the following formulae

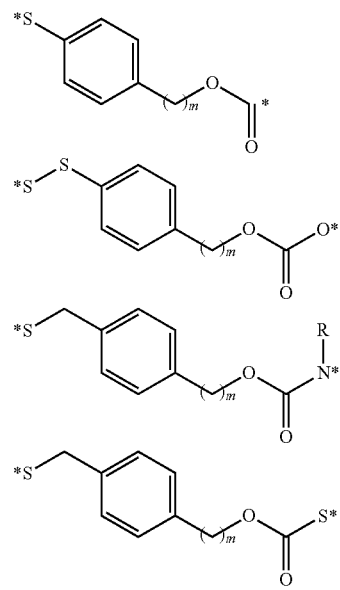

where m is an integer selected from 1 to about 4; R is an optionally substituted alkyl group, an optionally substituted acyl group, or a suitably selected nitrogen protecting group; and (*) indicates points of attachment for the drug, vitamin, imaging agent, diagnostic agent, other polyvalent linkers, or other parts of the conjugate.

Another illustrative mechanism involves an arrangement of the releasable and spacer linkers in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formula:

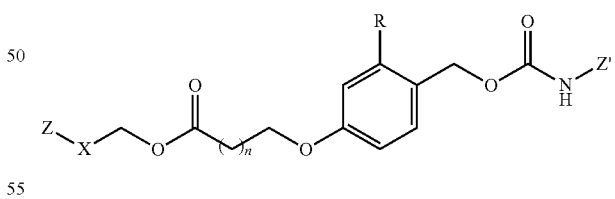

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and either of Z or Z' is the vitamin, or analog or derivative thereof, or the drug, or analog or derivative thereof, or a vitamin or drug moiety in conjunction with other portions of the polyvalent linker. It is appreciated that other substituents may be present on the aryl ring, the benzyl carbon, the carbamate nitrogen, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragementation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative polyvalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

In another embodiment, the polyvalent linker includes additional spacer linkers and releasable linkers connected to form a polyvalent 3-thiosuccinimid-1-ylalkyloxymethyloxy group, illustrated by the following formula

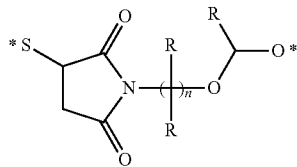

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes additional spacer linkers and releasable linkers connected to form a polyvalent 3-thiosuccinimid-1-ylalkylcarbonyl group, illustrated by the following formula

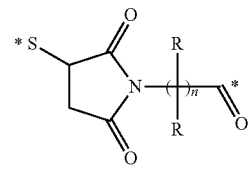

where n is an integer from 1 to 6, and the alkyl group is optionally substituted. The (*) symbols indicate points of attachment of the polyvalent linker fragment to other parts of the conjugates described herein. In another embodiment, the polyvalent linker includes spacer linkers and releasable linkers connected to form a polyvalent 3-thioalkylsulfonylalkyl(disubstituted silyl)oxy group, where the disubstituted silyl is substituted with alkyl and/or optionally substituted aryl groups.

In another embodiment, the polyvalent linker includes additional spacer linkers and releasable linkers connected to form a polyvalent dithioalkylcarbonylhydrazide group, or a polyvalent 3-thiosuccinimid-1-ylalkylcarbonylhydrazide, illustrated by the following formulae

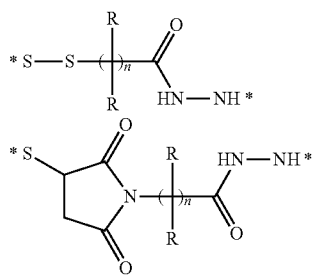

where n is an integer from 1 to 6, the alkyl group is optionally substituted, and the hydrazide forms an hydrazone with (B), (D), or another part of the polyvalent linker (L). The (*) symbols indicate points of attachment of the polyvalent linker fragment to other parts of the conjugates described herein.

In another embodiment, the polyvalent linker includes additional spacer linkers and releasable linkers connected to form a polyvalent 3-thiosuccinimid-1-ylalkyloxyalkyloxyalkylidene group, illustrated by the following formula

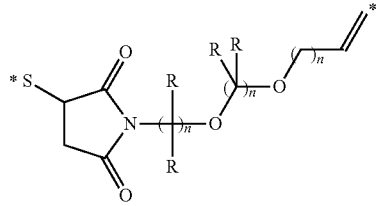

where each n is an independently selected integer from 1 to 6, each alkyl group independently selected and is optionally substituted, such as with alkyl or optionally substituted aryl, and where the alkylidene forms an hydrazone with (B), (D), or another part of the polyvalent linker (L). The (*) symbols indicate points of attachment of the polyvalent linker fragment to other parts of the conjugates described herein.

Additional illustrative additional spacer linkers include alkylene-amino-alkylenecarbonyl, alkylene-thio-carbonyl-alkylsuccinimid-3-yl, and the like, as further illustrated by the following formulae:

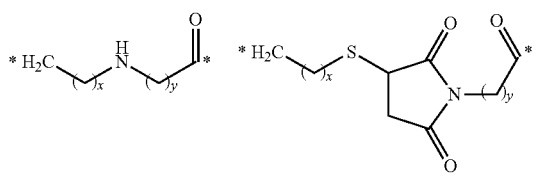 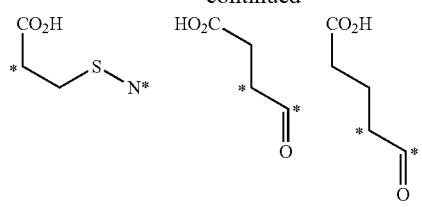

where the integers x and y are 1, 2, 3, 4, or 5:

In another illustrative embodiment, the linker includes one or more amino acids. In one variation, the linker includes a single amino acid. In another variation, the linker includes a peptide having from 2 to about 50, 2 to about 30, or 2 to about 20 amino acids. In another variation, the linker includes a peptide having from about 4 to about 8 amino acids. Such amino acids are illustratively selected from the naturally occurring amino acids, or stereoisomers thereof. The amino acid may also be any other amino acid, such as any amino acid having the general formula:

—N(R)—(CR'R'')$_q$—C(O)— where R is hydrogen, alkyl, acyl, or a suitable nitrogen protecting group, R' and R'' are hydrogen or a substituent, each of which is independently selected in each occurrence, and q is an integer such as 1, 2, 3, 4, or 5. Illustratively, R' and/or R'' independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In one variation, the releasable linker includes at least 2 amino acids selected from asparagine, aspartic acid, cysteine, glutamic acid, lysine, glutamine, arginine, serine, ornitine, and threonine. In another variation, the releasable linker includes between 2 and about 5 amino acids selected from asparagine, aspartic acid, cysteine, glutamic acid, lysine, glutamine, arginine, serine, omitine, and threonine. In another variation, the releasable linker includes a tripeptide, tetrapeptide, pentapeptide, or hexapeptide consisting of amino acids selected from aspartic acid, cysteine, glutamic acid, lysine, arginine, and ornitine, and combinations thereof.

In another illustrative aspect of the vitamin receptor binding drug delivery conjugate intermediate described herein, the drug, or an analog or a derivative thereof, includes an alkylthiol nucleophile.

Additional linkers are described in the following Tables, where the (*) atom is the point of attachment of additional spacer or releaseable linkers, the drug, and/or the binding ligand.

The following illustrative spacer linkers are described.

-continued

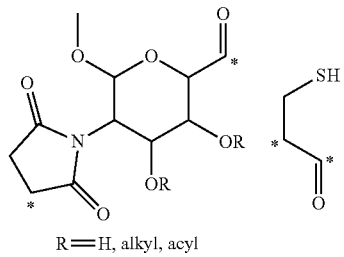

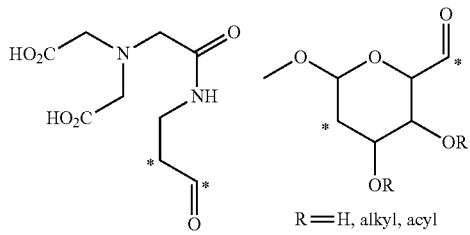

R=H, alkyl, acyl

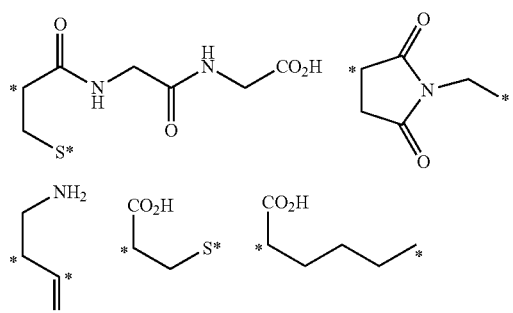

R=H, alkyl, acyl

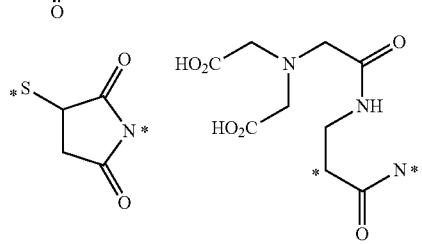

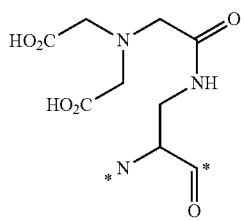

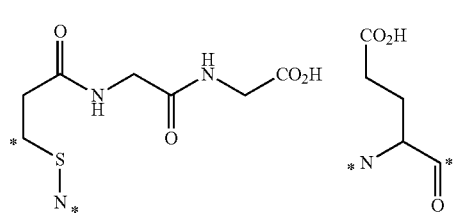

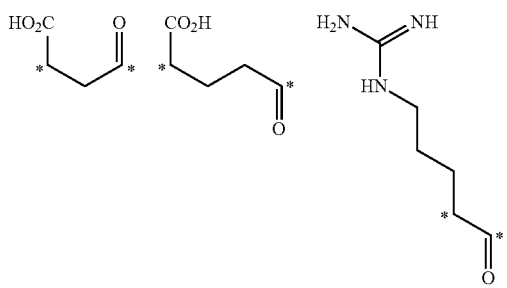

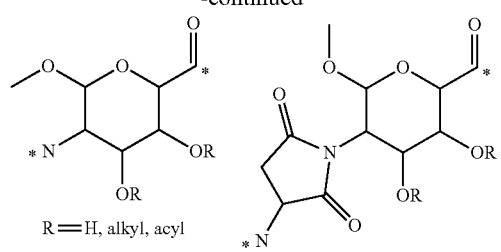
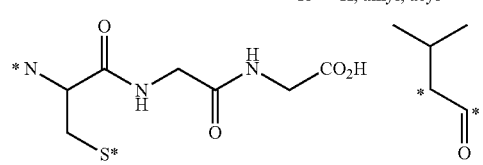
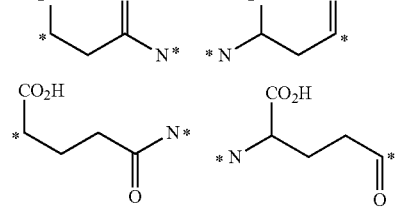
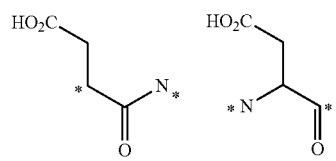
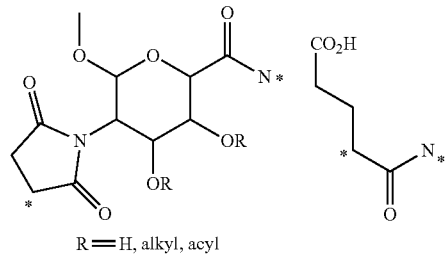
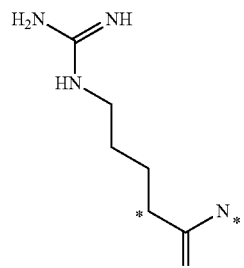
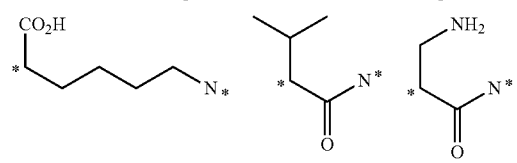
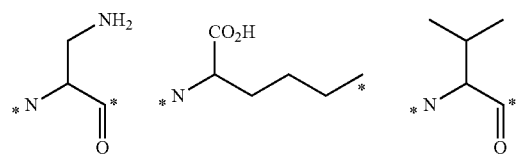
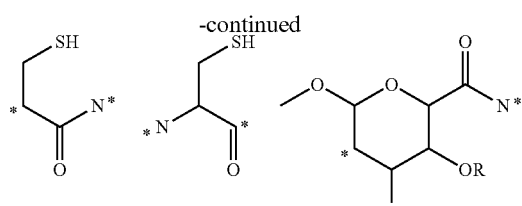
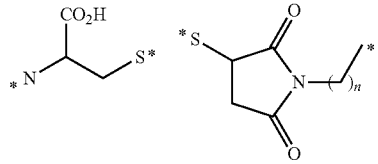
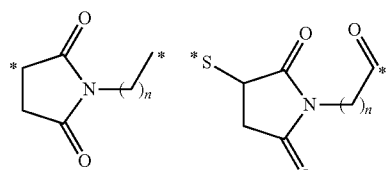
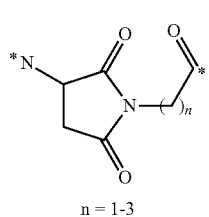
The following illustrative releasable linkers are described.
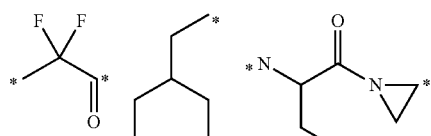
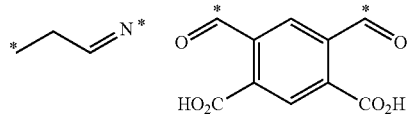
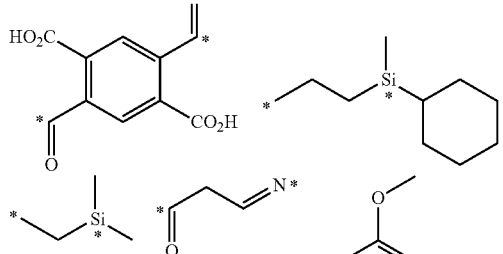
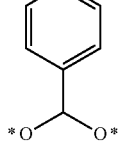

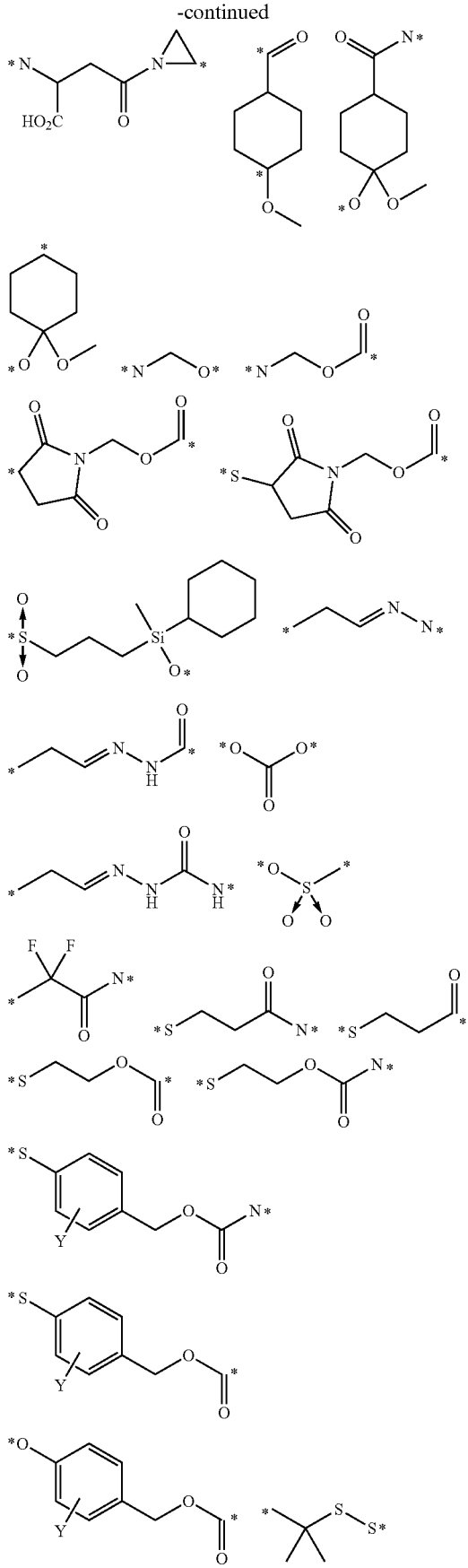

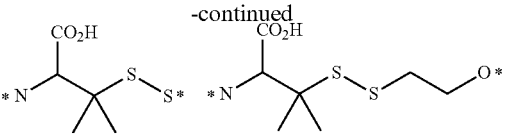

It is appreciated that such hydrophilic linkers may alter the stability, metabolism and tissue distribution of the conjugates, especially compared to other conjugate forms such as the peptidic based forms described in U.S. patent application Ser. No. 10/765,336. For example, it is understood that in certain situations, carbohydrate-protein interactions are weaker than peptide-protein interactions. Thus, it is appreciated that in various embodiments described herein, the conjugates may lead to lower binding of serum proteins. These and other physicochemical differences between the conjugates described herein and others already reported may include enhanced targeting to target cells and improved, i.e. more selective or differentially selective biodistribution profiles. The increased cyctotoxicity may be a natural consequence of the decreased serum protein binding or the better or differential biodistribution (i.e. less drug is wasted in non-specific compartments). This is especially true for the use of hydrophilic but neutral spacers. Without being bound by theory it is also suggested that the hydrophilic spacer linkers described herein may decrease toxicity that might be due at least in part to non-specific binding interactions.

In an alternate embodiment, drug is linked to a hydrophilic spacer linker, directly or indirectly, to accomplish the goal of decreasing liver clearance. It has been found herein that the attachment of hydrophilic groups, either releasable or not, and more specifically hydrophilic neutral groups, increases renal-specific delivery.

It has been observed that liver clearance of folate-drug conjugates possessing disulfide linkers and peptidic spacers retain residual and sometimes substantial unfavorable toxicity profiles. Including the hydrophilic spacers described herein also introduced vectors for kidney-specific delivery. It is therefore appreciated that including such linkers in targeted drug conjugates may decrease overall liver uptake and consequentially decrease overall toxicity. Without being bound by theory, it is appreciated that toxicity at MTD, such as with vinca alkaloid conjugates, may be caused by non-specific liver clearance, leading to metabolism, release of free drug, such as DAVLBH, into bile and then the intestine. The local toxicity as well as systemic toxicity (due to re-absorption) might then occur. By including hydrophilic linkers in the targeted and non-targeted conjugates described herein, it is believed that clearance through the kidney may preferentially occur, thus decreasing and/or avoiding concomitant liver metabolism based toxicity. Accordingly, measuring total bile clearance of the drug component, such as DAVLBH, from a series of drug-folate conjugates, may be used to predict which agent would be the least toxic.

As described above, the conjugates described herein may be used to deliver target agents A to cells in a selective or specific manner. In one aspect of such delivery, unwanted clearance mechanisms may also be avoided. It has been discovered that the hydrophilic spacer linkers described herein when used to form conjugates of receptor binding ligands B and agents A, can decrease the amount of clearance by the liver. It has further been discovered that these hydrophilic spacer linkers tend to favor clearance along renal pathways, such as the kidney. It has further been discovered that the conjugates described herein exhibit lower toxicity than the parent agents A by themselves when administered in the same way. Without being bound by theory, it is suggested that the lower toxicity arises from the observed decrease in liver clearance mechanism in favor of renal clearance mechanisms.

In another embodiment, compounds are described herein that have reduced uptake by the liver and are less likely to be cleared by the liver. In one aspect, such compounds are preferentially cleared by the renal processes as compared to hepatic processes. Accordingly, in another embodiment, non-targeted compounds of the following formula are described herein:

L-A where L is a hydrophilic spacer and A is diagnostic, therapeutic, or imaging agent. It is appreciated that such non-targeted compounds, though not targeted using a receptor binding ligand B, may nonetheless exhibit decreased toxicity than the parent agent A when delivered in the same manner. The non-targeted compounds, like the targeted conjugates described above include the hydrophilic spacer L. Therefore, the agent that does not reach the cell desirably treated will be cleared by ordinary metabolic and biological routes. However, it is appreciated that the presence of the hydrophilic spacer L will direct the clearance through renal pathways rather than hepatic pathways.

In another embodiment, multi-drug conjugates are described herein. Several illustrative configurations of such multi-drug conjugates are contemplated herein, and include the compounds and compositions described in PCT international publication No. WO 2007/022494, the disclosure of which is incorporated herein by reference. Illustratively, the polyvalent linkers may connect the receptor binding ligand B to the two or more agents A in a variety of structural configurations, including but not limited to the following illustrative general formulae:

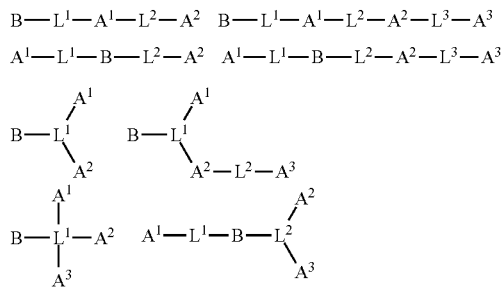

where B is the receptor binding ligand, each of ($L^1$), ($L^2$), and ($L^3$) is a polyvalent linker as described herein comprising a hydrophilic spacer linker, and optionally including one or more releasable linkers and/or additional spacer linkers, and each of ($A^1$), ($A^2$), and ($A^3$) is an agent A, or an analog or derivative thereof. Other variations, including additional agents A, or analogs or derivatives thereof, additional linkers, and additional configurations of the arrangement of each of (B), (L), and (A), are also contemplated herein.

In one variation, more than one receptor binding ligand B is included in the delivery conjugates described herein, including but not limited to the following illustrative general formulae:

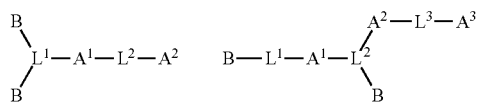

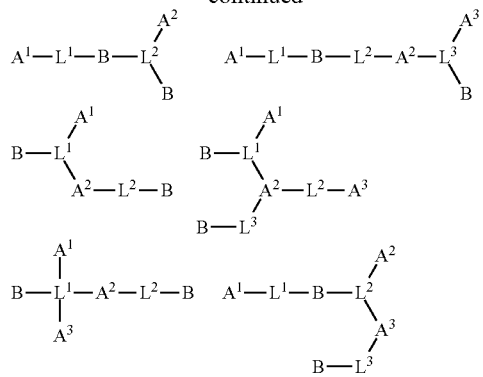

where each B is a receptor binding ligand, each of (L'), ($L^2$), and ($L^3$) is a polyvalent linker as described herein comprising a hydrophilic spacer linker, and optionally including one or more releasable linkers and/or additional spacer linkers, and each of ($A^1$), ($A^2$), and ($A^3$) is an agent A, or an analog or derivative thereof. Other variations, including additional agents A, or analogs or derivatives thereof, additional linkers, and additional configurations of the arrangement of each of (B), (L), and (A), are also contemplated herein. In one variation, the receptor binding ligands B are ligands for the same receptor, and in another variation, the receptor binding ligands B are ligands for different receptors.

In another illustrative embodiment, the drugs are selected based on activity against one or more populations of pathogenic cells with a particular mechanism of action. Illustrative mechanisms of action include alkylating agents, microtubule inhibitors, including those that stabilize and/or destabilize microtubule formation, including beta-tubulin agents, cyclin dependent kinase (CDK) inhibitors, topoisomerase inhibitors, protein synthesis inhibitors, protein kinase inhibitors, including Ras, Raf, PKC, PI3K, and like inhibitors, transcription inhibitor, antifolates, heat shock protein blockers, and the like.

Illustrative alkylating agents include, but are not limited to, mitomycins CBI, and the like. Illustrative cyclin dependent kinase (CDK) inhibitors include, but are not limited to, CYC202, seliciclib, R-roscovitine, AGM-1470, and the like. Illustrative topoisomerase inhibitors include, but are not limited to, doxorubicin, other anthracyclines, and the like. Illustrative protein synthesis inhibitors include, but are not limited to, bruceantin, and the like. Illustrative protein kinase inhibitors, including Ras, Raf, PKC, PI3K, and like inhibitors, include but are not limited to L-779,450, R115777, and the like. Illustrative transcription inhibitors include, but are not limited to, α-amanatin, actinomycin, and the like. Illustrative antifolates include, but are not limited to, methotrexate, and the like. Illustrative heat shock protein blockers include, but are not limited to, geldanamycin, and the like.

Illustrative microtubule inhibitors, including those that stabilize and/or destabilize microtubule formation, including β-tubulin agents, microtubule poisons, and the like. Illustrative microtubule poisons that bind to selected receptors include, but are not limited to, inhibitors biding to the *vinca* binding site such as arenastatin, dolastatin, halichondrin B, maytansine, phomopsin A, rhizoxin, ustiloxin, vinblastine, vincristine, and the like, stabilizers binding to the taxol binding site such as discodermalide, epothilone, taxol, paclitaxol, and the like, inhibitors binding to the colchicine binding site such as, colchicine, combretastatin, curacin A, podophyllotoxin, steganacine, and the like, and others binding to undefined sites such as cryptophycin, tubulysins, and the like.

In one embodiment, the tubulsyin is a naturally occurring tubulysin. In another embodiment, the tubulsyin is a synthetic or semi-synthetic tubulysin. Additional tubulysin that may be included in the conjugates described herein are described in PCT international application serial No. PCT/US2008/056824, the disclosure of which is incorporated herein by reference.

In one embodiment of the drug delivery conjugates described herein, at least one of the drugs is a microtubule inhibitor, or an analog or derivative thereof. In another embodiment, at least one of the drugs is a DNA alkylation agent. In another embodiment, at least one of the drugs is a DNA alkylation agent, and at least one other of the drugs is a microtubule inhibitor.

In another embodiment of the drug delivery conjugates described herein, at least one of the drugs is a P-glycoprotein (PGP) inhibitor. In another embodiment, at least one of the drugs included on the drug delivery conjugates described herein is a PGP inhibitor, and at least one other of the drugs included on the drug delivery conjugates is a PGP substrate. Illustratively in this latter embodiment, the PGP substrate is a DNA alkylating agent. Referring to this embodiment, it is appreciated that pairing a PGP inhibitor with a PGP substrate, such as a DNA alkylating agent including, but not limited to, any of the mitomycins like mitomycin C, mitomycin A, and the like may improve the overall performance of the drug that is otherwise a PGP substrate. In the releasable conjugates described herein, the PGP inhibitor drug and the PGP substrate drug are both released in the cell after endocytosis. In that manner, the PGP inhibitor drug may improve the overall efficacy and/or potency of the PGP substrate drug. In addition, the PGP inhibitor may reduces PGP expression, which in turn will decrease efflux of one or more of the drugs included on the multidrug conjugates described herein from the pathogenic cell. It is appreciated that the mitomycins, or analogs or derivatives thereof, such as mitomycin C may operate as a PGP inhibitor, or down-regulator of PGP. It is further appreciated that the *vinca* alkaloid, or analog or derivative thereof, such as vinblastine analogs and derivatives, may be a PGP substrate that is protected from efflux from the pathogenic cell by the PGP inhibitor or down-regulator.

In another embodiment of the drug delivery conjugates described herein, at least one of the drugs is a *vinca* alkaloid, or an analog or derivative thereof. *Vinca* alklaloids described herein include all members of the *vinca* indole-dihydroindole family of alkaloids, such as but not limited to vindesine, vinblastine, vincristine, catharanthine, vindoline, leurosine, vinorelbine, imidocarb, sibutramine, toltrazuril, vinblastinoic acid, and the like, and analogs and derivatives thereof.

In another embodiment, methods for treating diseases caused by or evidenced by pathogenic cell populations are described herein. The binding ligand (B) drug delivery conjugates can be used to treat disease states characterized by the presence of a pathogenic cell population in the host wherein the members of the pathogenic cell population have an accessible binding site for the binding ligand (B), or analog or derivative thereof, wherein the binding site is uniquely expressed, overexpressed, or preferentially expressed by the pathogenic cells. The selective elimination of the pathogenic cells is mediated by the binding of the ligand moiety of the binding ligand (B) drug delivery conjugate to a ligand receptor, transporter, or other surface-presented protein that specifically binds the binding ligand (B), or analog or derivative thereof, and which is uniquely expressed, overexpressed, or preferentially expressed by the pathogenic cells. A surface-presented protein uniquely expressed, overexpressed, or preferentially expressed by the pathogenic cells is a receptor not present or present at lower concentrations on non-pathogenic cells providing a means for selective elimination of the pathogenic cells.

For example, surface-expressed vitamin receptors, such as the high-affinity folate receptor, are overexpressed on cancer cells. Epithelial cancers of the ovary, mammary gland, colon, lung, nose, throat, and brain have all been reported to express elevated levels of the folate receptor. In fact, greater than 90% of all human ovarian tumors are known to express large amounts of this receptor. Accordingly, the binding ligand (B) drug delivery conjugates described herein can be used to treat a variety of tumor cell types, as well as other types of pathogenic cells, such as infectious agents, that preferentially express ligand receptors, such as vitamin receptors, and, thus, have surface accessible binding sites for ligands, such as vitamins, or vitamin analogs or derivatives. In one aspect, methods are described herein for targeting binding ligand-linker-drug conjugates to maximize targeting of the pathogenic cells for elimination.

The invention further contemplates the use of combinations of binding ligand-linker-drug conjugates to maximize targeting of the pathogenic cells for elimination.

The binding ligand (B) drug delivery conjugates described herein can be used for both human clinical medicine and veterinary applications. Thus, the host animal harboring the population of pathogenic cells and treated with the binding ligand (e.g., a vitamin) drug delivery conjugates can be human or, in the case of veterinary applications, can be a laboratory, agricultural, domestic, or wild animal. The methods described herein can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The methods are applicable to populations of pathogenic cells that cause a variety of pathologies in these host animals. The term pathogenic cells refers to for example cancer cells, infectious agents such as bacteria and viruses, bacteria- or virus-infected cells, activated macrophages capable of causing a disease state, and any other type of pathogenic cells that uniquely express, preferentially express, or overexpress binding ligand receptors, such as vitamin receptors or receptors that bind analogs or derivatives of vitamins. Pathogenic cells can also include any cells causing a disease state for which treatment with the binding ligand drug delivery conjugates described herein results in reduction of the symptoms of the disease. For example, the pathogenic cells can be host cells that are pathogenic under some circumstances such as cells of the immune system that are responsible for graft versus host disease, but not pathogenic under other circumstances.

Thus, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The methods can be utilized to treat such cancers as carcinomas, sarcomas, lymphomas, Hodgkin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of conjugate administration is a therapeutic response measured by reduction or elimination of tumor mass or of inhibition of tumor cell proliferation. In the case of a tumor, the elimination can be an elimination of cells of the primary tumor or of cells that have metastasized or are in the process of dissociating from the primary tumor. A prophylactic treatment with the binding ligand (B) drug delivery conjugate (e.g., a vitamin used as the binding ligand) to prevent return of a tumor after its removal by any therapeutic approach including surgical removal of the tumor, radiation therapy, chemotherapy, or biological therapy is also described. The prophylactic treatment can be an initial treatment with the binding ligand (B) drug delivery conjugate, such as treatment in a multiple dose daily regimen, and/or can be an additional treatment or series of treatments after an interval of days or months following the initial treatment(s). Accordingly, elimination of any of the pathogenic cell populations treated using the described methods includes reduction in the number of pathogenic cells, inhibition of proliferation of pathogenic cells, a prophylactic treatment that prevents return of pathogenic cells, or a treatment of pathogenic cells that results in reduction of the symptoms of disease.

In cases where cancer cells are being eliminated, the methods can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

The methods are also applicable to populations of pathogenic cells that cause a variety of infectious diseases. For example, the methods are applicable to such populations of pathogenic cells as bacteria, fungi, including yeasts, viruses, virus-infected cells, *mycoplasma*, and parasites. Infectious organisms that can be treated with the binding ligand (B) drug delivery conjugates described herein are any art-recognized infectious organisms that cause pathogenesis in an animal, including such organisms as bacteria that are gram-negative or gram-positive cocci or bacilli. For example, *Proteus* species, *Klebsiella* species, *Providencia* species, *Yersinia* species, *Erwinia* species, *Enterobacter* species, *Salmonella* species, *Serratia* species, Aerobacter species, *Escherichia* species, *Pseudomonas* species, *Shigella* species, *Vibrio* species, *Aeromonas* species, *Campylobacter* species, *Streptococcus* species, *Staphylococcus* species, *Lactobacillus* species, *Micrococcus* species, *Moraxella* species, *Bacillus* species, *Clostridium* species, *Corynebacterium* species, Eberthella species, *Micrococcus* species, *Mycobacterium* species, *Neisseria* species, *Haemophilus* species, *Bacteroides* species, *Listeria* species, Erysipelothrix species, *Acinetobacter* species, *Brucella* species, *Pasteurella* species, *Vibrio* species, *Flavobacterium* species, *Fusobacterium* species, *Streptobacillus* species, *Calymmatobacterium* species, *Legionella* species, *Treponema* species, *Borrelia* species, *Leptospira* species, *Actinomyces* species, *Nocardia* species, *Rickettsia* species, and any other bacterial species that causes disease in a host can be treated with the binding ligand drug delivery conjugates described herein.

Of particular interest are bacteria that are resistant to antibiotics such as antibiotic-resistant *Streptococcus* species and *Staphylococcus* species, or bacteria that are susceptible to antibiotics, but cause recurrent infections treated with antibiotics so that resistant organisms eventually develop. Bacteria that are susceptible to antibiotics, but cause recurrent infections treated with antibiotics so that resistant organisms eventually develop, can be treated with the binding ligand (B) drug delivery conjugates described herein in the absence of antibiotics, or in combination with lower doses of antibiotics than would normally be administered to a patient, to avoid the development of these antibiotic-resistant bacterial strains.

Viruses, such as DNA and RNA viruses, can also be treated with the described methods. Such viruses include, but are not limited to, DNA viruses such as papilloma viruses, parvoviruses, adenoviruses, herpesviruses and vaccinia viruses, and RNA viruses, such as arenaviruses, coronaviruses, rhinoviruses, respiratory syncytial viruses, influenza viruses, picornaviruses, paramyxoviruses, reoviruses, retroviruses, lentiviruses, and rhabdoviruses.

The methods are also applicable to any fungi, including yeasts, *mycoplasma* species, parasites, or other infectious organisms that cause disease in animals. Examples of fungi that can be treated with the methods and compositions include fungi that grow as molds or are yeastlike, including, for example, fungi that cause diseases such as ringworm, histoplasmosis, blastomycosis, aspergillosis, cryptococcosis, sporotrichosis, coccidioidomycosis, paracoccidioidomycosis, mucormycosis, chromoblastomycosis, dermatophytosis, protothecosis, fusariosis, *pityriasis*, mycetoma, paracoccidioidomycosis, phaeohyphomycosis, pseudallescheriasis, sporotrichosis, trichosporosis, *pneumocystis* infection, and candidiasis.

The methods can also be utilized to treat parasitic infections including, but not limited to, infections caused by tapeworms, such as *Taenia, Hymenolepsis, Diphyllobothrium*, and *Echinococcus* species, flukes, such as *Fasciolopsis, Heterophyes, Metagonimus, Clonorchis, Fasciola, Paragonimus*, and Schitosoma species, roundworms, such as *Enterobius, Trichuris, Ascaris, Ancylostoma, Necator, Strongyloides, Trichinella, Wuchereria, Brugia, Loa Onchocerca*, and *Dracunculus* species, ameba, such as *Naegleria* and *Acanthamoeba* species, and protozoans, such as *Plasmodium, Trypanosoma, Leishmania, Toxoplasma, Entamoeba, Giardia, Isospora, Cryptosporidium*, and Enterocytozoon species.

The pathogenic cells to which the binding ligand drug delivery conjugates described herein are directed can also be cells harboring endogenous pathogens, such as virus-, mycoplasma-, parasite-, or bacteria-infected cells, if these cells preferentially express ligand receptors, such as vitamin receptors.

In one embodiment, the binding ligand drug delivery conjugates can be internalized into the targeted pathogenic cells upon binding of the binding ligand moiety to a receptor, transporter, or other surface-presented protein that specifically binds the ligand and which is preferentially expressed on the pathogenic cells. Such internalization can occur, for example, through receptor-mediated endocytosis. If the binding ligand (B) drug delivery conjugate contains a releasable linker, the binding ligand moiety and the drug can dissociate intracellularly and the drug can act on its intracellular target.

In an alternate embodiment, the binding ligand moiety of the drug delivery conjugate can bind to the pathogenic cell placing the drug in close association with the surface of the pathogenic cell. The drug can then be released by cleavage of the releasable linker. For example, the drug can be released by a protein disulfide isomerase if the releasable linker is a disulfide group. The drug can then be taken up by the pathogenic cell to which the binding ligand (B) drug delivery conjugate is bound, or the drug can be taken up by another pathogenic cell in close proximity thereto. Alternatively, the drug could be released by a protein disulfide isomerase inside the cell where the releasable linker is a disulfide group. The drug may also be released by a hydrolytic mechanism, such as acid-catalyzed hydrolysis, as described above for certain beta elimination mechanisms, or by an anchimerically assisted cleavage through an oxonium ion or lactonium ion producing mechanism. The selection of the releasable linker or linkers will dictate the mechanism by which the drug is released from the conjugate. It is appreciated that such a selection can be pre-defined by the conditions wherein the drug conjugate will be used. Alternatively, the drug delivery conjugates can be internalized into the targeted cells upon binding, and the binding ligand and the drug can remain associated intracellularly with the drug exhibiting its effects without dissociation from the vitamin moiety.

In still another embodiment where the binding ligand is a vitamin, the vitamin-drug delivery conjugate can act through a mechanism independent of cellular vitamin receptors. For example, the drug delivery conjugates can bind to soluble vitamin receptors present in the serum or to serum proteins, such as albumin, resulting in prolonged circulation of the conjugates relative to the unconjugated drug, and in increased activity of the conjugates towards the pathogenic cell population relative to the unconjugated drug.

In another embodiment, where the linker does not comprise a releasable linker, the vitamin moiety of the drug delivery conjugate can bind to the pathogenic cell placing the drug on the surface of the pathogenic cell to target the pathogenic cell for attack by other molecules capable of binding to the drug. Alternatively, in this embodiment, the drug delivery conjugates can be internalized into the targeted cells upon binding, and the vitamin moiety and the drug can remain associated intracellularly with the drug exhibiting its effects without dissociation from the vitamin moiety.

In another embodiment of this invention, a cell receptor binding delivery conjugate of the general formula B-L-A is provided, where L is as defined herein, and A is a drug such as an immunogen. The immunogen can be a hapten, for example, fluorescein, dinitrophenyl, and the like. In this embodiment, the vitamin receptor binding drug delivery conjugate binds to the surface of the pathogenic cells and "labels" the cells with the immunogen, thereby triggering an immune response directed at the labeled pathogenic cell population. Antibodies administered to the host in a passive immunization or antibodies existing in the host system from a preexisting innate or acquired immunity bind to the immunogen and trigger endogenous immune responses. Antibody binding to the cell-bound vitamin-immunogen conjugate results in complement-mediated cytotoxicity, antibody-dependent cell-mediated cytotoxicity, antibody opsonization and phagocytosis, antibody-induced receptor clustering signaling cell death or quiescence, or any other humoral or cellular immune response stimulated by antibody binding to cell-bound ligand-immunogen conjugates. In cases where an immunogen can be directly recognized by immune cells without prior antibody opsonization, direct killing of the pathogenic cells can occur. This embodiment is described in more detail in U.S. patent application Ser. No. 09/822,379, incorporated herein by reference. It is appreciated that in certain variations of this embodiment where the drug is an immunogen, the polyvalent linker may also include releasable linkers, as described above, such as a vitamin receptor binding drug delivery conjugate of the general formula B-L-A where L is a linker that comprises one or more hydrophilic spacer linkers and a releaseable linker.

The binding ligand (B) drug delivery conjugates described herein comprise a binding ligand, a polyvalent linker (L), a drug, and, optionally, heteroatom linkers to link the binding ligand and the drug to the polyvalent linker (L). The polyvalent linker (L) can comprise a spacer linker, a releasable (i.e., cleavable) linker, and an heteroatom linker, or combinations thereof.

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

Further, the drug can be any drug known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell. Drugs suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cis-platin and other platinum compounds, tamoxiphen, taxol, paclitaxel, paclitaxel derivatives, Taxotere®, cyclophosphamide, daunomycin, daunorubicin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, analogs and derivative thereof such as deacetylvinblastine monohydrazide, and other *vinca* alkaloids, including those described in PCT international publication No. WO 2007/022493, the disclosure of which is incorporated herein by reference, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, maytansines, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

In another embodiment, the agent (A) is a drug selected from a *vinca* alkaloid, such as DAVLBH, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, everolimus, ispinesib, budesonide, dasatinib, an epothilone, a maytansine, and a tyrosine kinase inhibitor, including analogs and derivatives of the foregoing. In another embodiment, the conjugate includes at least two agents (A) selected from a *vinca* alkaloid, such as DAVLBH, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, everolimus, ispinesib, budesonide, dasatinib, an epothilone, a maytansine, and a tyrosine kinase inhibitor, including analogs and derivatives of the foregoing. In one variation, the agents (A) are the same. In another variation, the agents (A) are different.

In one embodiment, the drugs for use in the methods described herein remain stable in serum for at least 4 hours. In another embodiment the drugs have an $IC_{50}$ in the nanomolar range, and, in another embodiment, the drugs are water soluble. If the drug is not water soluble, the polyvalent linker (L) can be derivatized to enhance water solubility. The term "drug" also means any of the drug analogs or derivatives described hereinabove. It should be appreciated that in accordance with this invention, a drug analog or derivative can mean a drug that incorporates an heteroatom through which the drug analog or derivative is covalently bound to the polyvalent linker (L).

The binding ligand drug delivery conjugates can comprise a binding ligand (B), a bivalent linker (L), a drug, and, optionally, heteroatom linkers to link the binding ligand (B) receptor binding moiety and the drug to the bivalent linker (L). In one illustrative embodiment, it should be appreciated that a vitamin analog or derivative can mean a vitamin that incorporates an heteroatom through which the vitamin analog or derivative is covalently bound to the bivalent linker (L). Thus, in this illustrative embodiment, the vitamin can be covalently bound to the bivalent linker (L) through an heteroatom linker, or a vitamin analog or derivative (i.e., incorporating an heteroatom) can be directly bound to the bivalent linker (L). In similar illustrative embodiments, a drug analog or derivative is a drug, and a drug analog or derivative can mean a drug that incorporates an heteroatom through which the drug analog or derivative is covalently bound to the bivalent linker (L). Thus, in these illustrative aspects, the drug can be covalently bound to the bivalent linker (L) through an heteroatom linker, or a drug analog or derivative (i.e., incorporating an heteroatom) can be directly bound to the bivalent linker (L). The bivalent linker (L) can comprise a spacer linker, a releasable (i.e., cleavable) linker, and an heteroatom linker to link the spacer linker to the releasable linker in conjugates containing both of these types of linkers.

Generally, any manner of forming a conjugate between the bivalent linker (L) and the binding ligand (B), or analog or derivative thereof, between the bivalent linker (L) and the drug, or analog or derivative thereof, including any intervening heteroatom linkers, can be utilized. Also, any art-recognized method of forming a conjugate between the spacer linker, the releasable linker, and the heteroatom linker to form the bivalent linker (L) can be used. The conjugate can be formed by direct conjugation of any of these molecules, for example, through complexation, or through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

In another embodiment, the bivalent linker (L) includes a chain of atoms selected from C, N, O, S, Si, and P that covalently connects the binding ligand (B), the hydrophilic linker, and/or the agent (A). The linker may have a wide variety of lengths, such as in the range from about 2 to about 100 atoms. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, such that for example, alkanes, alkenes, alkynes, imines, and the like may be radicals that are included in the linker. In addition, it is to be understood that the atoms forming the linker may also be cyclized upon each other to form divalent cyclic structures that form the linker, including cyclo alkanes, cyclic ethers, cyclic amines, arylenes, heteroarylenes, and the like in the linker.

In another embodiment, pharmaceutical compositions comprising an amount of a binding ligand (B) drug delivery conjugate effective to eliminate a population of pathogenic cells in a host animal when administered in one or more doses are described. The binding ligand drug delivery conjugate is preferably administered to the host animal parenterally, e.g., intradermally, subcutaneously, intramuscularly, intraperitoneally, intravenously, or intrathecally. Alternatively, the binding ligand drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

In one illustrative aspect, at least one additional composition comprising a therapeutic factor can be administered to the host in combination or as an adjuvant to the above-detailed methodology, to enhance the binding ligand drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered binding ligand drug delivery conjugate.

In one illustrative aspect, therapeutically effective combinations of these factors can be used. In one embodiment, for example, therapeutically effective amounts of the therapeutic factor, for example, in amounts ranging from about 0.1 MIU/m²/dose/day to about 15 MIU/m²/dose/day in a multiple dose daily regimen, or for example, in amounts ranging from about 0.1 MIU/m²/dose/day to about 7.5 MIU/m²/dose/day in a multiple dose daily regimen, can be used along with the binding ligand drug delivery conjugates to eliminate, reduce, or neutralize pathogenic cells in a host animal harboring the pathogenic cells (MIU=million international units; m²=approximate body surface area of an average human).

In another embodiment, chemotherapeutic agents, which are, for example, cytotoxic themselves or can work to enhance tumor permeability, are also suitable for use in the described methods in combination with the binding ligand drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives, Taxotere®, cyclophosphamide, daunomycin, daunorubicin, doxorubicin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocoichicine, trityl cysteine, Halicondrin B, dolastatins such as dolastatin 10, amanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

The therapeutic factor can be administered to the host animal prior to, after, or at the same time as the binding ligand drug delivery conjugates and the therapeutic factor can be administered as part of the same composition containing the binding ligand drug delivery conjugate or as part of a different composition than the binding ligand drug delivery conjugate. Any such therapeutic composition containing the therapeutic factor at a therapeutically effective dose can be used.

Additionally, more than one type of binding ligand drug delivery conjugate can be used. Illustratively, for example, the host animal can be treated with conjugates with different vitamins, but the same drug in a co-dosing protocol. In other embodiments, the host animal can be treated with conjugates comprising the same binding ligand linked to different drugs, or various binding ligands linked to various drugs. In another illustrative embodiment, binding ligand drug delivery conjugates with the same or different vitamins, and the same or different drugs comprising multiple vitamins and multiple drugs as part of the same drug delivery conjugate could be used.

The unitary daily dosage of the binding ligand drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. In illustrative embodiments, effective doses can range, for example, from about 1 ng/kg to about 1 mg/kg, from about 1 µg/kg to about 500 µg/kg, from about 1 µg/kg to about 100 µg/kg, from about 1 µg/kg to about 50 µg/kg, and from about 1 µg/kg to about 10 µg/kg.

In another illustrative aspect, any effective regimen for administering the binding ligand drug delivery conjugates can be used. For example, the binding ligand drug delivery conjugates can be administered as single doses, or can be divided and administered as a multiple-dose daily regimen. In other embodiments, a staggered regimen, for example, one to three days per week can be used as an alternative to daily treatment, and such intermittent or staggered daily regimen is considered to be equivalent to every day treatment and within the scope of the methods described herein. In one embodiment, the host is treated with multiple injections of the binding ligand drug delivery conjugate to eliminate the population of pathogenic cells. In another embodiment, the host is injected multiple times (preferably about 2 up to about 50 times) with the binding ligand drug delivery conjugate, for example, at 12-72 hour intervals or at 48-72 hour intervals. In other embodiments, additional injections of the binding ligand drug delivery conjugate can be administered to the patient at an interval of days or months after the initial injections(s) and the additional injections prevent recurrence of the disease state caused by the pathogenic cells.

In one embodiment, vitamins, or analogs or derivatives thereof, that can be used in the binding ligand drug delivery conjugates include those that bind to receptors expressed specifically on activated macrophages, such as the folate receptor which binds folate, or an analog or derivative thereof. The folate-linked conjugates, for example, can be used to kill or suppress the activity of activated macrophages that cause disease states in the host. Such macrophage targeting conjugates, when administered to a patient suffering from an activated macrophage-mediated disease state, work to concentrate and associate the conjugated drug in the population of activated macrophages to kill the activated macrophages or suppress macrophage function. Elimination, reduction, or deactivation of the activated macrophage population works to stop or reduce the activated macrophage-mediated pathogenesis characteristic of the disease state being treated. Exemplary of diseases known to be mediated by activated macrophages include rheumatoid arthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD) and chronic inflammations. Administration of the drug delivery conjugate is typically continued until symptoms of the disease state are reduced or eliminated.

Illustratively, the binding ligand drug delivery conjugates administered to kill activated macrophages or suppress the function of activated macrophages can be administered parenterally to the animal or patient suffering from the disease state, for example, intradermally, subcutaneously, intramuscularly, intraperitoneally, or intravenously in combination with a pharmaceutically acceptable carrier. In another embodiment, the binding ligand drug delivery conjugates can be administered to the animal or patient by other medically useful procedures and effective doses can be administered in standard or prolonged release dosage forms. In another aspect, the therapeutic method can be used alone or in combination with other therapeutic methods recognized for treatment of disease states mediated by activated macrophages.

The drug delivery conjugates described herein can be prepared by art-recognized synthetic methods. The synthetic methods are chosen depending upon the selection of the optionally addition heteroatoms or the heteroatoms that are already present on the spacer linkers, releasable linkers, the drug, and/or or the binding ligand. In general, the relevant bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference. Additional details for preparing functional groups, including amides and esters, ketals and acetals, succinimides, silyloxys, hydrazones, acyl hydrazines, semicarbazones, disulfides, carbonates, sulfonates, and the like contained in the linker, including releasable linkers are described in U.S. patent application publication No. US 2005/0002942 A1, incorporated herein in its entirety by reference.

General formation of folate-peptides. The folate-containing peptidyl fragment Pte-Glu-(AA)$_n$-NH(CHR$_2$)CO$_2$H (3) is prepared by a polymer-supported sequential approach using standard methods, such as the Fmoc-strategy on an acid-sensitive Fmoc-AA-Wang resin (1), as shown in Scheme 1.

Scheme 1

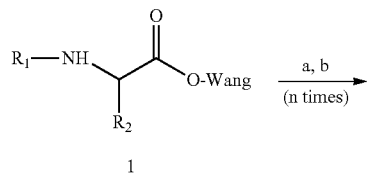

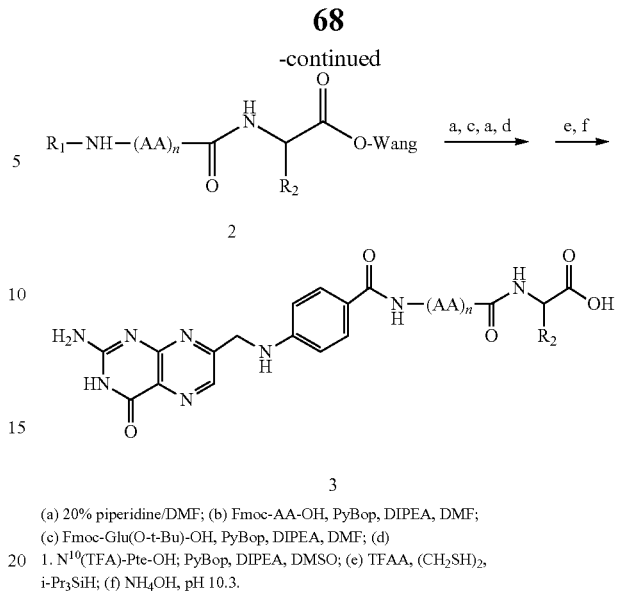

(a) 20% piperidine/DMF; (b) Fmoc-AA-OH, PyBop, DIPEA, DMF;
(c) Fmoc-Glu(O-t-Bu)-OH, PyBop, DIPEA, DMF; (d)
1. N$^{10}$(TFA)-Pte-OH; PyBop, DIPEA, DMSO; (e) TFAA, (CH$_2$SH)$_2$, i-Pr$_3$SiH; (f) NH$_4$OH, pH 10.3.

In this illustrative embodiment of the processes described herein, R$_1$ is Fmoc, R$_2$ is the desired appropriately-protected amino acid side chain, and DIPEA is diisopropylethylamine. Standard coupling procedures, such as PyBOP and others described herein or known in the art are used, where the coupling agent is illustratively applied as the activating reagent to ensure efficient coupling. Fmoc protecting groups are removed after each coupling step under standard conditions, such as upon treatment with piperidine, tetrabutylammonium fluoride (TBAF), and the like. Appropriately protected amino acid building blocks, such as Fmoc-Glu-OtBu, N$^{10}$-TFA-Pte-OH, and the like, are used, as described in Scheme 1, and represented in step (b) by Fmoc-AA-OH. Thus, AA refers to any amino acid starting material, that is appropriatedly protected. It is to be understood that the term amino acid as used herein is intended to refer to any reagent having both an amine and a carboxylic acid functional group separated by one or more carbons, and includes the naturally occurring alpha and beta amino acids, as well as amino acid derivatives and analogs of these amino acids. In particular, amino acids having side chains that are protected, such as protected serine, threonine, cysteine, aspartate, and the like may also be used in the folate-peptide synthesis described herein. Further, gamma, delta, or longer homologous amino acids may also be included as starting materials in the folate-peptide synthesis described herein. Further, amino acid analogs having homologous side chains, or alternate branching structures, such as norleucine, isovaline, β-methyl threonine, β-methyl cysteine, β,β-dimethyl cysteine, and the like, may also be included as starting materials in the folate-peptide synthesis described herein.

The coupling sequence (steps (a) & (b)) involving Fmoc-AA-OH is performed "n" times to prepare solid-support peptide 2, where n is an integer and may equal 0 to about 100. Following the last coupling step, the remaining Fmoc group is removed (step (a)), and the peptide is sequentially coupled to a glutamate derivative (step (c)), deprotected, and coupled to TFA-protected pteroic acid (step (d)). Subsequently, the peptide is cleaved from the polymeric support upon treatment with trifluoroacetic acid, ethanedithiol, and triisopropylsilane (step (e)). These reaction conditions result in the simultaneous removal of the t-Bu, t-Boc, and Trt protecting groups that may form part of the appropriately-protected amino acid side chain. The TFA protecting group is removed upon treatment with base (step (f)) to provide the folate-containing peptidyl fragment 3.

In addition, the following illustrative process may be used to prepare compounds described herein, where is an integer such as 1 to about 10.

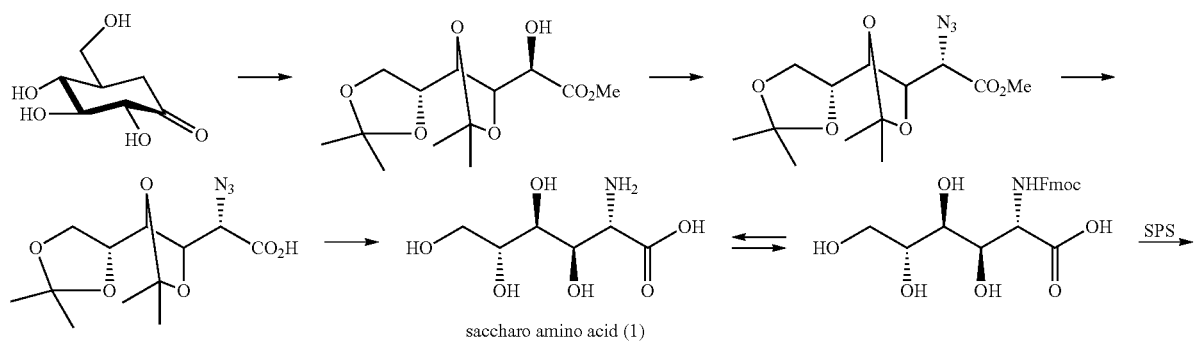

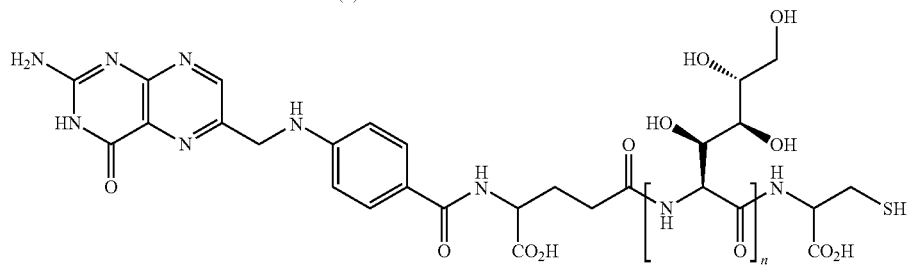

saccharo amino acid (1)

It is to be understood that although the foregoing synthetic process is illustrated for selected compounds, such as the particular saccharopeptides shown, additional analogous compounds may be prepared using the same or similar process by the routine selection of starting materials and the routine optimization of reaction conditions.

The compounds described herein may be prepared using conventional synthetic organic chemistry. In addition, the following illustrative process may be used to prepare compounds described herein, where is an integer such as 1 to about 10.

It is to be understood that although the foregoing synthetic process is illustrated for selected compounds, such as the particular saccharopeptides shown, additional analogous compounds may be prepared using the same or similar process by the routine selection of starting materials and the routine optimization of reaction conditions.

In addition, the following illustrative process may be used to prepare compounds described herein.

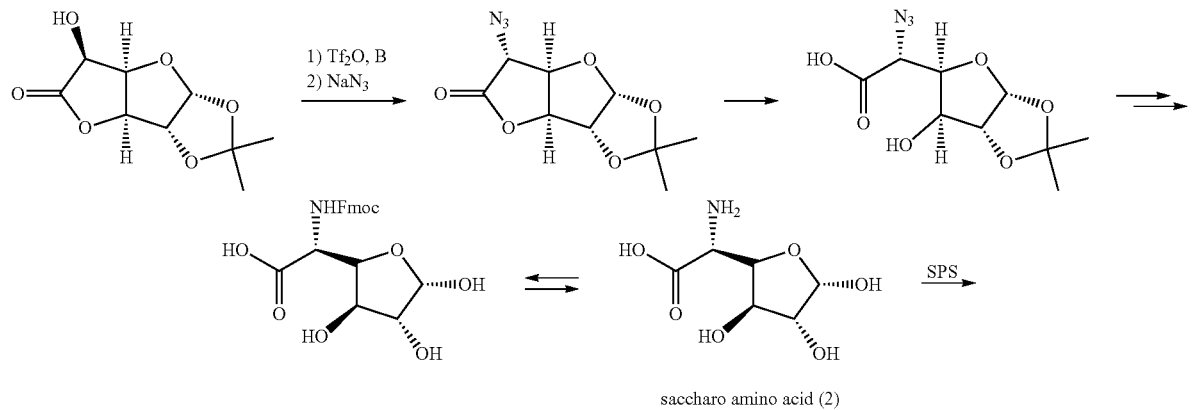

saccharo amino acid (2)

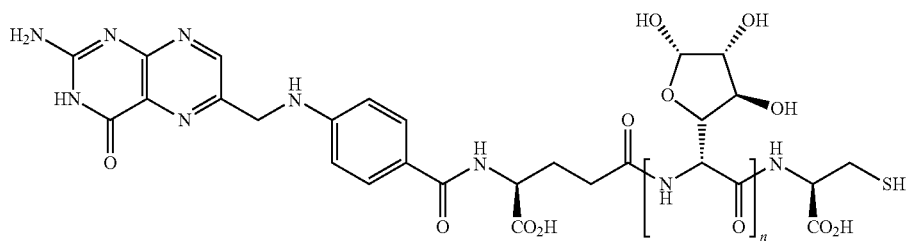

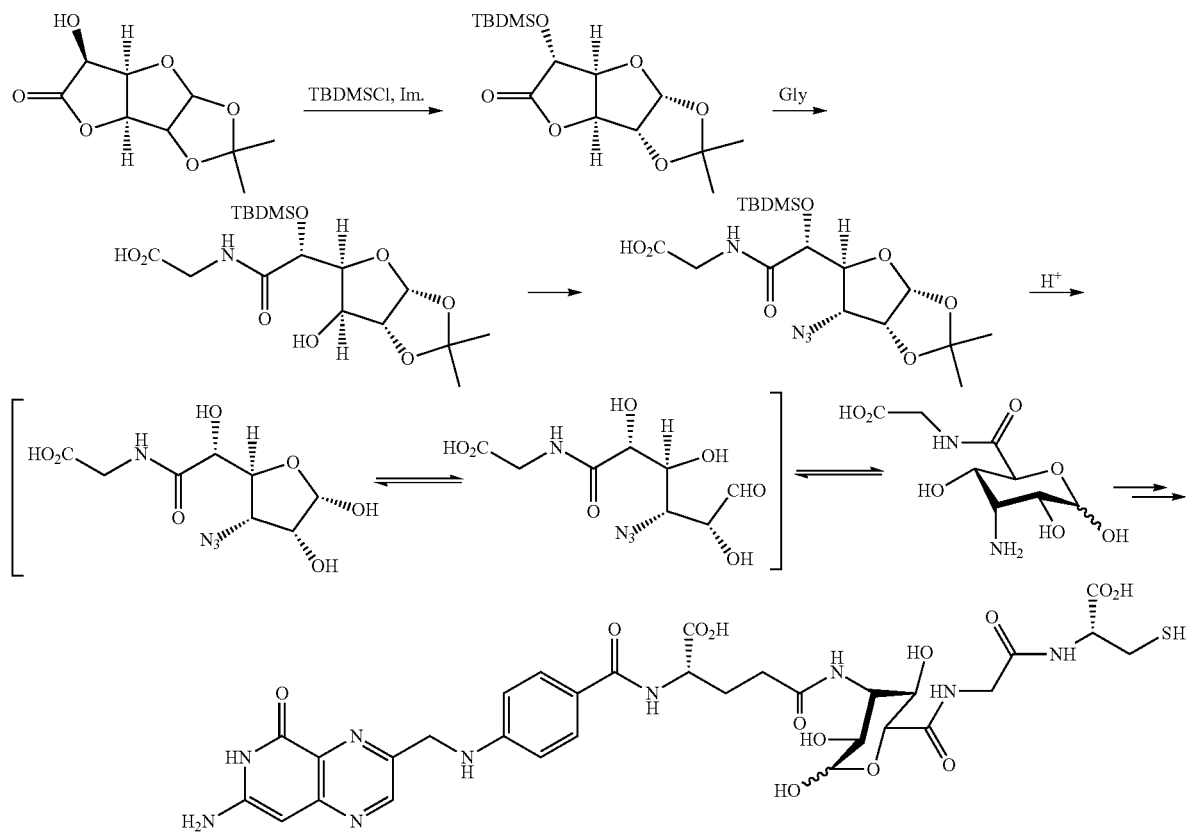

It is to be understood that although the foregoing synthetic process is illustrated for selected compounds, additional analogous compounds may be prepared using the same or similar process by the routine selection of starting materials and the routine optimization of reaction conditions.

In each of the foregoing synthetic processes, the intermediates may be coupled with any additional hydrophilic spacer linkers, other spacer linkers, releasable linkers, or the agent A. In variations of each of the foregoing processes, additional hydrophilic spacer linkers, other spacer linkers, or releasable linkers may be inserted between the binding ligand B and the indicated hydrophilic spacer linkers. In addition, it is to be understood that the left-to-right arrangement of the bivalent hydrophilic spacer linkers is not limiting, and accordingly, the agent A, the binding ligand B, additional hydrophilic spacer linkers, other spacer linkers, and/or releasable linkers may be attached to either end of the hydrophilic spacer linkers described herein.

Method Examples

Relative Affinity Assay. The affinity for folate receptors (FRs) relative to folate was determined according to a previously described method (Westerhof, G. R., J. H. Schornagel, et al. (1995) Mol. Pharm. 48: 459-471) with slight modification. Briefly, FR-positive KB cells were heavily seeded into 24-well cell culture plates and allowed to adhere to the plastic for 18 h. Spent incubation media was replaced in designated wells with folate-free RPMI (FFRPMI) supplemented with 100 nM $^3$H-folic acid in the absence and presence of increasing concentrations of test article or folic acid. Cells were incubated for 60 min at 37° C. and then rinsed 3 times with PBS, pH 7.4. Five hundred microliters of 1% SDS in PBS, pH 7.4, were added per well. Cell lysates were then collected and added to individual vials containing 5 mL of scintillation cocktail, and then counted for radioactivity, Negative control tubes contained only the $^3$H-folic acid in FFRPMI (no competitor). Positive control tubes contained a final concentration of 1 mM folic acid, and CPMs measured in these samples (representing non-specific binding of label) were subtracted from all samples. Notably, relative affinities were defined as the inverse molar ratio of compound required to displace 50% of $^3$H-folic acid bound to the FR on KB cells, and the relative affinity of folic acid for the FR was set to 1.

Inhibition of Cellular DNA Synthesis. The compounds described herein were evaluated using an in vitro cytotoxicity assay that predicts the ability of the drug to inhibit the growth of folate receptor-positive KB cells. The compounds were comprised of folate linked to a respective chemotherapeutic drug, as prepared according to the protocols described herein. The KB cells were exposed for up to 7 h at 37° C. to the indicated concentrations of folate-drug conjugate in the absence or presence of at least a 100-fold excess of folic acid. The cells were then rinsed once with fresh culture medium and incubated in fresh culture medium for 72 hours at 37° C. Cell viability was assessed using a $^3$H-thymidine incorporation assay.

In Vitro Concentration-Dependent Cytotoxic Activity. Cells were heavily seeded in 24-well Falcon plates and allowed to form nearly confluent monolayers overnight. Thirty minutes prior to the addition of test article, spent medium was aspirated from all wells and replaced with fresh folate-free RPMI (FFRPMI). Note, designated wells received media containing 100 μM folic acid; and, cells within the latter wells were used to determine the targeting specificity, since cytotoxic activity produced in the presence of excess folic acid (enables competition for FR binding) would signify the portion of the total activity that was unrelated to FR-specific delivery. Following one rinse with 1 mL of fresh FFRPMI containing 10% heat-inactivated fetal calf serum, each well received 1 mL of media containing increasing concentrations of test article (4 wells per sample) in the presence or absence of 100 μM free folic acid (a binding site competitor). Treated cells were pulsed for 2 h at 37° C., rinsed 4 times with 0.5 mL of media, and then chased in 1 mL of fresh media up to 70 h. Spent media was aspirated from all wells and replaced with fresh media containing 5 μCi/mL $^3$H-thymidine. Following a further 2 h 37° C. incubation, cells were washed 3 times with 0.5 mL of PBS and then treated with 0.5 mL of ice-cold 5% trichloroacetic acid per well. After 15 min, the trichloroacetic acid was aspirated and the cell material solubilized by the addition of 0.5 mL of 0.25 N sodium hydroxide for 15 min. Four hundred and fifty μL of each solubilized sample were transferred to scintillation vials containing 3 mL of Ecolume scintillation cocktail and then counted in a liquid scintillation counter. Final tabulated results were expressed as the percentage of $^3$H-thymidine incorporation relative to untreated controls.

As shown in the figures herein, dose-dependent cytotoxicity was measurable, and in most cases, the $IC_{50}$ values (concentration of drug conjugate required to reduce $^3$H-thymidine incorporation into newly synthesized DNA by 50%) were in the low nanomolar range. Furthermore, the cytotoxicities of these conjugates were reduced in the presence of excess free folic acid, indicating that the observed cell killing was mediated by binding to the folate receptor. The following table illustrated data for selected compounds against KB cells and against RAW264.7 cells The cells in the designated wells are used to determine the targeting specificity. Without being bound by theory it is suggested that the cytotoxic activity produced by test compounds in the presence of excess folic acid, i.e. where there is competition for FR binding, corresponds to the portion of the total activity that is unrelated to FR-specific delivery. Following one rinse with 1 mL of fresh FFRPMI containing 10% heat-inactivated fetal calf serum, each well receives 1 mL of medium containing increasing concentrations of test compound (4 wells per sample) in the presence or absence of 100 μM free folic acid as indicated. Treated cells are pulsed for 2 h at 37° C., rinsed 4 times with 0.5 mL of media, and then chased in 1 mL of fresh medium up to 70 h. Spent medium is aspirated from all wells and replaced with fresh medium containing 5 μCi/mL $^3$H-thymidine. Following a further 2 h 37° C. incubation, cells are washed 3 times with 0.5 mL of PBS and then treated with 0.5 mL of ice-cold 5% trichloroacetic acid per well. After 15 min, the trichloroacetic acid is aspirated and the cell material solubilized by the addition of 0.5 mL of 0.25 N sodium hydroxide for 15 min. A 450 μL aliquot of each solubilized sample is transferred to a scintillation vial containing 3 mL of Ecolume scintillation cocktail and then counted in a liquid scintillation counter. Final tabulated results are expressed as the percentage of $^3$H-thymidine incorporation relative to untreated controls.

Inhibition of Tumor Growth in Mice. Four to seven week-old mice (Balb/c or nu/nu strains) were purchased from Harlan Sprague Dawley, Inc. (Indianapolis, Ind.). Normal rodent chow contains a high concentration of folic acid (6 mg/kg chow); accordingly, mice used were maintained on the folate-free diet (Harlan diet # TD00434) for 1 week before tumor implantation to achieve serum folate concentrations close to the range of normal human serum. For tumor cell inoculation, $1\times10^6$ M109 cells (Balb/c strain) or $1\times10^6$ KB cells (nu/nu strain) in 100 μL were injected in

|  |  | KB Cells | | RAW264.7 Cells | |
|---|---|---|---|---|---|
| Conjugate Number | Base Drug(s) | $IC_{50}$ (nM) | Competable with xs folate | $IC_{50}$ (nM) | Competable with xs folate |
| EC0234 | DAVLBH | 56 | Yes | | |
| EC0246 | DAVLBH |  | Yes | | |
| EC0258 | DAVLBH | 8.4 | Yes | | |
| EC0262 | cryptophycin | 4 | Yes | | |
| EC0263 | DAVLBH | 11 | Yes | | |
| EC0409 | DAVLBH | 7 | Yes | | |
| EC0525 | Thio-bortezomib | | | 68 | Yes |
| EC0543 | Tubulysin A | 1.6 | Yes | | |
| EC0551 | Aminopterin | | | 1 | Yes |
| EC0552 | Rapamycin | | | 100 | Yes |
| EC0561 | Paclitaxel | 53 | Yes | | |
| EC0563 | Thiobortezomib + Rapamycin | | | 387 | Yes |
| EC0582 | Thio-bortezomib + Everolimus | | | 51 | Yes |
| EC0592 | α-amanatin | ~3 | Yes | 5 | Yes |
| EC0595 | Bis-Thio-bortezomib | | | 4 | Yes |
| EC0598 | Verucarin | | | 33 | Yes |
| EC0605 | Bis-Verucarin | | | 14 | Yes |
| EC0610 | Didemnin B | | | 4 | Yes |
| EC0647 | Bis-Aminopterin | | | 0.3 | Yes |

In Vitro Test against Various Cancer Cell Lines. Cells are heavily seeded in 24-well Falcon plates and allowed to form nearly confluent monolayers overnight. Thirty minutes prior to the addition of the test compound, spent medium is aspirated from all wells and replaced with fresh folate-deficient RPMI medium (FFRPMI). A subset of wells are designated to receive media containing 100 μM folic acid.

the subcutis of the dorsal medial area. Tumors were measured in two perpendicular directions every 2-3 days using a caliper, and their volumes were calculated as $0.5 \times L \times W^2$, where L=measurement of longest axis in mm and W=measurement of axis perpendicular to L in mm. Log cell kill (LCK) and treated over control (T/C) values were then calculated according to published procedures (see, e.g., Lee et al., "BMS-247550: a novel epothilone analog with a mode of action similar to paclitaxel but possessing superior antitumor efficacy" *Clin Cancer Res* 7:1429-1437 (2001); Rose, "Taxol-based combination chemotherapy and other in vivo preclinical antitumor studies" *J Natl Cancer Inst Monogr* 47-53 (1993)). Dosing solutions were prepared fresh each day in PBS and administered through the lateral tail vein of the mice. Dosing was initiated when the s.c. tumors had an average volume between 50-100 mm$^3$ (t$_o$), typically 8 days post tumor inoculation (PTI) for KB tumors, and 11 days PTI for M109 tumors.

General KB Tumor Assay. The anti-tumor activity of the compounds described herein, when administered intravenously (i.v.) to tumor-bearing animals, was evaluated in nu/nu mice bearing subcutaneous KB tumors. Approximately 8 days post tumor inoculation in the subcutis of the right axilla with 1×10$^6$ KB cells (average tumor volume at t$_o$=50-100 mm$^3$), in mice (5/group) were injected i.v. three times a week (TIW), for 3 weeks with 5 μmol/kg of the drug delivery conjugate or with an equivalent dose volume of PBS (control), unless otherwise indicated. Tumor growth was measured using calipers at 2-day or 3-day intervals in each treatment group. Tumor volumes were calculated using the equation V=a×b$^2$/2, where "a" is the length of the tumor and "b" is the width expressed in millimeters.

General M109 Tumors Assay. The anti-tumor activity of the compounds described herein, when administered intravenously (i.v.) to tumor-bearing animals, was evaluated in Balb/c mice bearing subcutaneous M109 tumors (a syngeneic lung carcinoma). Approximately 11 days post tumor inoculation in the subcutis of the right axilla with 1×10$^6$ M109 cells (average tumor volume at t$_o$=60 mm$^3$), mice (5/group) were injected i.v. three times a week (TIW), for 3 weeks with 1500 nmol/kg of the drug delivery conjugate or with an equivalent dose volume of PBS (control). Tumor growth was measured using calipers at 2-day or 3-day intervals in each treatment group. Tumor volumes were calculated using the equation V=a×b$^2$/2, where "a" is the length of the tumor and "b" is the width expressed in millimeters.

General 4T-1 Tumor Assay. Six to seven week-old mice (female Balb/c strain) were obtained from Harlan, Inc., Indianapolis, Ind. The mice were maintained on Harlan's folate-free chow for a total of three weeks prior to the onset of and during this experiment. Folate receptor-negative 4T-1 tumor cells (1×10$^6$ cells per animal) were inoculated in the subcutis of the right axilla. Approximately 5 days post tumor inoculation when the 4T-1 tumor average volume was ~100 mm$^3$, mice (5/group) were injected i.v. three times a week (TIW), for 3 weeks with 3 μmol/kg of drug delivery conjugate or with an equivalent dose volume of PBS (control), unless otherwise indicated herein. Tumor growth was measured using calipers at 2-day or 3-day intervals in each treatment group. Tumor volumes were calculated using the equation V=a×b$^2$/2, where "a" is the length of the tumor and "b" is the width expressed in millimeters.

Figure 8A:
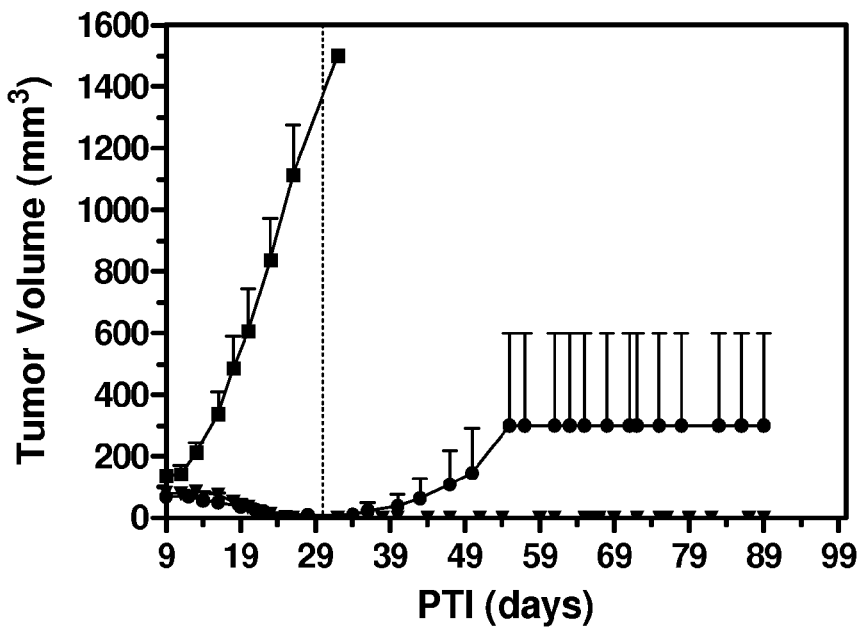
FIG. 8A shows the effect on tumor volume of EC0305 (●), EC0436 (▼) and PBS control (■) dosed at 2 μmol/kg TIW for two weeks (the vertical line indicates the last dosing day) for s.c. M109 tumors in Balb/c mice.
Figure 8B:
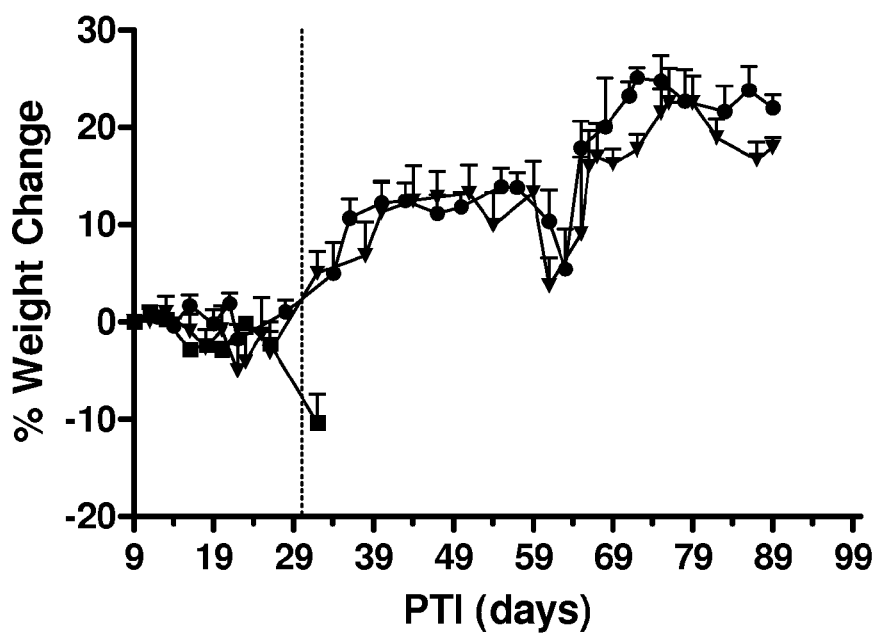
FIG. 8B shows the effect on percentage body weight change of EC0305 (●), EC0436 (▼) and PBS control (■) dosed at 2 μmol/kg TIW for two weeks (the vertical line indicates the last dosing day); indicating that no gross toxicity was observed during treatment.
Figure 10A:
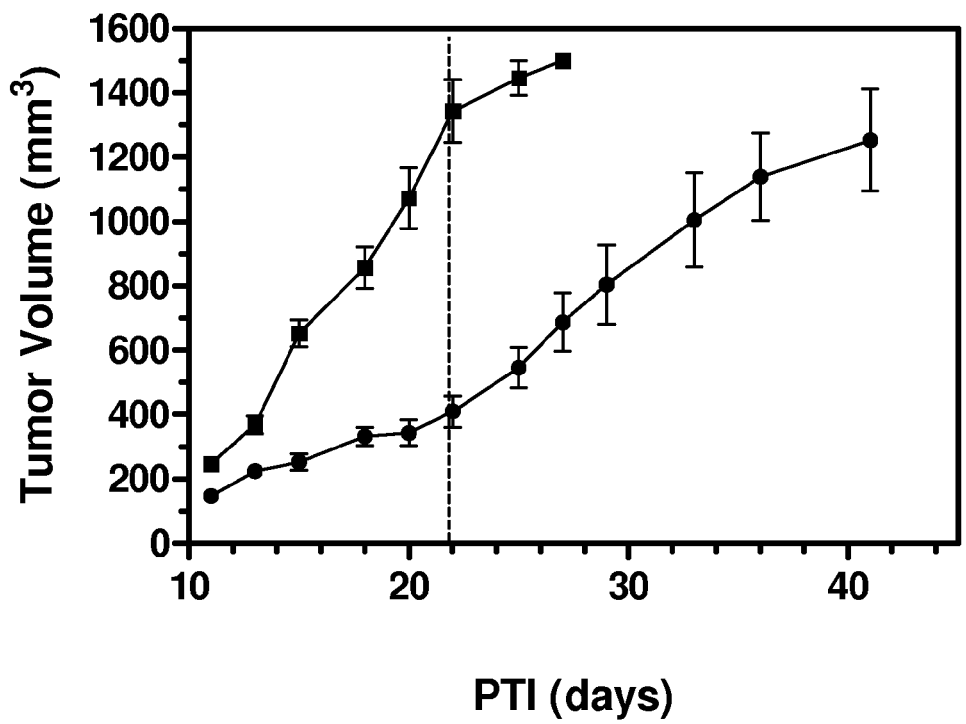
FIG. 10A shows the effect on s.c. KB tumors in nu/nu mice by EC0565 at 3 μmol/kg (qdx5 for two weeks) (●), compared to PBS treated controls (■). From the data, a Log Cell Kill (LCK) value of 1.2 can be determined (values greater than about 0.7 are indicative of an active anti-cancer compound).
Figure 10B:
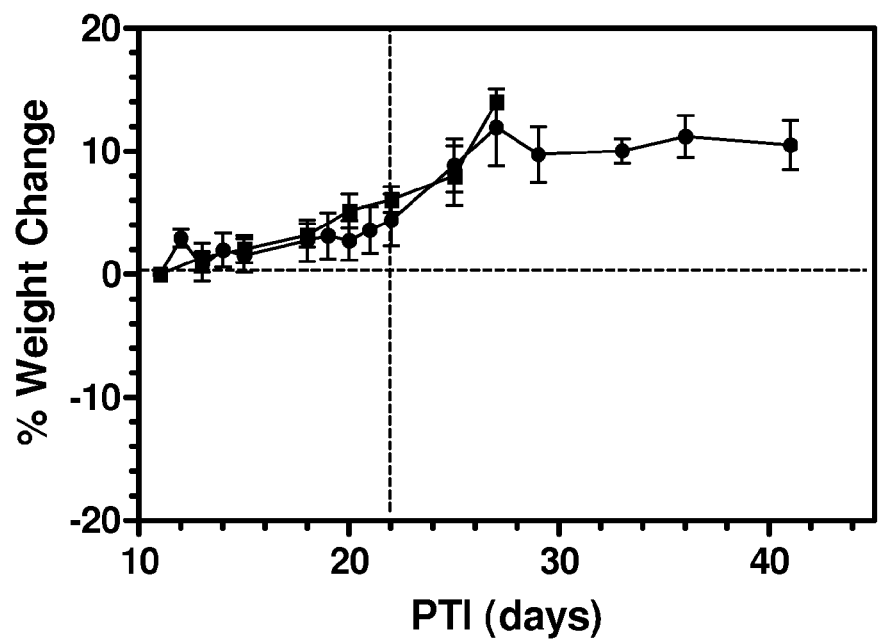
FIG. 10B shows the effect on percentage body weight change by EC0565 at 3 μmol/kg (qdx5 for two weeks) (●), compared to PBS treated controls (■); indicating that no gross toxicity was observed during treatment.

The data shown in FIGS. 3A, 4A, 5A, 6A, 7A, 8A, and 10A indicate that the conjugates described herein exhibit superior efficacy in the treatment of tumors compared to the corresponding unconjugated compounds. Treatment of Balb/c mice with s.c. M109 tumors with EC0396 and EC145 (FIG. 4A) led to complete responses in all treated animals (3/3 for EC0396 and 5/5 for EC145). In addition, after nearly 70 days, no recurrence of disease was observed. Similarly, treatment with EC0400 (FIG. 5A) led to a complete response and no recurrence of disease after nearly 70 days. Treatment with the conjugated compounds described herein including a hydrophilic spacer linker (e.g. EC0436) were superior to comparison conjugates lacking hydrophilic spacer linkers (e.g. EC0305) showed superior efficacy (FIG. 8A). EC0436 showed a complete response in 515 animals with no recurrence of disease after 90 days.

Drug Toxicity Determinations. Persistent drug toxicity was assessed by collecting blood via cardiac puncture and submitting the serum for independent analysis of blood urea nitrogen (BUN), creatinine, total protein, AST-SGOT, ALT-SGPT plus a standard hematological cell panel at Ani-Lytics. Inc. (Gaithersburg, Md.). In addition, histopathologic evaluation of formalin-fixed heart, lungs, liver, spleen, kidney, intestine, skeletal muscle and bone (tibia/fibula) were conducted by board-certified pathologists at Animal Reference Pathology Laboratories (ARUP; Salt Lake City, Utah).

Toxicity as Measured by Weight Loss. The percentage weight change was determined in mice (5 mice/group) on selected days post-tumor inoculation (PTI), compared to controls, and graphed. As shown in FIGS. 3B, 4B, 5B, 6B, 7B, 8B, and 10B, the conjugated compounds described herein showed equal or less toxicity compared to unconjugated compounds, as determined by percent weight loss.

Single and Multiple Dose MTD$_{app}$ on Mice. The compounds described herein may show a positive relationship between the number of hydrophilic spacer linkers included in the conjugate and the maximum tolerated dose on mice for a single dose. For example the following vinblastine conjugates described herein compared to a control conjugate are shown in the following table.

| Compound | No. of hydrophilic linkers | Single Dose MTD$_{app}$ (μmol/kg) |
|---|---|---|
| EC145 | 0 | 15 |
| EC0234 | 1 | 12* |
| EC0246 | 2 | <20** |
| EC0263 | 3 | >20 |

*dose limited by solubility;
**⅓ mice died at 20 μmol/kg.

EC0436 and Comparative Example EC0305 were also administered i.v. to Balb/c mice TIW for 1 week. The resulting MTD for the multiple dose was EC0305 (6 mmol/kg) and EC0436 (9 mmol/kg). The data indicate that EC0436 can be dosed at levels 50% greater than EC0305.

Serum Binding. Serum binding of Folate-DAVLBH conjugates containing hydrophilic spacer linkers compared to Comparative Example EC145 lacking a hydrophilic spacer linker 50 μM compound in serum with 30K NMWL filtration and evaluation by HPLC-UV detection (n=3).

| Compound | Human Serum (% Bound) | SD | Mouse Serum (% Bound) | SD |
|---|---|---|---|---|
| EC145 | 54.3 | 1.6 | 67.3 | 2.6 |
| EC0396 | 42.7 | 4.4 | 72.2 | 5.2 |
| EC0400 | 61.1 | 1.9 | 75.5 | 1.4 |

Bile Clearance. Comparison of Bile Clearance (% ID) of unconjugated drug, drug conjugate lacking a hydrophilic spacer linker, and conjugates described herein.

| Compound | Spacer | Bile clearance (% ID) |
|---|---|---|
| DAVLBH | None | 58.0 |
| EC145 | no hydrophilic spacer | 8.7 |

| Compound | Spacer | Bile clearance (% ID) |
|---|---|---|
| EC0234 | Mono-ribosyl | 10.6 |
| EC0246 | Bis-ribosyl | 4.7 |
| EC0258 | Tri-ribosyl | 3.2 |
| EC0434 | Tetra-ribosyl | 2.8 |
| EC0400 | Mono-glucuronide | 6.3 |
| EC0423 | Bis-glucuronide | 3.9 |
| EC0409 | PEG$_{12}$ | 7.9 |
| EC0429 | Piperazine/Asp | 8.6 |

Figure 11:
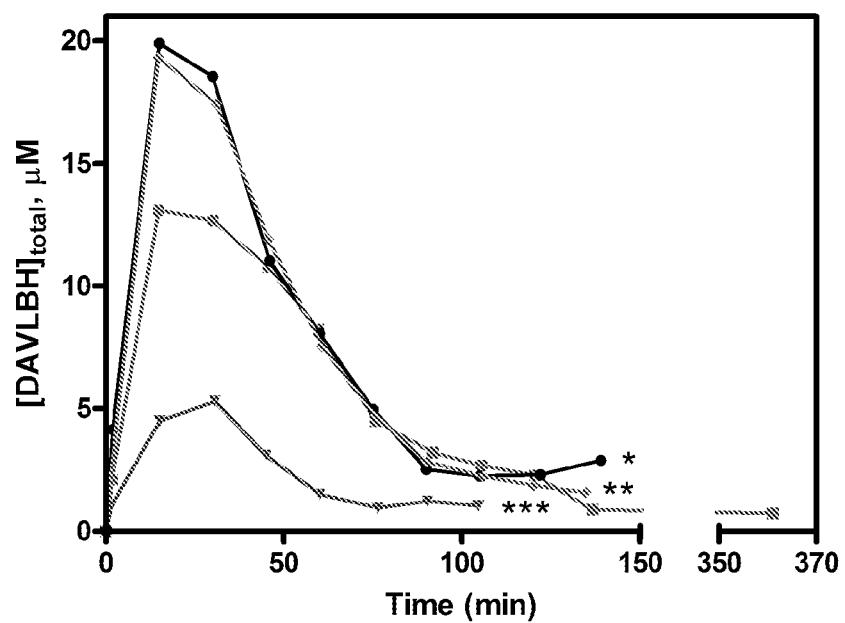
FIG. 11 shows the total DAVLBH biliary excretion from various DAVLBH conjugates at 2 μmol/kg i.v. bolus in a hepatobiliary excretion in bile duct assay in cannulated rats. The percent of total dose in the bile was measured for EC145=8.7% (●), EC0409=7.9% (♦), EC0429=8.6% (■), EC0434=2.8% (▼). In addition, EC145 shows an AUC=1092 (●); last time point collected was 139 min; and EC0434 shows an AUC=260 (■); the 120, 135, and 360 minute time points were all below level of quantitation, i.e. <0.65 μM.
Figure 12:
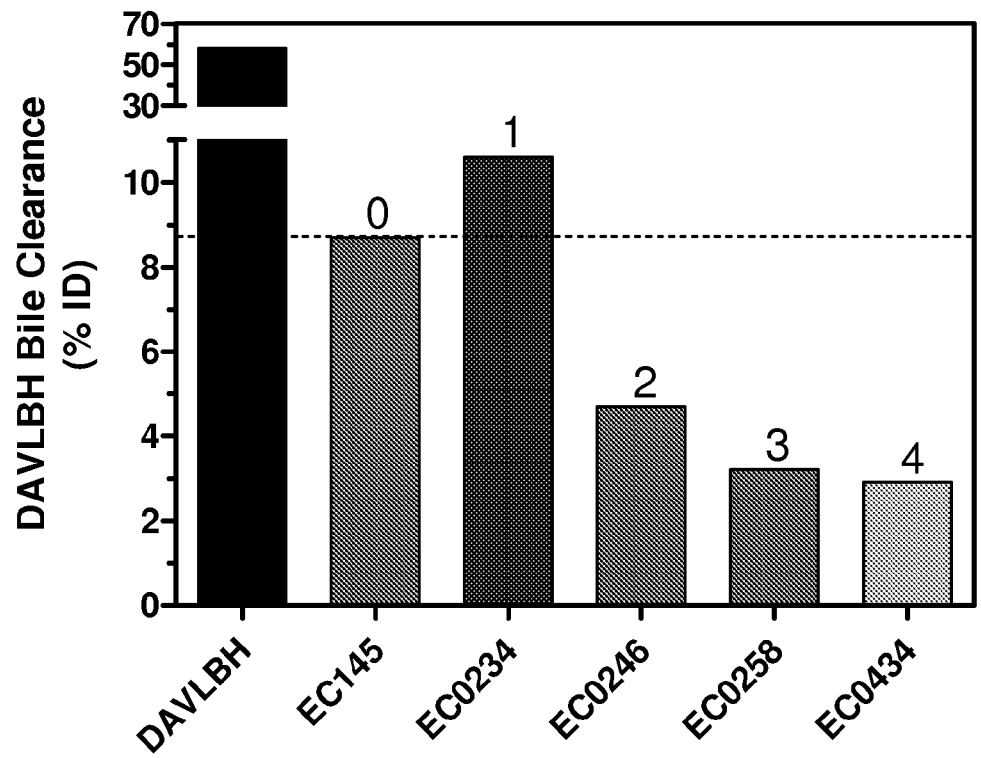
FIG. 12 shows the effect of ribose-based spacers on bile clearance and the impact of extended derivatization. The numbers above bars correspond to the number of hydrophilic spacers in the linker.
Figure 13:
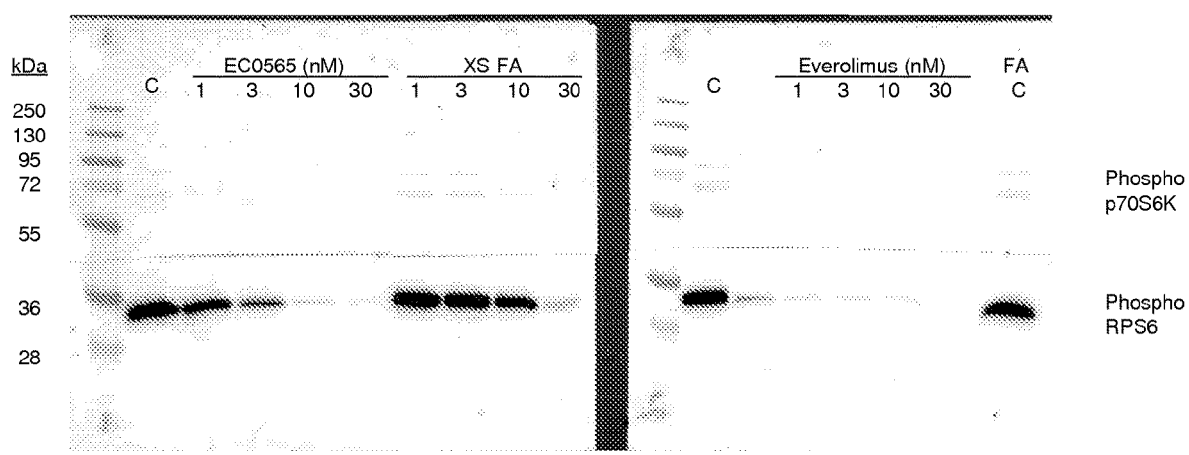
FIG. 13 shows that EC0565 induces dose-responsive inhibition of RPS6 and p70S6K in KB cells (1 h pulse/4 h chase) using a 30 min camera exposure, where C=Control (untreated cells); FAC=Folic acid control (100 μM).
Figure 14:
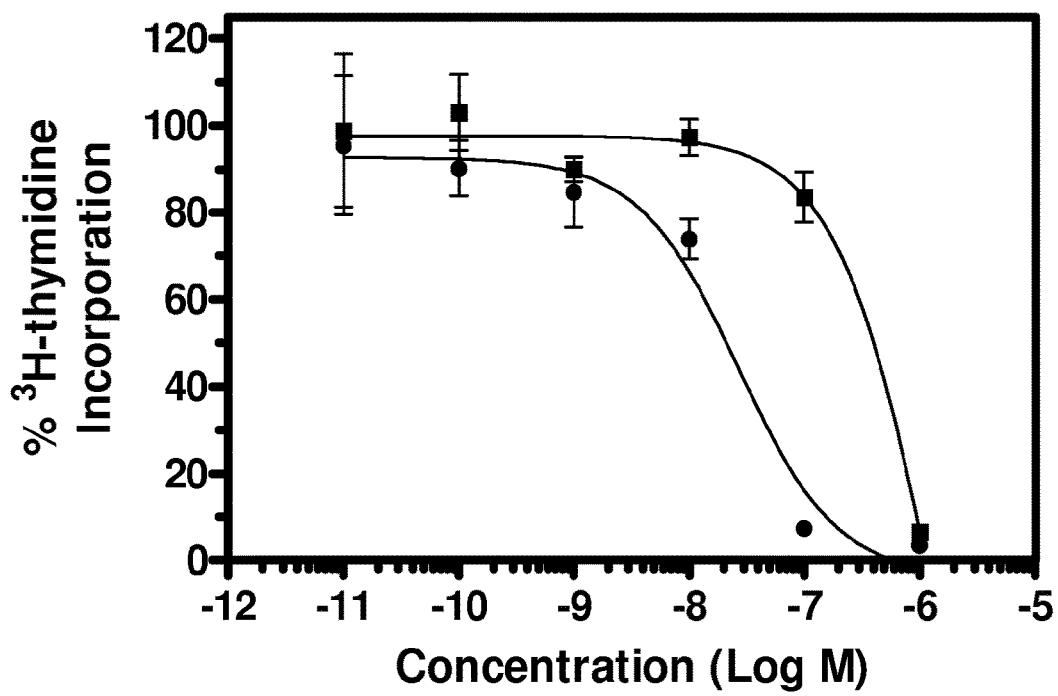
FIG. 14 shows the cytotoxicity of bortezomib versus the methylthiol bortezomib derivative (EC0501). $IC_{50}$ bortezomib, 20 nM (●); EC0501, 240 nM (■).
Figure 15:
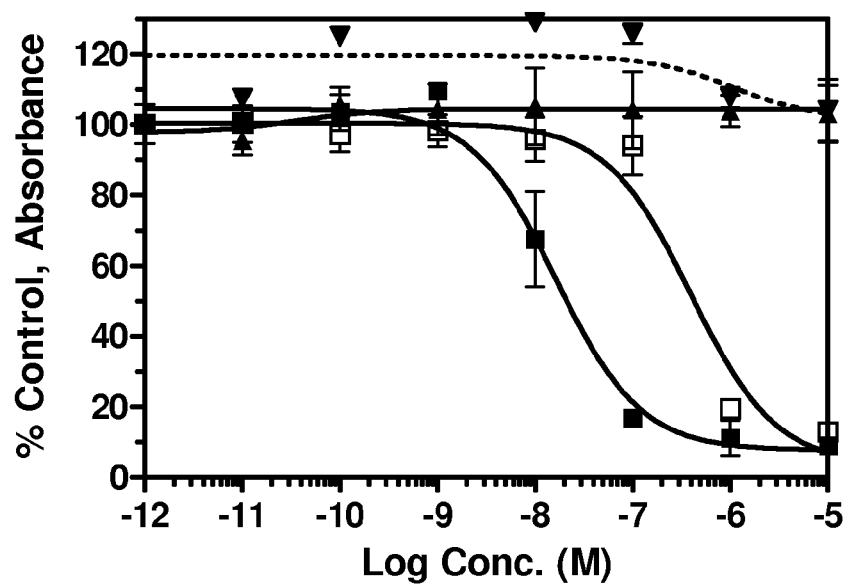
FIG. 15 shows that hydrophilic spacer linkers enable specific activity of mono- and bis-thio-velcade folate conjugates against RAW264.7 cells. Cell viability after a 5 h pulse, followed by a 72 h chase (MTT); bortezomib (■), EC0501 (□), EC0522 (▲), EC0522 plus excess folic acid (▽).
Figure 16:
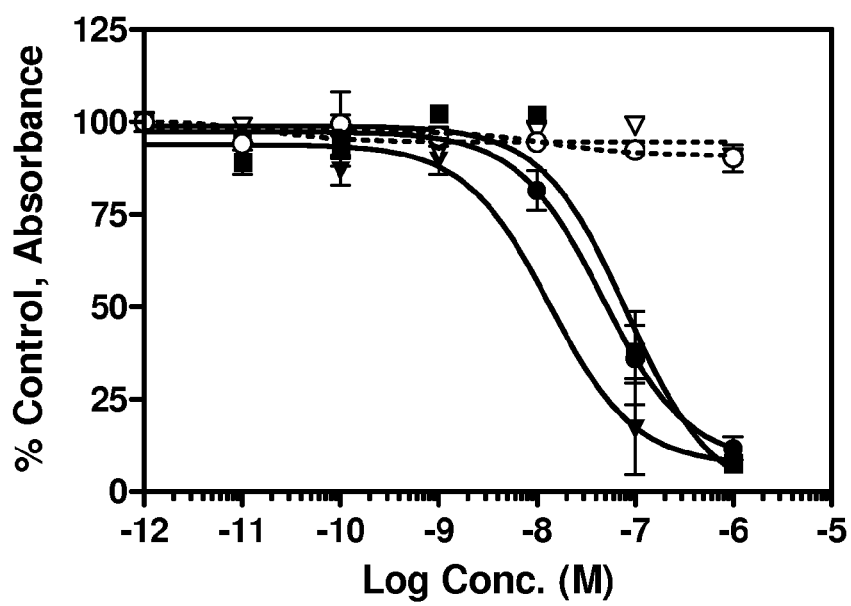
FIG. 16 shows cell viability (5 h pulse/72 h chase) (XTT) after treatment with EC0595 (13 nM IC50) (▼), EC0595 plus excess folic acid (▽), bortezomib (■), EC0525 (46 nM IC50) (●), EC0525 plus excess folic acid (○).
Figure 17:
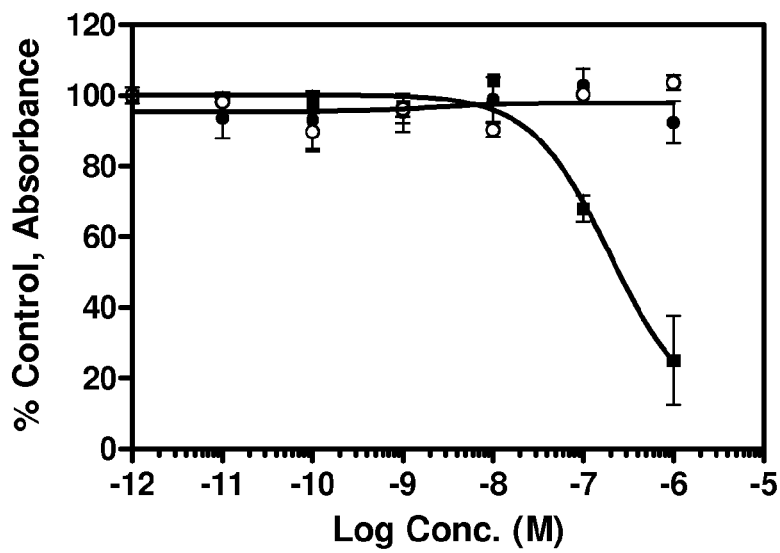
FIG. 17 shows cell viability after a 24 h incubation (XTT) with bortezomib (■), EC0587 (●), EC0587 plus excess folic acid (○).
Figure 18:
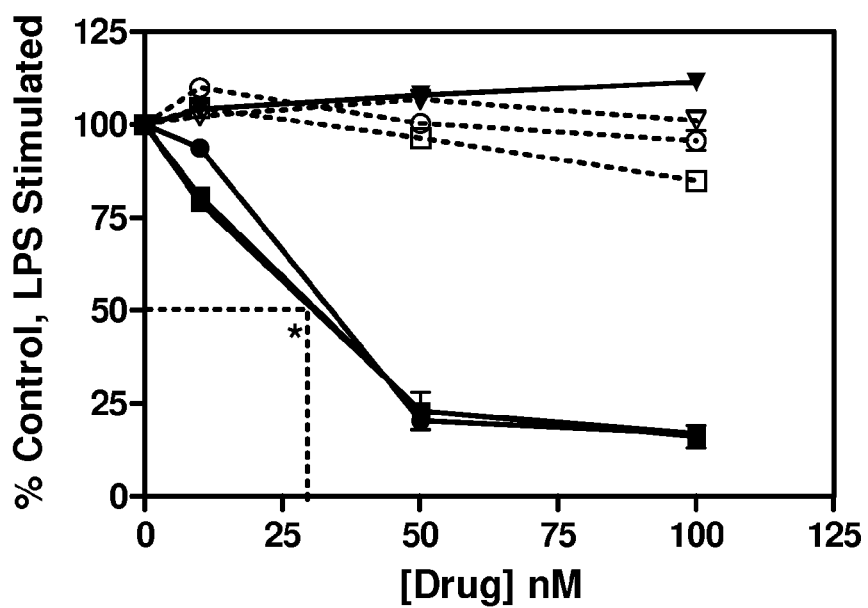
FIG. 18 shows inhibition of LPS stimulated proteosome activity in RAW 264.7 cells (5 h pulse/24 h chase), LPS 100 ng/mL, 30 m 20S proteosome/substrate reaction time by bortezomib (■), EC0522 (▼), EC0522 plus excess folic acid (∇), EC0525 (●), EC0525 plus excess folic acid (○), EC0595 (◆), EC0595 plus excess folic acid (□); $IC_{50}$ is ca. 30 nM for EC0595 and EC0525.
Figure 19:
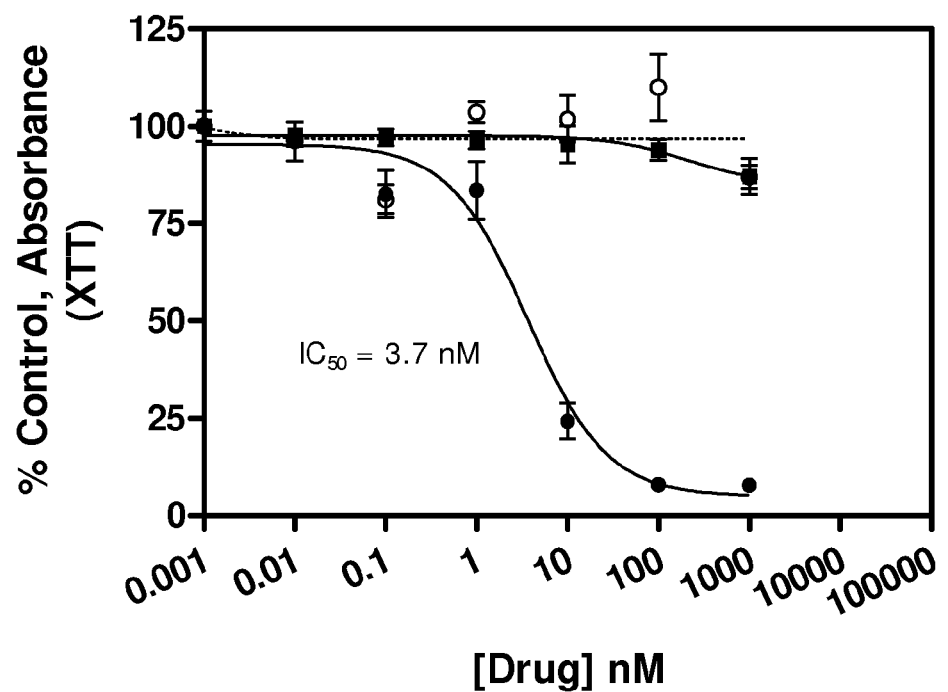
FIG. 19 shows activity against RAW cells (5 h pulse/72 h chase) after treatment with α-amantin (■), EC0592 ($IC_{50}$ 3.7 nM) (●), EC0592 plus excess folic acid (○).

The results shown in FIGS. 11 and 13 indicate a 76% decrease in the liver clearance of EC0434, which includes hydrophilic spacer linkers described herein, as compared to the standard EC145. Without being bound by theory, these results are believed to correspond to non-specific liver clearance, and accordingly, it is suggested that significantly lower doses of those conjugates that include the hydrophilic spacer linkers described herein may be administered compared to the corresponding conjugates that do not include such linkers. Further, without being bound by theory, it is suggested that hepatic clearance leads to the dose limiting GI-related toxicity that is observed with some conjugates.

Western Blot Analysis. The data shown in FIG. 13 indicate that EC0565 (folate-sugar-everolimus) can cause a dose-dependent, and specific knockdown of the downstream targets of mTOR (intracellular target for everolimus). Without being bound by theory, in it believed that folate delivers everolimus inside the cell where everolimus inhibits mTOR, which is the mammalian target of rapamycin and a ser/thr kinase. Inhibition of mTOR's downstream targets (P70 S6-kinase and Ribosomal S6) results, as shown on the Western blot.

Compound Examples

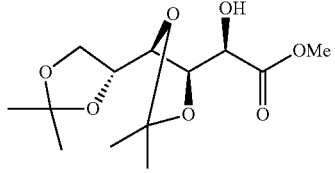

Example (3,4),(5,6)-Bisacetonide-D-Gluconic Acid Methyl Ester. In a dry 250 mL round bottom flask, under argon δ-gluconolactone (4.14 g, 23.24 mmol) was suspended in acetone-methanol (50 mL). To this suspension dimethoxypropane (17.15 mL, 139.44 mmol) followed by catalytic amount of p-toulenesulfonic acid (200 mg) were added. This solution was stirred at room temperature for 16 h. TLC (50% EtOAc in petroleum ether) showed that all of the starting material had been consumed and product had been formed. Acetone-methanol was removed under reduced pressure. The residue of the reaction was dissolved in EtOAc and washed with water. The organic layer was washed with brine, dried over Na$_2$SO$_4$, and concentrated to dryness. This material was then loaded onto a SiO$_2$ column and chromatographed (30% EtOAc in petroleum ether) to yield pure (3,4),(5,6)-bisacetonide-D-gluconic acid methyl ester (3.8 g, 56%) and regio-isomer (2,3), (5,6)-bisacetonide-D-gluconic acid methyl ester (0.71 g, 10%). $^1$H NMR data was in accordance with the required products. C$_{13}$H$_{22}$O$_7$; MW 290.31; Exact Mass: 290.14.

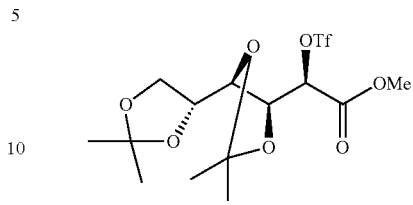

Example (3,4),(5,6)-Bisacetonide-2-OTf-D-Gluconic Acid Methyl Ester. In a dry 100 mL round bottom flask, under argon (3,4),(5,6)-bisacetonide-D-gluconic acid methyl ester (3.9 g, 13.43 mmol) was dissolved in methylene chloride (40 mL) and cooled to −20° C. to −25° C. To this solution pyridine (3.26 mL, 40.29 mmol) followed by triflic anhydride (3.39 mL, 20.15 mmol) were added. This white turbid solution was stirred at −20° C. for 1 h. TLC (25% EtOAc in petroleum ether) showed that all of the starting material had been consumed and product had been formed. The reaction mixture was poured into crushed-ice and extracted with diethyl ether. The organic layer was washed with water, brine, dried over Na$_2$SO$_4$, and concentrated to yield (3,4),(5,6)-bisacetonide-2-OTf-D-gluconic acid methyl ester (5.5 g, 97%). This material was used in the next reaction without further purification. C$_{14}$H$_{21}$F$_3$O$_9$S; MW 422.37; Exact Mass: 422.09.

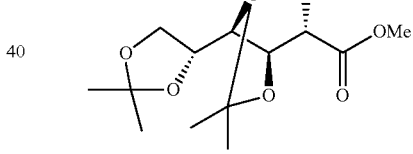

Example (3,4),(5,6)-Bisacetonide-2-Deoxy-2-Azido-D-Mannonic Acid Methyl Ester. In a dry 100 mL round bottom flask, under argon (3,4),(5,6)-bisacetonide-2-OTf-D-gluconic acid methyl ester (5.5 g g, 13.02 mmol) was dissolved in DMF (20 mL). To this solution NaN$_3$ (0.93 g, 14.32 mmol) was added. This solution was stirred at room temperature for 1 h. TLC (8% EtOAc in petroleum ether, triple run) showed that all of the starting material had been consumed and product had been formed. DMF was removed under reduced pressure. The reaction mixture was diluted with brine and extracted with EtOAc. The organic layer was washed with water, brine, dried over Na$_2$SO$_4$, and concentrated to dryness. This crude material was then loaded onto a SiO$_2$ column and chromatographed (20% EtOAc in petroleum ether) to yield pure (3,4),(5,6)-bisacetonide-2-deoxy-2-azido-D-mannonic acid methyl ester (3.8 g, 93%). $^1$H NMR data was in accordance with the product. C$_{13}$H$_{21}$N$_3$O$_6$; MW 315.32; Exact Mass: 315.14.

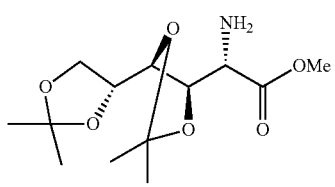

Example (3,4),(5,6)-Bisacetonide-2-Deoxy-2-Amino-D-Mannonic Acid Methyl Ester. In a Parr hydrogenation flask, (3,4),(5,6)-bisacetonide-2-deoxy-2-azido-D-mannonic acid methyl ester (3.5 g g, 11.10 mmol) was dissolved in methanol (170 mL). To this solution 10% Pd on carbon (800 mg, 5 mol %) was added. Hydrogenation was carried out using Parr-hydrogenator at 25 PSI for 1 h. TLC (10% methanol in methylene chloride) showed that all of the starting material had been consumed and product had been formed. The reaction mixture was filtered through a celite pad and concentrated to dryness. This crude material was then loaded onto a $SiO_2$ column and chromatographed (2% methanol in methylene chloride) to yield pure (3,4),(5,6)-bisacetonide-2-deoxy-2-amino-D-mannonic acid methyl ester (2.61 g, 81%). $^1$H NMR data was in accordance with the product. $C_{13}H_{23}NO_6S$ MW 289.32; Exact Mass: 289.15.

Example (3,4),(5,6)-Bisacetonide-2-Deoxy-2-Fmoc-Amino-D-Mannonic Acid. In a dry 100 mL round bottom flask, (3,4),(5,6)-bisacetonide-2-deoxy-2-amino-D-mannonic acid methyl ester (1.24 g, 4.29 mmol) was dissolved in THF/MeOH (20 mL/5 mL). To this solution LiOH.H$_2$O (215.8 mg, 5.14 mmol) in water (5 mL) was added. This light yellow solution was stirred at room temperature for 2 h. TLC (10% methanol in methylene chloride) showed that all of the starting material had been consumed and product had been formed. THF/MeOH was removed under reduced pressure. The aqueous phase was re-suspended in sat. NaHCO$_3$ (10 mL). To this suspension Fmoc-OSu (1.74 g, 5.14 mmol) in 1,4-dioxane (10 mL) was added. This heterogeneous solution was stirred at room temperature for 18 h. TLC (10% methanol in methylene chloride) showed that most of the starting material had been consumed and product had been formed. Dioxane was removed under reduced pressure. The aqueous layer was extracted with diethyl ether to remove less polar impurities. Then the aqueous layer was acidified to pH 6 using 0.2N HCl, and re-extracted with EtOAc. The EtOAc layer was washed with brine, dried over Na$_2$SO$_4$, and concentrated to yield (3,4),(5,6)-bisacetonide-2-deoxy-2-Fmoc-amino-D-mannonic acid (1.6 g, 76%). This material was used in the next reaction without further purification. $^1$H NMR data was in accordance with the product. $C_{27}H_{31}NO_8$; MW 497.54; Exact Mass: 497.20.

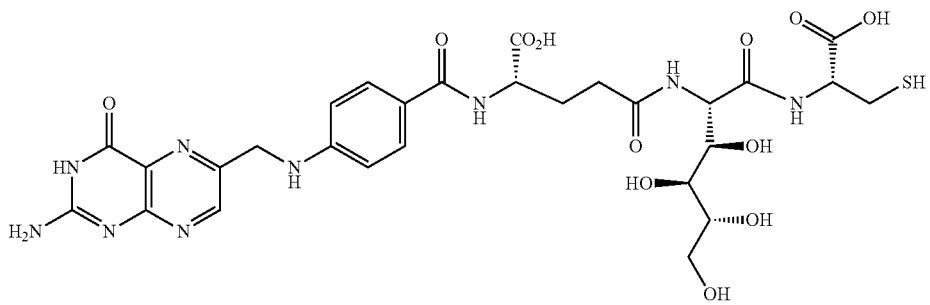 [SMILES: Nc1nc2ncc(CNc3ccc(C(=O)N[C@@H](CCC(=O)N[C@H](C(=O)N[C@@H](CS)C(=O)O)[C@@H](O)[C@H](O)[C@H](O)CO)C(=O)O)cc3)nc2c(=O)[nH]1]

Example

EC0233 was synthesized by SPPS in three steps according to the general peptide synthesis procedure described herein starting from H-Cys(4-methoxytrityl)-2-chlorotrityl-Resin, and the following SPPS reagents:

| Reagents | mmol | Equivalent | MW | amount |
|---|---|---|---|---|
| H-Cys(4-methoxytrityl)-2-chlorotrityl-Resin (loading 0.56 mmol/g) | 0.56 | | | 1.0 g |
| (3,4), (5,6)-bisacetonide-2-deoxy-2-Fmoc-amino-D-mannonic acid | 0.7 | 1.25 | 497.54 | 0.348 g |
| Fmoc-Glu-OtBu | 1.12 | 2 | 425.5 | 0.477 g |
| N$^{10}$TFA-Pteroic Acid (dissolve in 10 ml DMSO) | 0.70 | 1.25 | 408 | 0.286 g |
| DIPEA | 2.24 | 4 | 129.25 (d = 0.742) | 0.390 mL |
| PyBOP | 1.12 | 2 | 520 | 0.583 g |

Coupling steps. In a peptide synthesis vessel add the resin, add the amino acid solution, DIPEA, and PyBOP. Bubble argon for 1 hr. and wash 3× with DMF and IPA. Use 20% piperdine in DMF for Fmoc deprotection, 3× (10 min), before each amino acid coupling. Continue to complete all 3 coupling steps. At the end wash the resin with 2% hydrazine in DMF 3× (5 min) to cleave TFA protecting group on Pteroic acid.

Cleavage step. Cleavage Reagent: 92.5% (50 ml) TFA, 2.5% (1.34 ml) H$_2$O, 2.5% (1.34 ml) triisopropylsilane, 2.5% (1.34 ml) ethanedithiol. Add 25 ml cleavage reagent and bubble argon for 20 min, drain, and wash 3× with remaining reagent. Rotavap until 5 ml remains and precipitate in ethyl ether. Centrifuge and dry.

HPLC Purification step. Column: Waters NovaPak $C_{18}$ 300×19 mm; Buffer A=10 mM ammonium acetate, pH 5; B=ACN; Method: 1% B to 20% B in 40 minutes at 15 ml/min; yield ~202 mg, 50%. $C_{28}H_{35}N_9O_{12}S$; MW 721.70; Exact Mass: 721.21.

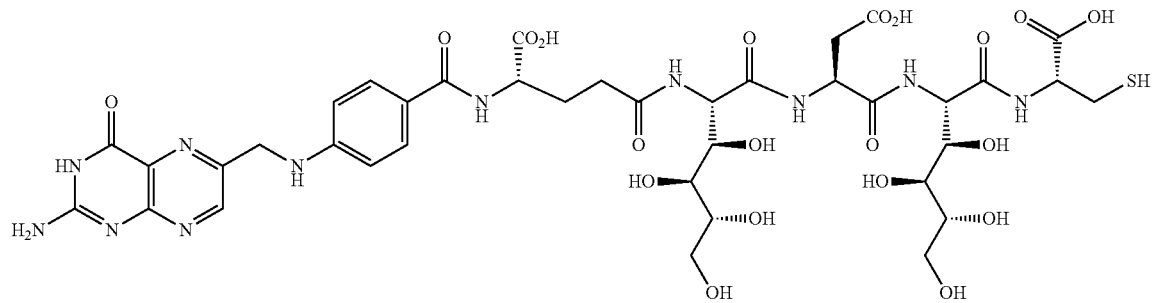 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@@H](CS)C(=O)O)[C@@H](O)[C@H](O)[C@H](O)CO)[C@@H](O)[C@H](O)[C@H](O)CO)C(=O)O)cc3)nc2c(=O)[nH]1]

Example

Bis-Saccharo-Folate Linker EC0244. EC0244 was synthesized by SPPS in five steps according to the general peptide synthesis procedure described herein starting from H-Cys(4-methoxytrityl)-2-chlorotrityl-Resin, and the following SPPS reagents:

| Reagents | mmol | Equivalent | MW | amount |
|---|---|---|---|---|
| H-Cys(4-methoxytrityl)-2-chlorotrityl-Resin (loading 0.56 mmol/g) | 0.56 | | | 1.0 g |
| (3,4), (5,6)-bisacetonide-2-deoxy-2-Fmoc-amino-D-mannonic acid | 0.7 | 1.25 | 497.54 | 0.348 g |
| Fmoc-Asp(OtBu)-OH | 1.12 | 2 | 411.5 | 0.461 g |
| (3,4), (5,6)-bisacetonide-2-deoxy-2-Fmoc-amino-D-mannonic acid | 0.7 | 1.25 | 497.54 | 0.348 g |
| Fmoc-Glu-OtBu | 1.12 | 2 | 425.5 | 0.477 g |
| $N^{10}$TFA-Pteroic Acid (dissolve in 10 ml DMSO) | 0.70 | 1.25 | 408 | 0.286 g |
| DIPEA | 2.24 | 4 | 129.25 (d = 0.742) | 0.390 mL |
| PyBOP | 1.12 | 2 | 520 | 0.583 g |

The Coupling steps, Cleavage step, Cleavage Reagent, and HPLC Purification step were identical to those described above; yield ~284 mg, 50%. $C_{38}H_{51}N_{11}O_{20}S$; MW 1013.94; Exact Mass: 1013.30.

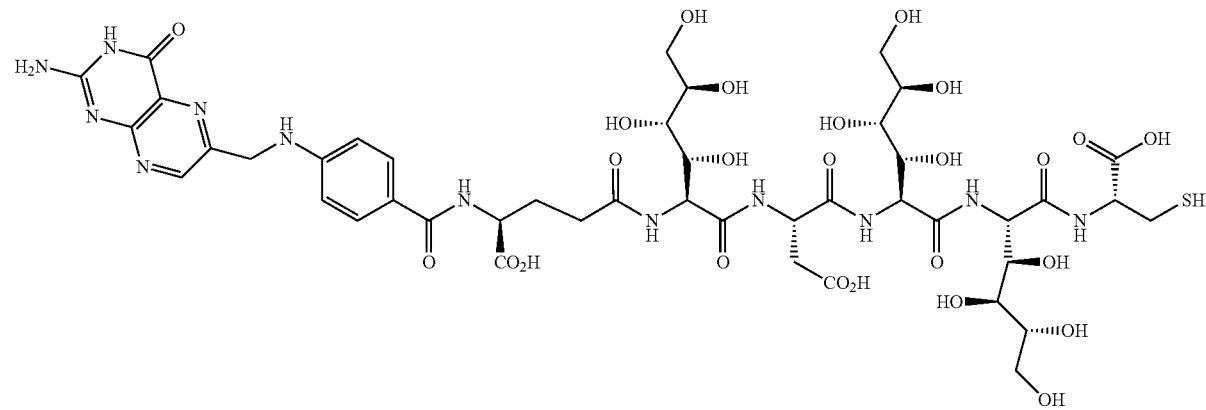 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@H](C(=O)N[C@@H](CS)C(=O)O)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]

Example

EC0257 was synthesized by SPPS in six steps according to the general peptide synthesis procedure described herein starting from H-Cys(4-methoxytrityl)-2-chlorotrityl-Resin, and the following SPPS reagents:

| Reagents | mmol | Equivalent | MW | amount |
|---|---|---|---|---|
| H-Cys(4-methoxytrityl)-2-chlorotrityl-Resin (loading 0.56 mmol/g) | 0.2 | | | 0.333 g |
| (3,4), (5,6)-bisacetonide-2-deoxy-2-Fmoc-amino-D-mannonic acid | 0.25 | 1.25 | 497.54 | 0.124 g |
| (3,4), (5,6)-bisacetonide-2-deoxy-2-Fmoc-amino-D-mannonic acid | 0.25 | 1.25 | 497.54 | 0.124 g |
| Fmoc-Asp(OtBu)-OH | 0.4 | 2 | 411.5 | 0.165 g |
| (3,4), (5,6)-bisacetonide-2-deoxy-2-Fmoc-amino-D-mannonic acid | 0.25 | 1.25 | 497.54 | 0.124 g |
| Fmoc-Glu-OtBu | 0.4 | 2 | 425.5 | 0.170 g |
| $N^{10}$TFA-Pteroic Acid (dissolve in 10 ml DMSO) | 0.25 | 1.25 | 408 | 0.119 g |
| DIPEA | 0.8 | 4 | 129.25 (d = 0.742) | 0.139 mL |
| PyBOP | 0.4 | 2 | 520 | 0.208 g |

The Coupling steps, Cleavage step, Cleavage Reagent, and HPLC Purification step were identical to those described above; yield ~170 mg, 71%. $C_{44}H_{62}N_{12}O_{25}S$; MW 1191.09; Exact Mass: 1190.37.

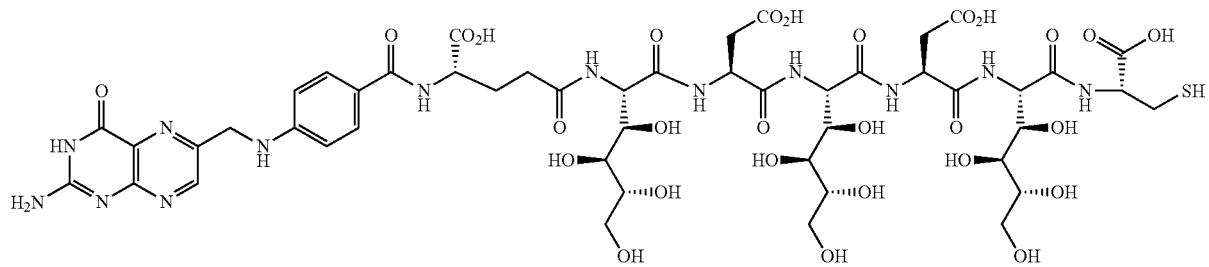 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@@H](CC(=O)O)C(=O)N[C@H](C(=O)N[C@@H](CS)C(=O)O)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]

Example

EC0261 was synthesized by SPPS in seven steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.56 mmol/g) | 0.2 | | | 0.333 g |
| (3,4), (5,6)-bisacetonide-2-deoxy-2-Fmoc-amino-D-mannonic acid | 0.25 | 1.25 | 497.54 | 0.124 g |
| Fmoc-Asp(OtBu)-OH | 0.4 | 2 | 411.5 | 0.165 g |
| (3,4), (5,6)-bisacetonide-2-deoxy-2-Fmoc-amino-D-mannonic acid | 0.25 | 1.25 | 497.54 | 0.124 g |
| Fmoc-Asp(OtBu)-OH | 0.4 | 2 | 411.5 | 0.165 g |
| (3,4), (5,6)-bisacetonide-2-deoxy-2-Fmoc-amino-D-mannonic acid | 0.25 | 1.25 | 497.54 | 0.124 g |
| Fmoc-Glu-OtBu | 0.4 | 2 | 425.5 | 0.170 g |
| $N^{10}$TFA-Pteroic Acid (dissolve in 10 ml DMSO) | 0.25 | 1.25 | 408 | 0.119 g |
| DIPEA | 0.8 | 4 | 129.25 (d = 0.742) | 0.139 mL |
| PyBOP | 0.4 | 2 | 520 | 0.208 g |

The Coupling steps, Cleavage step, Cleavage Reagent, and HPLC Purification step were identical to those described above; yield ~170 mg, 65%. $C_{48}H_{67}N_{13}O_{28}S$; MW 1306.18; Exact Mass: 1305.39.

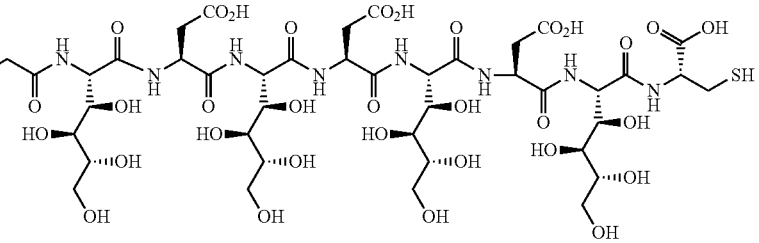

Example

Tetra-Saccharo-Tris-Asp-Folate Linker EC0268. EC0268 was synthesized by SPPS in nine steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.56 mmol/g) | 0.1 | | | 0.167 g |
| (3,4), (5,6)-bisacetonide-2-deoxy-2-Fmoc-amino-D-mannonic acid | 0.125 | 1.25 | 497.54 | 0.062 g |
| Fmoc-Asp(OtBu)-OH | 0.2 | 2 | 411.5 | 0.082 g |
| (3,4), (5,6)-bisacetonide-2-deoxy-2-Fmoc-amino-D-mannonic acid | 0.125 | 1.25 | 497.54 | 0.062 g |
| Fmoc-Asp(OtBu)-OH | 0.2 | 2 | 411.5 | 0.082 g |
| (3,4), (5,6)-bisacetonide-2-deoxy-2-Fmoc-amino-D-mannonic acid | 0.125 | 1.25 | 497.54 | 0.062 g |

-continued

| Reagents | mmol | equivalent | MW | Amount |
|---|---|---|---|---|
| 2-deoxy-2-Fmoc-amino-D-mannonic acid | | | | |
| Fmoc-Asp(OtBu)-OH | 0.2 | 2 | 411.5 | 0.082 g |
| (3,4), (5,6)-bisacetonide-2-deoxy-2-Fmoc-amino-D-mannonic acid | 0.125 | 1.25 | 497.54 | 0.062 g |
| Fmoc-Glu-OtBu | 0.2 | 2 | 425.5 | 0.085 g |
| N$^{10}$TFA-Pteroic Acid (dissolve in 10 ml DMSO) | 0.125 | 1.25 | 408 | 0.059 g |
| DIPEA | 0.4 | 4 | 129.25 (d = 0.742) | 0.070 mL |
| PyBOP | 0.2 | 2 | 520 | 0.104 g |

The Coupling steps, Cleavage step, Cleavage Reagent, and HPLC Purification step were identical to those described above; yield ~100 mg, 63%. $C_{94}H_{125}N_{19}O_{37}S_2$; MW 2177.24; Exact Mass: 2175.79.

The following illustrative examples may be prepared according to the procedure for EC0268:

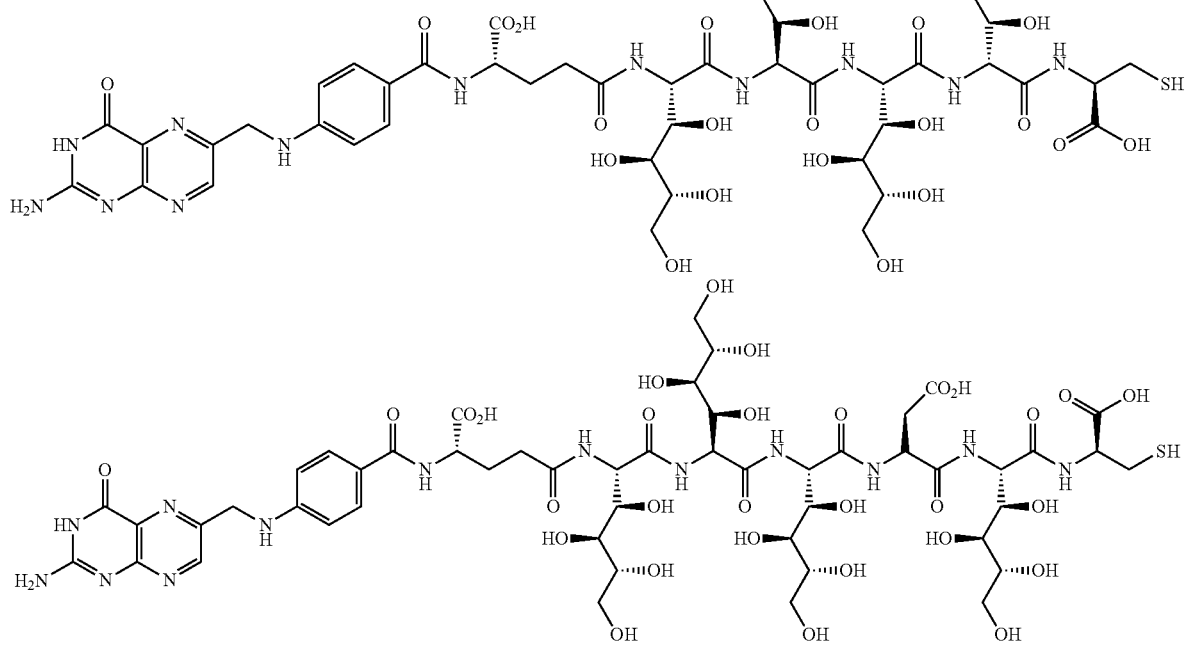

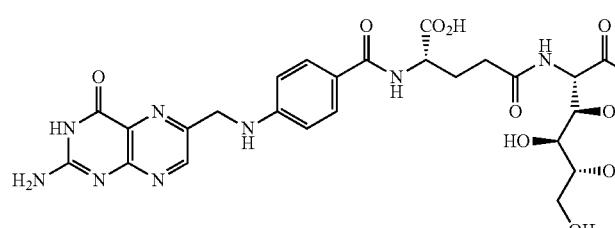
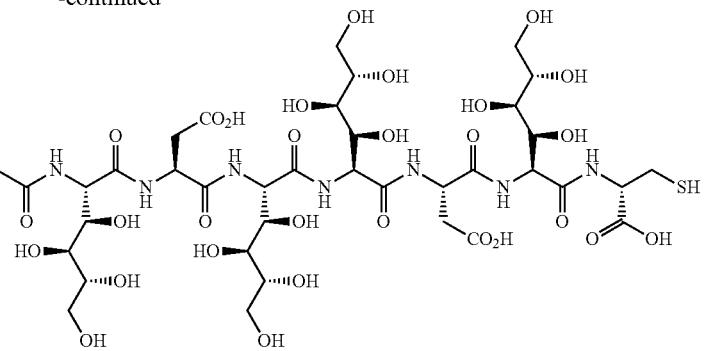

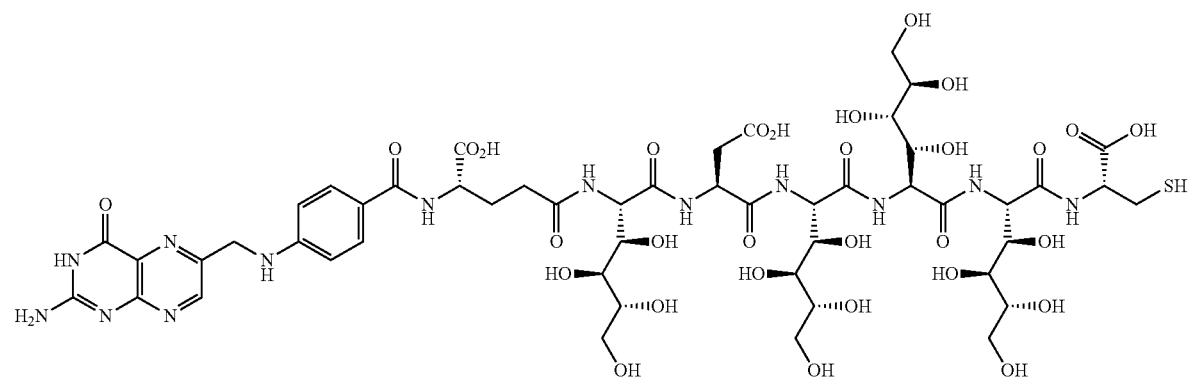

Example

Tetra-Saccharo-Asp-Folate Linker EC0463. EC0463 was synthesized by SPPS in seven steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.56 mmol/g) | 0.1 | | | 0.167 g |
| (3,4), (5,6)-bisacetonide-2-deoxy-2-Fmoc-amino-D-mannonic acid | 0.125 | 1.25 | 497.54 | 0.062 g |
| (3,4), (5,6)-bisacetonide-2-deoxy-2-Fmoc-amino-D-mannonic acid | 0.125 | 1.25 | 497.54 | 0.062 g |
| (3,4), (5,6)-bisacetonide-2-deoxy-2-Fmoc-amino-D-mannonic acid | 0.125 | 1.25 | 497.54 | 0.062 g |
| Fmoc-Asp(OtBu)-OH | 0.2 | 2 | 411.5 | 0.082 g |
| (3,4), (5,6)-bisacetonide-2-deoxy-2-Fmoc-amino-D-mannonic acid | 0.125 | 1.25 | 497.54 | 0.062 g |
| Fmoc-Glu-OtBu | 0.2 | 2 | 425.5 | 0.085 g |
| $N^{10}$TFA-Pteroic Acid (dissolve in 10 ml DMSO) | 0.125 | 1.25 | 408 | 0.059 g |
| DIPEA | 0.4 | 4 | 129.25 (d = 0.742) | 0.070 mL |
| PyBOP | 0.2 | 2 | 520 | 0.104 g |

The Coupling steps, Cleavage step, Cleavage Reagent, and HPLC Purification step were identical to those described above; yield ~63 mg, 46%. $C_{50}H_{73}N_{13}O_{30}S$; MW 1368.25; Exact Mass. 1367.43.

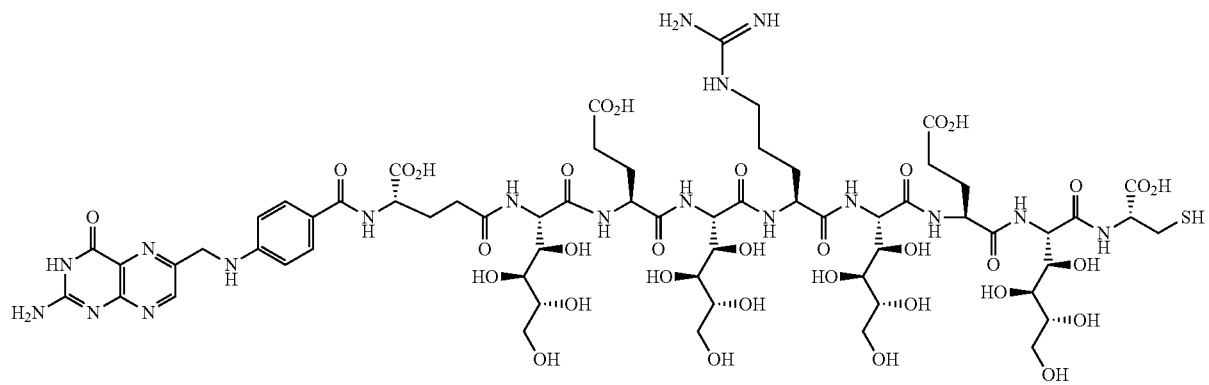 [SMILES: N=C(N)NCCC[C@H](NC(=O)[C@@H](NC(=O)[C@H](CCC(=O)O)NC(=O)[C@@H](NC(=O)CC[C@H](NC(=O)c1ccc(NCc2cnc3nc(N)[nH]c(=O)c3n2)cc1)C(=O)O)[C@@H](O)[C@H](O)[C@H](O)CO)[C@@H](O)[C@H](O)[C@H](O)CO)C(=O)N[C@H](C(=O)N[C@@H](CCC(=O)O)C(=O)N[C@H](C(=O)N[C@@H](CS)C(=O)O)[C@@H](O)[C@H](O)[C@H](O)CO)[C@@H](O)[C@H](O)[C@H](O)CO]

Example

Tetra-Saccharo-Bis-α-Glu-Arg-Folate Linker EC0480. EC0480 was synthesized by SPPS in nine steps according to the general peptide synthesis procedure described herein starting from H-Cys(4-methoxytrityl)-2-chlorotrityl-Resin, and the following SPPS reagents:

The Coupling steps, Cleavage step, Cleavage Reagent, and HPLC Purification step were identical to those described above; yield ~100 mg, 33%. $C_{62}H_{94}N_{18}O_{20}S$; MW 1667.58; Exact Mass: 1666.59.

Example

Tetra-Saccharo-Bis-Asp-Folate Linker EC0452:

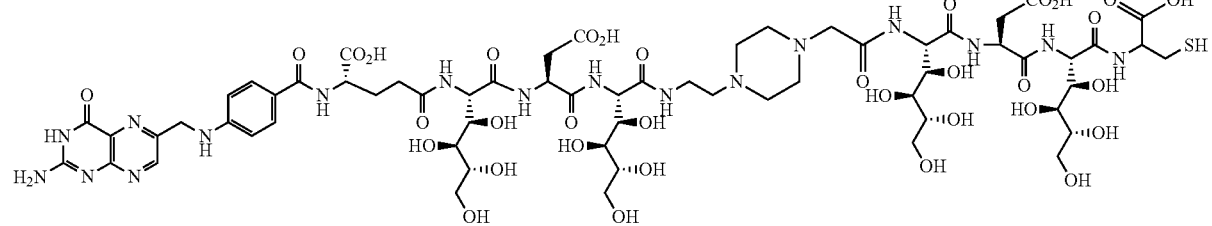

| Reagents | mmol | equivalent | MW | Amount |
|---|---|---|---|---|
| H-Cys(4-methoxytrityl)-2-chlorotrityl-Resin (loading 0.56 mmol/g) | 0.2 | | | 0.333 g |
| (3,4), (5,6)-bisacetonide-2-deoxy-2-Fmoc-amino-D-mannonic acid | 0.250 | 1.25 | 497.54 | 0.124 g |
| Fmoc-Glu(OtBu)-OH | 0.4 | 2 | 425.5 | 0.170 g |
| (3,4), (5,6)-bisacetonide-2-deoxy-2-Fmoc-amino-D-mannonic acid | 0.250 | 1.25 | 497.54 | 0.124 g |
| Fmoc-Arg(Pbf)-OH | 0.4 | 2 | 648.78 | 0.260 g |
| (3,4), (5,6)-bisacetonide-2-deoxy-2-Fmoc-amino-D-mannonic acid | 0.250 | 1.25 | 497.54 | 0.124 g |
| Fmoc-Glu(OtBu)-OH | 0.4 | 2 | 425.5 | 0.170 g |
| (3,4), (5,6)-bisacetonide-2-deoxy-2-Fmoc-amino-D-mannonic acid | 0.250 | 1.25 | 497.54 | 0.124 g |
| Fmoc-Glu-OtBu | 0.4 | 2 | 425.5 | 0.170 g |
| $N^{10}$TFA-Pteroic Acid (dissolve in 10 ml DMSO) | 0.250 | 1.25 | 408 | 0.119 g |
| DIPEA | 0.8 | 4 | 129.25 (d = 0.742) | 0.139 mL |
| PyBOP | 0.4 | 2 | 520 | 0.208 g |

Example

Tetra-Saccharo-Bis-Asp-Folate Linker EC0452. EC0452 was synthesized by SPPS in nine steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.6 mmol/g) | 0.15 | | | 0.250 g |
| (3,4), (5,6)-bisacetonide-2-deoxy-2-Fmoc-amino-D-mannonic acid | 0.188 | 1.25 | 497.54 | 0.094 g |
| Fmoc-Asp(OtBu)-OH | 0.3 | 2 | 411.5 | 0.123 g |
| (3,4), (5,6)-bisacetonide-2-deoxy-2-Fmoc-amino-D-mannonic acid | 0.188 | 1.25 | 497.54 | 0.094 g |
| Fmoc-4-(2-aminoethyl)-1-carboxymethyl-piperazine dihydrochloride | 0.3 | 2 | 482.42 | 0.145 g |
| (3,4), (5,6)-bisacetonide-2-deoxy-2-Fmoc-amino-D-mannonic acid | 0.188 | 1.25 | 497.54 | 0.094 g |

| Reagents | mmol | equivalent | MW | Amount |
|---|---|---|---|---|
| Fmoc-Asp(OtBu)-OH | 0.3 | 2 | 411.5 | 0.123 g |
| (3,4), (5,6)-bisacetonide-2-deoxy-2-Fmoc-amino-D-mannonic acid | 0.188 | 1.25 | 497.54 | 0.094 g |
| Fmoc-Glu-OtBu | 0.3 | 2 | 425.5 | 0.128 g |
| $N^{10}$TFA-Pteroic Acid (dissolve in 10 ml DMSO) | 0.188 | 1.25 | 408 | 0.077 g |

| Reagents | mmol | equivalent | MW | Amount |
|---|---|---|---|---|
| DIPEA | 0.6 | 4 | 129.25 (d = 0.742) | 0.105 mL |
| PyBOP | 0.3 | 2 | 520 | 0.156 g |

The Coupling steps, Cleavage step, and Cleavage Reagent were identical to those described above. HPLC Purification step. Column: Waters NovaPak $C_{18}$ 300×19 mm; Buffer A=10 mM ammonium acetate, pH 5; B=ACN; Method: 1% B to 20% B in 40 minutes at 25 ml/min; yield ~98 mg, 40%. $C_{62}H_{93}N_{17}O_{34}S$; MW 1652.56; Exact Mass: 1651.58.

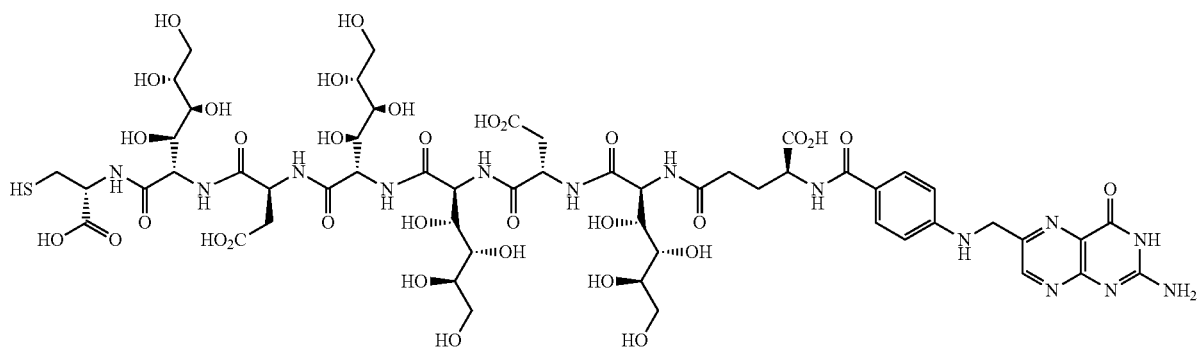 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@H](C(=O)N[C@@H](CC(=O)O)C(=O)N[C@H](C(=O)N[C@@H](CS)C(=O)O)[C@@H](O)[C@H](O)[C@H](O)CO)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]

Example

Tetra-Saccharo-bis-Asp-Folate Linker EC0457. EC0457 was synthesized by SPPS in eight steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.6 mmol/g) | 0.20 | | | 0.333 g |
| (3,4), (5,6)-bisacetonide-2-deoxy-2-Fmoc-amino-D-mannonic acid | 0.25 | 1.25 | 497.54 | 0.124 g |
| Fmoc-Asp(OtBu)-OH | 0.30 | 1.5 | 411.5 | 0.123 g |
| (3,4), (5,6)-bisacetonide-2-deoxy-2-Fmoc-amino-D-mannonic acid | 0.25 | 1.25 | 497.54 | 0.124 g |
| (3,4), (5,6)-bisacetonide-2-deoxy-2-Fmoc-amino-D-mannonic acid | 0.25 | 1.25 | 497.54 | 0.124 g |
| Fmoc-Asp(OtBu)-OH | 0.30 | 1.5 | 411.5 | 0.123 g |
| (3,4), (5,6)-bisacetonide-2-deoxy-2-Fmoc-amino-D-mannonic acid | 0.25 | 1.25 | 497.54 | 0.124 g |
| Fmoc-Glu-OtBu | 0.30 | 1.5 | 425.5 | 0.128 g |
| $N^{10}$TFA-Pteroic Acid (dissolve in 10 ml DMSO) | 0.25 | 1.25 | 408 | 0.102 g |
| DIPEA | | 2 eq. of amino acid | 129.25 (d = 0.742) | 87 μL or 105 μL |
| PyBOP | | 2 eq. of amino acid | 520 | 260 mg or 312 mg |

The Coupling steps, Cleavage step, and Cleavage Reagent were identical to those described above. HPLC Purification step. Column: Waters NovaPak $C_{18}$ 300×19 mm; Buffer A=10 mM ammonium acetate, pH 5; B=ACN; Method: 0% B to 20% B in 40 minutes at 25 ml/min; yield ~210 mg, 71%. $C_{54}H_{78}N_{14}O_{33}S$; MW 1483.34; Exact Mass: 1482.46.

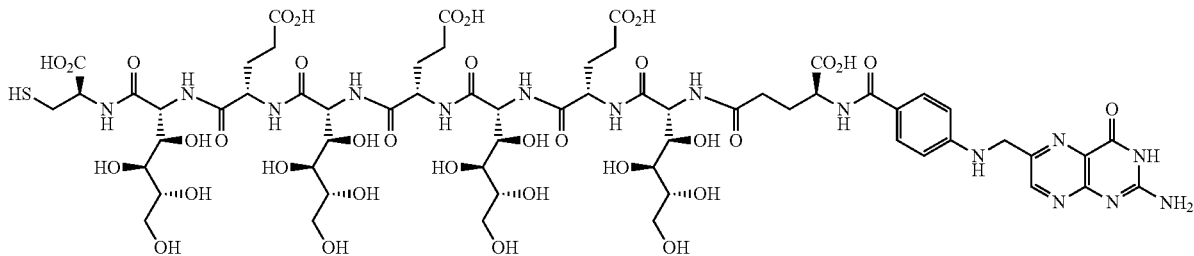 [SMILES: Nc1nc2ncc(CNc3ccc(C(=O)N[C@@H](CCC(=O)N[C@@H](C(=O)N[C@@H](CCC(=O)O)C(=O)N[C@@H](C(=O)N[C@@H](CCC(=O)O)C(=O)N[C@@H](C(=O)N[C@@H](CCC(=O)O)C(=O)N[C@@H](C(=O)N[C@@H](CS)C(=O)O)[C@@H](O)[C@H](O)[C@H](O)CO)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]

Example

Tetra-Saccharo-tris-Glu-Folate Linker EC0477. EC0477 was synthesized by SPPS in nine steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.6 mmol/g) | 0.20 | | | 0.333 g |
| (3,4), (5,6)-bisacetonide-2-deoxy-2-Fmoc-amino-D-mannonic acid | 0.25 | 1.25 | 497.54 | 0.124 g |
| Fmoc-Glu(OtBu)-OH | 0.30 | 1.5 | 425.5 | 0.128 g |
| (3,4), (5,6)-bisacetonide-2-deoxy-2-Fmoc-amino-D-mannonic acid | 0.25 | 1.25 | 497.54 | 0.124 g |
| Fmoc-Glu(OtBu)-OH | 0.30 | 1.5 | 425.5 | 0.128 g |
| (3,4), (5,6)-bisacetonide-2-deoxy-2-Fmoc-amino-D-mannonic acid | 0.25 | 1.25 | 497.54 | 0.124 g |
| Fmoc-Glu(OtBu)-OH | 0.30 | 1.5 | 425.5 | 0.128 g |
| (3,4), (5,6)-bisacetonide-2-deoxy-2-Fmoc-amino-D-mannonic acid | 0.25 | 1.25 | 497.54 | 0.124 g |
| Fmoc-Glu-OtBu | 0.30 | 1.5 | 425.5 | 0.128 g |
| $N^{10}$TFA-Pteroic Acid (dissolve in 10 ml DMSO) | 0.25 | 1.25 | 408 | 0.102 g |
| DIPEA | | 2 eq. of amino acid | 129.25 (d = 0.742) | 87 µL or 105 µL |
| PyBOP | | 1 eq. of amino acid | 520 | 130 mg or 156 mg |

The Coupling steps, Cleavage step, and Cleavage Reagent were identical to those described above. HPLC Purification step. Column: Waters NovaPak $C_{18}$ 300×19 mm; Buffer A=10 mM ammonium acetate, pH 5; B=ACN; Method: 0% B to 20% B in 40 minutes at 25 ml/min; yield ~220 mg, 67%. $C_{61}H_{89}N_{15}O_{36}S$; MW 1640.50; Exact Mass: 1639.53.

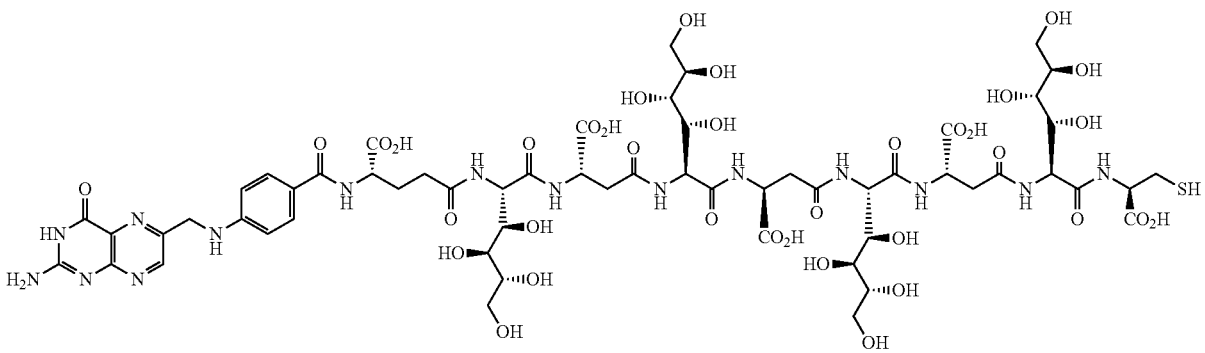 [SMILES: Nc1nc2ncc(CNc3ccc(C(=O)N[C@@H](CCC(=O)N[C@H](C(=O)N[C@@H](CC(=O)N[C@H](C(=O)N[C@@H](CC(=O)N[C@H](C(=O)N[C@@H](CC(=O)N[C@H](C(=O)N[C@@H](CS)C(=O)O)[C@@H](O)[C@H](O)[C@H](O)CO)C(=O)O)[C@@H](O)[C@H](O)[C@H](O)CO)C(=O)O)[C@@H](O)[C@H](O)[C@H](O)CO)C(=O)O)[C@@H](O)[C@H](O)[C@H](O)CO)C(=O)O)cc3)nc2c(=O)[nH]1]

Example

EC0453 was synthesized by SPPS according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.56 mmol/g) | 0.162 | | | 0.290 g |
| (3,4), (5,6)-bisacetonide-2-deoxy-2-Fmoc-amino-D-mannonic acid | 0.203 | 1.25 | 497.54 | 0.101 g |
| Fmoc-Asp(OtBu)-OH | 0.324 | 2 | 411.5 | 0.133 g |
| (3,4), (5,6)-bisacetonide-2-deoxy-2-Fmoc-amino-D-mannonic acid | 0.203 | 1.25 | 497.54 | 0.101 g |
| Fmoc-Asp(OtBu)-OH | 0.324 | 2 | 411.5 | 0.133 g |
| (3,4), (5,6)-bisacetonide-2-deoxy-2-Fmoc-amino-D-mannonic acid | 0.203 | 1.25 | 497.54 | 0.101 g |
| Fmoc-Asp(OtBu)-OH | 0.324 | 2 | 411.5 | 0.133 g |
| (3,4), (5,6)-bisacetonide-2-deoxy-2-Fmoc-amino-D-mannonic acid | 0.203 | 1.25 | 497.54 | 0.101 g |
| Fmoc-Glu-OtBu | 0.324 | 2 | 425.5 | 0.138 g |
| $N^{10}$TFA-Pteroic Acid (dissolve in 10 ml DMSO) | 0.203 | 1.25 | 408 | 0.083 g |
| DIPEA | | 2 eq of AA | | 71 µL or 85 µL |
| PyBOP | | 1 eq of AA | | 211 mg or 253 mg |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Cleavage Reagent: 92.5% TFA, 2.5% $H_2O$, 2.5% triisopropylsilane, 2.5% ethanedithiol. Treat the resin with cleavage reagent 3 times (15 min, 5 min, 5 min) with argon bubbling, drain, collect, and combine the solution. Rotavap until 5 ml remains and precipitate in diethyl ether (35 mL). Centrifuge, wash with diethyl ether, and dry. The crude solid was purified by HPLC.

HPLC Purification step, Column: Waters Xterra Prep MS $C_{18}$ 10 µl 19×250 mm; Solvent A: 10 mM ammonium acetate, pH 5; Solvent B: ACN; Method: 5 min 0% B to 40 min 20% B 25 mL/min; Fractions containing the product was collected and freeze-dried to give ~60 mg EC0453 (23% yield). $^1$H NMR and LC/MS were consistent with the product. $C_{58}H_{83}N_{15}O_{36}S$; MW 1598.43; Exact Mass: 1597.48. C, 43.58; H, 5.23; N, 13.14; O, 36.03; S, 2.01.

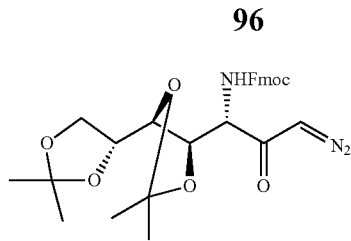

Example (3,4),(5,6)-Bisacetonide-2-deoxy-2-Fmoc-amino-D-Mannonic acid-diazo-ketone. In a dry 100 mL round bottom flask, (3,4),(5,6)-bisacetonide-2-deoxy-2-Fmoc-amino-D-mannonic acid (1.0 g, 2.01 mmol) was dissolved in THF (10 mL, not fully dissolved) under Argon atmosphere. The reaction mixture was cooled to −25° C. To this solution NMM (0.23 mL, 2.11 mmol) and ethylchloroformate (228.98 mg, 2.11 mmol) were added. This solution was stirred at −20° C. for 30 min. The resulting white suspension was allowed to warm to 0° C., and a solution of diazomethane in ether was added until yellow color persisted. Stirring was continued as the mixture was allowed to warm to room temperature. Stirred for 2 h, excess diazomethane was destroyed by the addition of few drops of acetic acid with vigorous stirring. The mixture was diluted with ether, washed with sat, aq. $NaHCO_3$ solution, sat. aq. $NH_4Cl$, brine, dried over $Na_2SO_4$, and concentrated to dryness. This crude material was then loaded onto a $SiO_2$ column and chromatographed (30% EtOAc in petroleum ether) to yield pure (3,4),(5,6)-bisacetonide-2-deoxy-2-Fmoc-amino-D-mannonic acid-diazo-ketone (0.6 g, 57%). $^1$H NMR data was in accordance with the product. $C_{28}H_{31}N_3O_7$; MW 521.56; Exact Mass: 521.22.

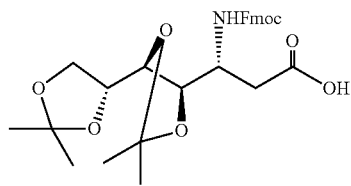

Example (3R,4R,5S,6R)-(4,5),(6,7)-Bisacetonide-3-Fmoc-Amino-Heptanoic acid. In a dry 25 mL round bottom flask, (3,4),(5,6)-bisacetonide-2-deoxy-2-Fmoc-amino-D-mannonic acid-diazo-ketone (0.15 g, 0.29 mmol) was dissolved in THF (1.6 mL) under Argon atmosphere. To this solution silver trifluoroacetate (6.6 mg, 0.03 mmol) in water (0.4 mL) was added in the dark. The resulting mixture was stirred at room temperature for 16 h. TLC (10% MeOH in methylene chloride) showed that all of the starting material had been consumed and product had been formed. Solvent (THF) was removed under reduced pressure, the residue was diluted with water (pH was 3.5-4.0) and extracted with EtOAc. The organic layer was washed with brine, dried over $Na_2SO_4$, and concentrated to dryness. This crude material was then loaded onto a $SiO_2$ column and chromatographed (gradient elution from 1% MeOH in methylene chloride to 5% MeOH in methylene chloride) to yield pure (3R,4R,5S,6R)-(4,5),(6,7)-bisacetonide-3-Fmoc-amino-heptanoic acid (0.10 g, 68%). $^1$H NMR data was in accordance with the product. $C_{28}H_{33}NO_8$; MW 511.56; Exact Mass: 511.22.

with 100 mL liquid ammonia, warmed up to room temperature and heated to 160° C./850 PSI for 2 hours. The reaction vessel was cooled to room temperature and released the pressure. Evaporation of the solvent gave brownish syrup, and minimum amount of isopropyl alcohol was added to make the homogeneous solution with reflux. The solution was cooled to −20° C. and the resulting solid was filtered to give 8.3 g of solid. The mother liquid was evaporated, and to the resulting residue, ether was added and refluxed until homogeneous solution was achieved. The solution was then cooled to −20° C. and the resulting solid was filtered to give 4.0 g product. The solid was combined and recrystallized in isopropyl alcohol to give 11.2 g (59%) of the white amide product. $C_{12}H_{21}NO_6$; MW 275.30; Exact Mass: 275.14.

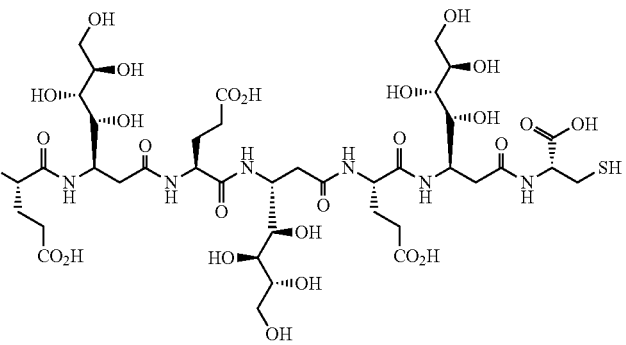

Example

Tetra-Homosaccharo-Tris-αGlu-Folate Spacer EC0478. EC0478 was synthesized by SPPS in nine steps according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.56 mmol/g) | 0.1 | | | 0.167 g |
| Homo sugar | 0.12 | 1.2 | 511.56 | 0.061 g |
| Fmoc-Glu(OtBu)-OH | 0.2 | 2 | 425.5 | 0.085 g |
| Homo sugar | 0.12 | 1.2 | 511.56 | 0.061 g |
| Fmoc-Glu(OtBu)-OH | 0.2 | 2 | 425.5 | 0.085 g |
| Homo sugar | 0.12 | 1.2 | 511.56 | 0.061 g |
| Fmoc-Glu(OtBu)-OH | 0.2 | 2 | 425.5 | 0.085 g |
| Homo sugar | 0.12 | 1.2 | 511.56 | 0.061 g |
| Fmoc-Glu-OtBu | 0.2 | 2 | 425.5 | 0.085 g |
| $N^{10}$TFA-Pteroic Acid•TFA (dissolve in 10 ml DMSO) | 0.12 | 1.2 | 408 | 0.049 g |
| DIPEA | 0.4 | 4 | 129.25 (d = 0.742) | 0.070 mL |
| PyBOP | 0.2 | 2 | 520 | 0.104 g |

The Coupling steps, Cleavage step, and Cleavage Reagent were identical to those described above. HPLC Purification step: Column: Waters NovaPak $C_{18}$ 300×19 mm; Buffer A=10 mM ammonium acetate, pH 5; B=ACN; Method: 100% A for 5 min then 0% B to 20% B in 20 minutes at 26 ml/min; yield ~88 mg, 52%. $C_{65}H_{97}N_{15}O_{36}S$; MW 1696.61; Exact Mass: 1695.59.

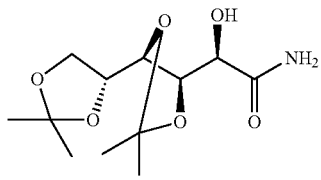

Example (3,4),(5,6)-Bisacetonide-D-Gluconic Amide. 20 g of the methyl ester was dissolved in 100 mL methanol, cooled the high-pressure reaction vessel with dry ice/acetone, charged

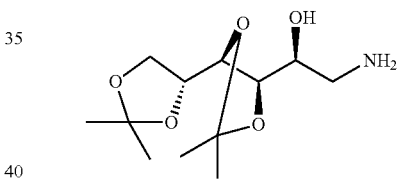

Example (3,4),(5,6)-Bisacetonide-1-Deoxy-1-Amino-D-Glucitol. In a dry 100 mL round bottom flask, under argon, LiAlH$_4$ (450 mg, 11.86 momol)) was dissolved in THF (10 mL) and cooled to 0° C. To this suspension (3,4),(5,6)-bisacetonide-D-gluconic amide (1.09 g, 3.96 mmol) in THF (30 mL) was added very slowly over 15 min. This mixture was refluxed for 5 h. TLC (10% MeOH in methylene chloride) showed that all of the starting material had been consumed and product had been formed. The reaction mixture was cooled to room temperature, and then cooled to ice-bath temperature, diluted with diethyl ether (40 mL), slowly added 0.5 mL of water, 0.5 mL of 15% aq. NaOH, and then added 1.5 mL of water. The reaction mixture was warmed to room temperature and stirred for 30 min. MgSO$_4$ was added and stirred for additional 15 min and filtered. The organic layer was concentrated to dryness to yield (3,4),(5,6)-bisacetonide-1-deoxy-1-amino-D-glucitol. $^1$H NMR data was in accordance with the product. $C_{12}H_{23}NO_5$; MW 261.31; Exact Mass: 261.16.

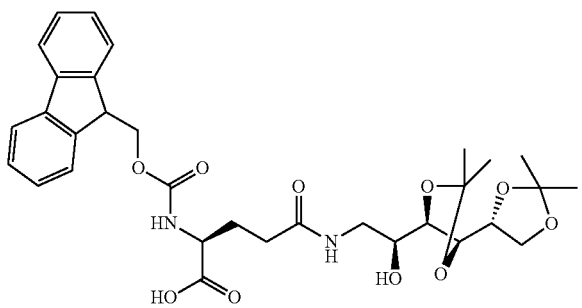

Example

EC0475. O-Allyl protected Fmoc-Glu (2.17 g, 1 eq), PyBOP (2.88 g, 1 eq), and DIPEA (1.83 mL, 2 eq) were added to a solution of (3,4),(5,6)-bisacetonide-1-deoxy-1-amino-D-glucitol (1.4 g, 5.3 mmol) in dry DMF (6 mL) and the mixture was stirred at RT under Ar for 2 h. The solution was diluted with EtOAc (50 mL), washed with brine (10 mL×3), organic layer separated, dried (MgSO$_4$), filtered and concentrated to give a residue, which was purified by a flash column (silica gel, 60% EtOAc/petro-ether) to afford 1.72 g (50%) allyl-protected EC0475 as a solid. Pd(Ph$_3$)$_4$ (300 mg, 0.1 eq) was added to a solution of allyl-protected EC0475 (1.72 g, 2.81 mmol) in NMM/AcOH/CHCl$_3$ (2 mL/4 mL/74 mL). The resulting yellow solution was stirred at RT under Ar for 1 h, to which was added a second portion of Pd(Ph$_3$)$_4$ (300 mg, 0.1 eq). After stirring for an additional 1 h, the mixture was washed with 1 N HCl (50 mL×3) and brine (50 mL), organic layer separated, dried (MgSO4), filtered, and concentrated to give a yellow foamy solid, which was subject to chromatography (silica gel, 1% MeOH/CHCl$_3$ followed by 3.5% MeOH/CHCl$_3$) to give 1.3 g (81%) EC0475 as a solid material. MW 612.67; Exact Mass: 612.27.

Example

Tetra-Saccharoglutamate-Bis-αGlu-Folate Spacer EC0491. EC0491 was synthesized by SPPS in eight steps according to the general peptide synthesis procedure described herein starting from H-Cys(4-methoxytrityl)-2-chlorotrityl-Resin, and the following SPPS reagents:

| Reagents | Mmol | equivalent | MW | Amount |
|---|---|---|---|---|
| H-Cys(4-methoxytrityl)-2-chlorotrityl-Resin (loading 0.56 mmol/g) | 0.1 | | | 0.167 g |
| EC0475 | 0.13 | 1.3 | 612.67 | 0.080 g |
| Fmoc-Glu(OtBu)-OH | 0.2 | 2 | 425.5 | 0.085 g |
| EC0475 | 0.13 | 1.3 | 612.67 | 0.080 g |
| EC0475 | 0.13 | 1.3 | 612.67 | 0.080 g |
| Fmoc-Glu(OtBu)-OH | 0.2 | 2 | 425.5 | 0.085 g |
| EC0475 | 0.13 | 1.3 | 612.67 | 0.080 g |
| Fmoc-Glu-OtBu | 0.2 | 2 | 425.5 | 0.085 g |
| N$^{10}$TFA-Pteroic Acid•TFA (dissolve in 10 ml DMSO) | 0.2 | 2 | 408 | 0.105 g |
| DIPEA | 0.4 | 4 | 129.25 (d = 0.742) | 0.070 mL |
| PyBOP | 0.2 | 2 | 520 | 0.104 g |

The Coupling steps, Cleavage step, and Cleavage Reagent were identical to those described above. HPLC Purification step: Column: Waters NovaPak C$_{18}$ 300×19 mm; Buffer A=10 mM ammonium acetate, pH 5; B=ACN; Method: 100% A for 5 min then 0% B to 20% B in 20 minutes at 26 ml/min; yield ~100 mg, 51%. C$_{76}$H$_{118}$N$_{18}$O$_{41}$S; MW 1971.91; Exact Mass: 1970.74.

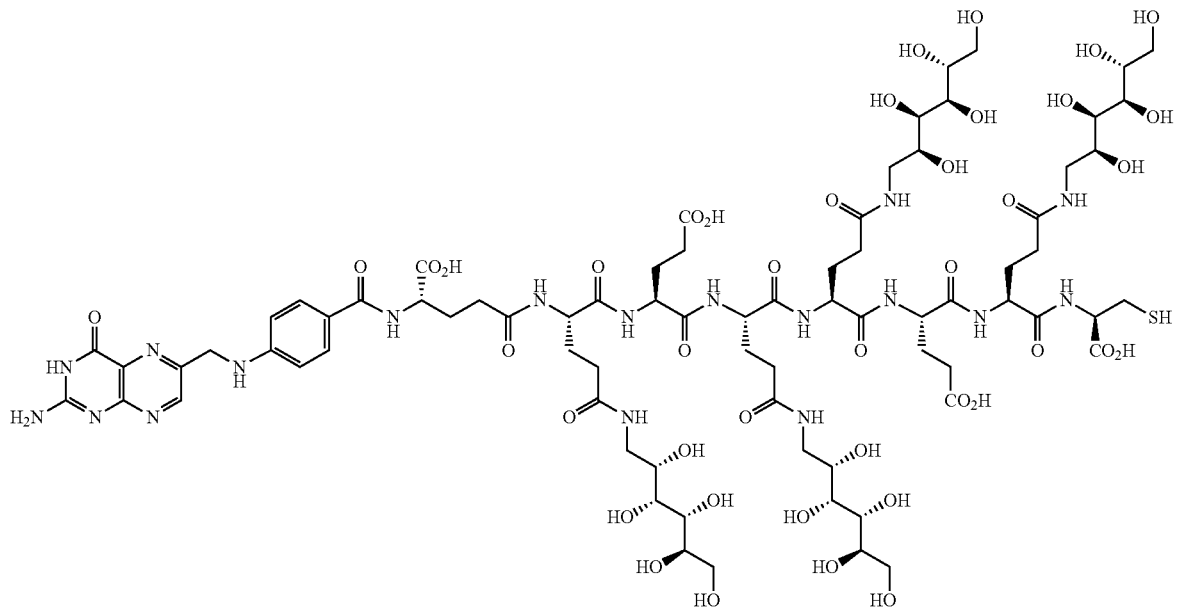 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

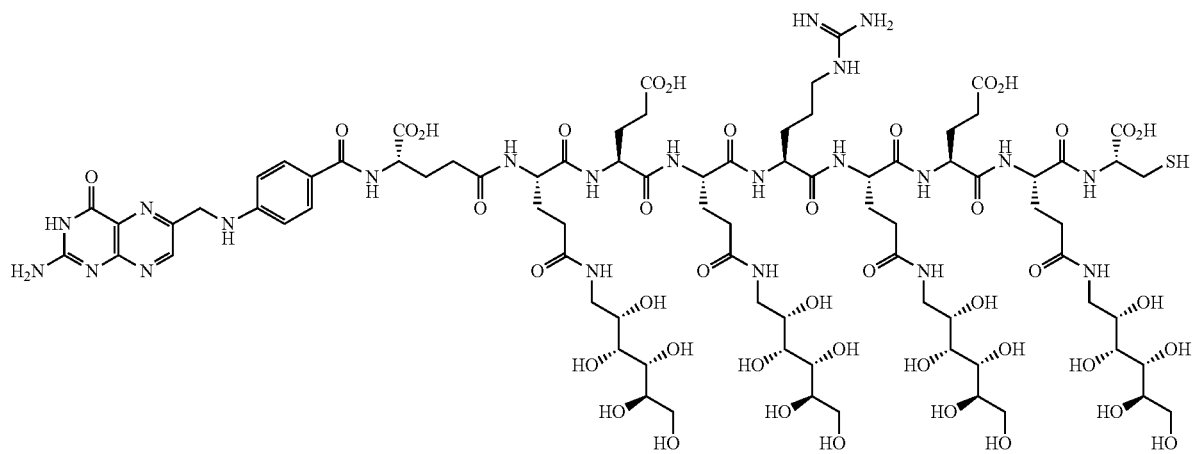 [SMILES: N=C(N)NCCC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c1ccc(NCc2cnc3nc(N)[nH]c(=O)c3n2)cc1)C(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O]

Example

EC0479 was synthesized by SPPS according to the general peptide synthesis procedure described herein starting from H-Cys(4-methoxytrityl)-2-chlorotrityl-Resin, and the following SPPS reagents:

| Reagents | mmol | equivalent | MW | Amount |
|---|---|---|---|---|
| H-Cys(4-methoxytrityl)-2-chlorotrityl-Resin (loading 0.6 mmol/g) | 0.094 | | | 0.16 g |
| EC0475 | 0.13 | 1.4 | 612.67 | 0.082 g |
| Fmoc-Glu(OtBu)-OH | 0.19 | 2.0 | 425.47 | 0.080 g |
| EC0475 | 0.13 | 1.4 | 612.67 | 0.082 g |
| Fmoc-Arg(Pbf)-OH | 0.19 | 2.0 | 648.77 | 0.12 g |
| EC0475 | 0.13 | 1.4 | 612.67 | 0.082 g |
| Fmoc-Glu(OtBu)-OH | 0.19 | 2.0 | 425.47 | 0.080 g |
| EC0475 | 0.13 | 1.4 | 612.67 | 0.082 g |
| Fmoc-Glu-OtBu | 0.19 | 2.0 | 425.47 | 0.080 g |
| $N^{10}$TFA-Pteroic Acid (dissolve in 10 ml DMSO) | 0.16 | 1.7 | 408.29 | 0.066 g |
| DIPEA | | 2.0 eq of AA | | 41 µL or 49 µL |
| PyBOP | | 1.0 eq of AA | | 122 mg or 147 mg |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent for 15 min with argon bubbling, drain, wash the resin once with cleavage reagent, and combine the solution. Rotavap until 5 ml remains and precipitate in diethyl ether (35 mL). Centrifuge, wash with diethyl ether, and dry. The crude solid was purified by HPLC.

HPLC Purification step, Column: Waters Atlantis Prep T3 10 µm OBD 19×250 mm; Solvent A: 10 mM ammonium acetate, pH 5; Solvent B: ACN; Method: 5 min 0% B to 20 min 20% B 26 mL/min. Fractions containing the product was collected and freeze-dried to give ~70 mg EC0479 (35% yield). $^1$H NMR and LC/MS were consistent with the product. MW 2128.10: Exact Mass: 2126.84.

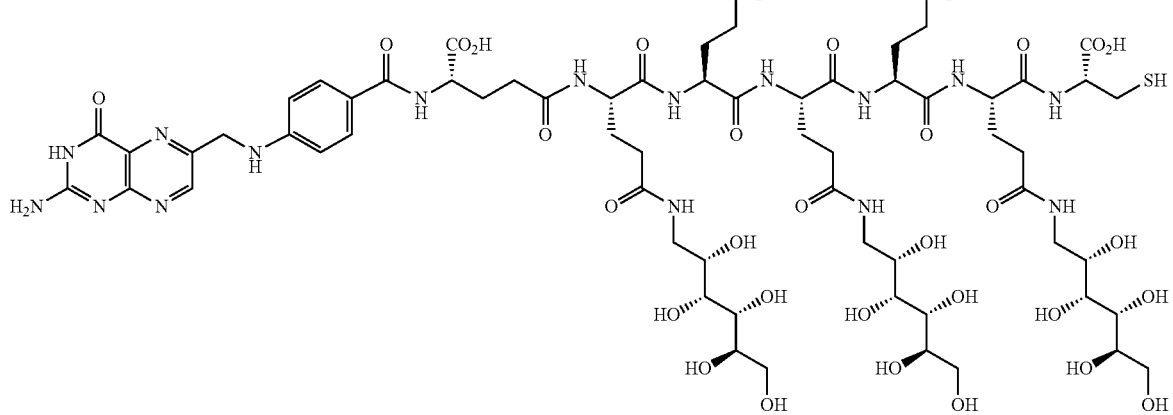

EC0488. This compound was prepared by SPPS according to the general peptide synthesis procedure described herein starting from H-Cys(4-methoxytrityl)-2-chlorotrityl-Resin, and the following SPPS reagents:

| Reagents | mmol | equivalent | MW | amount |
|---|---|---|---|---|
| H-Cys(4-methoxytrityl)-2-chlorotrityl-Resin (loading 0.6 mmol/g) | 0.10 | | | 0.17 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu(OtBu)-OH | 0.19 | 1.9 | 425.47 | 0.080 g |
| EC0475 | 0.13 | 1.3 | 612.67 | 0.082 g |
| Fmoc-Glu-OtBu | 0.19 | 1.9 | 425.47 | 0.080 g |
| $N^{10}$TFA-Pteroic Acid (dissolve in 10 ml DMSO) | 0.16 | 1.6 | 408.29 | 0.066 g |
| DIPEA | | 2.0 eq of AA | | |
| PyBOP | | 1.0 eq of AA | | |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×). IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent 3× (10 min, 5 min, 5 min) with argon bubbling, drain, wash the resin once with cleavage reagent, and combine the solution. Rotavap until 5 ml remains and precipitate in diethyl ether (35 mL). Centrifuge, wash with diethyl ether, and dry. About half of the crude solid (~100 mg) was purified by HPLC.

HPLC Purification step, Column: Waters Xterra Prep MS C18 10 µm 19×250 mm; Solvent A: 10 mM ammonium acetate, pH 5; Solvent B: ACN; Method: 5 min 0% B to 25 min 20% B 26 mL/min. Fractions containing the product was collected and freeze-dried to give 43 mg EC0488 (51% yield). $^1$H NMR and LC/MS (exact mass 1678.62) were consistent with the product. MW 1679.63; Exact Mass: 1678.62.

The following Examples of binding ligand-linker intermediates, EC0233, EC0244, EC0257, and EC0261, were prepared as described herein.

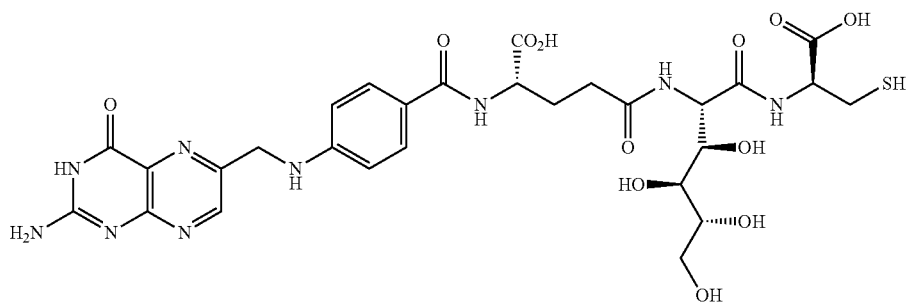 [SMILES: Nc1nc2ncc(CNc3ccc(C(=O)N[C@@H](CCC(=O)N[C@H](C(=O)N[C@H](CS)C(=O)O)[C@@H](O)[C@H](O)[C@H](O)CO)C(=O)O)cc3)nc2c(=O)[nH]1]

EC0233: $C_{28}H_{35}N_9O_{12}S$; MW 721.70; Exact Mass: 721.21

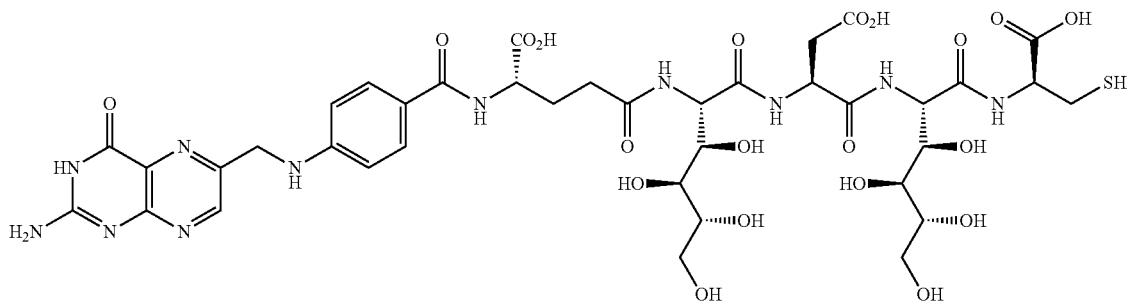 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@H](CS)C(=O)O)[C@@H](O)[C@H](O)[C@H](O)CO)[C@@H](O)[C@H](O)[C@H](O)CO)C(=O)O)cc3)nc2c(=O)[nH]1]

EC0244: $C_{38}H_{51}N_{11}O_{20}S$; MW 1013.94; Exact Mass: 1013.30
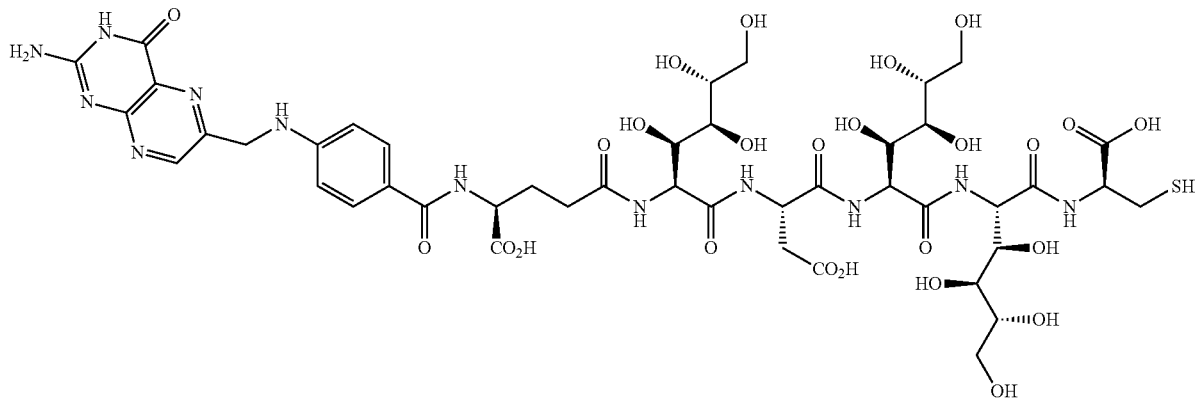 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@H](C(=O)N[C@H](CS)C(=O)O)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]
EC0257: $C_{44}H_{62}N_{12}O_{25}S$; MW 1191.09; Exact Mass: 1190.37
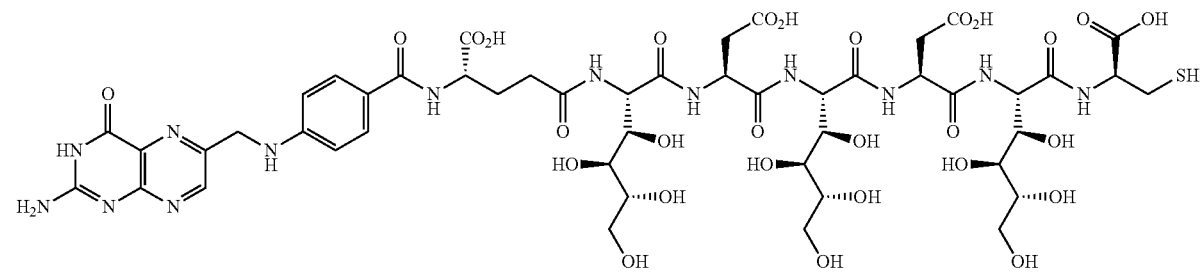 [SMILES: Nc1nc2ncc(CNc3ccc(C(=O)N[C@@H](CCC(=O)N[C@H](C(=O)N[C@@H](CC(=O)O)C(=O)N[C@H](C(=O)N[C@@H](CC(=O)O)C(=O)N[C@H](C(=O)N[C@H](CS)C(=O)O)[C@@H](O)[C@H](O)[C@H](O)CO)[C@@H](O)[C@H](O)[C@H](O)CO)[C@@H](O)[C@H](O)[C@H](O)CO)C(=O)O)cc3)nc2c(=O)[nH]1]
EC0261: $C_{48}H_{67}N_{13}O_{28}S$; MW 1306.18; Exact Mass: 1305.39
The following Examples of illustrative intermediates were prepared as described herein.
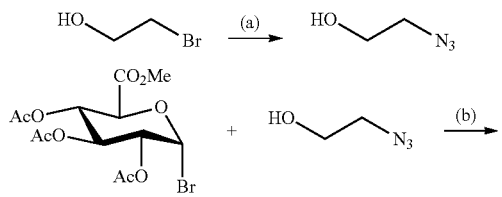
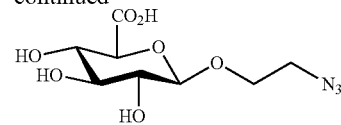
Huisgen azide for forming 1,2,3-triazole; (a) $NaN_3$; (b) $Ag_2CO_3$, DCM, molecular sieves; (c) LiOH, MeOH, $H_2O$.

EC0501 Thio bortezomib
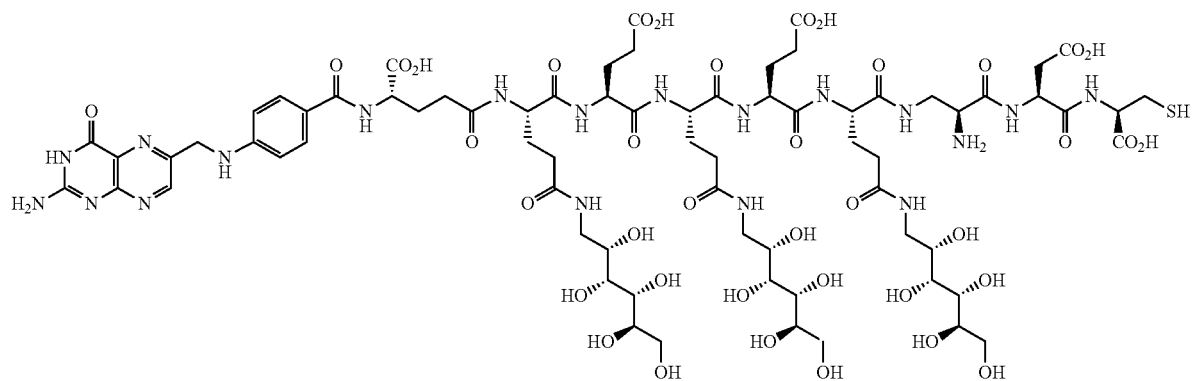
EC0536 Conjugate intermediate
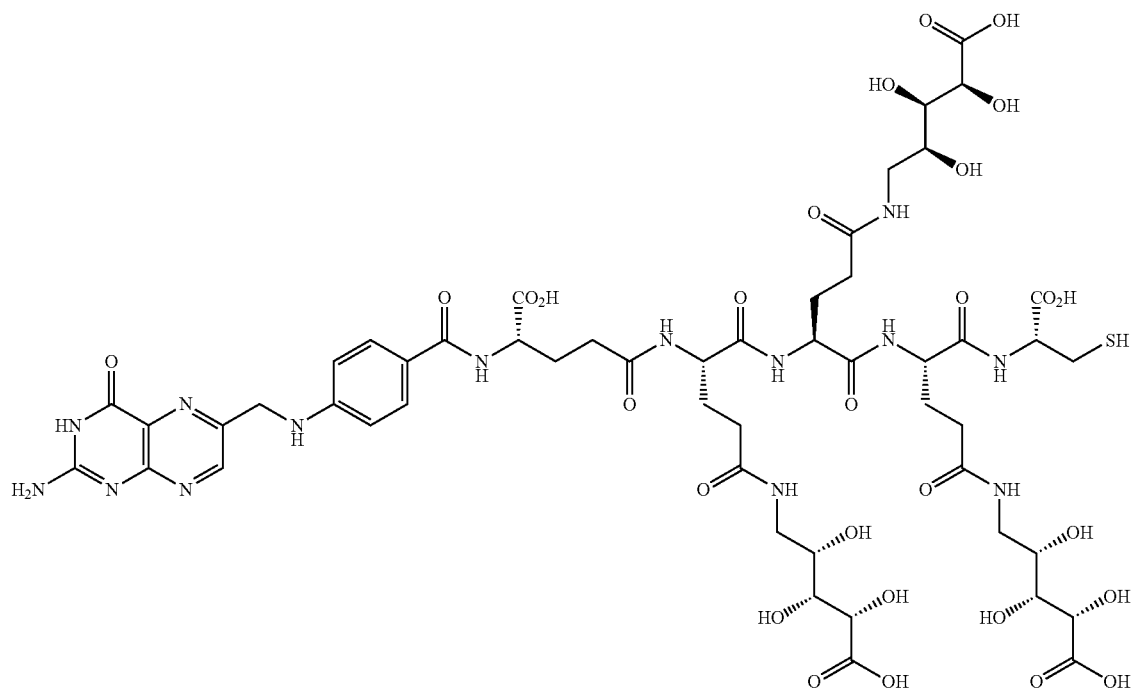 [SMILES: Nc1nc2ncc(CNc3ccc(C(=O)N[C@@H](CCC(=O)N[C@@H](CCC(=O)NC[C@H](O)[C@@H](O)[C@H](O)C(=O)O)C(=O)N[C@@H](CCC(=O)NC[C@H](O)[C@@H](O)[C@H](O)C(=O)O)C(=O)N[C@@H](CCC(=O)NC[C@H](O)[C@@H](O)[C@H](O)C(=O)O)C(=O)N[C@@H](CS)C(=O)O)C(=O)O)cc3)nc2c(=O)[nH]1]
EC0632 Conjugate intermediate. C52H72N14O28S, MW 1373.27, Exact Mass: 1372.44, prepared from the corresponding tert-butyl protected carboxylates.

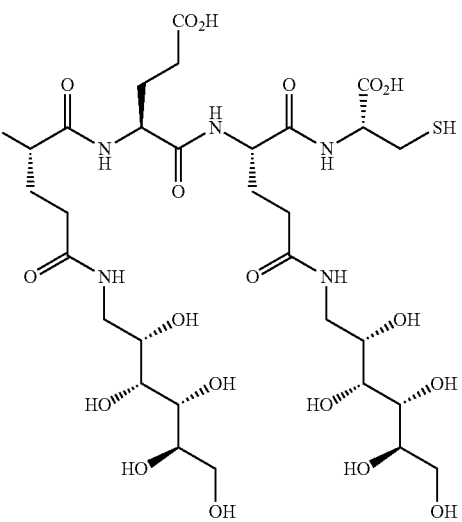
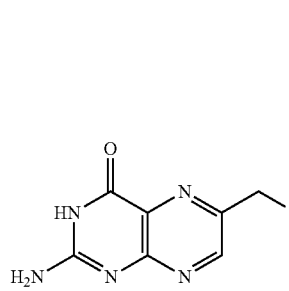

EC0669 Conjugate intermediate. C49H71N13O24S, MW 1258.23, Exact Mass: 1257.45

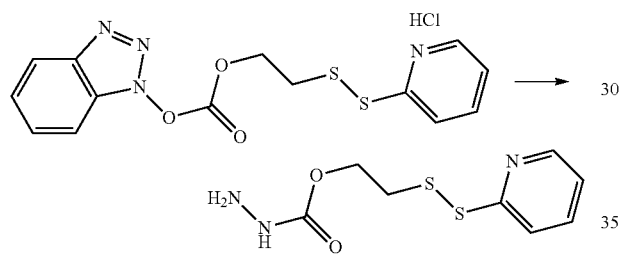

Example

Synthesis of Coupling Reagent EC0311. DIPEA (0.60 mL) was added to a suspension of HOBt-OCO$_2$—(CH$_2$)$_2$—SS-2-pyridine HCl (685 mg, 91%) in anhydrous DCM (5.0 mL) at 0° C., stirred under argon for 2 minutes, and to which was added anhydrous hydrazine (0.10 mL). The reaction mixture was stirred under argon at 0° C. for 10 minutes and room temperature for an additional 30 minutes, filtered, and the filtrate was purified by flash chromatography (silica gel, 2% MeOH in DCM) to afford EC0311 as a clear thick oil (371 mg), solidified upon standing.

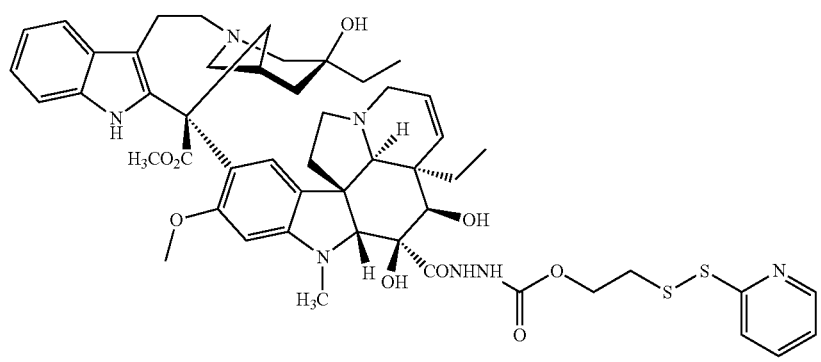

Example

Vinblastine Pyridinyl Disulfide. 2-[(Benzotriazole-1-yl-(oxycarbonyloxy)-ethyldisulfanyl]-pyridine HCl (601 mg) and 378 μL of DIPEA were sequentially added to a solution of desacetyl vinblastine hydrazide (668 mg) in 5 ml of DCM at 0° C. The reaction was allowed to warm to room temperature and stirred for 3 hours. TLC (15% MeOH in DCM) showed complete conversion. The mixture was purified by silica gel chromatography (1:9 MeOH/DCM). The combined fractions were evaporated, redissolved in DCM and washed with 10% $Na_2CO_3$, brine, dried ($MgSO_4$), and evaporated to 550 mg (80%); HPLC-RT 12.651 min., 91% pure, $^1$H HMR spectrum consistent with the assigned structure, and MS (ESI+): 984.3, 983.3, 982.4, 492.4, 491.9, 141.8. Additional details of this procedure are described in U.S. patent application publication No. US 2005/0002942 A1.

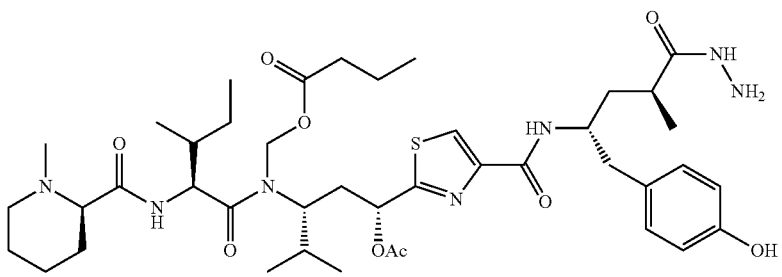 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NN)cs1)C(C)C]

Example

Preparation of Tubulysin Hydrazides. Illustrated by preparing EC0347. N,N-Diisopropylethylamine (DIPEA, 6.1 μL) and isobutyl chloroformate (3.0 μL) were added with via syringe in tandem into a solution of tubulysin B (0.15 mg) in anhydrous EtOAc (2.0 mL) at −15° C. After stirring for 45 minutes at −15° C. under argon, the reaction mixture was cooled down to −20° C. and to which was added anhydrous hydrazine (5.0 μL). The reaction mixture was stirred under argon at −20° C. for 3 hours, quenched with 1.0 mM sodium phosphate buffer (pH 7.0, 1.0 mL), and injected into a preparative HPLC for purification. Column: Waters XTerra Prep MS $C_{18}$ 10 19×250 mm; Mobile phase A: 1.0 mM sodium phosphate buffer, pH 7.0; Mobile phase B: acetonitrile; Method: 10% B to 80% B over 20 minutes, flow rate=25 mL/min. Fractions from 15.14-15.54 minutes were collected and lyophilized to produce EC0347 as a white solid (2.7 mg). The foregoing method is equally applicable for preparing other tubulysin hydrazides by the appropriate selection of the tubulysin starting compound.

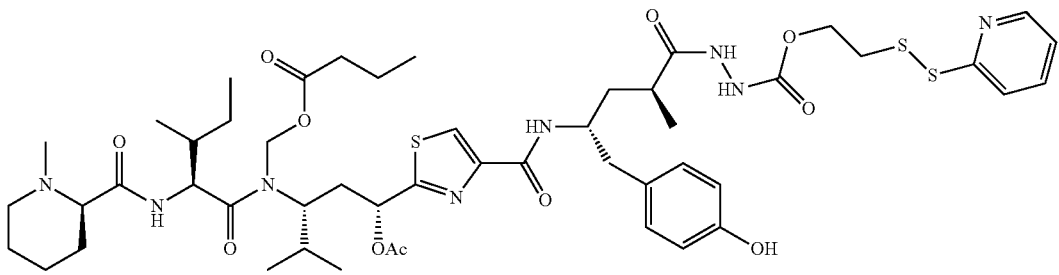 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSc2ccccn2)cs1)C(C)C]

Example

Preparation of Tubulysin Disulfides (stepwise process). Illustrated for EC0312. DIPEA (36 µL) and isobutyl chloroformate (13 µL) were added with the help of a syringe in tandem into a solution of tubulysin B (82 mg) in anhydrous EtOAc (2.0 mL) at −15° C. After stirring for 45 minutes at −15° C. under argon, to the reaction mixture was added a solution of EC0311 in anhydrous EtOAc (1.0 mL). The resulting solution was stirred under argon at −15° C. for 15 minutes and room temperature for an additional 45 minutes, concentrated, and the residue was purified by flash chromatography (silica gel, 2 to 8% MeOH in DCM) to give EC0312 as a white solid (98 mg). The foregoing method is equally applicable for preparing other tubulysin derivatives by the appropriate selection of the tubulysin starting compound.

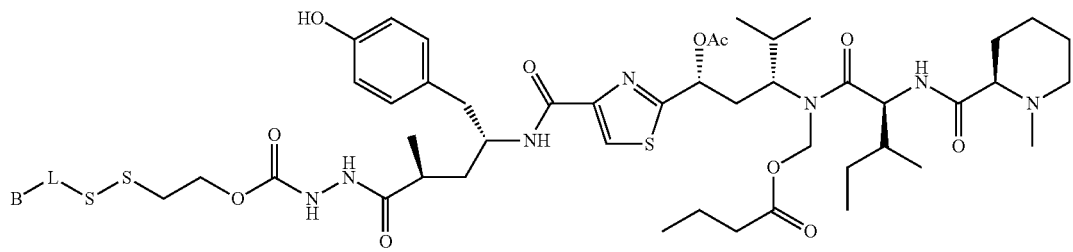

Example

General Synthesis of Disulfide Containing Tubulysin Conjugates. Illustrated with EC0312. A binding ligand-linker intermediate containing a thiol group is taken in deionized water (ca. 20 mg/mL, bubbled with argon for 10 minutes prior to use) and the pH of the suspension was adjusted by saturated $NaHCO_3$ (bubbled with argon for 10 minutes prior to use) to about 6.9 (the suspension may become a solution when the pH increased). Additional deionized water is added (ca. 20-25%) to the solution as needed, and to the aqueous solution is added immediately a solution of EC0312 in THF (ca. 20 mg/mL). The reaction mixture becomes homogenous quickly. After stirring under argon, e.g. for 45 minutes, the reaction mixture is diluted with 2.0 mM sodium phosphate buffer (pH 7.0, ca 150 volume percent) and the THF is removed by evacuation. The resulting suspension is filtered and the filtrate may be purified by preparative HPLC (as described herein). Fraction are lyophilized to isolate the conjugates. The foregoing method is equally applicable for preparing other tubulysin conjugates by the appropriate selection of the tubulysin starting compound.

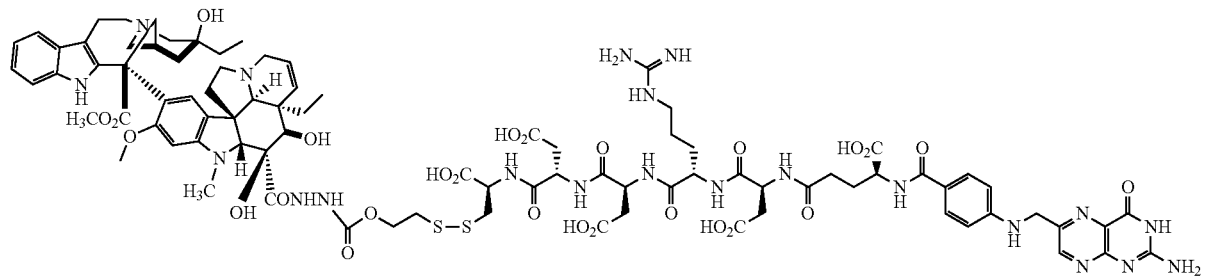

Comparative Vinblastine Example

EC145 lacking a hydrophilic spacer linker. Peptidyl fragment Pte-Glu-Asp-Arg-Asp-Asp-Cys-OH (Example 13) in THF was treated with either the thiosulfonate-activated vinblastine or vinblastine pyridinyl disulfide as a yellow solution resulting from dissolution in 0.1 M $NaHCO_3$ at pH>6.5 under argon. Lyophilization and HPLC gave a 70% yield; selected $^1H$ NMR ($D_2O$) δ 8.67 (s, 1H, FA H-7), 7.50 (br s, 1H, VLB H-11'), 7.30-7.40 (br s, 1H, VLB H-14'), 7.35 (d, 2H, J=7.8 Hz, FA H-12 &16), 7.25 (m, 1H, VLB H-13'), 7.05 (br s, 1H, VLB H-12'), 6.51 (d, 2H, J=8.7 Hz, FA H-13 &15), 6.4 (s, 2H, VLB H-14 & 17), 5.7 (m, 1H, VLB olefin), 5.65 (m, 1H, VLB H-7), 5.5 (d, 1H, VLB olefin), 5.5 (m, 1H, VLB H-6), 4.15 (m, 1H, VLB H-8'), 3.82 (s, 3H, VLB $C_{18'}$—$CO_2CH_3$), 3.69 (s, 3H, VLB $C_{16}$—$OCH_3$), 2.8 (s, 3H, VLB N—$CH_3$), 1.35 (br s, 1H, VLB H-3'), 1.15 (m, 1H, VLB H-2'), 0.9 (t, 3H, J=7 Hz, VLB H-21'), 0.55 (t, 3H, J=6.9 Hz, VLB H-21); LCMS (ESI, m+$H^+$) 1918.

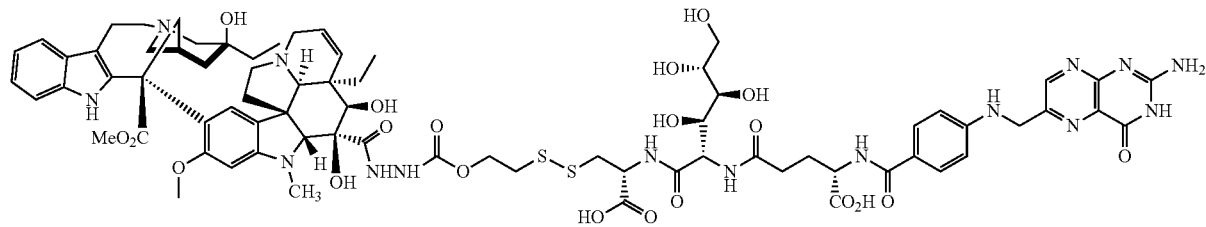

Example

EC0234 (Mono-Saccharo-Folate Vinblastine Conjugate) including a hydrophilic spacer linker. In a polypropylene centrifuge bottle, folate linker (EC0233, 22 mg, 0.030 mmol) was dissolved in 2 mL of water and bubbled with argon for 10 min. In another flask, a 0.1N $NaHCO_3$ solution was argon bubbled for 10 min. pH of the linker solution was carefully adjusted to 6.9 using the 0.1N $NaHCO_3$ solution. The vinblastine pyridinyl disulfide (27 mg, 0.028 mmol) in 2 mL of tetrahydrofuran (THF) was added slowly to the above solution. The resulting clear solution was stirred under argon for 15 min to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column $C_{18}$, 19×300 mM). Elution with 1 mM sodium phosphate pH=7.0 and acetonitrile resulted in pure fractions containing the product. Vinblastine-saccharo-folate conjugate (EC0234) was isolated after freeze-drying for 48 h (34 mg, 76%). $^1H$ NMR data was in accordance with the folate conjugate. $C_{74}H_{93}N_{15}O_{21}S_2$; MW 1592.75; Exact Mass: 1591.61.

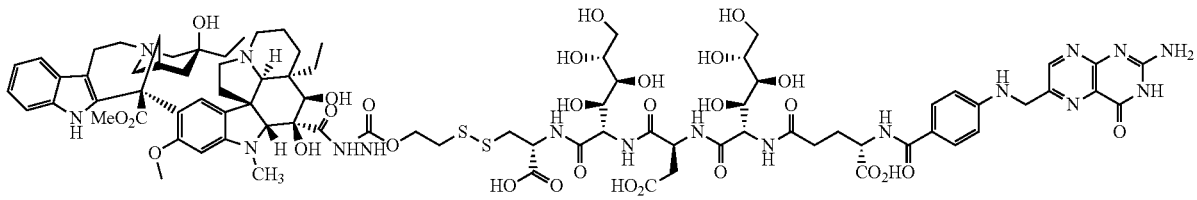

Example

EC0246 (Bis-Saccharo-Folate Vinblastine Conjugate). In a polypropylene centrifuge bottle, folate linker (EC0244, 30 mg, 0.030 mmol) was dissolved in 5 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (27 mg, 0.028 mmol) in 5 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-bis-saccharo-folate conjugate (EC0246) was isolated after freeze-drying for 48 h (34 mg, 66%). $^1$H NMR data was in accordance with the folate conjugate. C$_{84}$H$_{109}$N$_{17}$O$_{29}$S$_2$: MW 1884.99: Exact Mass: 1883.70.

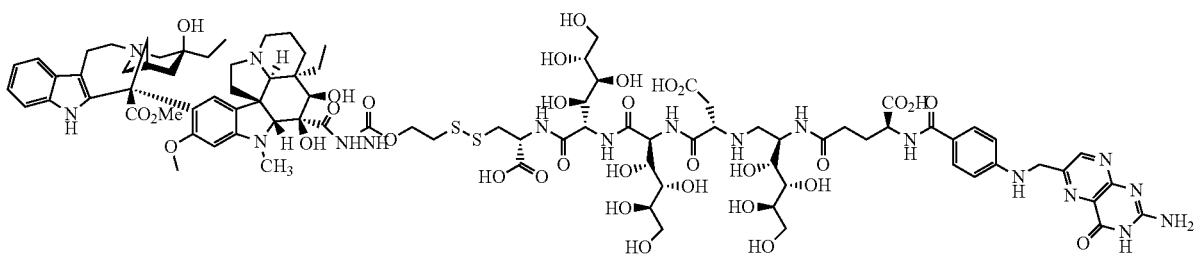

Example

EC0258 (Tris-Saccharo-Asp-Folate Vinblastine Conjugate). In a polypropylene centrifuge bottle, folate linker (EC0257, 37 mg, 0.031 mmol) was dissolved in 5 mL of water and bubbled with argon for 10 mM. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (27.5 mg, 0.028 mmol) in 5 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tris-saccharo-Asp-folate conjugate (EC0258) was isolated after freeze-drying for 48 h (36 mg, 62%). $^1$H NMR data was in accordance with the folate conjugate. C$_{90}$H$_{120}$N$_{18}$O$_{34}$S$_2$; MW 2062.15; Exact Mass: 2060.77.

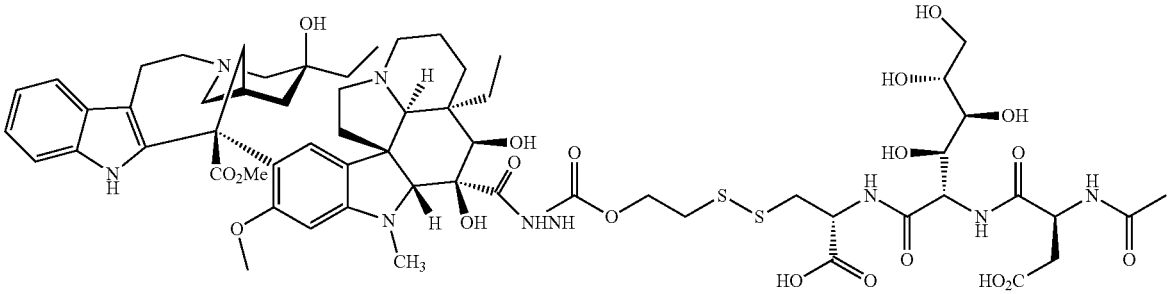

-continued

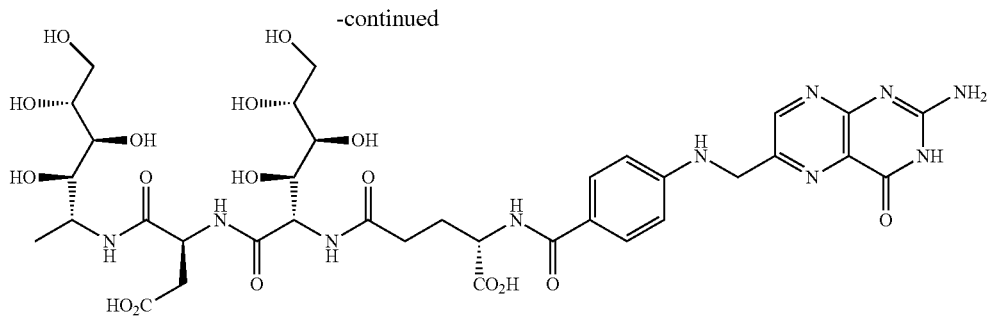

Example 15

EC0263 (Tris-Saccharo-Bis-Asp-Folate Vinblastine Conjugate). In a polypropylene centrifuge bottle, folate linker (EC0261, 37 mg, 0.029 mmol) was dissolved in 5 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (25.5 mg, 0.026 mmol) in 5 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tris-saccharo-bis-Asp-folate conjugate (EC0263) was isolated after freeze-drying for 48 h (36 mg, 64%). $^1$H NMR data was in accordance with the folate conjugate. C$_{94}$H$_{125}$N$_{19}$O$_{37}$S$_2$; MW 2177.24; Exact Mass: 2175.79.

Example

EC0434 (Tetra-Saccharo-Tris-Asp-Folate Vinblastine Conjugate). In a polypropylene centrifuge bottle, folate linker (EC0268, 20 mg, 0.012 mmol) was dissolved in 3 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (12 mg, 0.012 mmol) in 3 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-saccharo-tris-Asp-folate conjugate (EC0434) was isolated after freeze-drying for 48 h (26 mg, 62%). $^1$H NMR data was in accordance with the folate conjugate. C$_{104}$H$_{141}$N$_{21}$O$_{45}$S$_2$; MW 2469.48; Exact Mass: 2467.88.

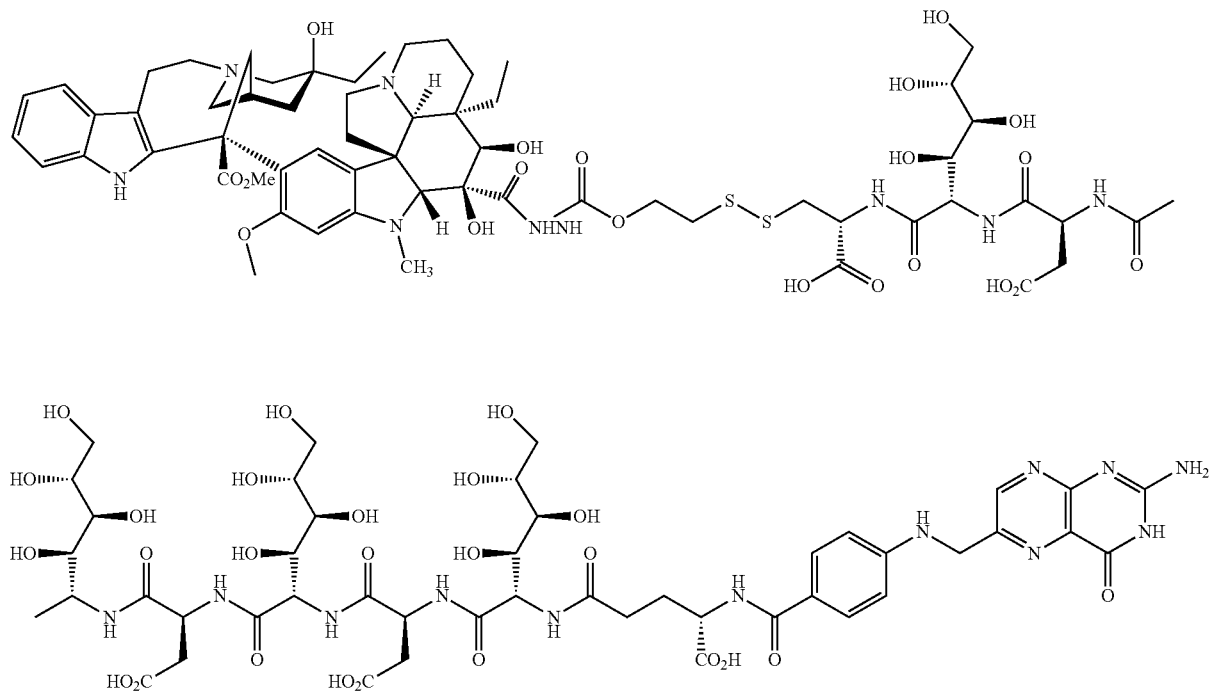

121

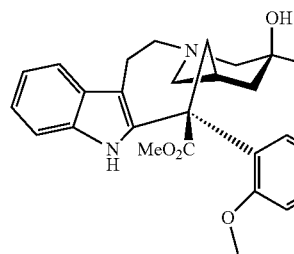

122

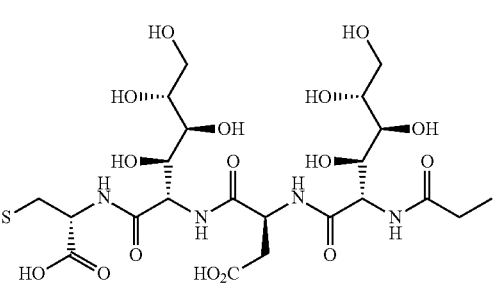

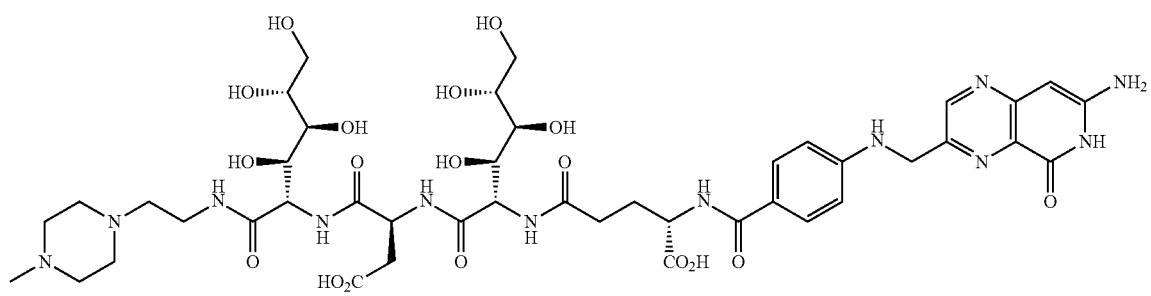

Example 30

EC0454 (Tetra-Saccharo-Bis-Asp-Folate Vinblastine Conjugate). In a polypropylene centrifuge bottle, folate linker (EC0452, 34 mg, 0.02 mmol) was dissolved in 3 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (20 mg, 0.02 mmol) in 3 mL of tetrahydrofuran (THF) was added slowly to the above solution. The resulting clear solution was stirred under argon for 15 min to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-saccharo-bis-Asp-folate conjugate (EC0454) was isolated after freeze-drying for 48 h (35 mg, 70%). $^1$H NMR data was in accordance with the folate conjugate. C$_{108}$H$_{151}$N$_{23}$O$_{43}$S$_2$; MW 2523.62; Exact Mass: 2521.98.

Example 30

EC0455 (Tetra-Saccharo-bis-Asp-Folate Vinblastine Conjugate). In a polypropylene centrifuge bottle, folate linker (EC0457, 20 mg, 0.013 mmol) was dissolved in 1.5 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (18 mg, 0.018 mmol) in 1.5 mL of tetrahydrofuran (THF) was added slowly to the above solution. The resulting clear solution was stirred under argon for 30 min. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-saccharo-bis-Asp-folate conjugate (EC0455) was isolated after freeze-drying for 48 h (19 mg, 62%). $^1$H NMR data was in accordance with the folate conjugate. C$_{100}$H$_{136}$N$_{20}$O$_{42}$S$_2$; MW 2354.39.

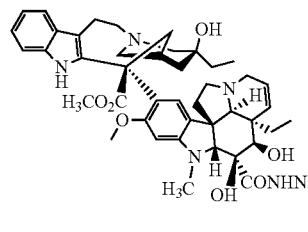
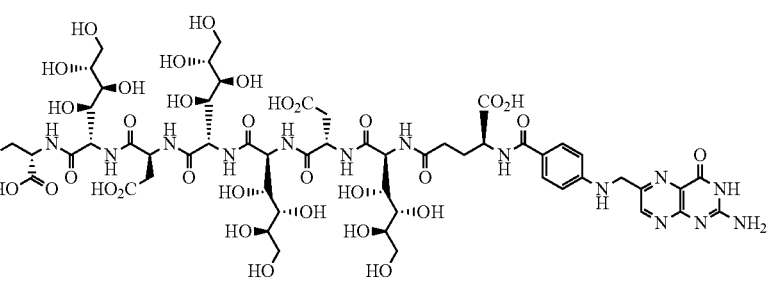

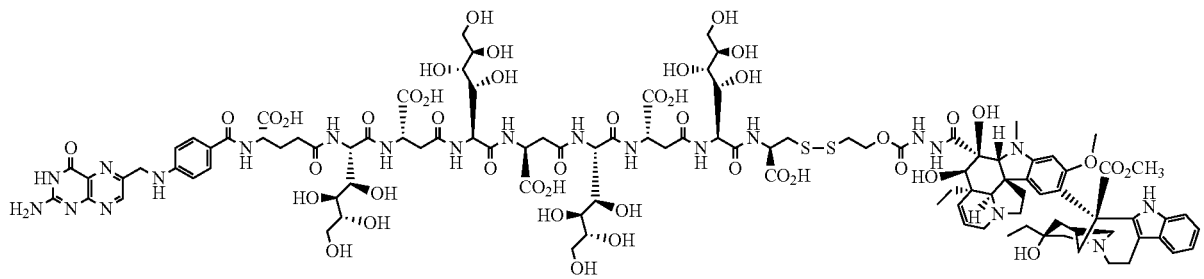

Example

EC0456. In a polypropylene centrifuge bottle, folate linker (EC0453, 46 mg, 0.029 mmol) was dissolved in 3 mL of water, which had been bubbled with argon for 10 min. In another flask, a saturated $NaHCO_3$ solution was argon bubbled for 10 min. The pH of the linker solution was carefully adjusted, with argon bubbling, to 6.9 using the $NaHCO_3$ solution. The vinblastine pyridinyl disulfide (32 mg, 1.1 eq) in 3 mL of tetrahydrofuran (THF) was added quickly to the above solution. The resulting clear solution was stirred under argon. Progress of the reaction was monitored by analytical HPLC (2 mM phosphate buffer, pH=7.0 and acetonitrile). After 30 min, to the reaction was added 12 mL 2 mM phosphate buffer (pH 7), the resulting cloudy solution filtered, and the filtrate was injected on a prep-HPLC: Column: Waters Xterra Prep MS $C_{18}$ 10 μm 19×250 mm; Solvent A: 2 mM sodium phosphate, pH 7; Solvent B: ACN; Method: 5 mM 1% B to 40 mM 80% B 25 mL/min. Fractions containing EC0456 were collected and freeze-dried to afford 41.6 mg fluffy yellow solid, consisting of 30 mg EC0456 (42% yield) and 11.6 sodium phosphate salt. $^1$H NMR and LC/MS were consistent with the product. $C_{104}H_{141}N_{21}O_{45}S_2$; MW 2469.48; Exact Mass: 2467.88. C, 50.58; H, 5.76; N, 11.91; O, 29.15; S, 2.60.

Example

EC0481. In a polypropylene centrifuge bottle, folate linker (EC0479, 12 mg, 0.0058 mmol) was dissolved in 2.5 mL of water, which had been bubbled with argon for 10 min. In another flask, a saturated $NaHCO_3$ solution was argon bubbled for 10 min. The pH of the linker solution was carefully adjusted, with argon bubbling, to 6.9 using the $NaHCO_3$ solution. The vinblastine pyridinyl disulfide (5.7 mg, 1.0 eq) in 2.5 mL of tetrahydrofuran (THF) was added quickly to the above solution. The resulting clear solution was stirred under argon. Progress of the reaction was monitored by analytical HPLC (2 mM phosphate buffer, pH=7.0 and acetonitrile). After 20 mM, to the reaction was added 12 mL 2 mM phosphate buffer (pH 7), the resulting cloudy solution filtered, and the filtrate was injected on a prep-HPLC: Column: Waters Atlantis Prep T3 10 μm OBD 19×250 mm; Solvent A: 2 mM sodium phosphate, pH 7; Solvent B: ACN; Method: 5 min 1% B to 25 mM 50% B 26 mL/min. Fractions containing EC0481 were collected and freeze-dried to afford 15.5 mg fluffy yellow solid, consisting of 10.5 mg EC0481 (60% yield) and 5.0 sodium phosphate salt. $^1$H NMR and LC/MS were consistent with the product. MW 2999.15; Exact Mass: 2997.24.

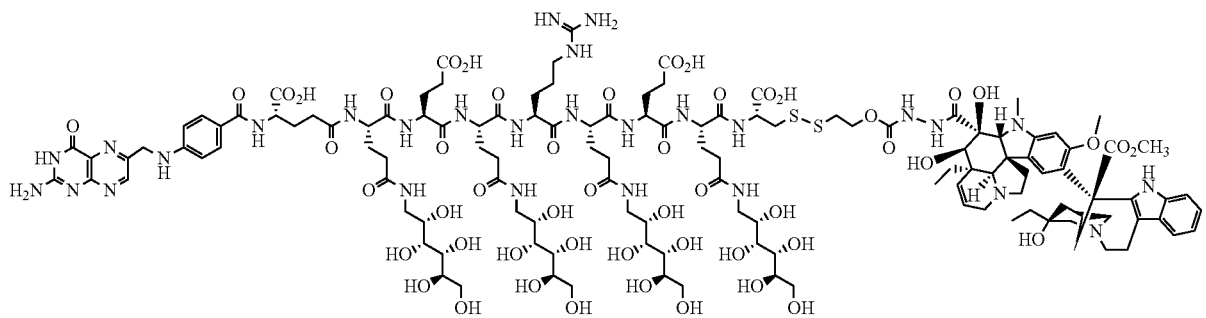

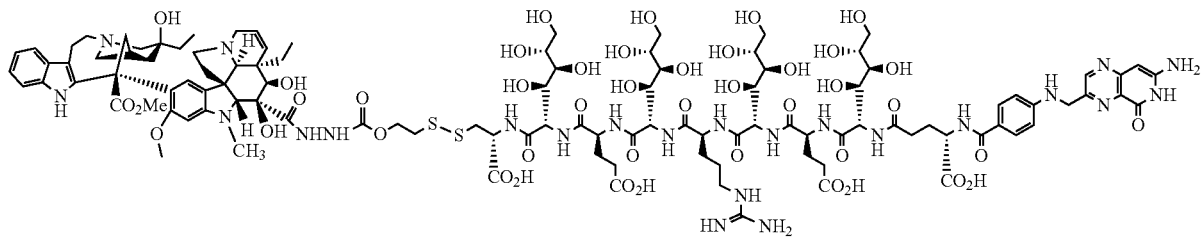

Example

EC0484 (Tetra-Saccharo-Bis-α-Glu-Arg-Folate Vinblastine Conjugate). In a polypropylene centrifuge bottle, folate linker (EC0480, 15 mg, 0.009 mmol) was dissolved in 3 mL of water and bubbled with argon for 10 mM. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (8.8 mg, 0.009 mmol) in 3 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-saccharo-bis-α-Glu-Arg-folate conjugate (EC0484) was isolated after freeze-drying for 48 h (16 mg, 70%). $^1$H NMR data was in accordance with the folate conjugate. $C_{108}H_{152}N_{24}O_{43}S_2$; MW 2538.63; Exact Mass: 2536.99.

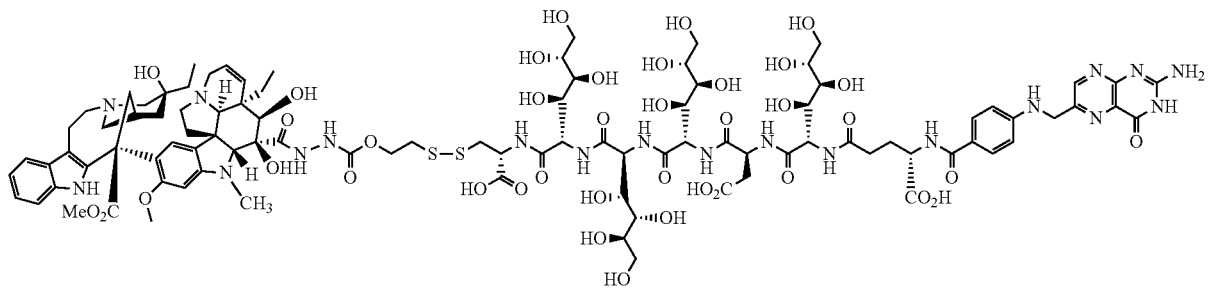

Example

EC0487 (Tetra-Saccharo-Asp-Folate Vinblastine Conjugate). In a polypropylene centrifuge bottle, folate linker (EC0463, 21 mg, 0.015 mmol) was dissolved in 3 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (15 mg, 0.015 mmol) in 3 mL of tetrahydrofuran (THF) was added slowly to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (Atlantis Column, 19×300 mM). Elution with 1 mM sodium phosphate pH=7.0 and acetonitrile resulted in pure fractions containing the product. Vinblastine-tetra-saccharo-Asp-folate conjugate (EC0487) was isolated after freeze-drying for 48 h (28 mg, 84%). $^1$H NMR data was in accordance with the folate conjugate. $C_{96}H_{131}N_{19}O_{39}S_2$; MW 2239.30; Exact Mass: 2237.83.

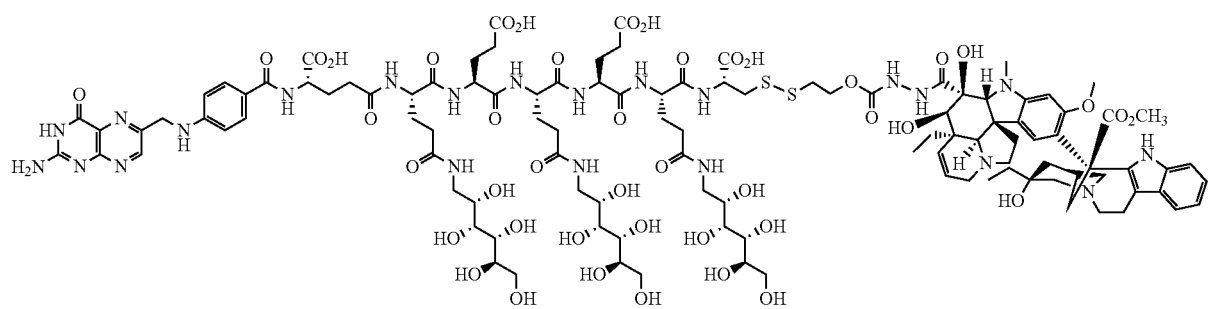

Example

EC0489. In a polypropylene centrifuge bottle, folate linker (EC0488, 26 mg, 0.015 mmol) was dissolved in 2.5 mL of water, which had been bubbled with argon for 10 mM. In another flask, a saturated NaHCO$_3$ solution was argon bubbled for 10 min. The pH of the linker solution was carefully adjusted, with argon bubbling, to 6.9 using the NaHCO$_3$ solution. The vinblastine pyridinyl disulfide (15 mg, 1.0 eq) in 2.5 mL of tetrahydrofuran (THF) was added quickly to the above solution. The resulting clear solution was stirred under argon. Progress of the reaction was monitored by analytical HPLC (2 mM phosphate buffer, pH=7.0 and acetonitrile). After 20 mM, to the reaction was added 12 mL 2 mM phosphate buffer (pH 7), the resulting cloudy solution filtered, and the filtrate was injected on a prep-HPLC: Column: Waters Xterra Prep MS C, 10 μm 19×250 mm; Solvent A: 2 mM sodium phosphate, pH 7; Solvent B: ACN; Method: 5 mM 1% B to 25 min 50% B 26 mL/min. Fractions containing EC0489 were collected and freeze-dried to afford 35 mg fluffy yellow solid, consisting of 27.5 mg EC0489 (71% yield) and 7.5 sodium phosphate salt. $^1$H NMR and LC/MS were consistent with the product. MW 2550.68; Exact Mass: 2549.01.

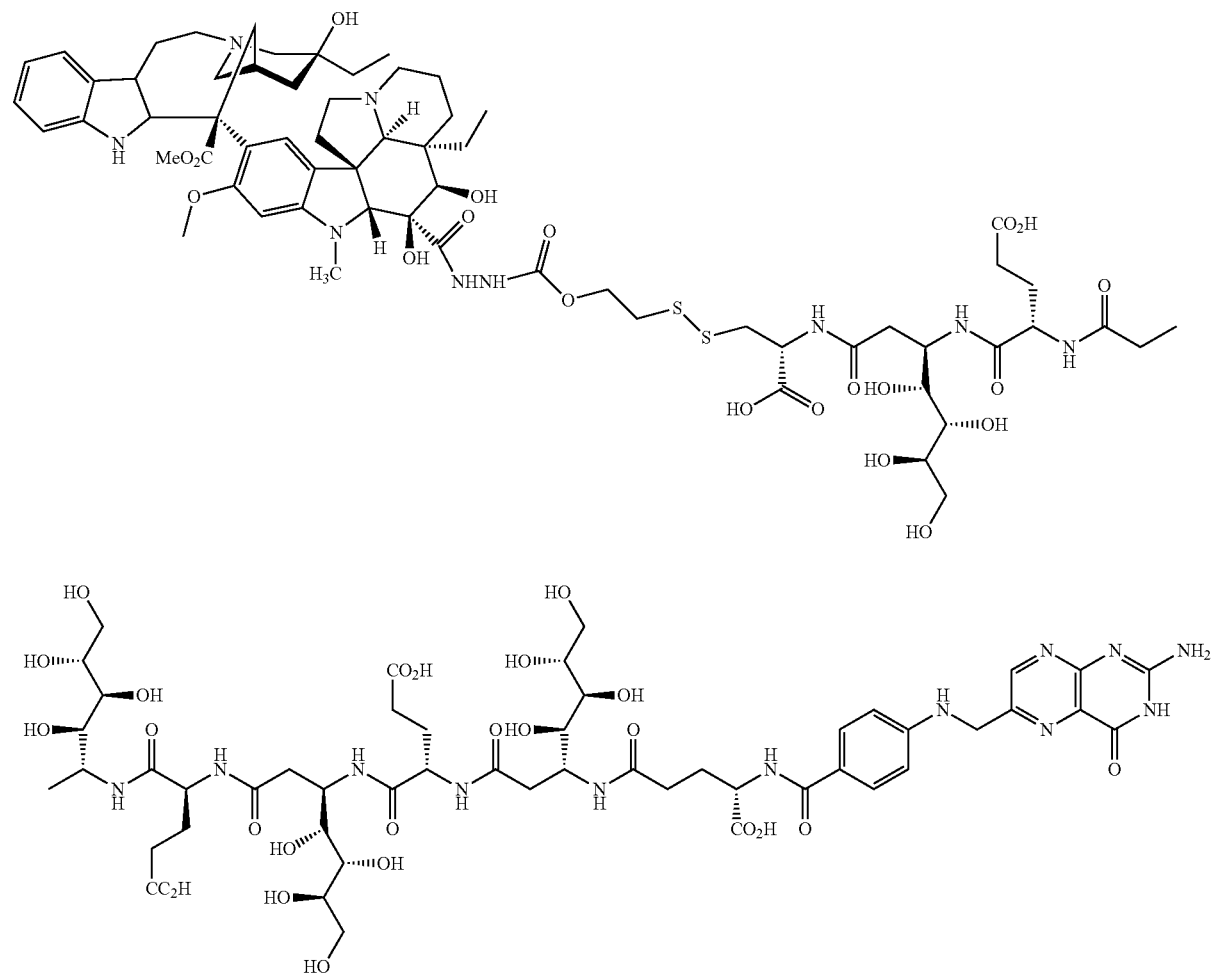

Example

EC0490 (Tetra-HomoSaccharo-Tris-αGlu-Folate Vinblastine Conjugate). In a polypropylene centrifuge bottle, folate linker (EC0478, 22 mg, 0.013 mmol) was dissolved in 3 mL of water and bubbled with argon for 10 min. In another flask, a 0.1N $NaHCO_3$ solution was argon bubbled for 10 min. pH of the linker solution was carefully adjusted to 6.9 using the 0.1N $NaHCO_3$ solution. The vinblastine pyridinyl disulfide (mg, mmol) in 3 mL of tetrahydrofuran (THF) was added slowly to the above solution. The resulting clear solution was stirred under argon for 15 min to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column $C_{18}$, 19×300 mM). Elution with 1 mM sodium phosphate pH=7.0 and acetonitrile resulted in pure fractions containing the product. Vinblastine-tetra-Homosaccharo-tris-Glu-folate conjugate (EC0490) was isolated after freeze-drying for 48 h (15 mg, 45%). $^1$H NMR data was in accordance with the folate conjugate. $C_{111}H_{155}N_{21}O_{45}S_2$; MW 2567.66; Exact Mass: 2565.99.

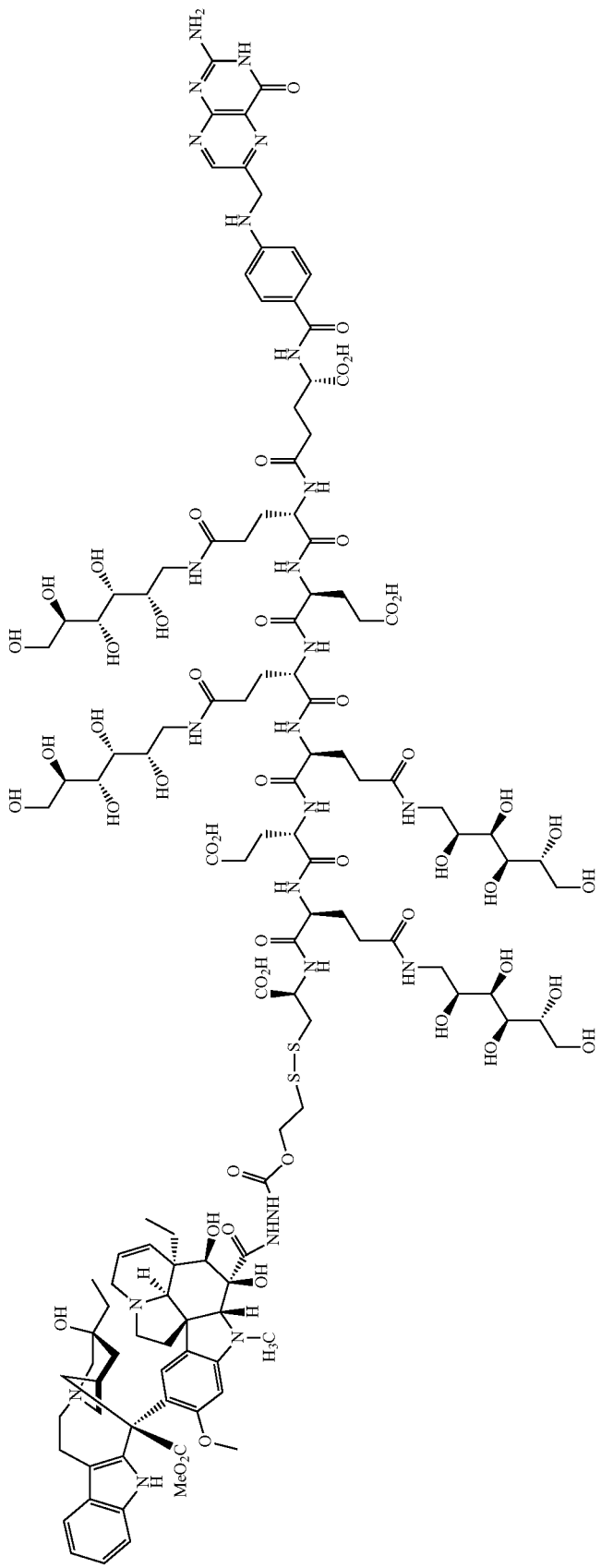

Example

EC0492 (Tetra-HomoSaccharo-Tris-αGlu-Folate Vinblastine Conjugate). In a polypropylene centrifuge bottle, folate linker (EC0491, 26 mg, 0.013 mmol) was dissolved in 3 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (13 mg, 0.013 mmol) in 3 mL of tetrahydrofuran (THF) was added to the above solution. The resulting clear solution was stirred under argon for 15 mM to 1 h. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-homosaccharo-tris-Glu-folate conjugate (EC0492) was isolated after freeze-drying for 48 h (22 mg, 60%). $^1$H NMR data was in accordance with the folate conjugate. C$_{122}$H$_{176}$N$_{24}$O$_{50}$S$_2$; MW 2842.97; Exact Mass: 2841.14.

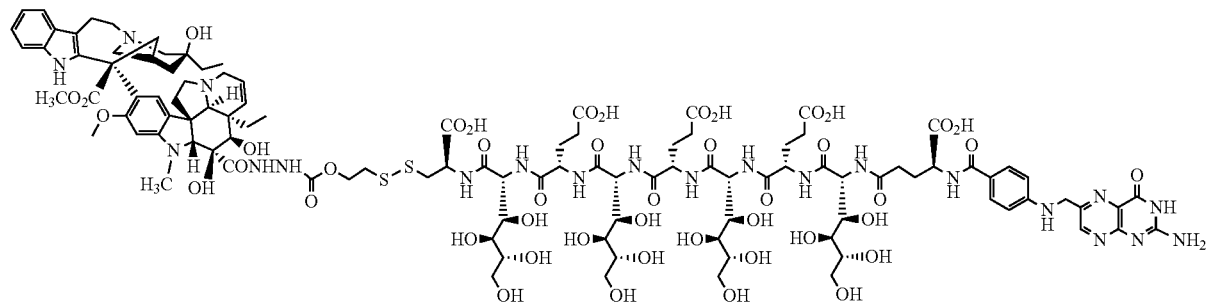

Example

EC0493 (Tetra-Saccharo-tris-Glu-Folate Vinblastine Conjugate). In a polypropylene centrifuge bottle, folate linker (EC0477, 25 mg, 0.015 mmol) was dissolved in 1.5 mL of water and bubbled with argon for 10 min. In another flask, a 0.1N NaHCO$_3$ solution was argon bubbled for 10 min. pH of the linker solution was carefully adjusted to 6.9 using the 0.1N NaHCO$_3$ solution. The vinblastine pyridinyl disulfide (20 mg, 0.020 mmol) in 1.5 mL of tetrahydrofuran (THF) was added slowly to the above solution. The resulting clear solution was stirred under argon for 30 min. Progress of the reaction was monitored by analytical HPLC (10 mM ammonium acetate, pH=7.0 and acetonitrile). THF was removed under reduced pressure and the aqueous solution was filtered and injected on a prep-HPLC column (X-terra Column C$_{18}$, 19×300 mM). Elution with 1 mM sodium phosphate pH=7.0 and acetonitrile resulted in pure fractions containing the product. Vinblastine-tetra-saccharo-tris-Glu-folate conjugate (EC0493) was isolated after freeze-drying for 48 h (23 mg, 61%). $^1$H NMR data was in accordance with the folate conjugate. C$_{107}$H$_{147}$N$_{21}$O$_{45}$S$_2$; MW 2511.56; Exact Mass: 2509.93.

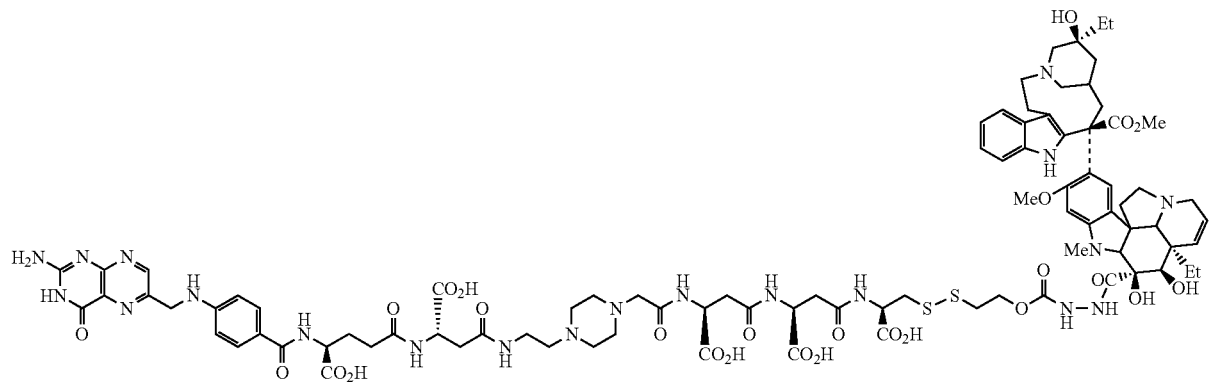

Example

EC0429. This Example including an oligoamide hydrophilic spacer represented by the aminoethylpiperazinylacetamide of Asp-Asp-Cys, was prepared using the processes described herein.

The following illustrative examples of glucuronide compounds, EC0400 and EC0423, where the saccharide based group is illustratively introduced using click chemistry, were also prepared as described herein.

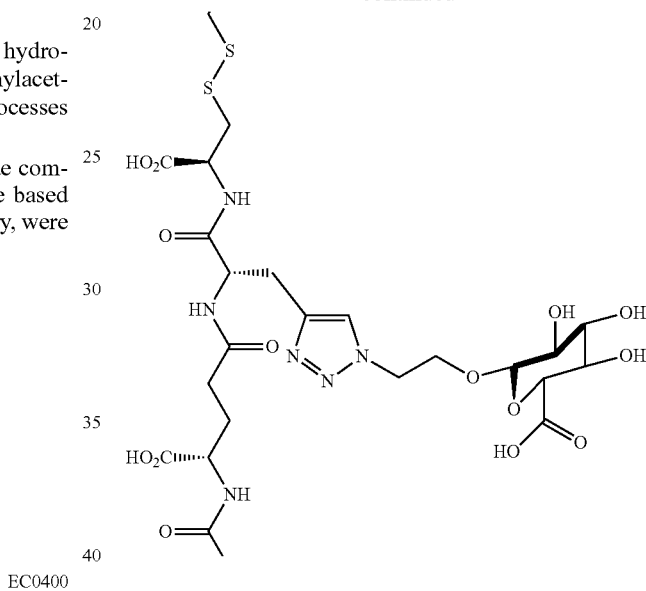

EC0400

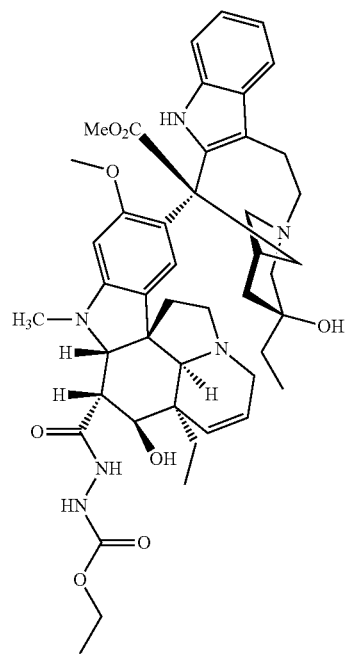

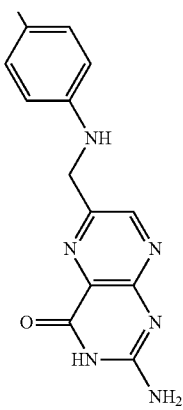

137
-continued
EC0423
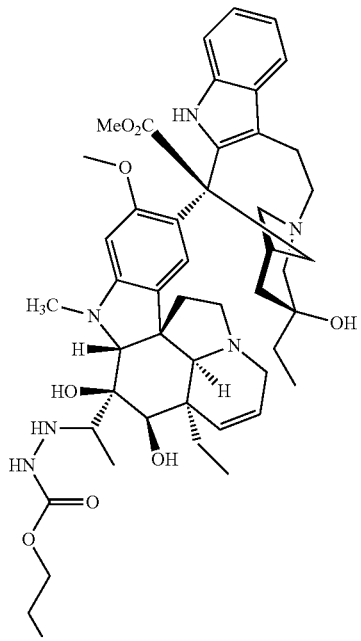
138
-continued
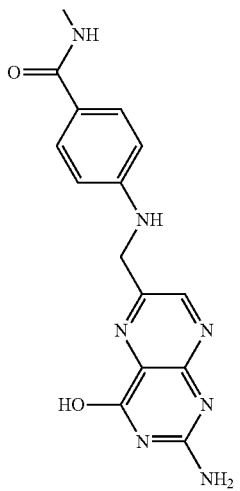
The following illustrative examples of PEG-spacer compounds, EC0367 and EC0409, were also prepared as described herein.
EC0367
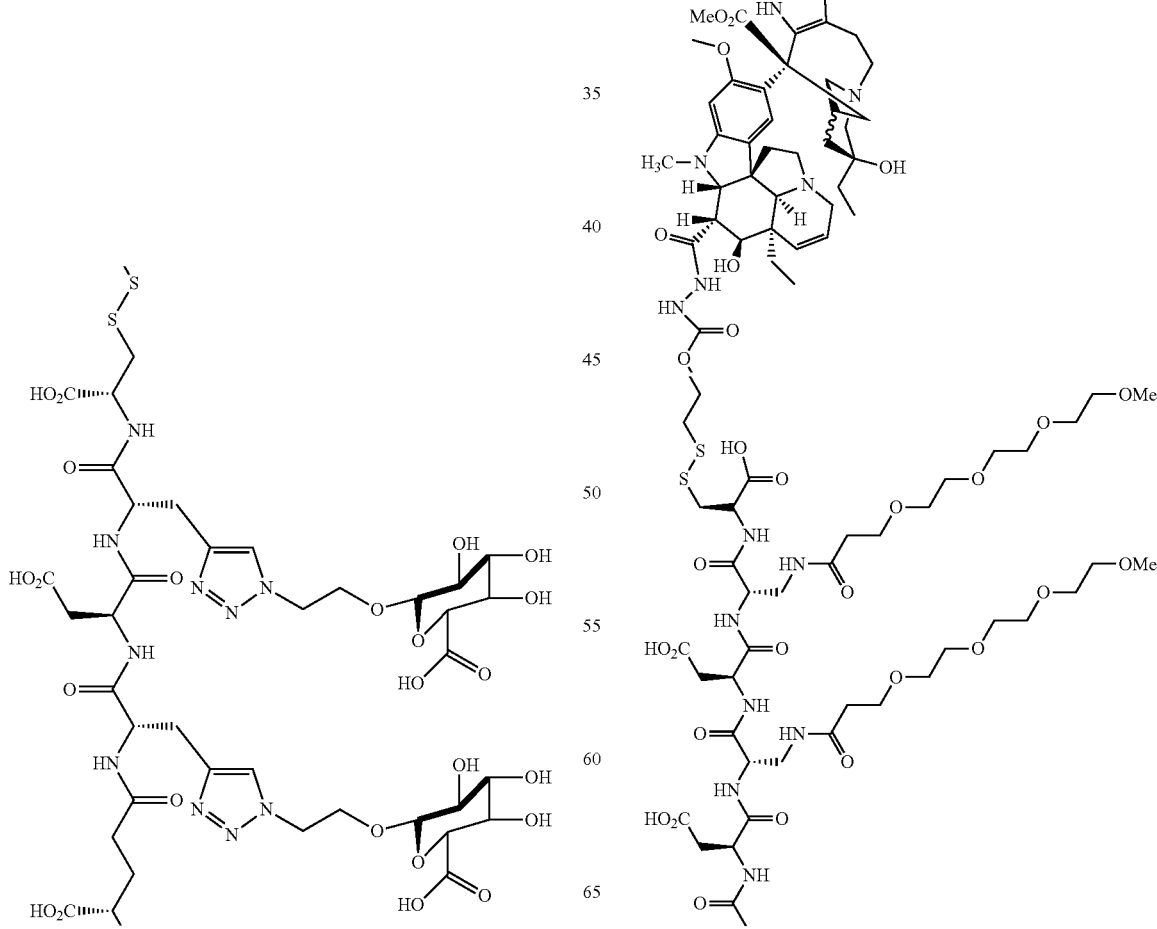

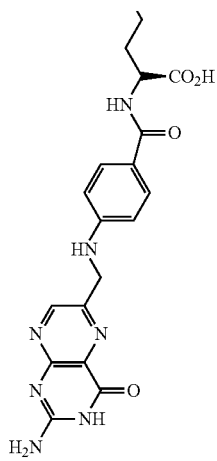

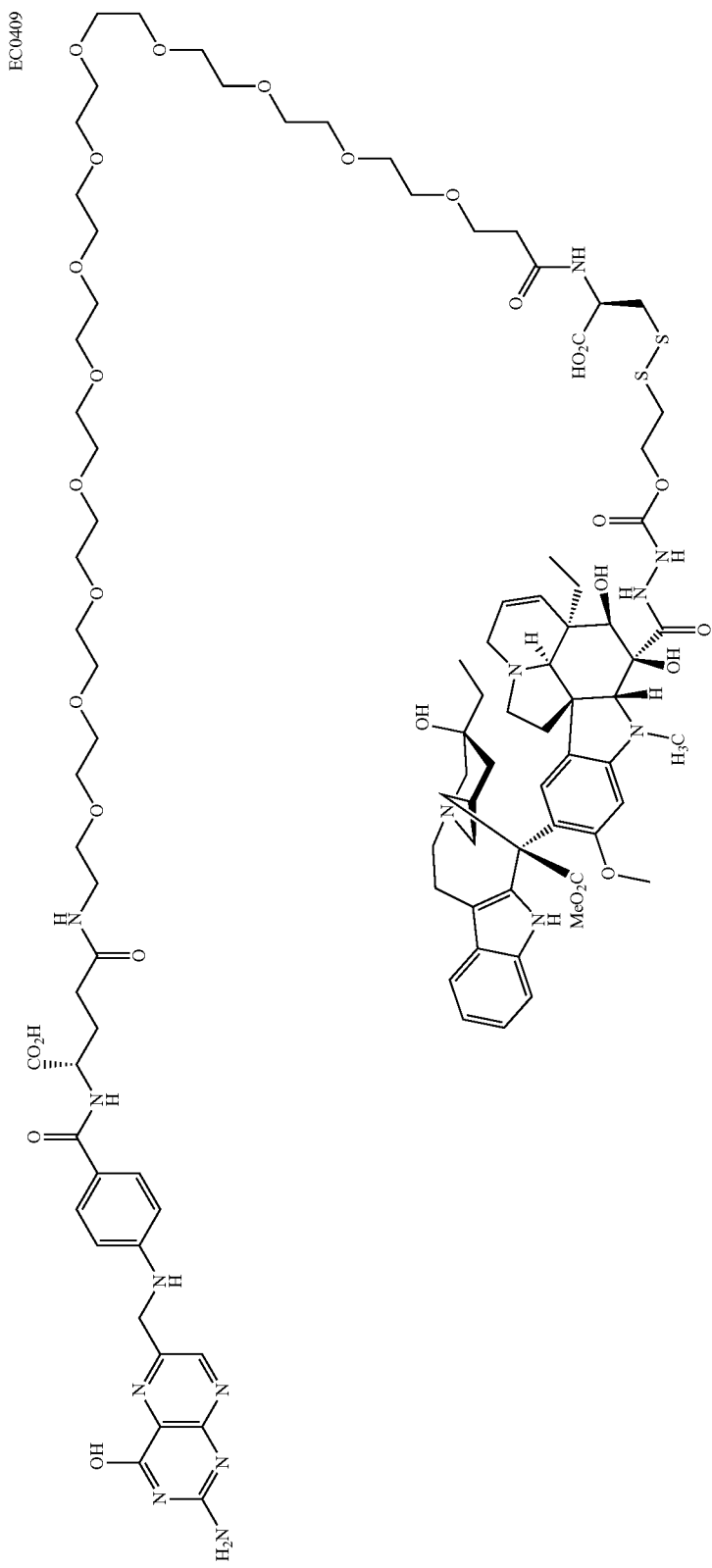

The following illustrative examples of sulfuric acid alkyl ester compounds, EC0418 and EC0428, where the sulfuric acid fragment is illustratively introduced via click chemistry, were prepared as described herein.

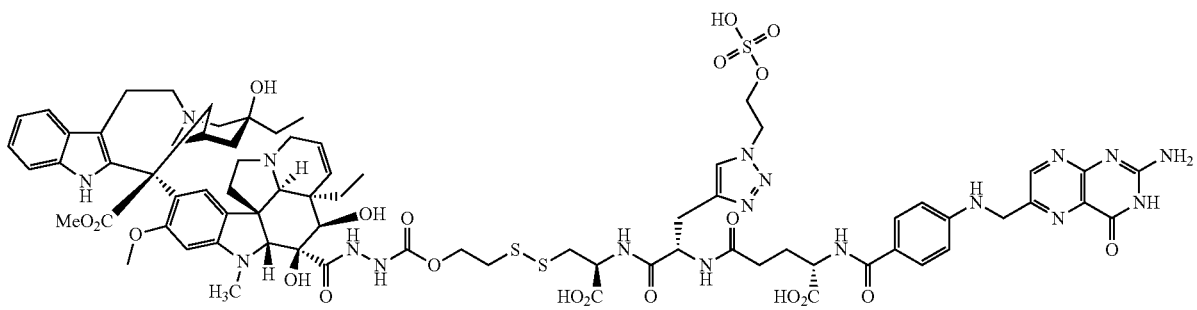

EC0418 Conjugate of DAVLBH

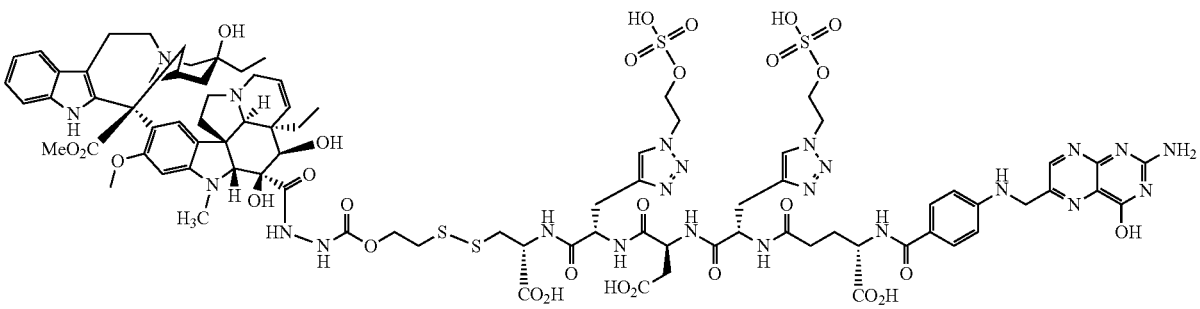

EC0428 Conjugate of DAVLBH The following illustrative examples of additional oligoamide spacer compounds, where the oligoamide includes an EDTE derivative were prepared as described herein.

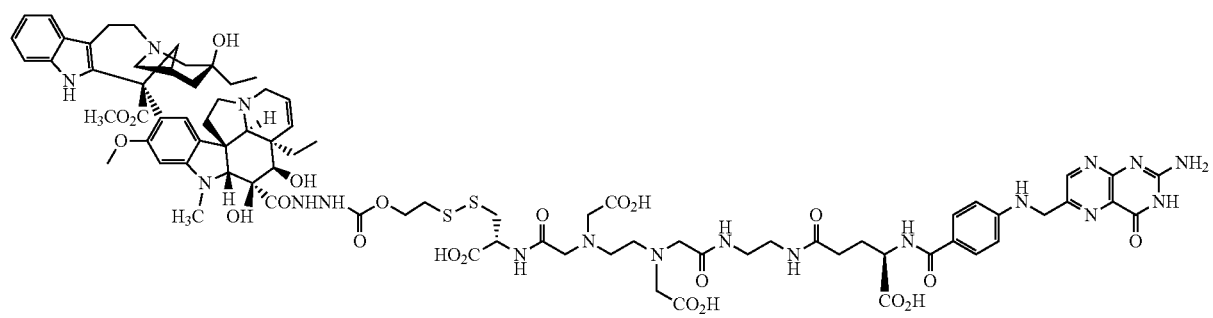

EC0396 Conjugate of DAVLBH

The following illustrative examples of β-alkyl glycosides of 2-deoxyhexapyranose compounds and PEG-linked compounds may be prepared as described herein, using click chemistry to attach the hydrophilic groups onto the spacer linker.

Conjugate of DAVLBH including a β-alkyl 2-deoxyglucose

Conjugate of DAVLBH including a β-alkyl 2-deoxyglucuronide.

Conjugate of DAVLBH including a PEG.

Conjugate of DAVLBH including a β-alkyl mannopyranoside.
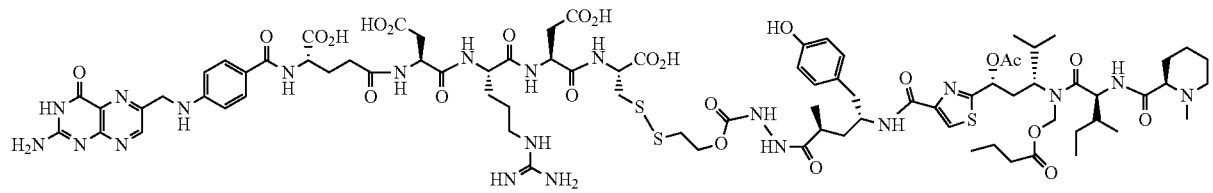 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CC(=O)O)NC(=O)[C@H](CCCNC(=N)N)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cs1)C(C)C]

Comparative Tubulysin Example

EC0305 lacking a hydrophilic spacer linker. EC89 (86 mg) was taken in deionized water (4.0 mL, bubbled with argon for 10 minutes prior to use) and the pH of the suspension was adjusted by saturated $NaHCO_3$ (bubbled with argon for 10 minutes prior to use) to about 6.9 (the suspension became a solution when the pH increased). Additional deionized water was added to the solution to make a total volume of 5.0 mL and to the aqueous solution was added immediately a solution of EC0312 (97 mg) in THF (5.0 mL). The reaction mixture became homogenous quickly. After stirring under argon for 45 minutes, the reaction mixture was diluted with 2.0 mM sodium phosphate buffer (pH 7.0, 15 mL) and the THF was removed on a Rotavapor. The resulting suspension was filtered and the filtrate was injected into a preparative HPLC for purification (Column: Waters XTerra Prep MS $C_{18}$ 10 μm, 19×250 mm; Mobile phase A: 2.0 mM sodium phosphate buffer, pH 7.0; Mobile phase B: acetonitrile; Method: 5% B to 80% B over 25 minutes, flow rate=25 mL/min). Fractions from 10.04-11.90 minutes were collected and lyophilized to give EC0305 as a pale yellow fluffy solid (117 mg).

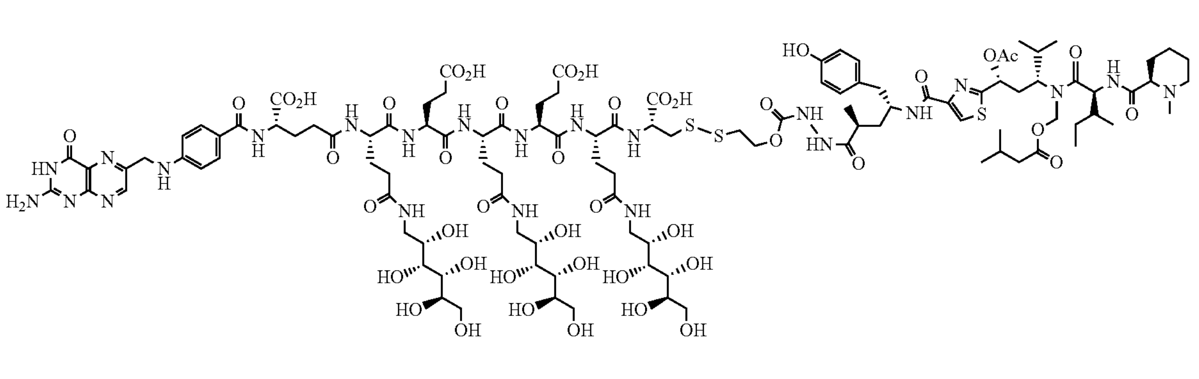 [SMILES: CCC(C)[C@H](NC(=O)[C@H]1CCCCN1C)C(=O)N(COC(=O)CC(C)C)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cs1)C(C)C]

Example

General Method 2 for Preparing Conjugates having a hydrophilic spacer linker (one-pot). Illustrated with preparation of EC0543. DIPEA (7.8 μL) and isobutyl chloroformate (3.1 μL) were added with the help of a syringe in tandem into a solution of tubulysin A (18 mg) in anhydrous EtOAc (0.50 mL) at −15° C. After stirring for 35 minutes at −15° C. under argon, to the reaction mixture was added a solution of EC0311 (5.8 mg) in anhydrous EtOAc (0.50 mL). The cooling was removed and the reaction mixture was stirred under argon for an additional 45 minutes, concentrated, vacuumed, and the residue was dissolved in THF (2.0 mL). Meanwhile, EC0488 (40 mg) was dissolved in deionized water (bubbled with argon for 10 minutes prior to use) and the pH of the aqueous solution was adjusted to 6.9 by saturated $NaHCO_3$. Additional deionized water was added to the EC0488 solution to make a total volume of 2.0 mL and to which was added immediately the THF solution containing the activated tubulysin. The reaction mixture, which became homogeneous quickly, was stirred under argon for 50 minutes and quenched with 2.0 mM sodium phosphate buffer (pH 7.0, 15 mL). The resulting cloudy solution was filtered and the filtrate was injected into a preparative HPLC for purification. Column: Waters XTerra Prep MS $C_{18}$ 10 μm, 19×250 mm; Mobile phase A: 2.0 mM sodium phosphate buffer, pH 7.0; Mobile phase B: acetonitrile; Method: 1% B for 5 minutes, then 1% B to 60% B over the next 30 minutes, flow rate 26 mL/min. Fractions from 20.75-24.50 minutes were collected and lyophilized to afford EC0543 as a pale yellow fluffy solid (26 mg). The foregoing method is equally applicable for preparing other tubulysin conjugates by the appropriate selection of the tubulysin starting compound.

The following additional illustrative examples of tubulysin conjugates including a hydrophilic spacer linker were prepared using the process and syntheses described herein from tubulysins.

149 150
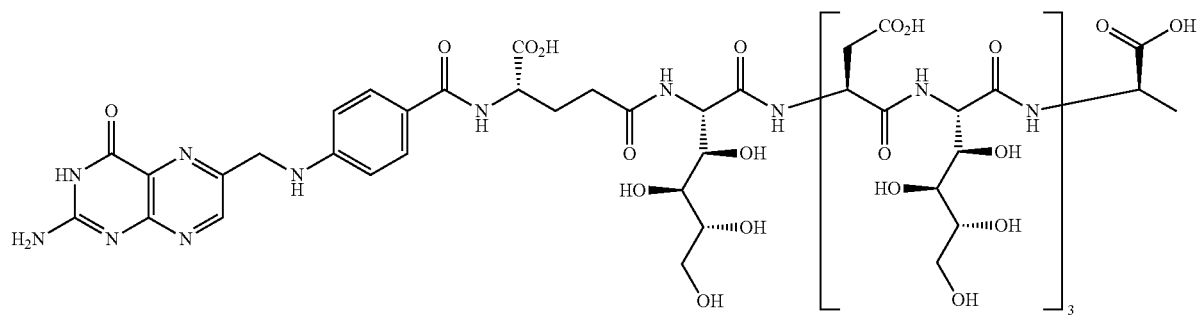
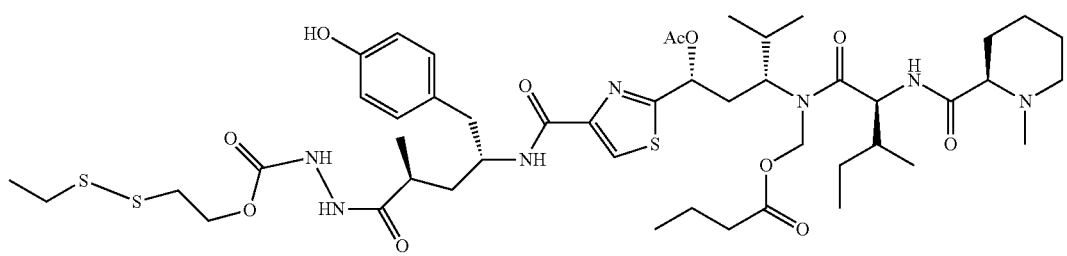
EC0436 Conjugate of Tubulysin
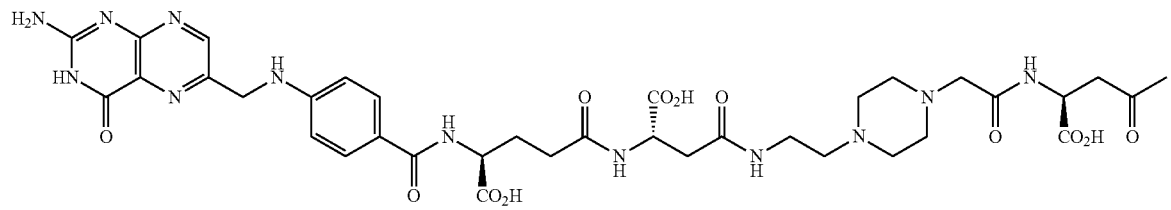
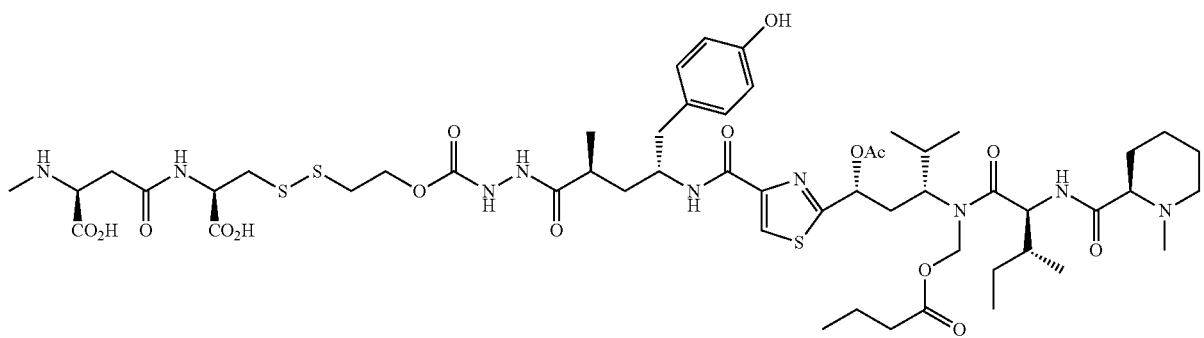

EC0444 Conjugate of Tubulysin
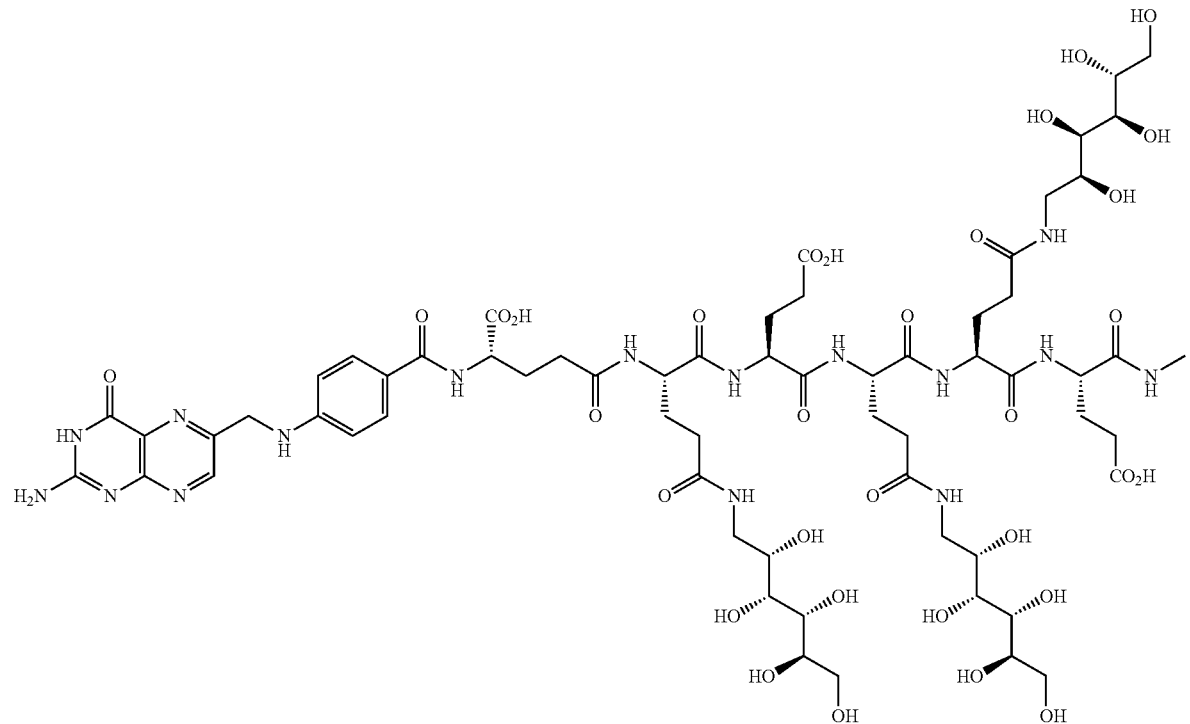
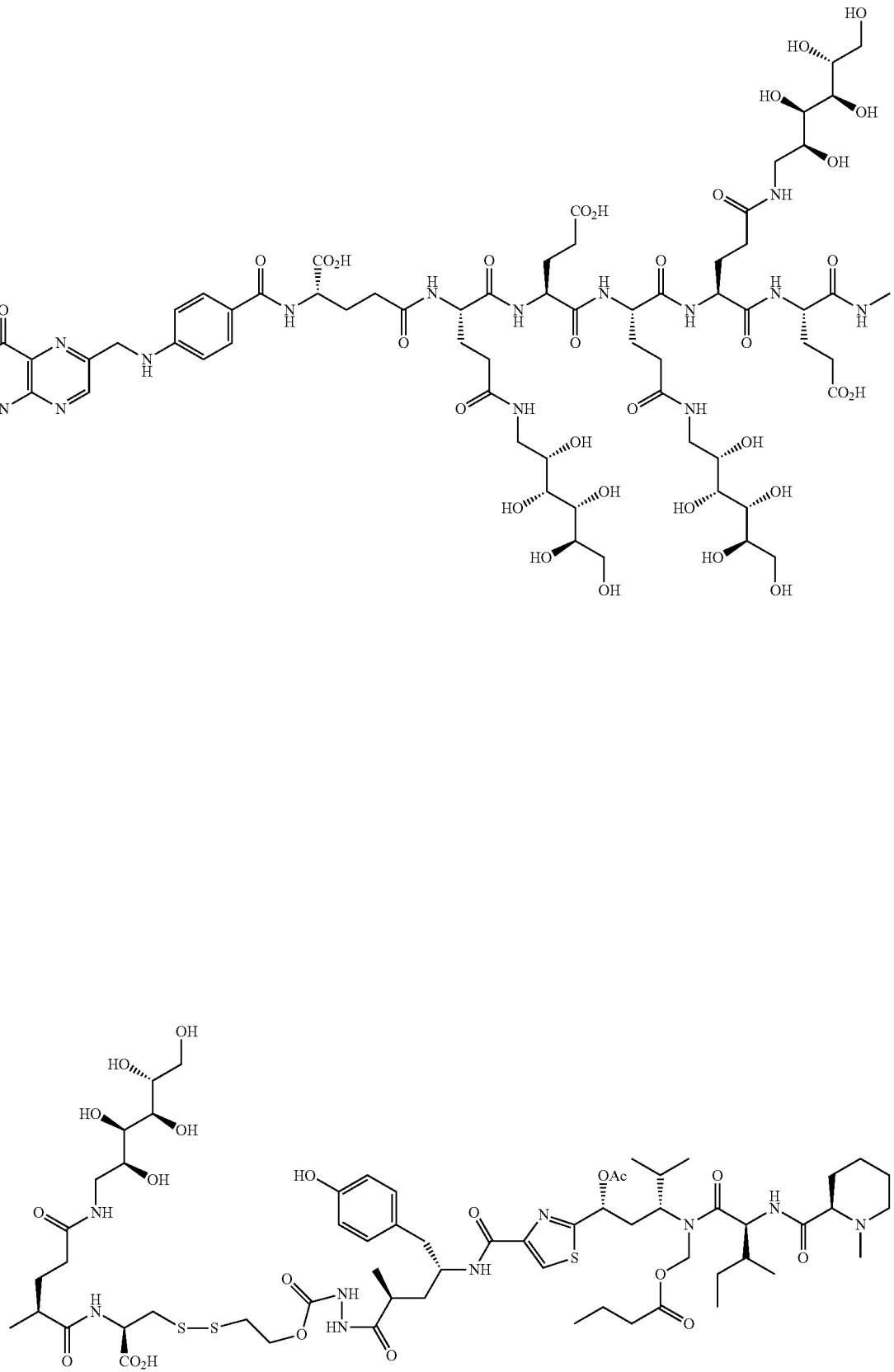

153

EC0530 Conjugate of Tubulysin

154

EC0531 Conjugate of Tubulysin
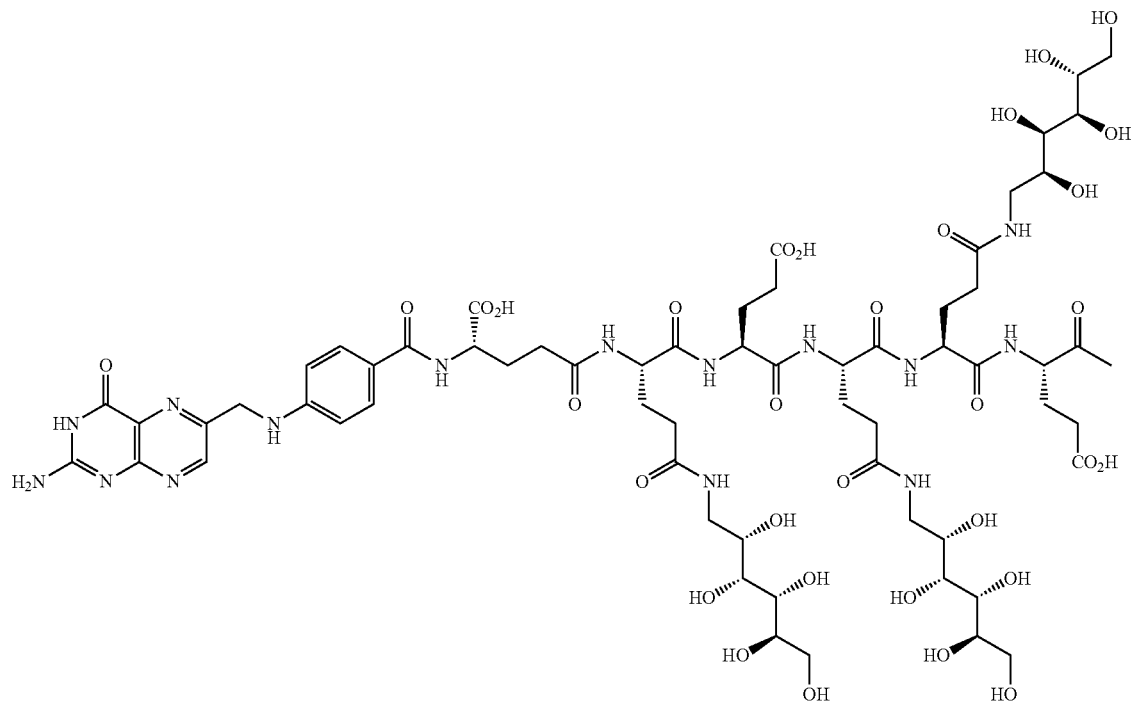
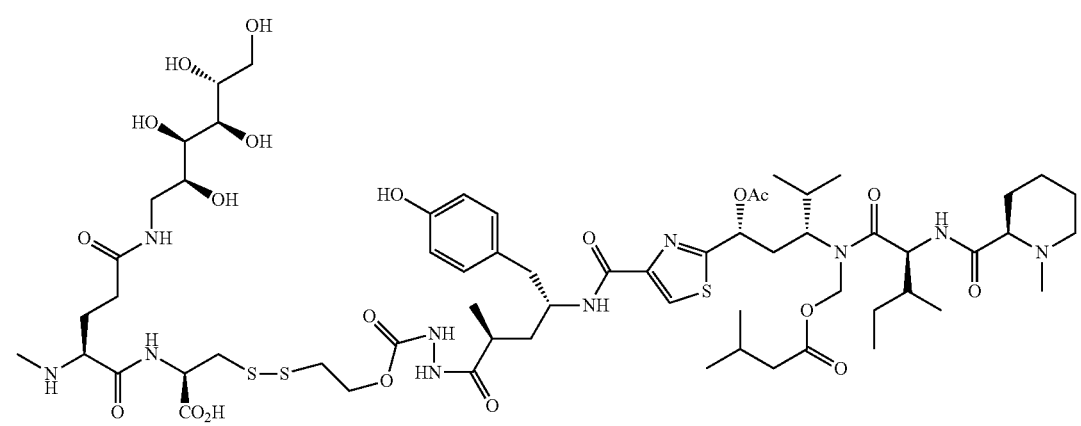
EC0533 Conjugate of Tubulysin
The following Examples were also prepared as described herein.
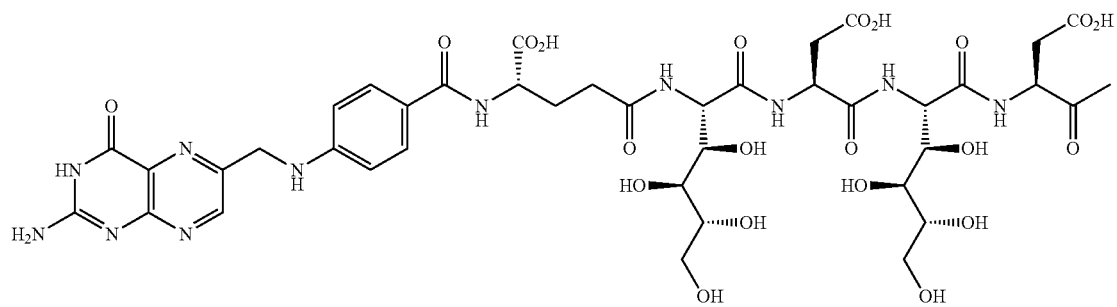

-continued

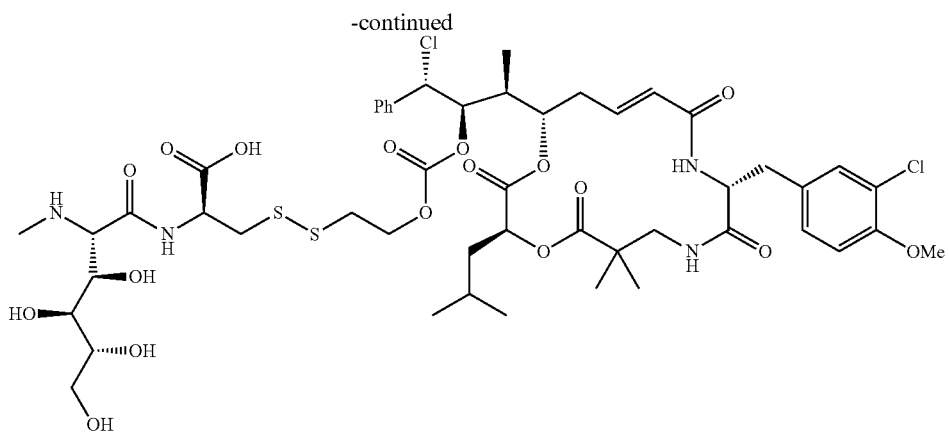

EC0262 Cryptophycin-Carbonate-CH$_2$CH$_2$—SS-Cys-Saccharo-Asp-Saccharo-Asp-Saccharo-Folate Conjugate. C$_{87}$H$_{115}$Cl$_2$N$_{15}$O$_{38}$S$_2$; MW 2113.96; Exact Mass: 2111.63

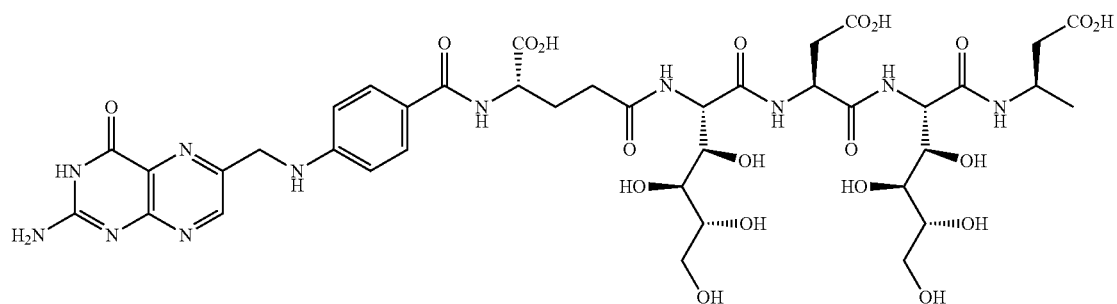

EC0278

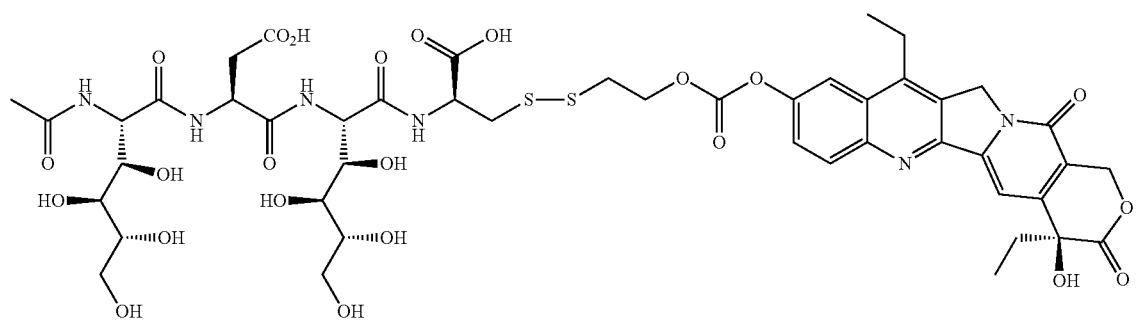

Comparative Bortezomib Examples

The following Comparative Examples of bortezomib (Velcade) conjugates (EC0522 and EC0587) lacking a hydrophilic spacer linker were also prepared as described herein and in US Patent Application Publication Serial No. 2005/0002942.

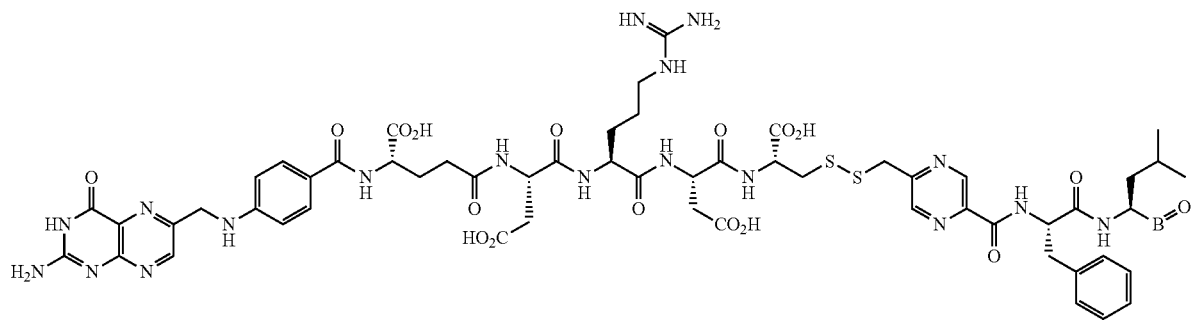 [SMILES: CC(C)C[C@@H](B=O)NC(=O)[C@H](Cc1ccccc1)NC(=O)c1cnc(CSSC[C@H](NC(=O)[C@H](CC(=O)O)NC(=O)[C@H](CCCNC(=N)N)NC(=O)[C@H](CC(=O)O)NC(=O)CC[C@H](NC(=O)c2ccc(NCc3cnc4nc(N)[nH]c(=O)c4n3)cc2)C(=O)O)C(=O)O)cn1]

EC0522 C56H69BN18O17S2, C, 50.15; H, 5.19; B, 0.81; N, 18.80; O, 20.28; S, 4.78, MW 1341.20, Exact Mass: 1340.46

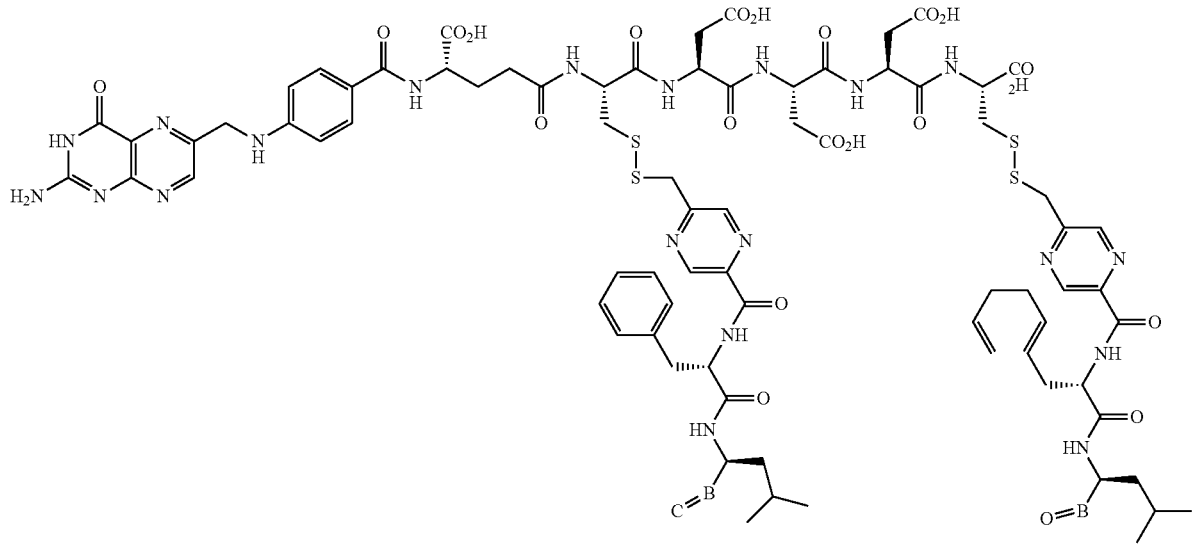 [SMILES: C=B[C@H](CC(C)C)NC(=O)[C@H](Cc1ccccc1)NC(=O)c1cnc(CSSC[C@H](NC(=O)CC[C@H](NC(=O)c2ccc(NCc3cnc4nc(N)[nH]c(=O)c4n3)cc2)C(=O)O)C(=O)N[C@@H](CC(=O)O)C(=O)N[C@@H](CC(=O)O)C(=O)N[C@@H](CC(=O)O)C(=O)N[C@@H](CSSCc2cnc(C(=O)N[C@@H](C/C=C/CCC=C)C(=O)N[C@H](B=O)CC(C)C)cn2)C(=O)O)cn1]

EC0587 C77H90B2N20O23S4, MW 1813.55, Exact Mass: 1812.56

The following Examples of bortezomib conjugates including a hydrophilic spacer linker were also prepared as described herein.

velcade conjugates, the boronic acid and the linker may form intermolecular interactions with the carbohydrate side chains. Illustratively, the boronic acid forms boronate ester complexes with one or two hydroxyl groups. Such ester complexes may be formed with vicinal hydroxyls as well as with 1,3-hydroxyls. It is appreciated that the boronate ester complexes may form at the end of the carbohydrate fragment, or in the interior of the carbohydrate fragment. It is

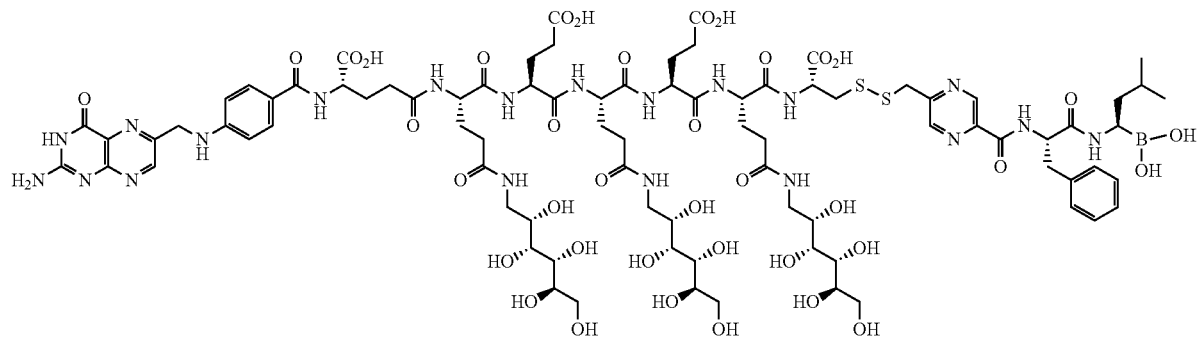 [SMILES: CC(C)C[C@H](NC(=O)[C@H](Cc1ccccc1)NC(=O)c1cnc(CSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cn1)B(O)O]

EC0525 Conjugate of bortezomib (Velcade). C85H119BN20O36S2, MW 2071.91, Exact Mass: 2070.76. Without being bound by theory, it is appreciated that in the further appreciated that in aqueous solution, the boronate ester complexes may be in equilibrium with the boronic acid.

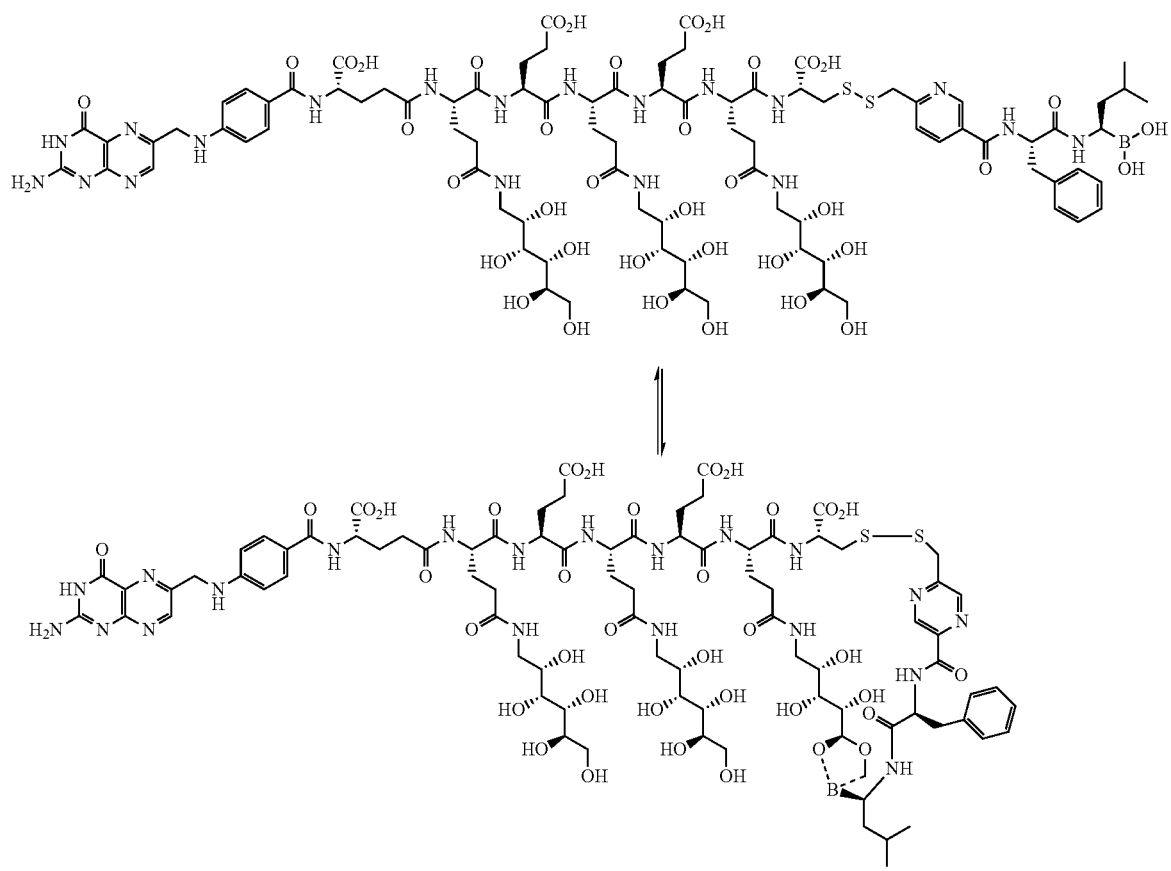
161
162
EC0525 (hydrated). C85H119BN20O36S2, MW 2071.91, Exact Mass: 2070.76; EC0525 (coordinated). C85H123BN20O38S2, MW 2107.94, Exact Mass: 2106.78.

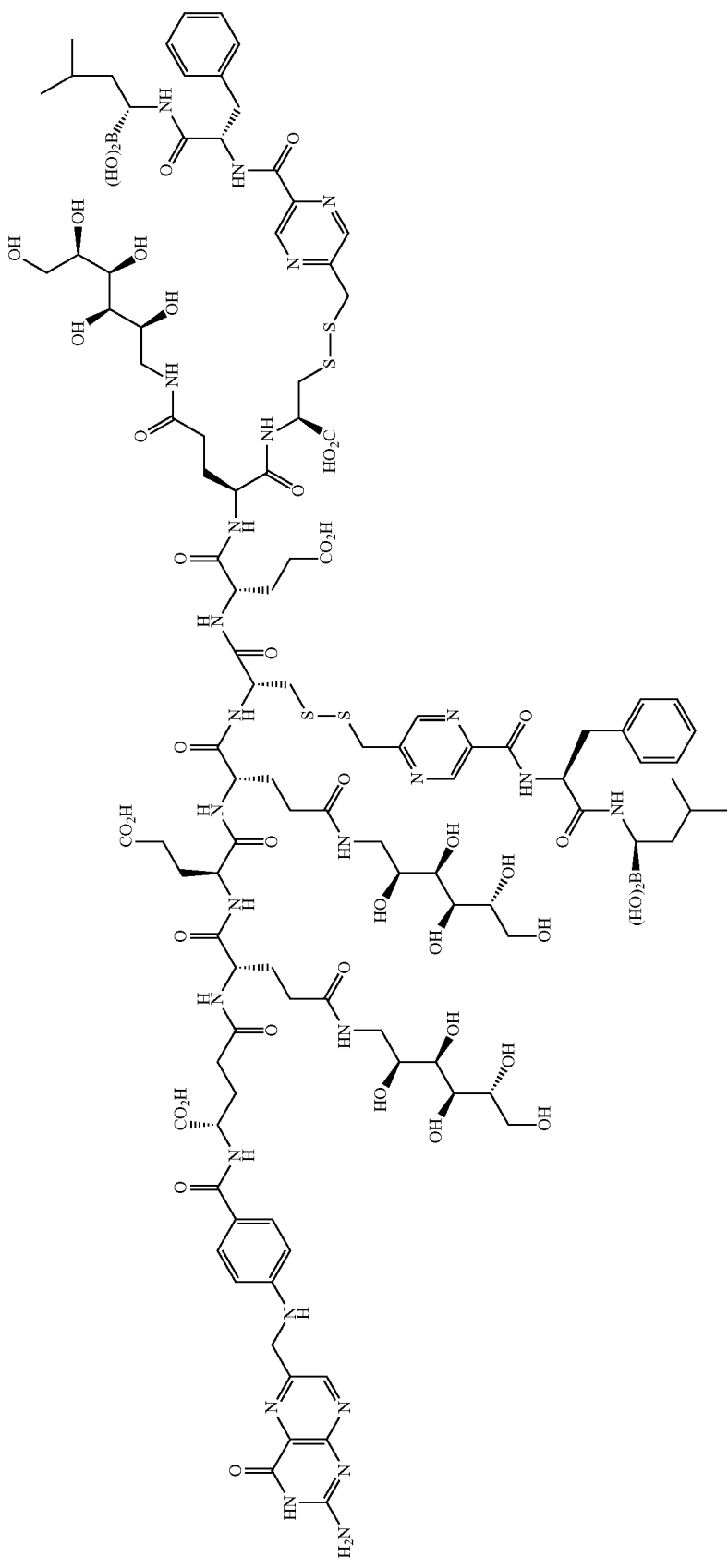

EC0595 Bis-bortezomib conjugate. C108H145B2N25O39S4, MW 2567.34, Exact Mass: 2565.92

Comparative α-Amantin Example

The following Comparative Example of an α-amantin conjugate lacking a hydrophilic spacer linker was also prepared as described herein and in US Patent Application Publication Serial No. 2005/0002942.

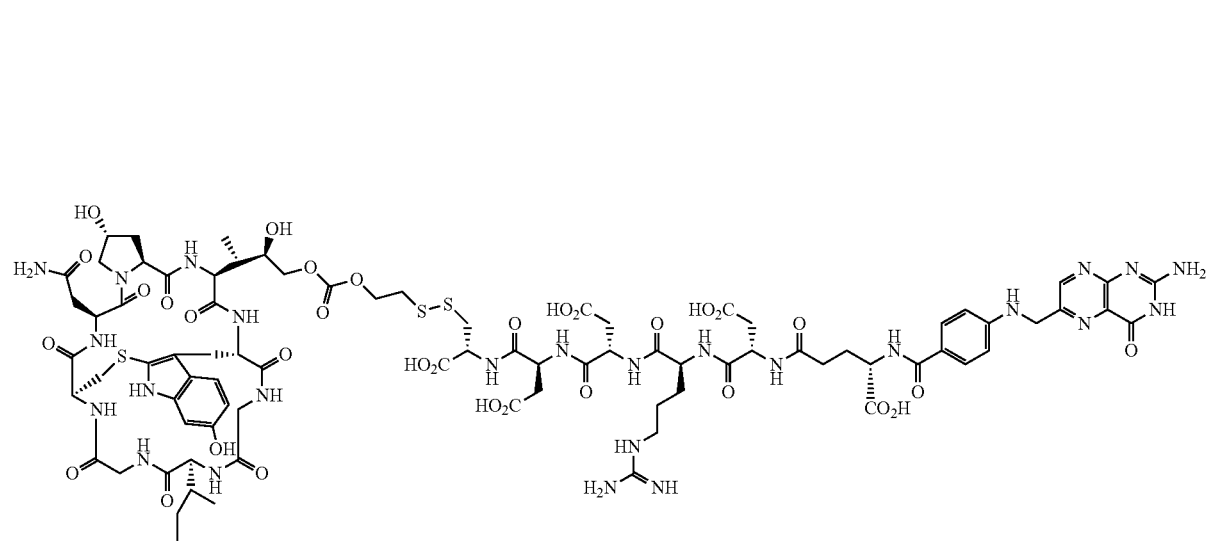 [SMILES: CCC(C)[C@@H]1NC(=O)CNC(=O)[C@@H]2Cc3c([nH]c4cc(O)ccc34)SC[C@@H](NC(=O)CNC1=O)C(=O)N[C@@H](CC(N)=O)C(=O)N1C[C@H](O)C[C@H]1C(=O)N[C@@H]([C@H](C)[C@@H](O)COC(=O)OCCSSC[C@H](NC(=O)[C@H](CC(=O)O)NC(=O)[C@H](CC(=O)O)NC(=O)[C@H](CCCNC(=N)N)NC(=O)[C@H](CC(=O)O)NC(=O)CC[C@H](NC(=O)c1ccc(NCc3cnc4nc(N)[nH]c(=O)c4n3)cc1)C(=O)O)C(=O)O)C(=O)N2]

EC0323 was not competitive with folic acid, and exhibited the same IC50 with and without excess folic acid present.

The following Examples of an α-amantin conjugate including a hydrophilic spacer linker was also prepared as described herein.

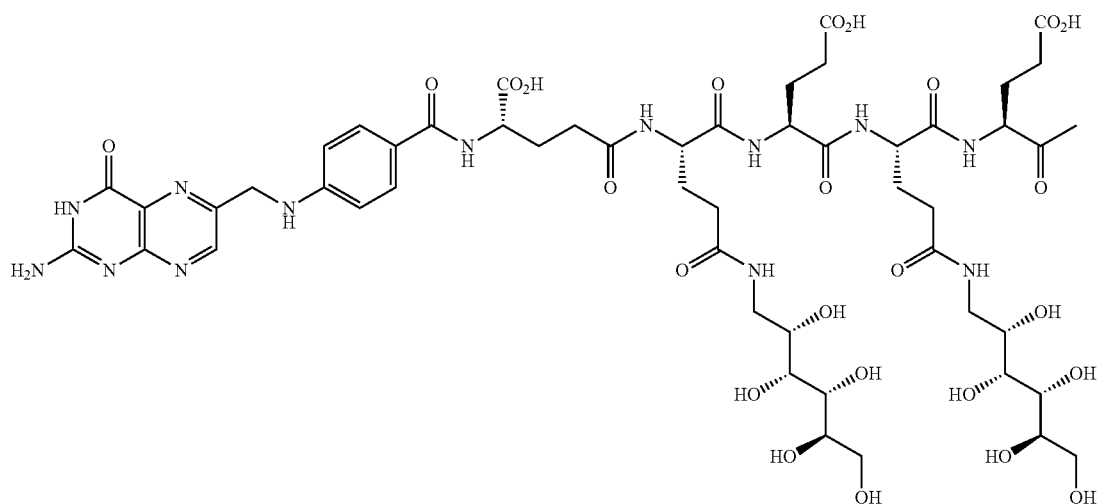

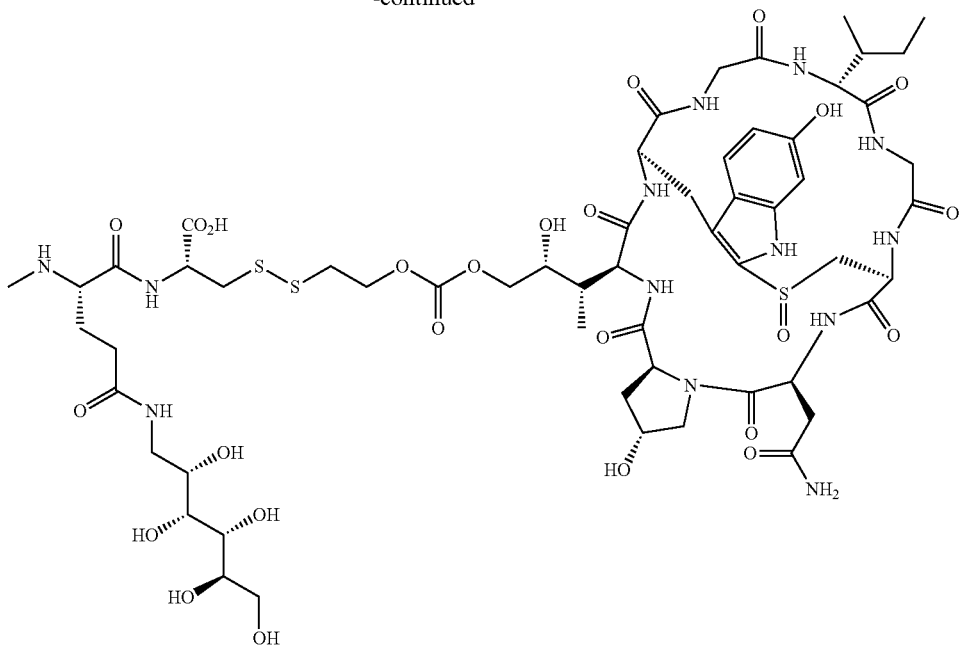
EC0592 Conjugate of α-amanitin. C107H154N26O50S3, MW 2700.71, Exact Mass: 2698.95. EC0592 shows an IC50 of ~3 nM, which may be competed with excess folic acid, against KB cells in 3H-thymidine incorporation assay.
The following Examples of illustrative conjugates were prepared as described herein.
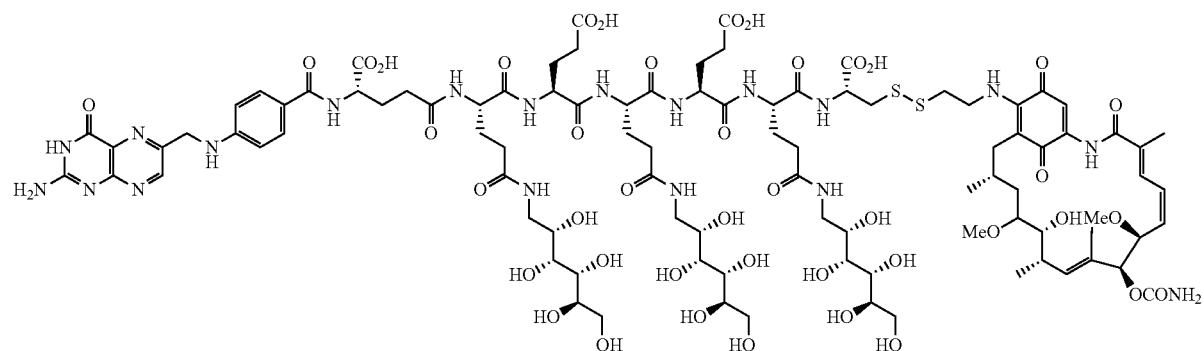
EC0535 Conjugate of geldanomycin. C95H139N19O42S2, MW 2283.35, Exact Mass: 2281.88
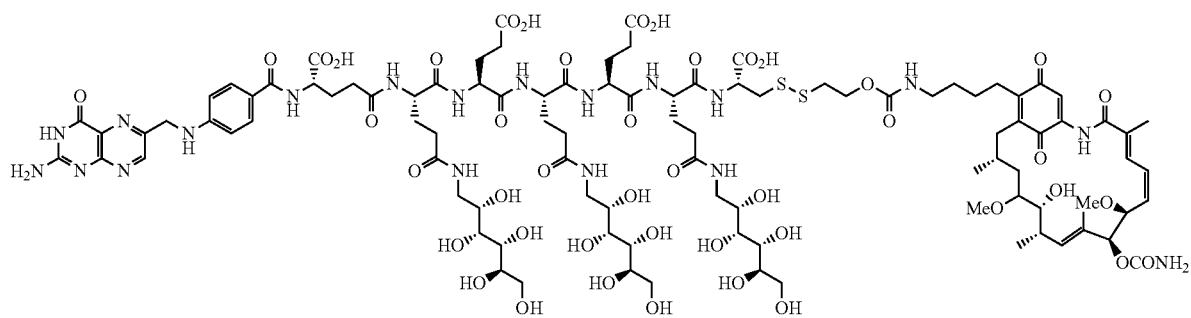

EC0568 Conjugate of geldanomycin.
C99H146N20O44S2, MW 2384.46, Exact Mass: 2382.92
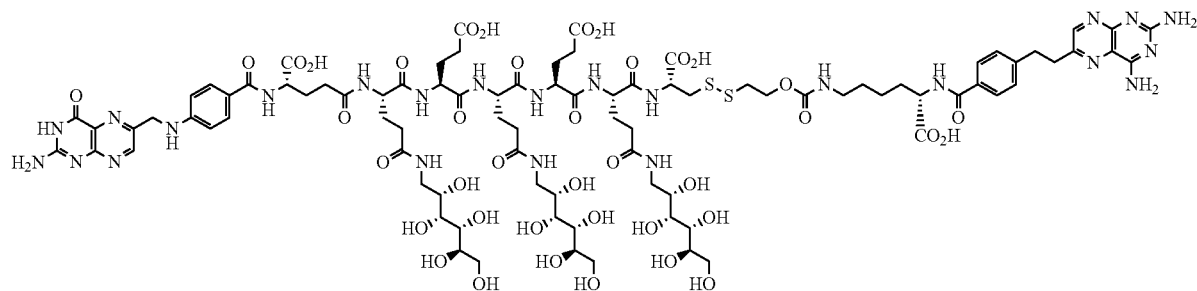 [SMILES: Nc1nc(N)c2nc(CCc3ccc(C(=O)N[C@@H](CCCCNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c4ccc(NCc5cnc6nc(N)[nH]c(=O)c6n5)cc4)C(=O)O)C(=O)O)C(=O)O)cc3)cnc2n1]
EC0539 Conjugate of lysine analog of aminopterin.
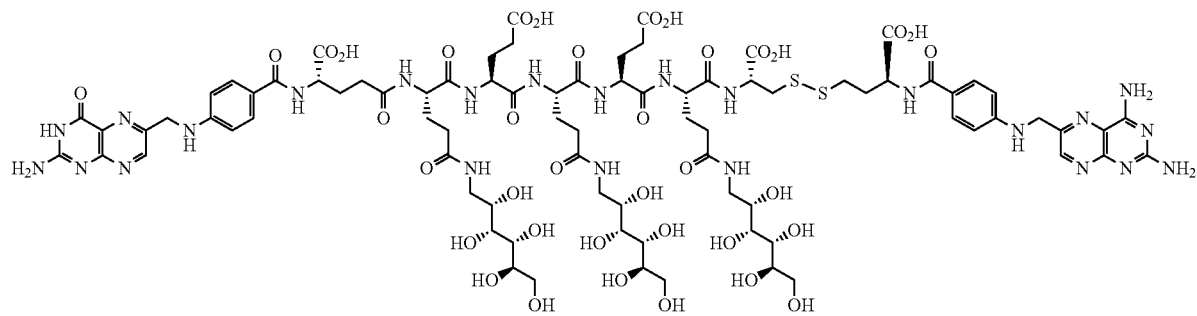 [SMILES: Nc1nc(N)c2nc(CNc3ccc(C(=O)N[C@@H](CCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c4ccc(NCc5cnc6nc(N)[nH]c(=O)c6n5)cc4)C(=O)O)C(=O)O)C(=O)O)cc3)cnc2n1]
EC0544 Conjugate of cysteine analog of aminopterin.
C83H116N24O37S2, C, 47.33; H, 5.55; N, 15.96; O, 28.11;
S, 3.05, MW 2106.08, Exact Mass: 2104.74
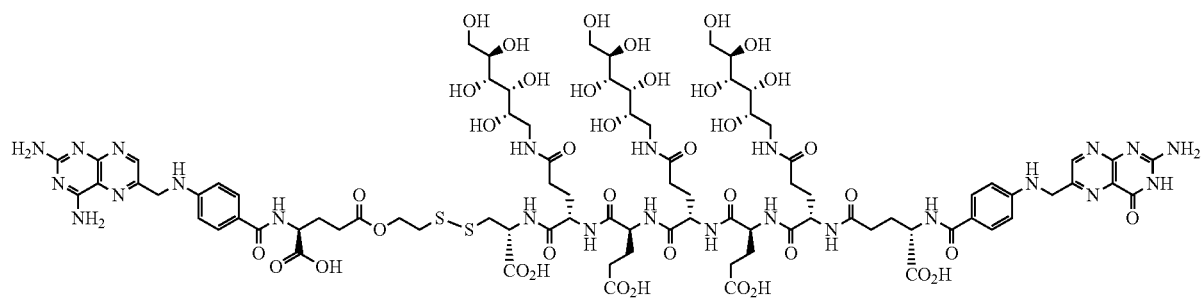 [SMILES: Nc1nc(N)c2nc(CNc3ccc(C(=O)N[C@@H](CCC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c4ccc(NCc5cnc6nc(N)[nH]c(=O)c6n5)cc4)C(=O)O)C(=O)O)C(=O)O)cc3)cnc2n1]
EC0551 Conjugate of aminopterin. C86H120N24O39S2,
C, 47.42; H, 5.55; N, 15.43; O, 28.65; S, 2.94, MW 2178.14,
Exact Mass: 2176.76

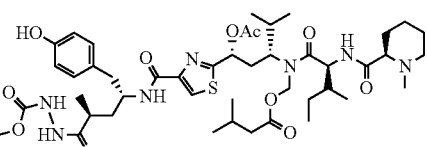
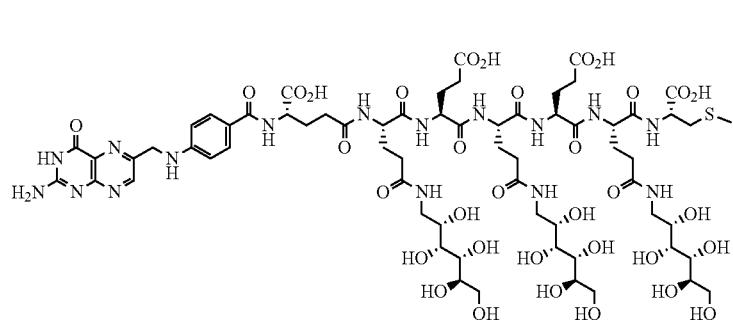
EC0543 Conjugate of tubulysin A. C111H167N23O45S3,
C, 50.50; H, 6.38; N, 12.20; O, 27.27; S, 3.64, MW 2639.84,
m/z: 2639.07 (100.0%), 2638.06 (80.8%), 2640.07 (79.6%)
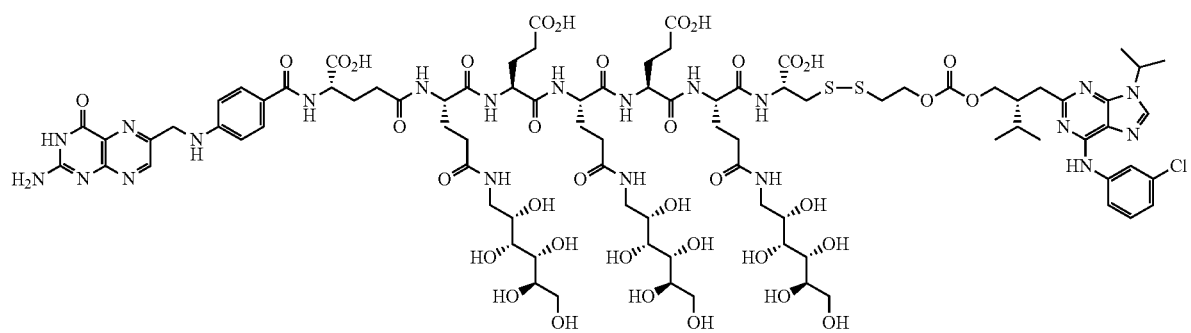 [SMILES: CC(C)[C@H](COC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c1ccc(NCc2cnc3nc(N)[nH]c(=O)c3n2)cc1)C(=O)O)C(=O)O)Cc1nc(Nc2cccc(Cl)c2)c2ncn(C(C)C)c2n1]
EC0545 Conjugate of purvalanol A.
C87H125ClN22O37S2; MW 2170.63, Exact Mass: 2168.77
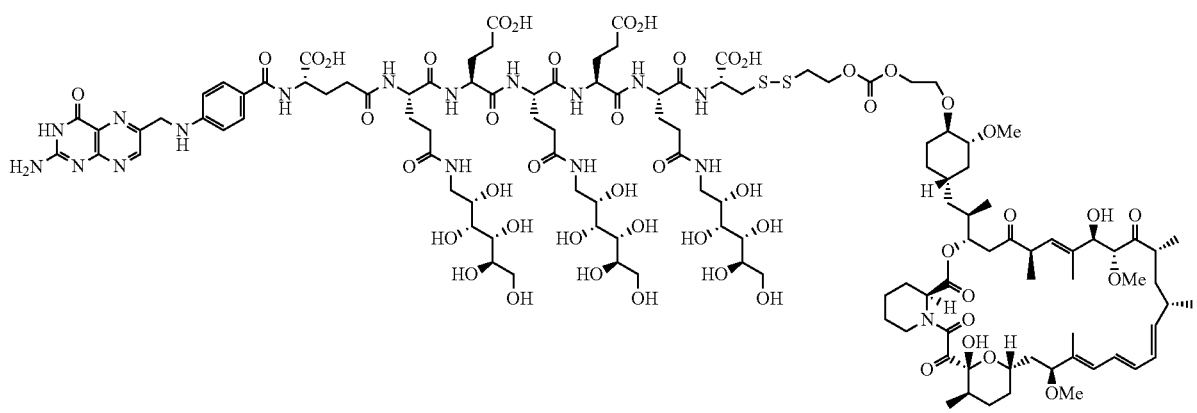 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCOC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c3ccc(NCc4cnc5nc(N)[nH]c(=O)c5n4)cc3)C(=O)O)C(=O)O)[C@H](OC)C2)CC(=O)[C@H](C)/C=C(\C)[C@@H](O)[C@@H](OC)C(=O)[C@H](C)C[C@H](C)/C=C/C=C/C=C/1C]
EC0565 Conjugate of everolimus. C121H183N17O50S2,
MW 2739.96, Exact Mass: 2738.17

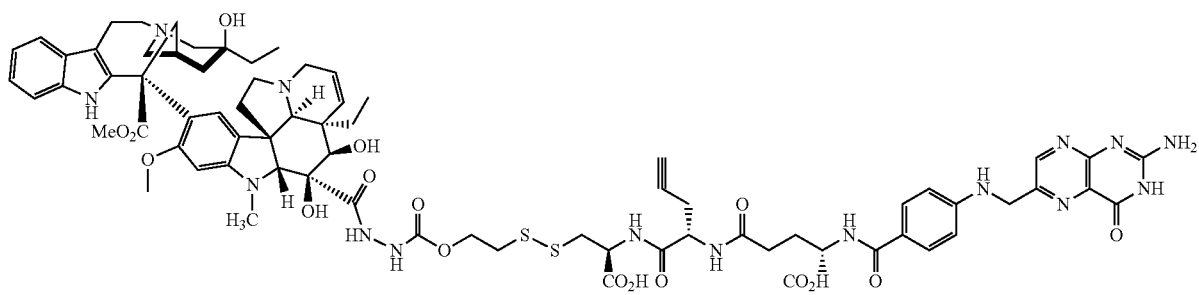
Conjugate of DAVLBH.
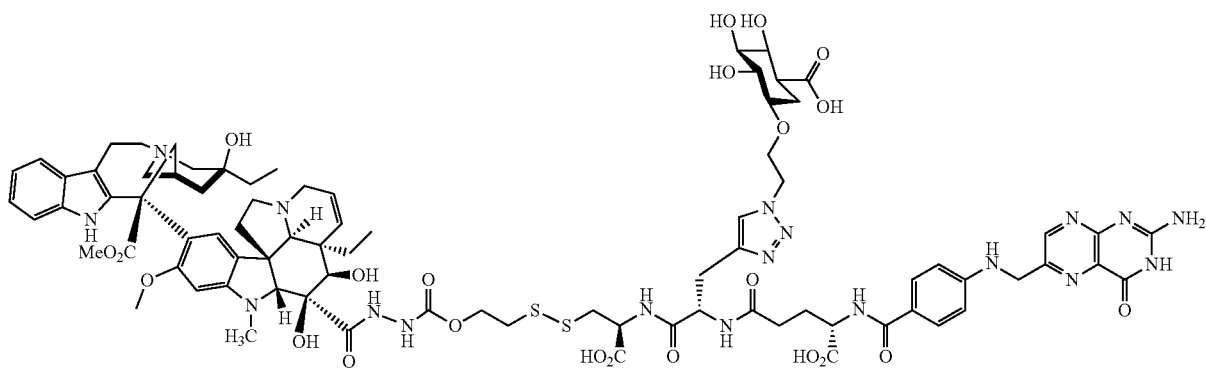
EC0400 Conjugate of DAVLBH. Prepared by Huisgen cyclization of corresponding alkyne and azidoethylcarbohydrate; 2 eq. Na ascorbate, 1 eq. CuSO4.5H2O, THF/water (1:1); 5 eq. Na aAscorbate, 2.5 eq. CuSO4.5H2O, THF/water (9:1); (10 mg). C81H100N18O24S2, C, 54.84; H, 5.68; N, 14.21; O, 21.65; S, 3.62, MW 1773.90, Exact Mass: 1772.66
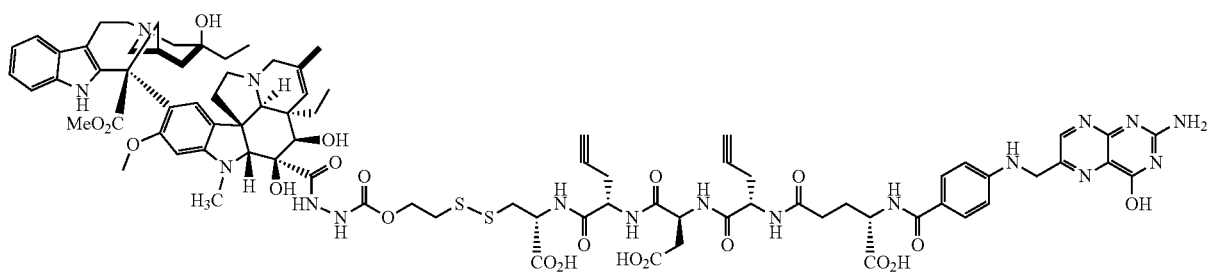
Conjugate of DAVLBH. Prepared from EC0419. C82H97N17O21S2, MW 1720.88, Exact Mass: 1719.65 (90 mg).

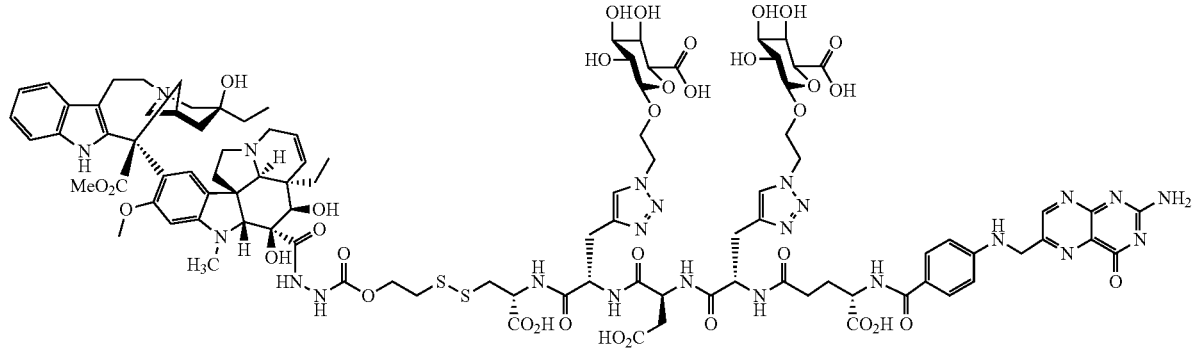
EC0423 Conjugate of DAVLBH. Prepared by Huisgen cyclization; C98H123N23O35S2, C, 52.38; H, 5.52; N, 14.34; O, 24.92; S, 2.85, MW 2247.29, Exact Mass: 2245.80

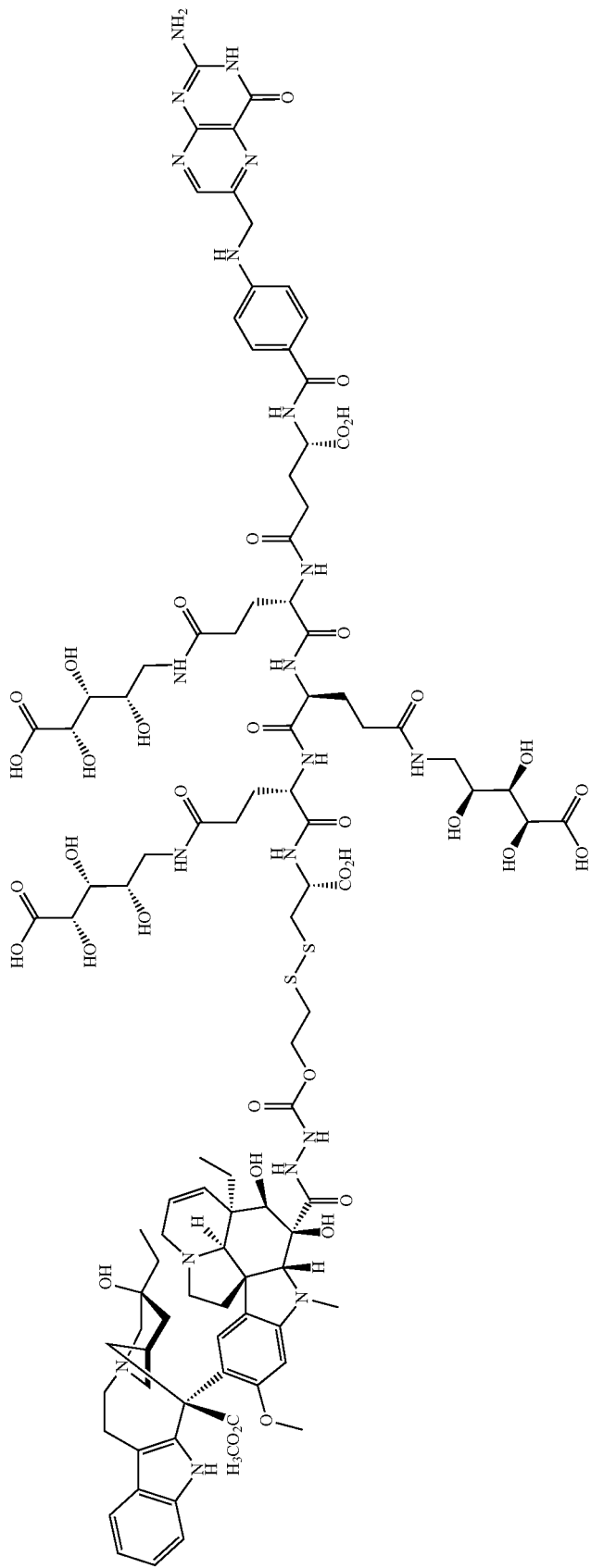

EC0637 Conjugate of DAVLBH. C98H130N20O37S2, MW 2244.32, Exact Mass: 2242.83
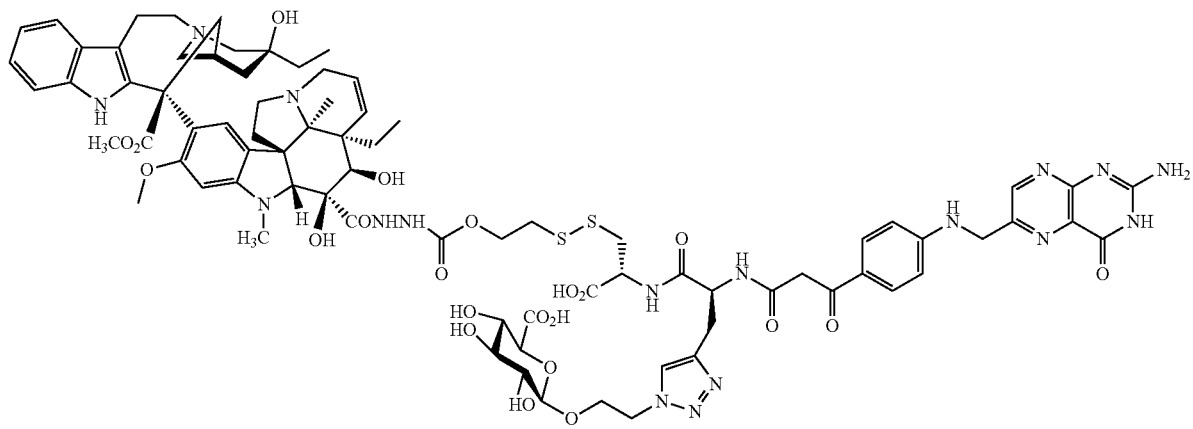
Conjugate of DAVLBH.
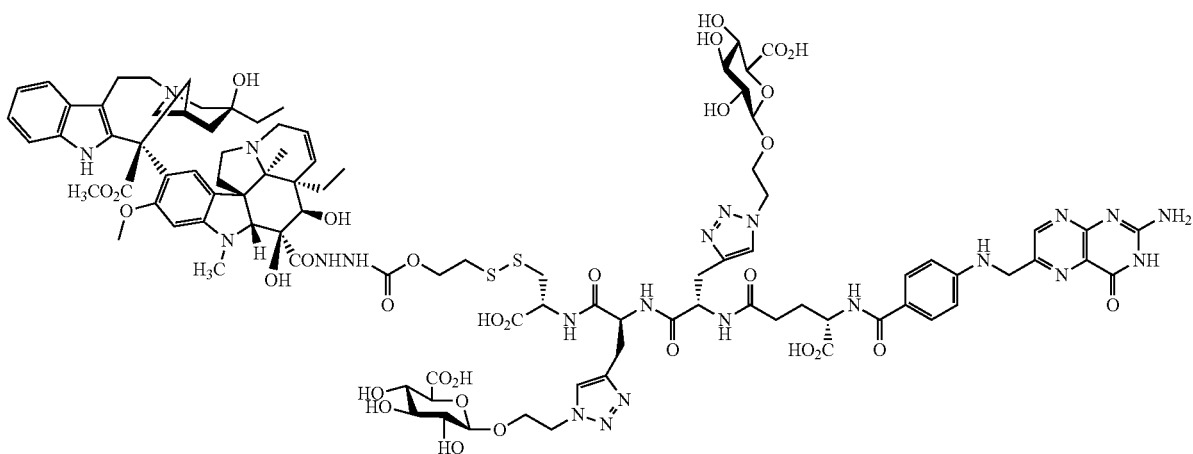
Conjugate of DAVLBH.
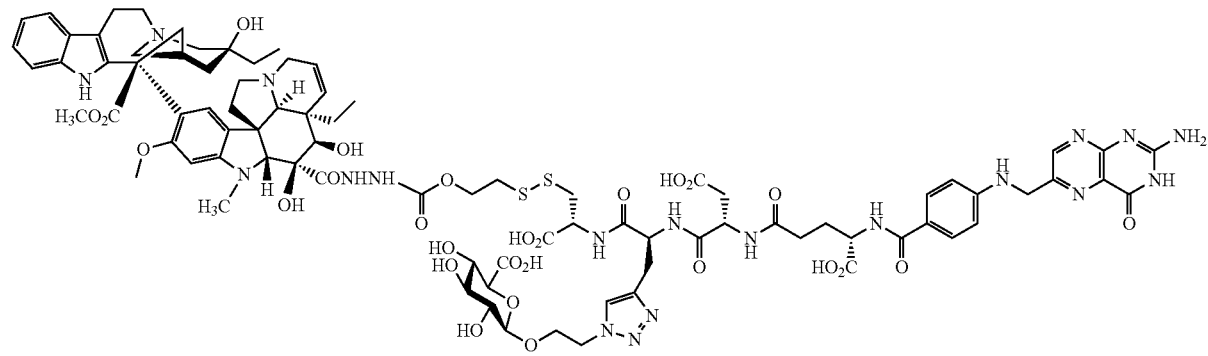

Conjugate of DAVLBH.
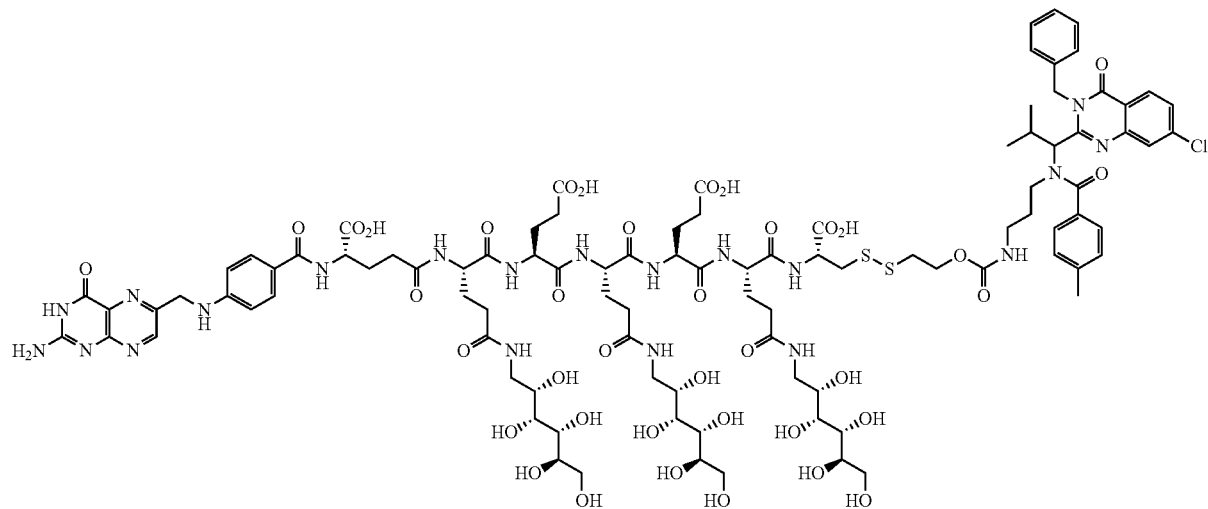 [SMILES: Cc1ccc(C(=O)N(CCCNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)C(c2nc3cc(Cl)ccc3c(=O)n2Cc2ccccc2)C(C)C)cc1]
EC0581 Conjugate of ispinesib. C98H133ClN20O38S2,
MW 2298.80, Exact Mass: 2296.82
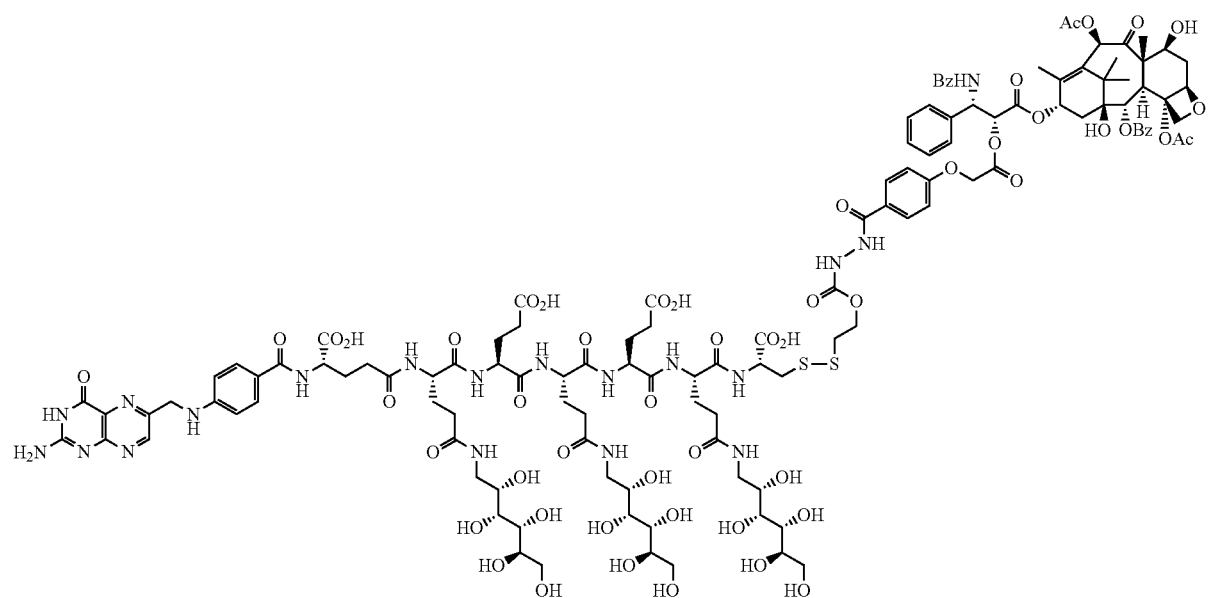
EC0561 Conjugate of paclitaxel. C124H159N19O53S2,
MW 2827.82, Exact Mass: 2825.98

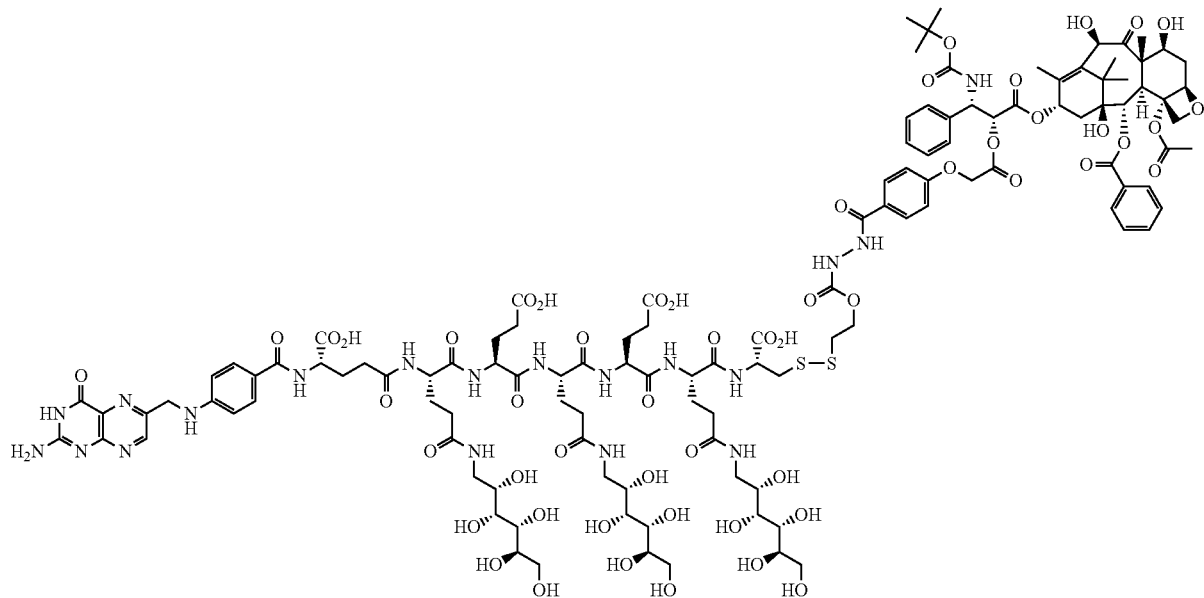 [SMILES: CC(=O)O[C@@]12CO[C@@H]1C[C@H](O)[C@@]1(C)C(=O)[C@H](O)C3=C(C)[C@@H](OC(=O)[C@H](OC(=O)COc4ccc(C(=O)NNC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c5ccc(NCc6cnc7nc(N)[nH]c(=O)c7n6)cc5)C(=O)O)C(=O)O)cc4)[C@@H](NC(=O)OC(C)(C)C)c4ccccc4)C[C@@](O)([C@@H](OC(=O)c4ccccc4)[C@H]21)C3(C)C]
EC0594 Conjugate of docetaxel. C120H161N19O53S2,
MW 2781.79, Exact Mass: 2779.99
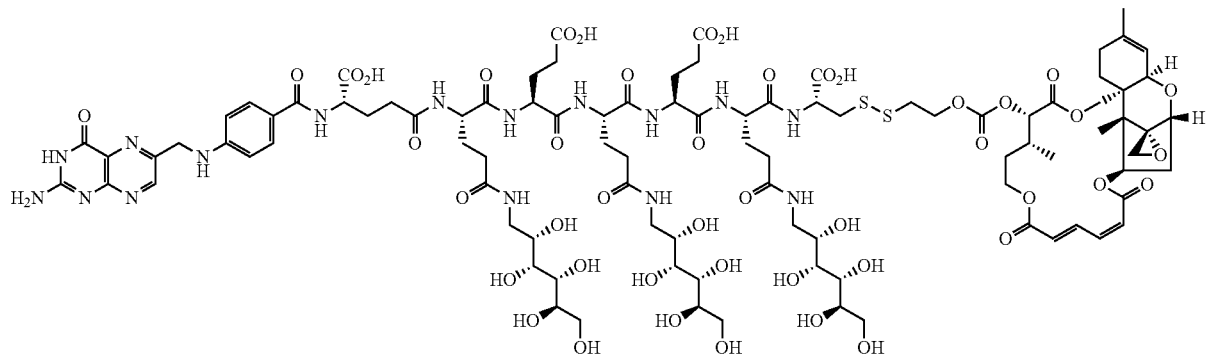 [SMILES: CC1=C[C@H]2O[C@@H]3C[C@H]4OC(=O)/C=C\C=C\C(=O)OCC[C@@H](C)[C@H](OC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c5ccc(NCc6cnc7nc(N)[nH]c(=O)c7n6)cc5)C(=O)O)C(=O)O)C(=O)OC[C@@]2(CC1)[C@]4(C)[C@]31CO1]
EC0598 Conjugate of Verucarin. C95H134N16O45S2,
MW 2284.29, Exact Mass: 2282.81
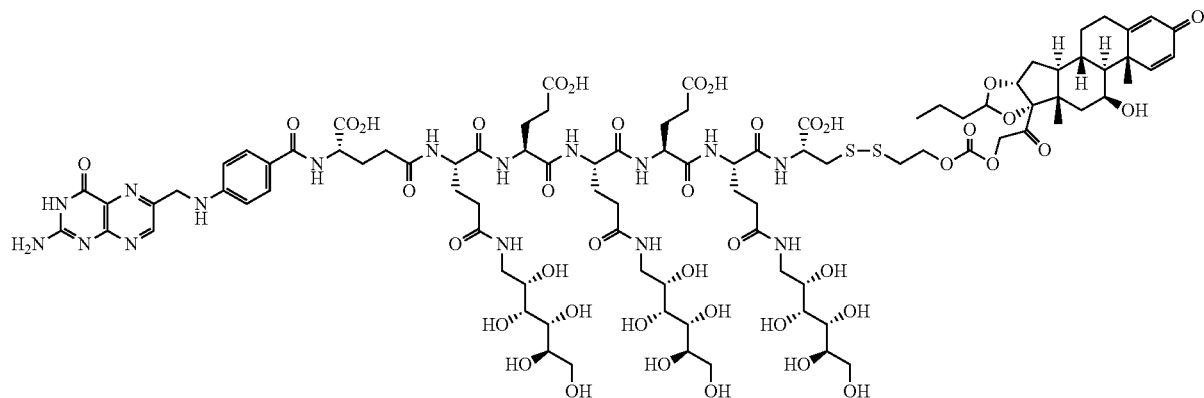

EC0600 Conjugate of Budesonide. C93H134N16O42S2, C, 50.49; H, 6.11; N, 10.13; 0, 30.37; S, 2.90, MW 2212.27, Exact Mass: 2210.83
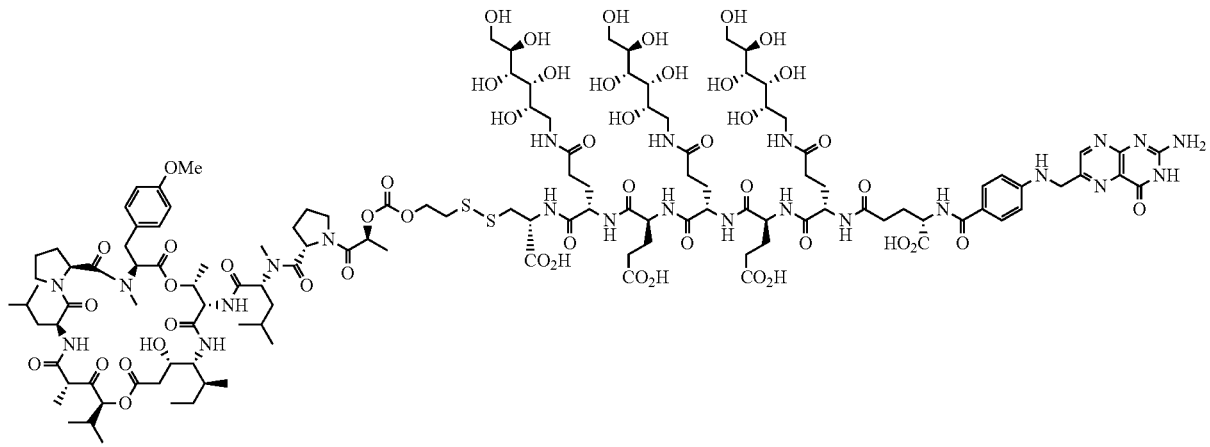
EC0610 Conjugate of Didemnin B. C125H189N23O51S2, MW 2894.09, Exact Mass: 2892.23
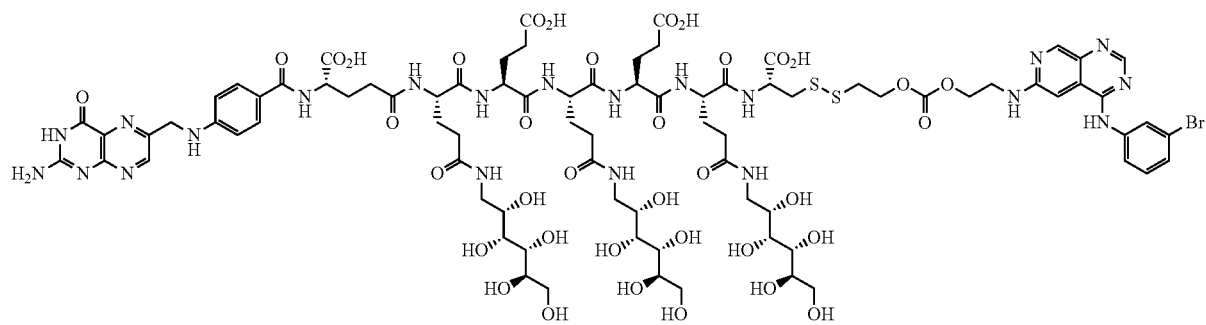 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CSSCCOC(=O)OCCNc4cc5c(Nc6cccc(Br)c6)ncnc5cn4)C(=O)O)C(=O)O)cc3)nc2c(=O)[nH]1]
EC0631 Conjugate of the tyrosine kinase inhibitor 4-[(3-bromophenyl)amino]-6-[(2-hydroxyethyl-amino]pyrido[3,4-d]pyrimidine, C83H114BrN21O37S2, MW 2141.95, Exact Mass: 2139.63
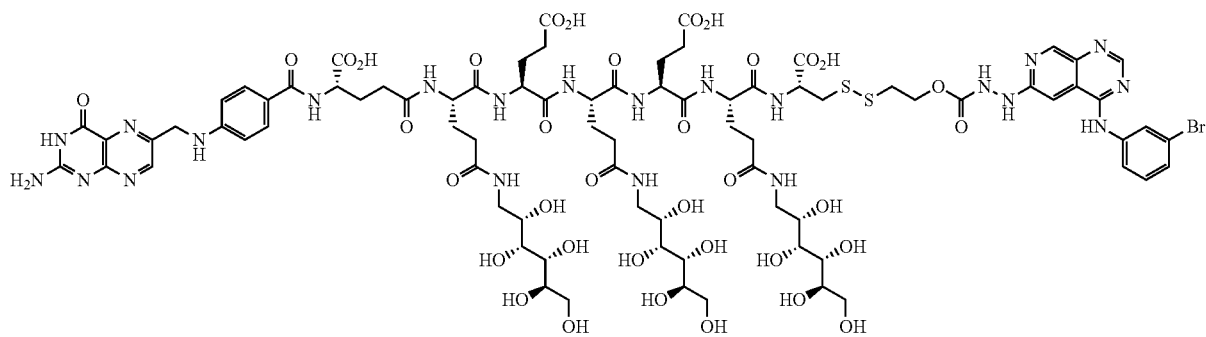 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CSSCCOC(=O)NNc4cc5c(Nc6cccc(Br)c6)ncnc5cn4)C(=O)O)C(=O)O)cc3)nc2c(=O)[nH]1]
EC0640: Conjugate of 4-[(3-Bromophenyl)amino]-6-hydrazino-pyrido[3,4-d]pyrimidine

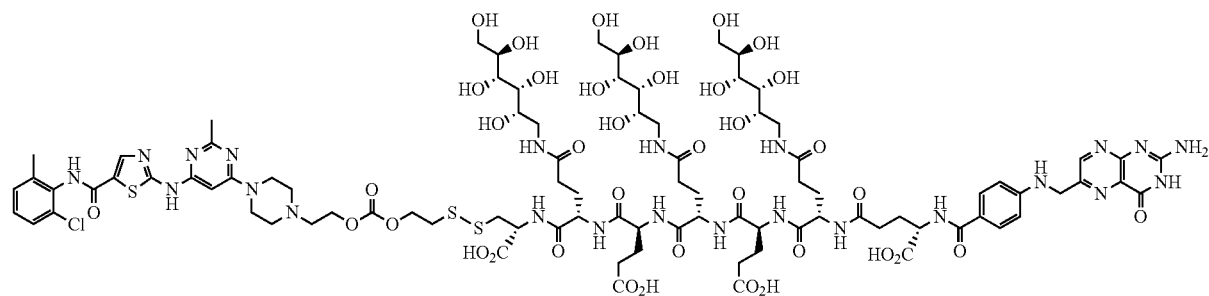 [SMILES: Cc1nc(Nc2ncc(C(=O)Nc3c(C)cccc3Cl)s2)cc(N2CCN(CCOC(=O)OCCSSC[C@H](NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c3ccc(NCc4cnc5nc(N)[nH]c(=O)c5n4)cc3)C(=O)O)C(=O)O)CC2)n1]
EC0663 Conjugate of Dasatinib. C90H126ClN23O38S3,
MW 2269.74, Exact Mass: 2267.75
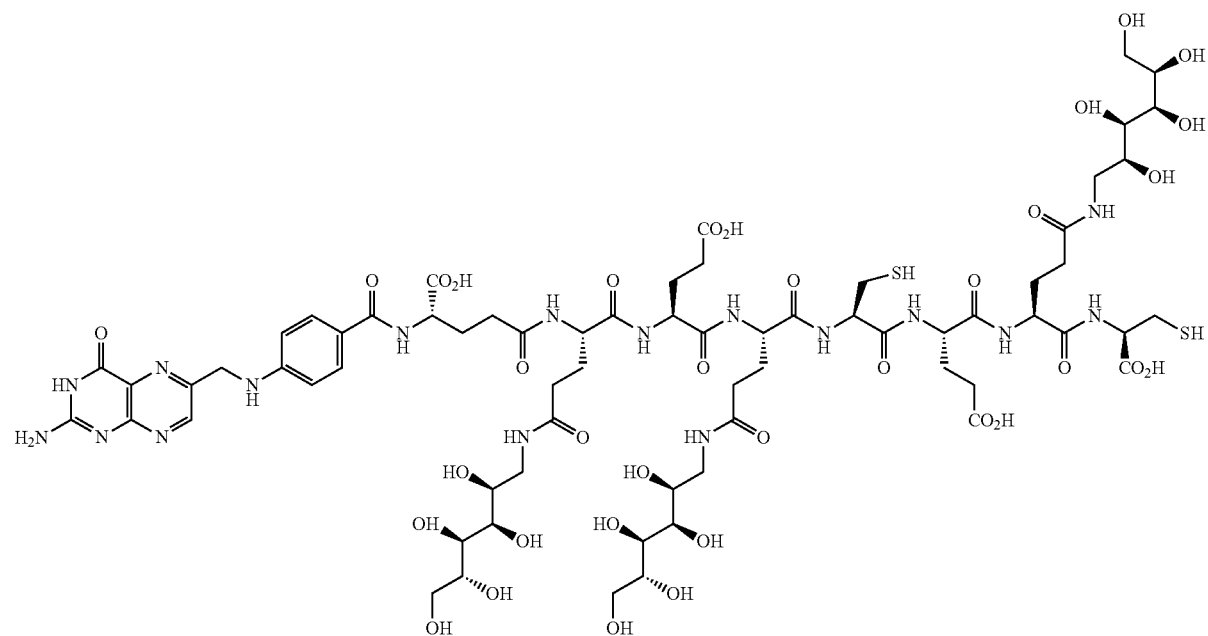 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]
EC0593 Multidrug intermediate for two drugs.
C68H103N17O35S2, MW 1782.77, Exact Mass: 1781.62
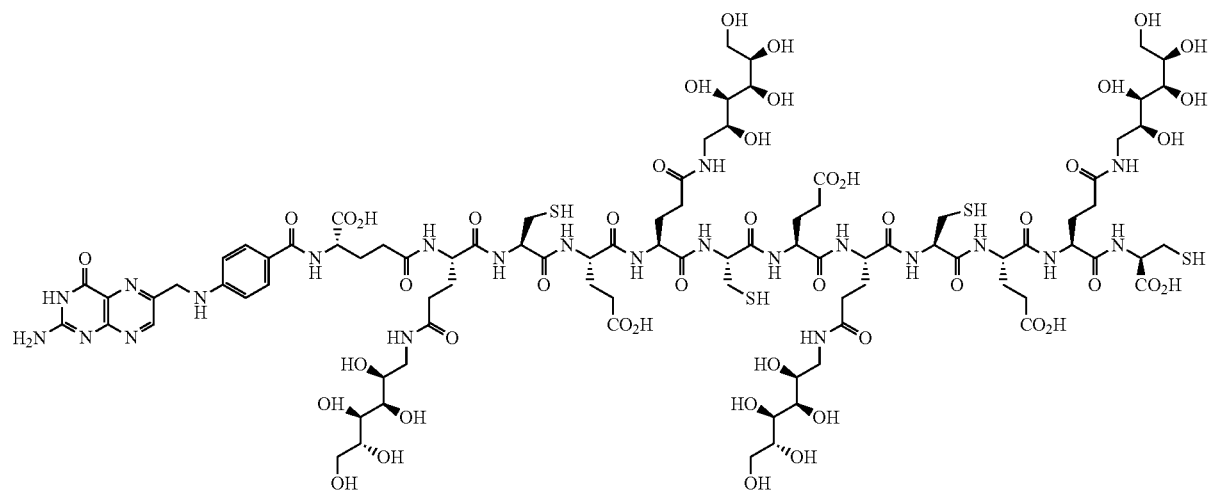 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CS)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0613 Multidrug intermediate for three drugs. C90H140N22O47S4, MW 2410.45, Exact Mass: 2408.81
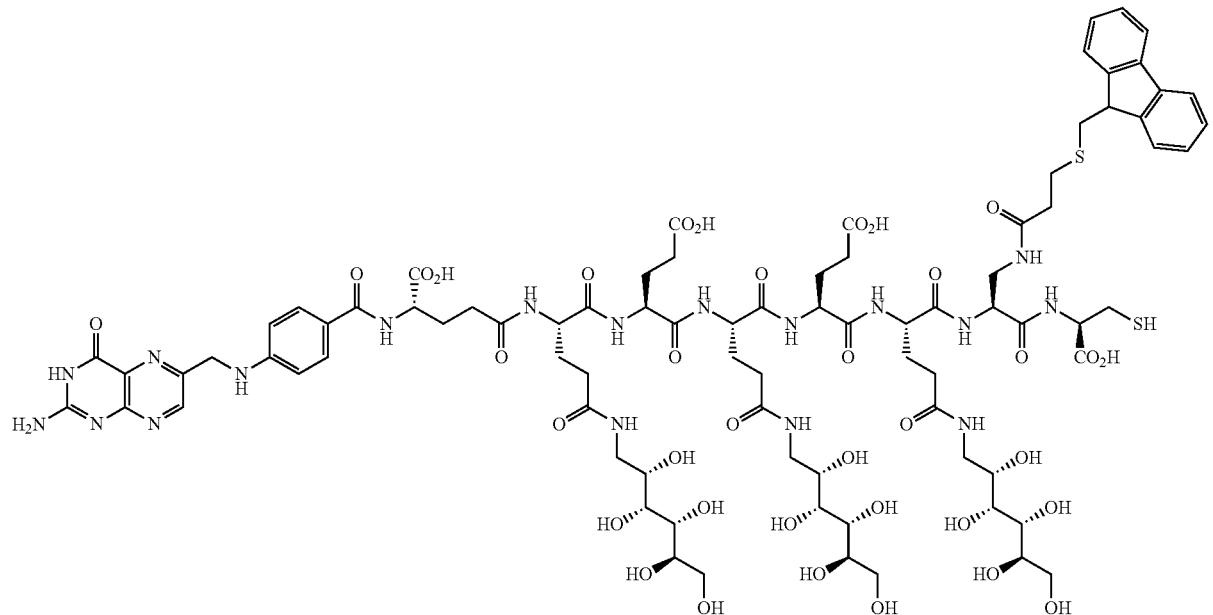 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CNC(=O)CCSCC4c5ccccc5-c5ccccc54)C(=O)N[C@@H](CS)C(=O)O)C(=O)O)cc3)nc2c(=O)[nH]1]
EC0542 Optionally selective multidrug intermediate for two drugs. C85H118N18O36S2, C, 50.24; H, 5.85; N, 12.41; O, 28.34; S, 3.16, MW 2032.08, Exact Mass: 2030.74
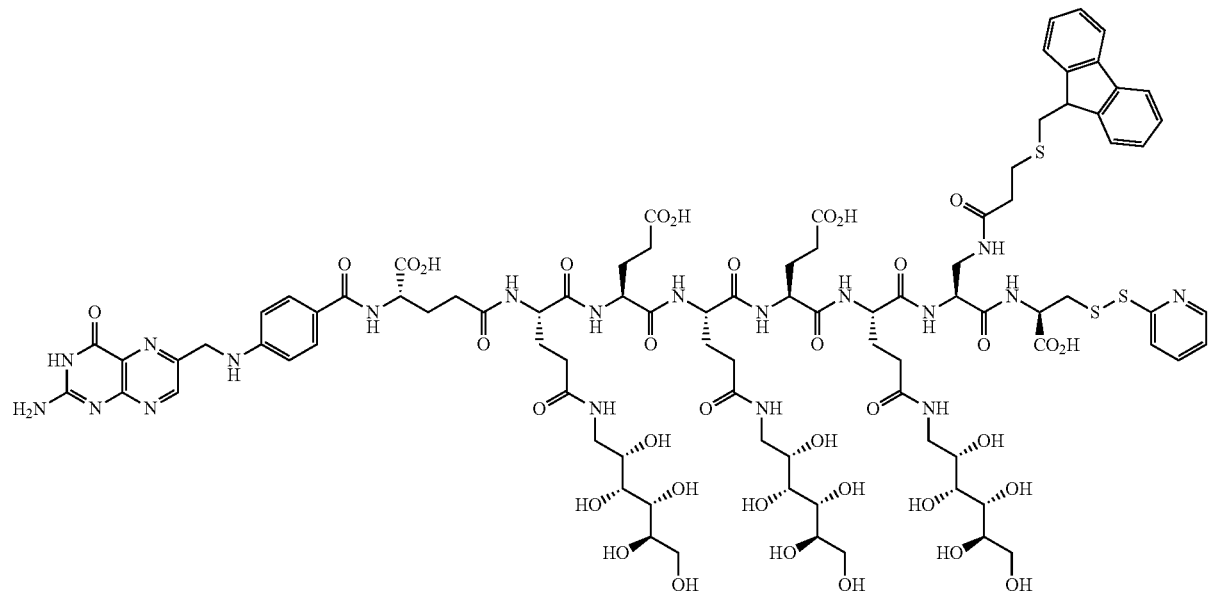 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CNC(=O)CCSCC4c5ccccc5-c5ccccc54)C(=O)N[C@@H](CSSc4ccccn4)C(=O)O)C(=O)O)cc3)nc2c(=O)[nH]1]
EC0559 Optionally selective multidrug intermediate for two drugs. C90H121N19O36S3, MW 2141.22, Exact Mass: 2139.74

191 192
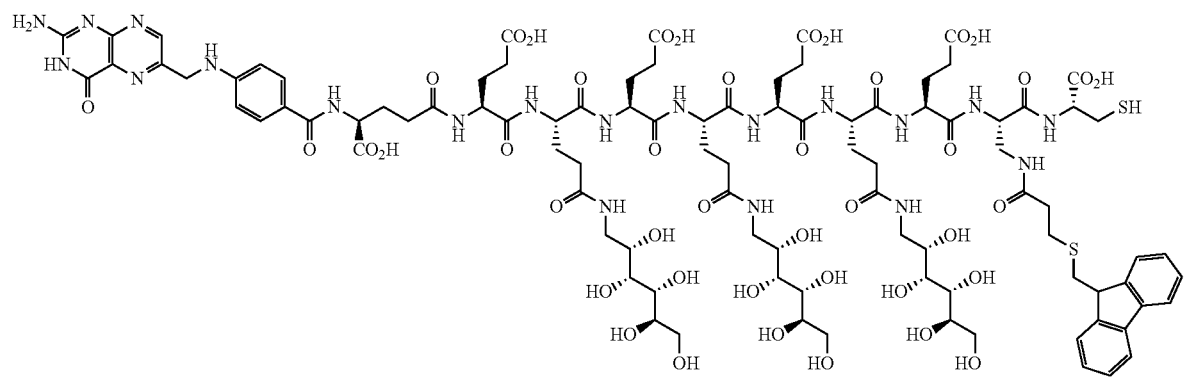 [SMILES: Nc1nc2ncc(CNc3ccc(C(=O)N[C@@H](CCC(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CNC(=O)CCSCC4c5ccccc5-c5ccccc54)C(=O)N[C@@H](CS)C(=O)O)C(=O)O)cc3)nc2c(=O)[nH]1]
EC0682 Optionally selective multidrug intermediate for two drugs. C95H132N20O42S2, MW 2290.30, Exact Mass: 2288.82

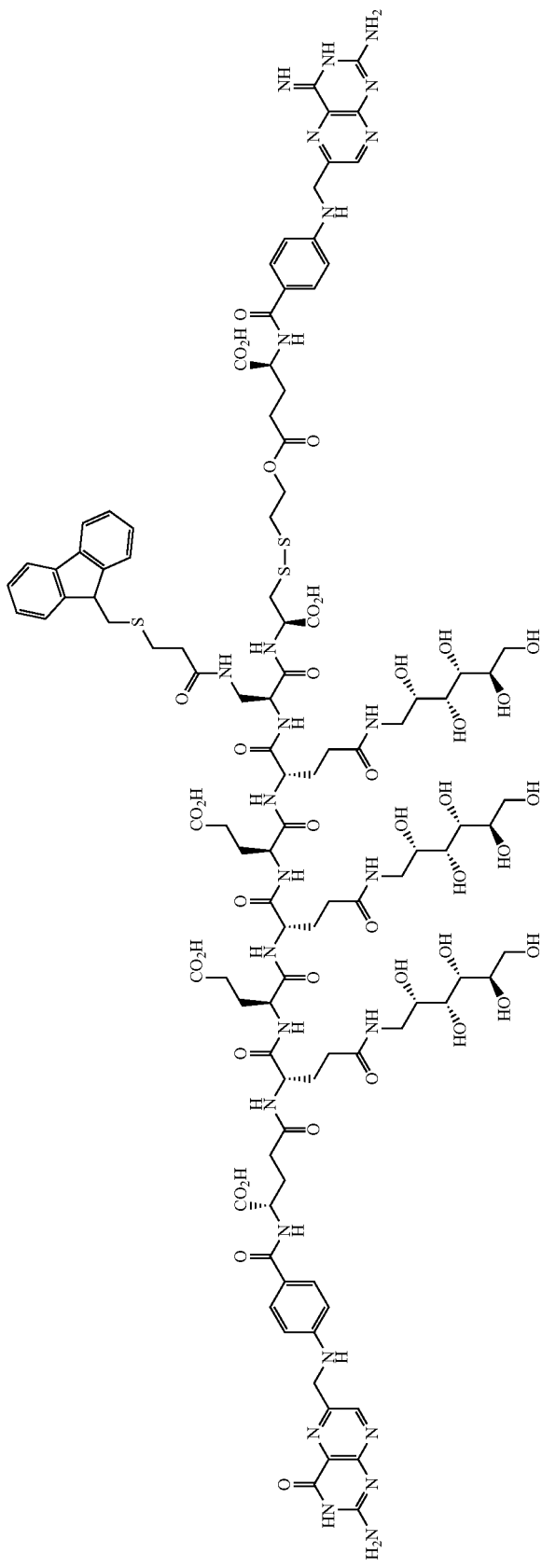

EC0646 Conjugate of Aminopterin and intermediate for multidrug conjugate. C106H140N26O41S3, MW 2530.59, Exact Mass: 2528.88
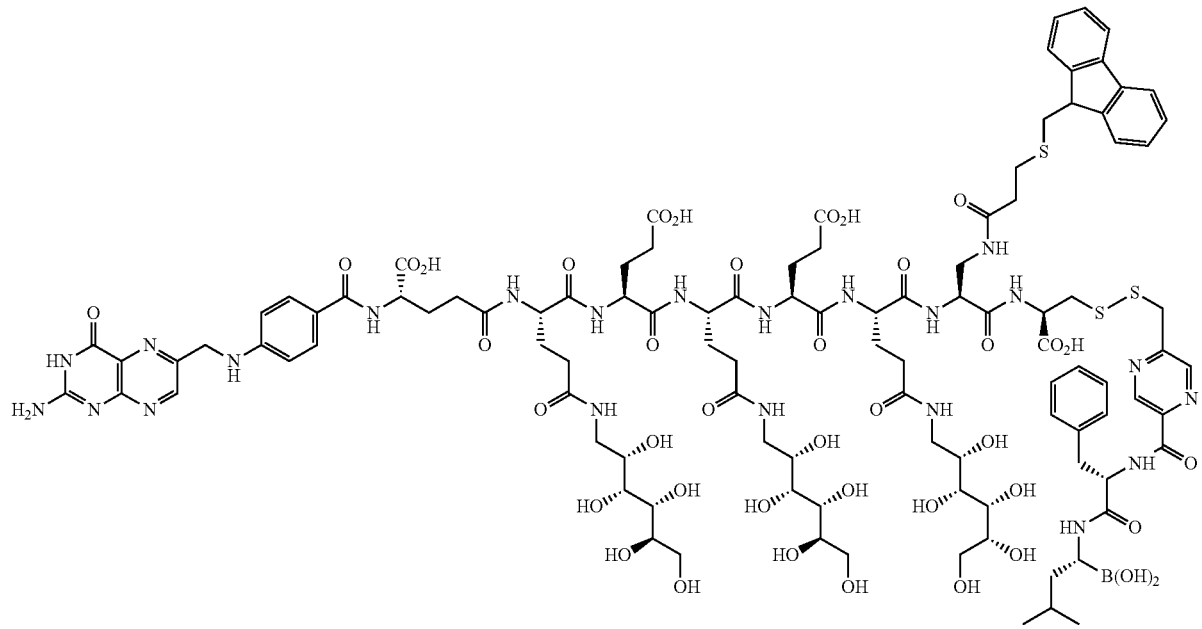 [SMILES: CC(C)C[C@H](NC(=O)[C@H](Cc1ccccc1)NC(=O)c1cnc(CSSC[C@H](NC(=O)[C@H](CNC(=O)CCSCC2c3ccccc3-c3ccccc32)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)cn1)B(O)O]
EC0555 Conjugate of Bortezomib (Velcade) and intermediate for multidrug conjugate. C105H139BN22O38S3, C, 52.02; H, 5.78; B, 0.45; N, 12.71; O, 25.08; S, 3.97, MW 2424.36, Exact Mass: 2422.89

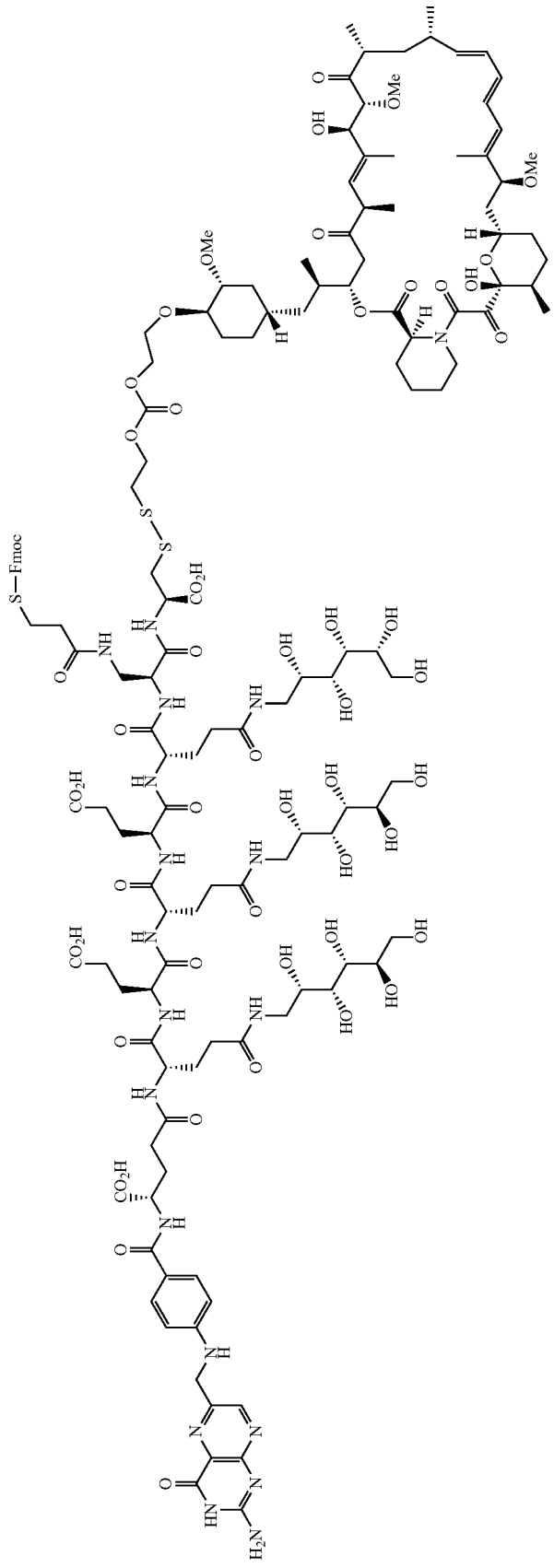

EC0606 Conjugate of Everolimus and intermediate for multidrug conjugate. C141H203N19O52S3, C, 54.76; H, 6.62; N, 8.61; O, 26.90; S, 3.11, MW 3092.42, Exact Mass: 3090.30

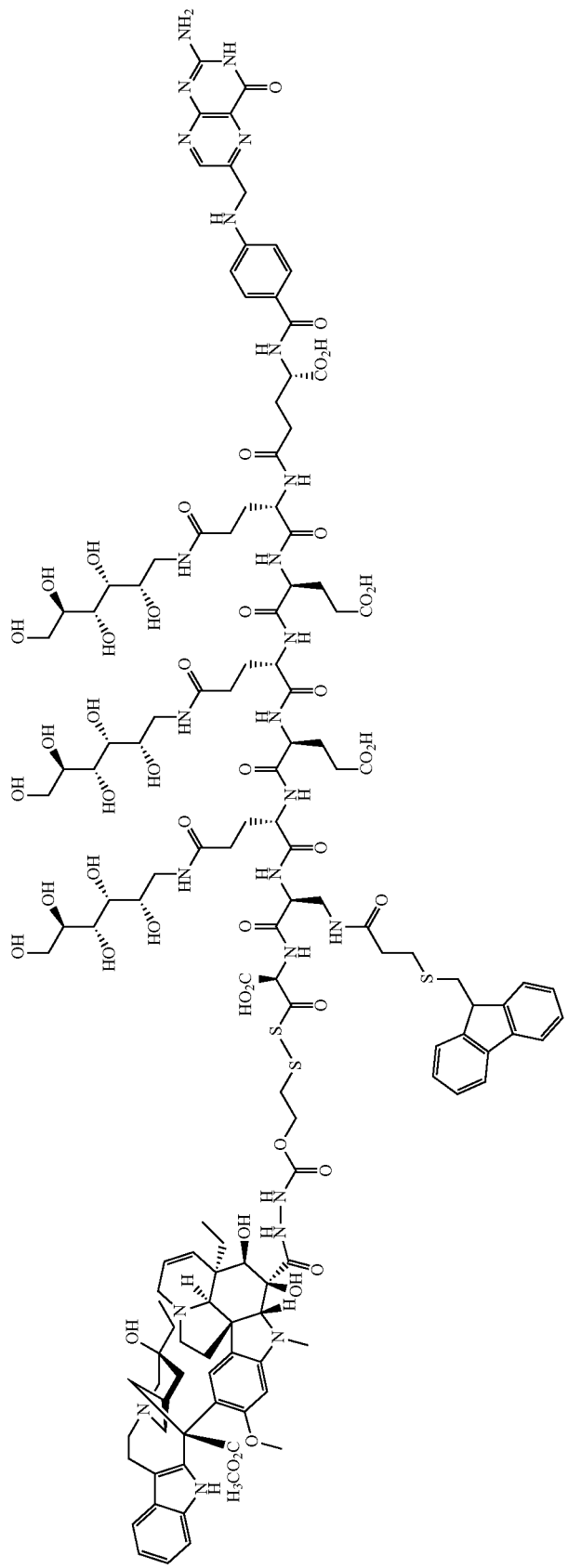

EC0633 Conjugate of DAVLBH and intermediate for multidrug conjugate. C131H176N24O45S3, MW 2903.13, Exact Mass: 2901.14
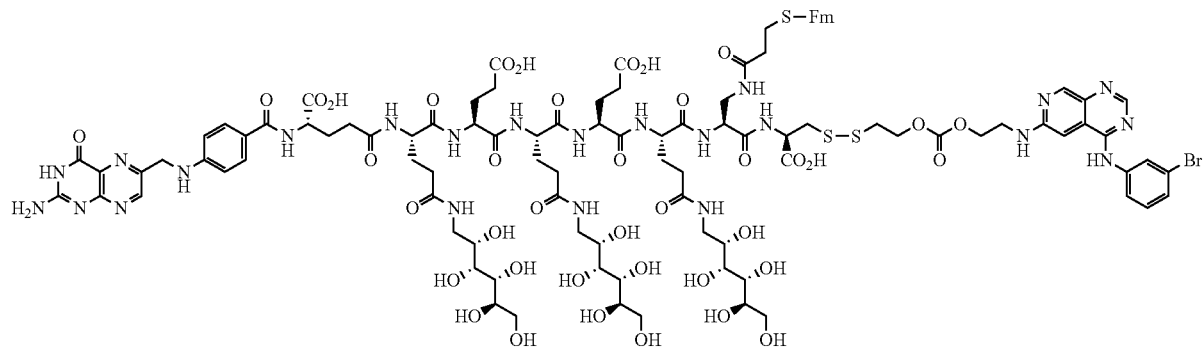
EC0661 Conjugate of 4-[(3-Bromophenyl)amino]-6-amino-pyrido[3,4-d]pyrimidine and intermediate for multidrug conjugate. C145H209BrN24O55S4, MW 3376.51, Exact Mass: 3373.24
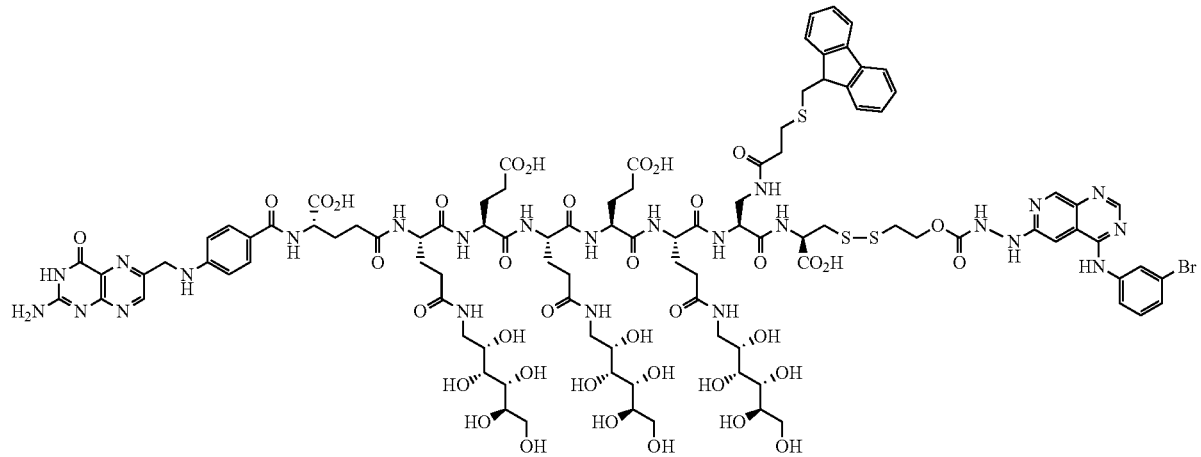 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CNC(=O)CCSCC4c5ccccc5-c5ccccc54)C(=O)N[C@@H](CSSCCOC(=O)NNc4cc5c(Nc6cccc(Br)c6)ncnc5cn4)C(=O)O)C(=O)O)cc3)nc2c(=O)[nH]1]
EC0679 Conjugate of 4-[(3-Bromophenyl)amino]-6-hydrazino-pyrido[3,4-d]pyrimidine and intermediate for multidrug conjugate. C101H131BrN24O38S3, MW 2465.36, Exact Mass: 2462.74
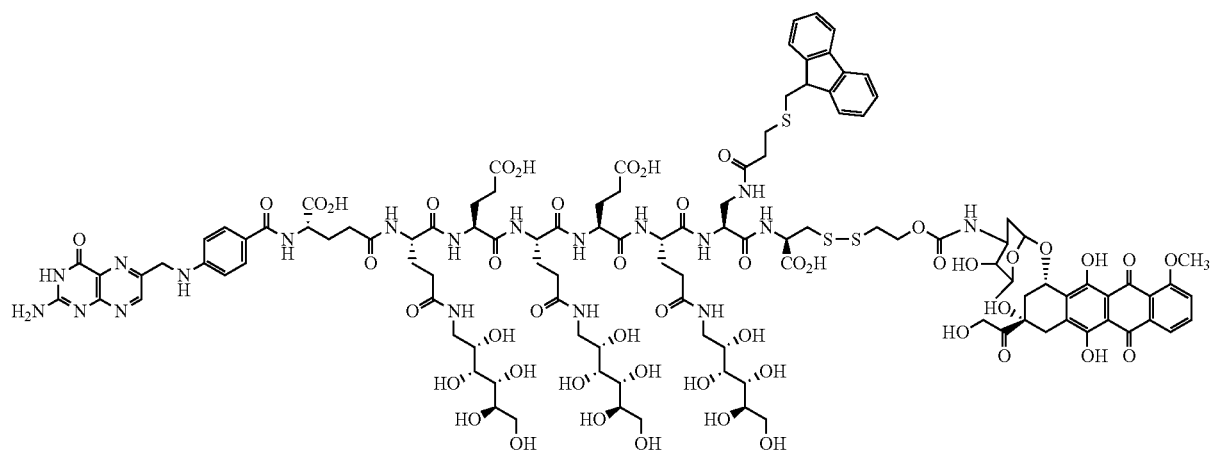 [SMILES: COc1cccc2c1C(=O)c1c(O)c3c(c(O)c1C2=O)C[C@@](O)(C(=O)CO)C[C@@H]3OC1CC(NC(=O)OCCSSC[C@H](NC(=O)[C@H](CNC(=O)CCSCC2c3ccccc3-c3ccccc32)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)[C@H](CCC(=O)O)NC(=O)[C@H](CCC(=O)NC[C@H](O)[C@@H](O)[C@H](O)[C@H](O)CO)NC(=O)CC[C@H](NC(=O)c2ccc(NCc3cnc4nc(N)[nH]c(=O)c4n3)cc2)C(=O)O)C(=O)O)C(O)C(C)O1]

EC0693 Conjugate of Doxorubicin and intermediate for multidrug conjugate. C115H149N19O49S3, MW 2677.71, Exact Mass: 2675.89

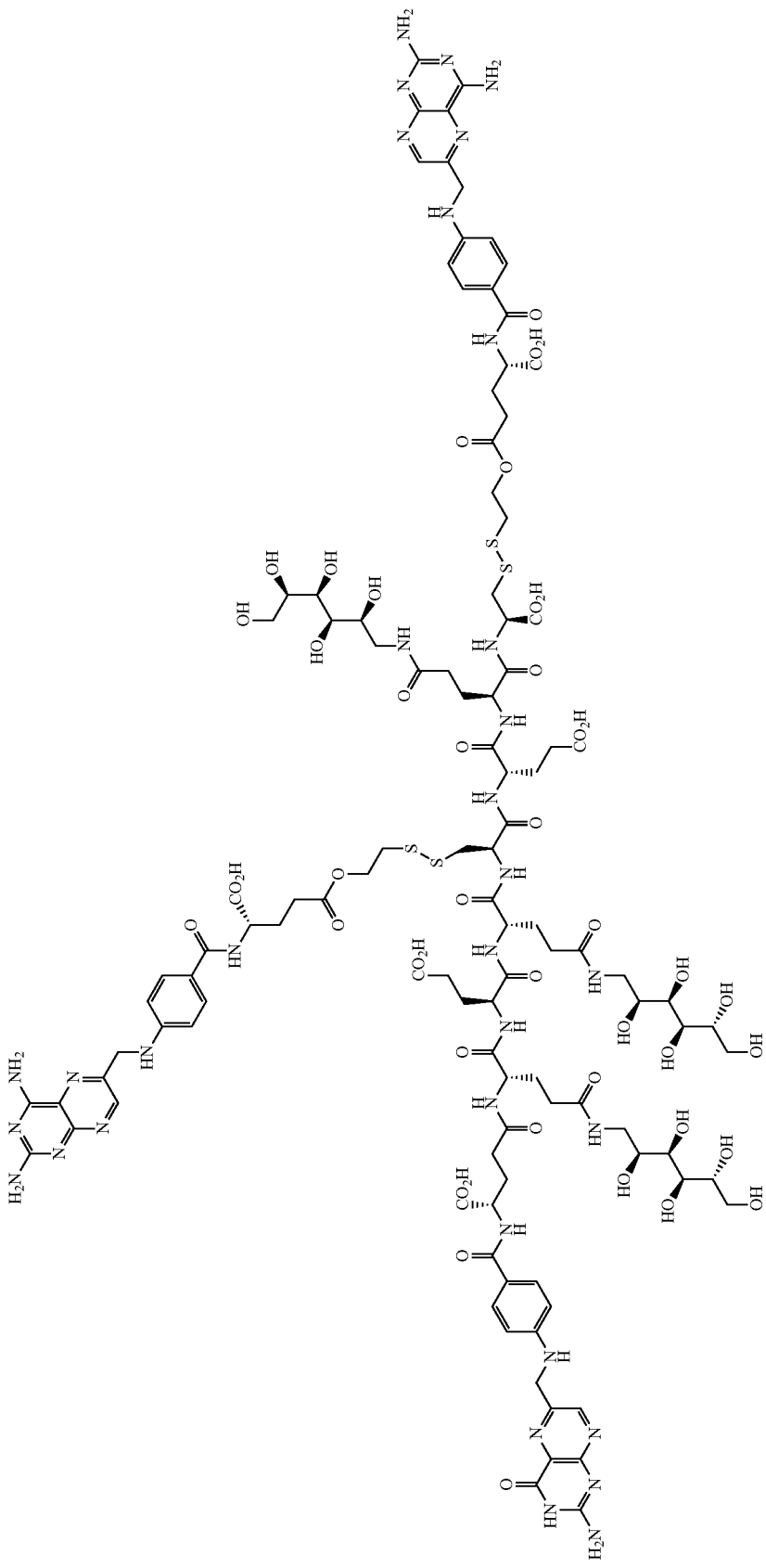

EC0647 Bis aminopterin conjugate. C110H147N33O45S4, MW, 2779.80, Exact Mass: 2777.9112, m/z: 2778.91 (100.0%), 2777.91 (74.4%), 2779.92 (62.2%)
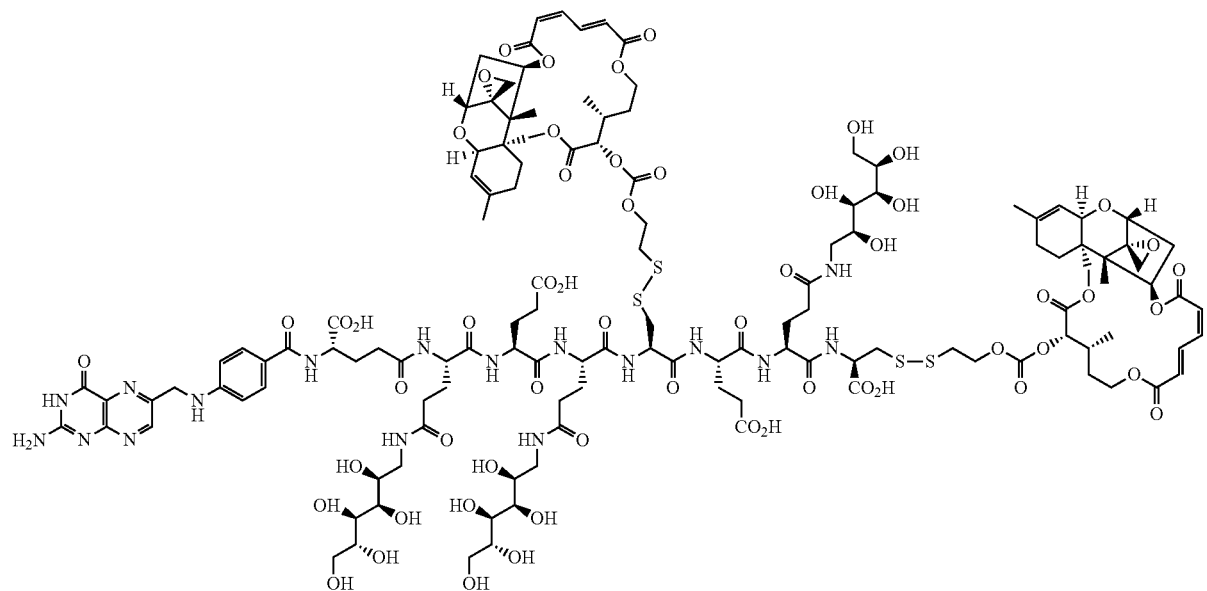
EC0605 Bis-verucarin conjugate.
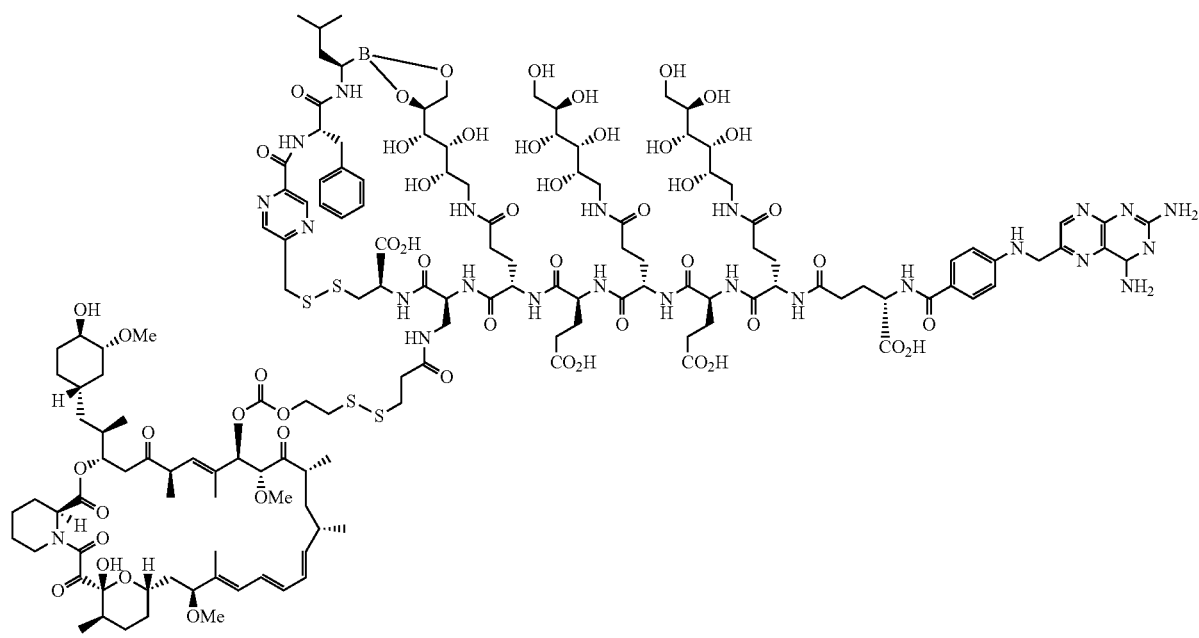
EC0563 Conjugate of Bortezomib and Rapamycin.

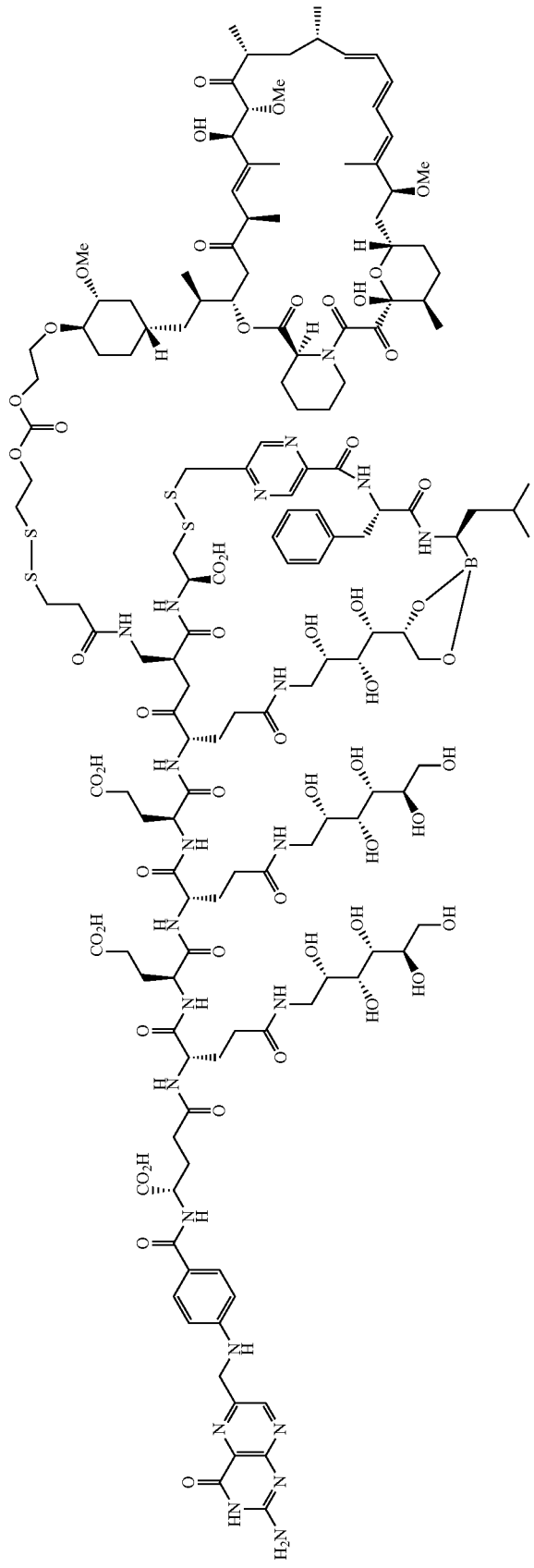

EC0582 Conjugate of Bortezomib and Everolimus. C147H214BN23O54S4, C, 53.40; H, 6.52; B, 0.33; N, 9.74; O, 26.13; S, 3.88, MW 3306.47, Exact Mass: 3304.37

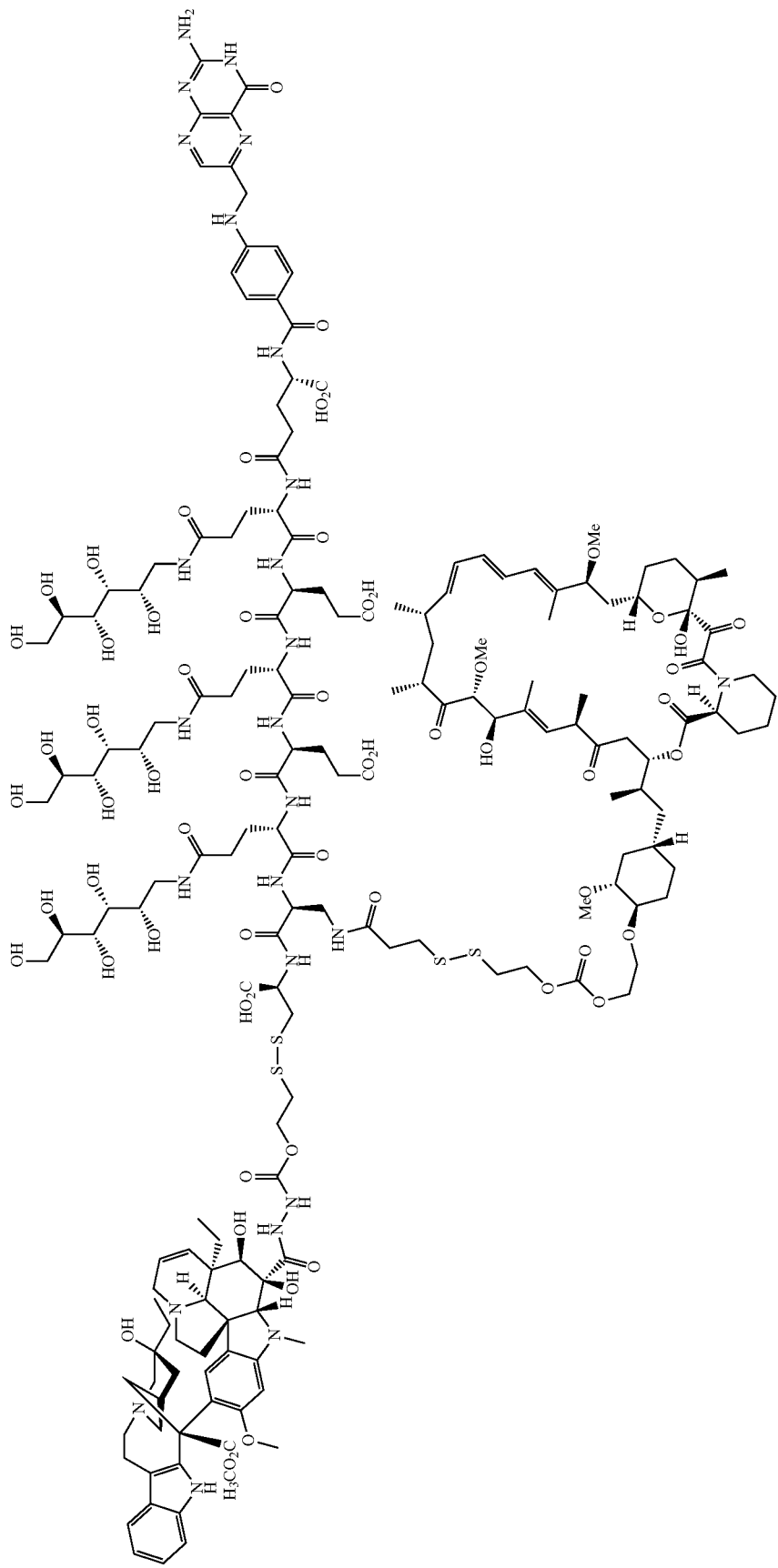

EC0636 Conjugate of DAVLBH and Everolimus.
C173H251N25O61S4, MW 3785.23, Exact Mass: 3782.62
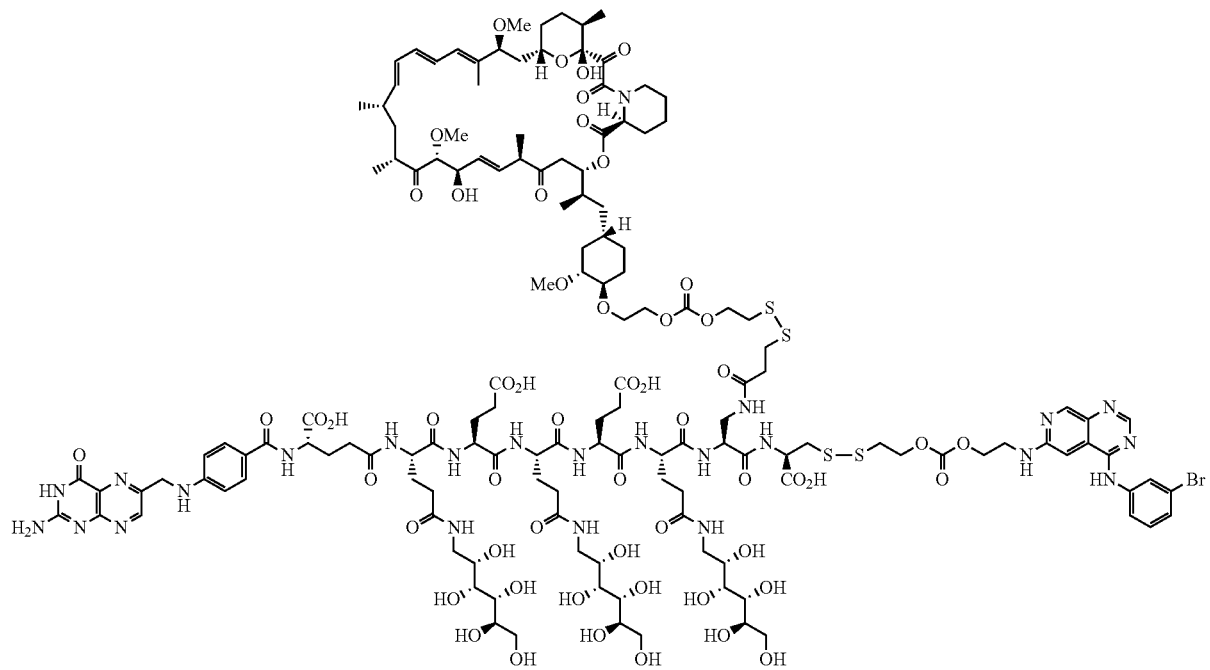
EC0664 Conjugate of Everolimus and 4-[(3-Bromophenyl)amino]-6-amino-pyrido[3,4-d]pyrimidine.
C145H209BrN24O55S4, MW 3376.51, Exact Mass: 3373.24
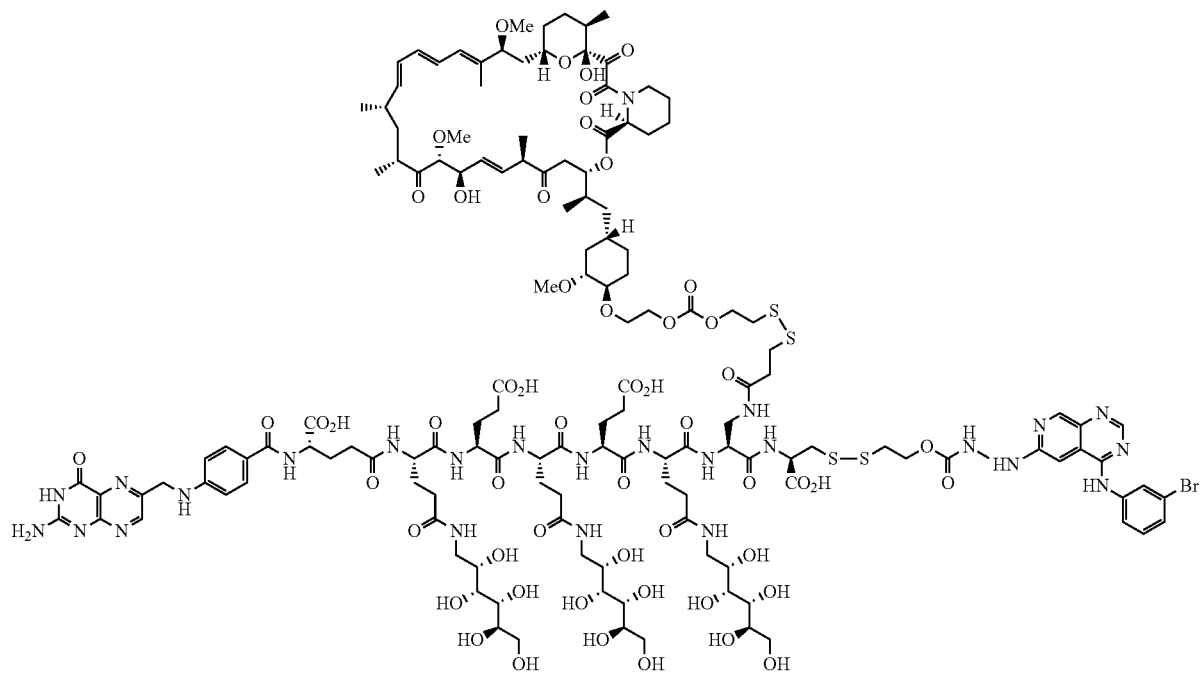
EC0680 Conjugate of Everolimus and 4-[(3-Bromophenyl)amino]-6-hydrazino-pyrido[3,4-d]pyrimidine.
C143H206BrN25O54S4, MW 3347.47, Exact Mass: 3344.22

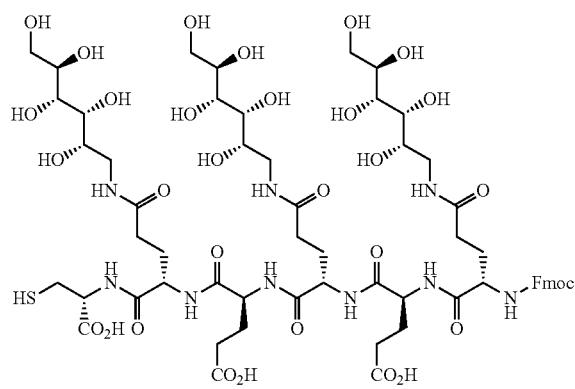
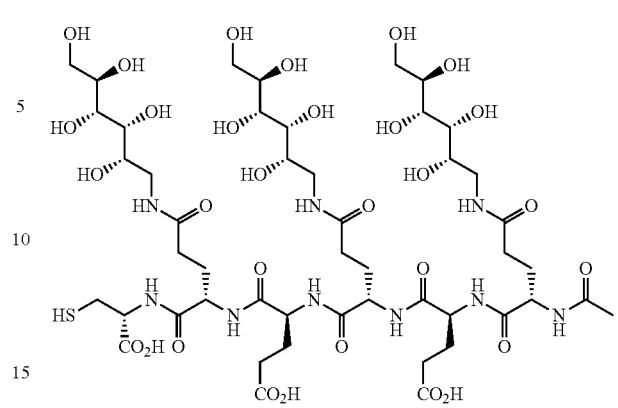
EC0584 Intermediate for optional non-targeted delivery.
C61H91N9O31S. MW 1478.48, Exact Mass: 1477.55
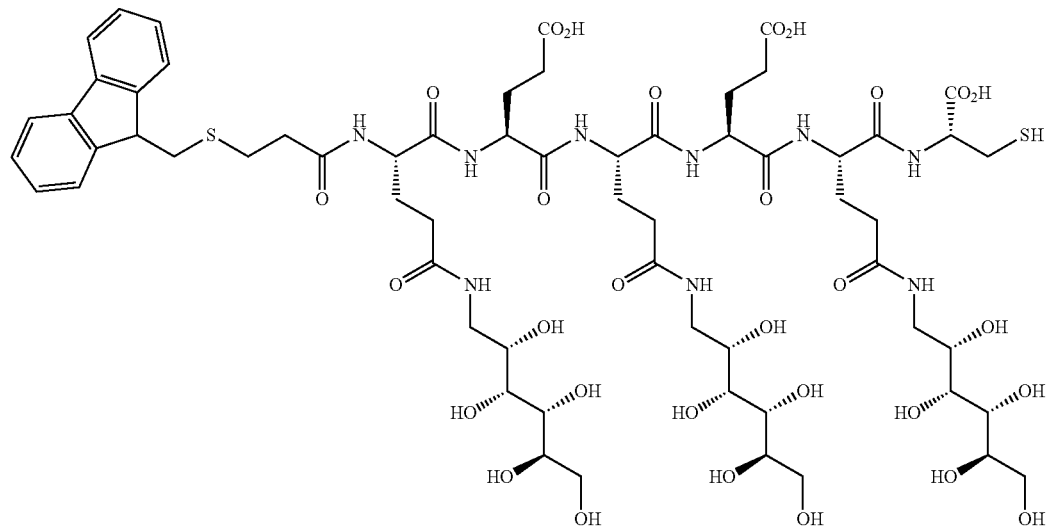 [SMILES: O=C(O)CC[C@H](NC(=O)[C@H](CCC(=O)NC[C@H](O)[C@@H](O)[C@H](O)[C@H](O)CO)NC(=O)CCSCC1c2ccccc2-c2ccccc21)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O]
EC0634 Intermediate for optional non-targeted delivery.
C63H95N9O30S2, MW 1522.60, Exact Mass: 1521.56
EC0586 Intermediate for optional non-target delivery.
C48H83N9O30S, MW 1298.28, Exact Mass: 1297.50
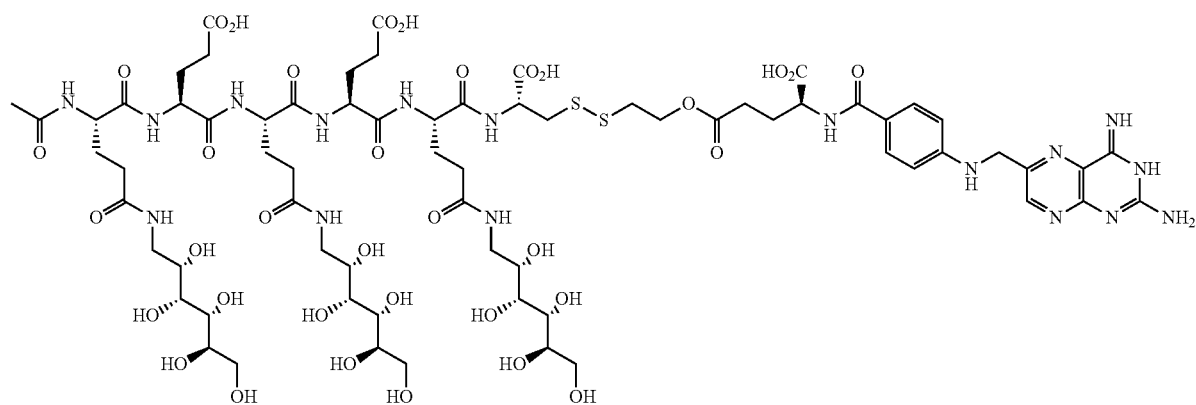

EC0588 Aminopterin conjugate intermediate for optional non-targeted delivery. C69H105N17O35S2, MW 1796.79, Exact Mass: 1795.64

$-N(R^{4a})S(O)_2-$, $-C(R^{6b})(R^{7b})-$, $-N(C\equiv CH)-$, $-N(CH_2C\equiv CH)-$, $C_1-C_{12}$ alkylene, and $C_1-C_{12}$ alkyneoxy, where Z is oxygen or sulfur;

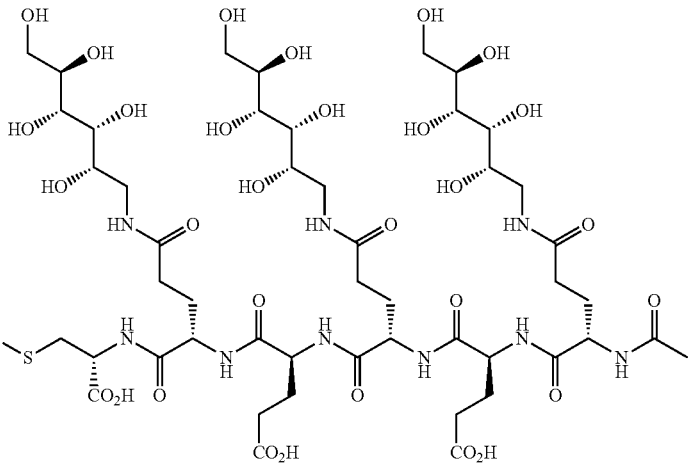 [SMILES: CC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O]

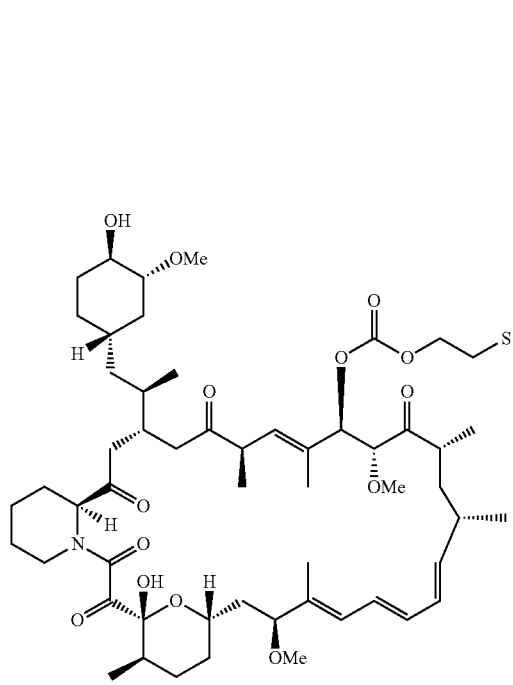

EC0591 Rapamycin conjugate intermediate for optional non-targeted delivery. C102H164N10O45S2, C, 52.93; H, 7.14; N, 6.05; O, 31.11; S, 2.77, MW 2314.57, Exact Mass: 2313.03

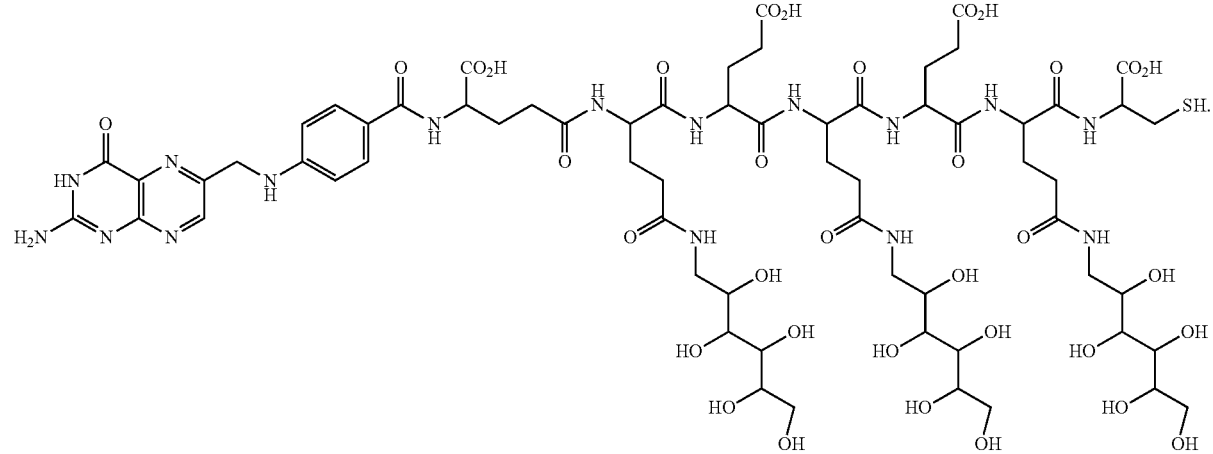

21. A compound of the formula
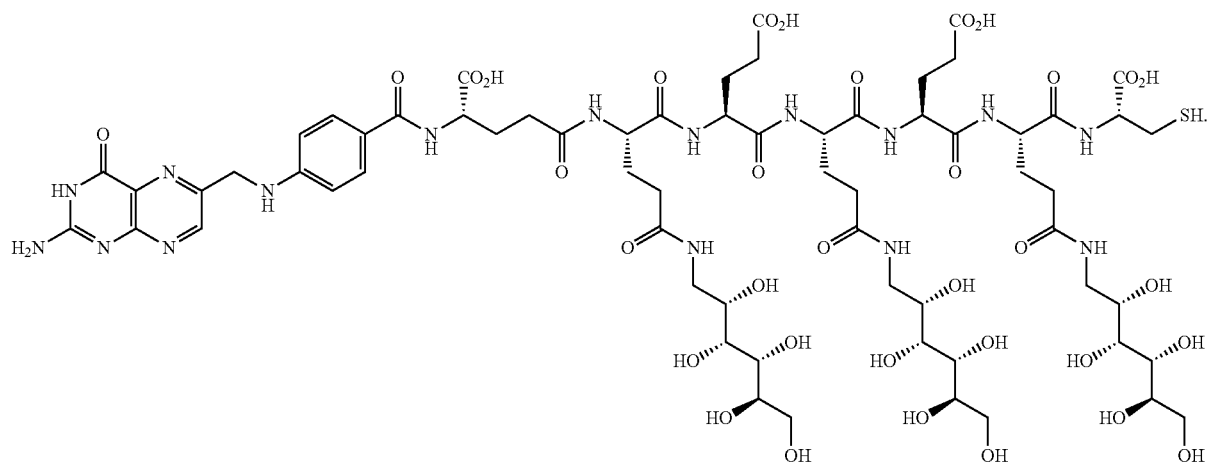

The invention claimed is:

1. A compound of the formula

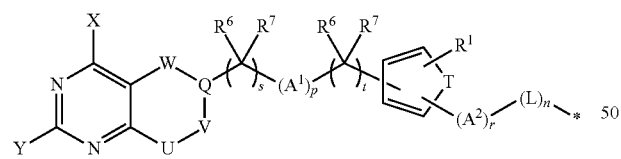

wherein X and Y are each-independently selected from the group consisting of halo, $R^2$, $OR^2$, $SR^3$, and $NR^4R^5$;

U, V, and W represent divalent moieties each independently selected from the group consisting of $-(R^{6a})C=$, $-N=$, $-(R^{6a})C(R^{7a})-$, and $-N(R^{4a})-$; Q is selected from the group consisting of C and CH; T is selected from the group consisting of S, O, N, and $-C=C-$;

$A^1$ and $A^2$ are each independently selected from the group consisting of oxygen, sulfur, $-C(Z)-$, $-C(Z)O-$, $-OC(Z)-$, $-N(R^{4b})-$, $-C(Z)N(R^{4b})-$, $-N(R^{4b})$ $C(Z)-$, $-OC(Z)N(R^{4b})-$, $-N(R^{4b})C(Z)O-$, $-N(R^{4b})C(Z)N(R^{5b})-$, $-S(O)-$, $-S(O)_2-$, $R^1$ is selected-from the group consisting of hydrogen, halo, $C_1-C_{12}$ alkyl, and $C_1-C_{12}$ alkoxy;

$R^2$, $R^3$, $R^4$, $R^{4a}$, $R^{4b}$, $R^5$, $R^{5b}$, $R^{6b}$, and $R^{7b}$ are each independently selected from the group consisting of hydrogen, $C_1-C_{12}$ alkyl, $C_1-C_{12}$ alkoxy, $C_1-C_{12}$ alkanoyl, $C_1-C_{12}$ alkenyl, $C_1-C_{12}$ alkynyl, ($C_1-C_{12}$ alkoxy)carbonyl, and ($C_1-C_{12}$ alkylamino)carbonyl;

$R^6$ and $R^7$ are each independently selected from the group consisting of hydrogen, halo, $C_1-C_{12}$ alkyl, and $C_1-C_{12}$ alkoxy; or, $R^6$ and $R^7$ are taken together to form a carbonyl group; $R^{6a}$ and $R^{7a}$ are each independently selected from the group consisting of hydrogen, halo, $C_1-C_{12}$ alkyl, and $C_1-C_{12}$ alkoxy; or $R^{6a}$ and $R^{7a}$ are taken together to form a carbonyl group;

L is a divalent linker comprising at least three hydrophilic spacer linkers that are polyhydroxyl groups;

n is 1;
p is 1;
r is 1;
s is 1;
t is 0;

* indicates a point of attachment to an additional spacer linker selected from the group consisting of aspartic acid, glutamic acid, lysine, cysteine, norleucine, isovaline, β-methyl threonine, β-methyl cystein, and β,β-dimethyl cystein, or a stereoisomer thereof, wherein at least one polyhydroxyl group is selected from the group consisting of

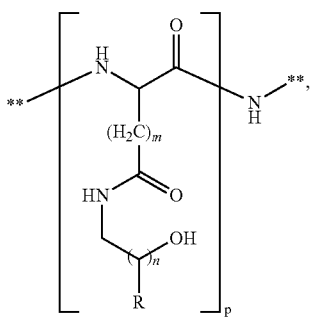

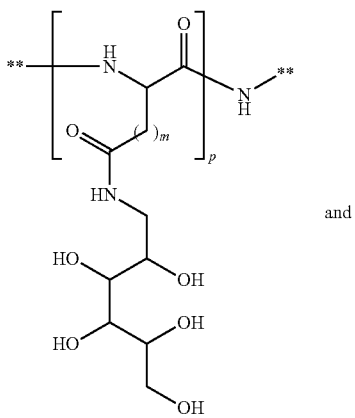

and wherein each ** represents a point of attachment to an additional spacer linker.

2. The compound of claim 1, wherein at least one polyhydroxyl group is of the formula

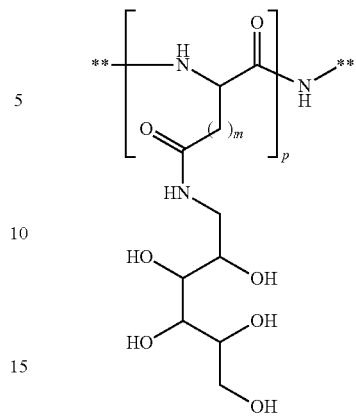

wherein each ** represents a point of attachment to an additional spacer linker.

3. The compound of claim 2, wherein L further comprises a $L^a$, wherein $L^a$ is a naturally occurring amino acid, or a stereoisomer thereof, covalently linked to $A^2$ through the alpha-amino group of the naturally occurring amino acid by an amide bond.

4. The compound of claim 3, wherein the naturally occurring amino acid is aspartic acid, glutamic acid, lysine or cysteine.

5. The compound of claim 3, wherein the naturally occurring amino acid is glutamic acid.

6. The compound of claim 1, wherein L further comprises at least one $L_s$ selected from the group consisting of aspartic acid, glutamic acid, lysine and cysteine, or a stereoisomer thereof.

7. The compound of claim 6, wherein the at least one $L_s$ is glutamic acid.

8. The compound of claim 5, wherein L further comprises at least one $L_s$ selected from the group consisting of aspartic acid, glutamic acid, lysine and cysteine, or a stereoisomer thereof.

9. The compound of claim 8, wherein the at least one $L_s$ is glutamic acid.

10. A compound of the formula

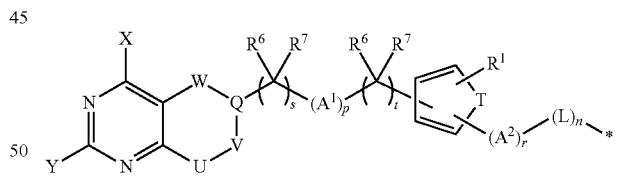

wherein X and Y are each-independently selected from the group consisting of halo, $R^2$, $OR^2$, $SR^3$, and $NR^4R^5$;

U, V, and W represent divalent moieties each independently selected from the group consisting of —($R^{6a}$)C=, —N=, —($R^{6a}$)C($R^{7a}$)—, and —N($R^{4a}$)—; Q is selected from the group consisting of C and CH; T is selected from the group consisting of S, O, N, and —C=C—;

$A^1$ is independently selected from the group consisting of oxygen, sulfur, —C(Z)—, —C(Z)O—, —OC(Z)—, —N($R^{4b}$)—, —C(Z)N($R^{4b}$)—, —N($R^{4b}$)C(Z)—, —OC(Z)N($R^{4b}$)—, —N($R^{4b}$)C(Z)O—, —N($R^{4b}$)C(Z)N($R^{5b}$)—, —S(O)—, —S(O)$_2$—, —N($R^{4a}$)S(O)$_2$—, —C($R^{6b}$)($R^{7b}$)—, —N(C≡CH)—, —N(CH$_2$C≡CH)—, $C_1$-$C_{12}$ alkylene, and $C_1$-$C_{12}$ alkyeneoxy;

A² is —C(Z)— and Z is oxygen;

R¹ is selected-from the group consisting of hydrogen, halo, $C_1$-$C_{12}$ alkyl, and $C_1$-$C_{12}$ alkoxy;

R², R³, R⁴, R⁴ᵃ, R⁴ᵇ, R⁵, R⁵ᵇ, R⁶ᵇ, and R⁷ᵇ are each independently selected from the group consisting of hydrogen, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

R⁶ and R⁷ are each independently selected from the group consisting of hydrogen, halo, $C_1$-$C_{12}$ alkyl, and $C_1$-$C_{12}$ alkoxy; or, R⁶ and R⁷ are taken together to form a carbonyl group; R⁶ᵃ and R⁷ᵃ are each independently selected from the group consisting of hydrogen, halo, $C_1$-$C_{12}$ alkyl, and $C_1$-$C_{12}$ alkoxy; or R⁶ᵃ and R⁷ᵃ are taken together to form a carbonyl group;

L is a divalent linker comprising at least three hydrophilic spacer linkers that are polyhydroxyl groups;

n is 1;
p is 1;
r is 1;
s is 1;
t is 0; and

* indicates a point of attachment to an additional spacer linker selected from the group consisting of aspartic acid, glutamic acid, lysine and cysteine, norleucine, isovaline, β-methyl threonine, β-methyl cystein, β,β-dimethyl cystein, or a stereoisomer thereof.

11. The compound of claim 9, wherein A² is —C(Z)—, wherein Z is oxygen.

12. The compound of claim 1, wherein A¹ is —N(R⁴ᵇ)—, and R⁴ᵇ is H.

13. The compound of claim 11, wherein A¹ is —N(R⁴ᵇ)—, and R⁴ᵇ is H.

14. The compound of claim 1, wherein each R⁶ and R⁷ is H.

15. The compound of claim 1, wherein U and W are —N═.

16. The compound of claim 11, wherein V is —(R⁶ᵃ)C═, wherein R⁶ᵃ is H.

17. The compound of claim 13, wherein U and W are —N═, and V is —(R⁶ᵃ)C═, wherein R⁶ᵃ is H.

18. A compound of the formula

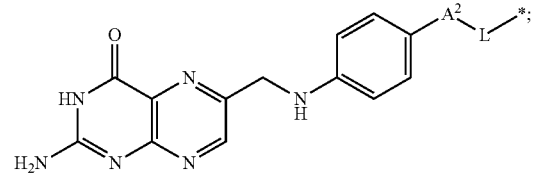

wherein A² is selected from the group consisting of oxygen, sulfur, —C(Z)—, —C(Z)O—, —OC(Z)—, —N(R⁴ᵇ)—, —C(Z)N(R⁴ᵇ)—, —N(R⁴ᵇ)C(Z)—, —OC(Z)N(R⁴ᵇ)—, —N(R⁴ᵇ)C(Z)O—, —N(R⁴ᵇ)C(Z)N(R⁵ᵇ)—, —S(O)—, —S(O)₂—, —N(R⁴ᵃ)S(O)₂—, —C(R⁶ᵇ)(R⁷ᵇ)—, —N(C≡CH)—, —N(CH₂C≡CH)—, $C_1$-$C_{12}$ alkylene, and $C_1$-$C_{12}$ alkyeneoxy, where Z is oxygen or sulfur;

R⁴ᵃ, R⁴ᵇ, R⁵ᵇ, R⁶ᵇ, and R⁷ᵇ are each independently selected from the group consisting of hydrogen, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

L is a divalent linker comprising at least three hydrophilic spacer linkers that are polyhydroxyl groups; and

* indicates a point of attachment to an additional spacer linker selected from the group consisting of aspartic acid, glutamic acid, lysine, cysteine, norleucine, isovaline, β-methyl threonine, and β-methyl cystein, β,β-dimethyl cystein, or a stereoisomer thereof.

19. The compound of claim 17, of the formula

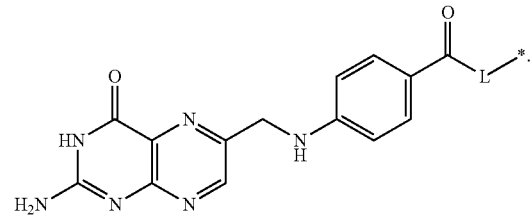

20. A compound of the formula